(12) United States Patent
Rabinovich et al.

(10) Patent No.: US 11,141,434 B2
(45) Date of Patent: Oct. 12, 2021

(54) PROGRAMMED DEATH 1 LIGAND 1 (PD-L1) BINDING PROTEINS AND METHODS OF USE THEREOF

(71) Applicant: Iovance Biotherapeutics, Inc., San Carlos, CA (US)

(72) Inventors: Brian Rabinovich, Winchester, MA (US); Natalia Martin-Orozco, Acton, MA (US); Laszlo Radvanyi, Acton, MA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 218 days.

(21) Appl. No.: 16/316,019

(22) PCT Filed: Jul. 7, 2017

(86) PCT No.: PCT/US2017/041241
§ 371 (c)(1),
(2) Date: Jan. 7, 2019

(87) PCT Pub. No.: WO2018/009894
PCT Pub. Date: Jan. 11, 2018

(65) Prior Publication Data
US 2019/0298770 A1 Oct. 3, 2019

Related U.S. Application Data

(60) Provisional application No. 62/359,612, filed on Jul. 7, 2016.

(51) Int. Cl.
| | | |
|---|---|---|
| *C07K 16/28* | (2006.01) | |
| *A61K 35/17* | (2015.01) | |
| *A61P 35/00* | (2006.01) | |
| *C12N 5/0783* | (2010.01) | |

(52) U.S. Cl.
CPC .............. *A61K 35/17* (2013.01); *A61P 35/00* (2018.01); *C07K 16/2818* (2013.01); *C07K 16/2827* (2013.01); *C12N 5/0638* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,766,106 A | 8/1988 | Katre et al. |
| 4,902,502 A | 2/1990 | Nitecki et al. |
| 5,089,261 A | 2/1992 | Nitecki et al. |
| 5,206,344 A | 4/1993 | Katre et al. |
| 5,877,293 A | 3/1999 | Adair et al. |
| 5,886,152 A | 3/1999 | Nakatani et al. |
| 6,054,297 A | 4/2000 | Carter et al. |
| 6,706,289 B2 | 3/2004 | Lewis et al. |
| 7,943,743 B2 | 5/2011 | Korman et al. |
| 8,008,449 B2 | 8/2011 | Korman et al. |
| 8,034,334 B2 | 10/2011 | Dudley et al. |
| 8,383,099 B2 | 2/2013 | Dudley et al. |
| 8,809,050 B2 | 8/2014 | Vera et al. |
| 8,956,860 B2 | 2/2015 | Vera et al. |
| 9,074,185 B2 | 7/2015 | Dudley et al. |
| 9,844,569 B2 | 12/2017 | Gros et al. |
| 2005/0106717 A1 | 5/2005 | Wilson et al. |
| 2011/0052530 A1 | 3/2011 | Dudley et al. |
| 2011/0136228 A1 | 6/2011 | Vera et al. |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2014/0328791 A1 | 11/2014 | Bossard et al. |
| 2014/0377739 A1 | 12/2014 | Welch et al. |
| 2015/0175966 A1 | 6/2015 | Vera et al. |
| 2016/0010058 A1 | 1/2016 | Gros et al. |
| 2016/0137731 A1 | 5/2016 | Freeman et al. |
| 2016/0208216 A1 | 7/2016 | Vera et al. |
| 2016/0215262 A1 | 7/2016 | Powell |

(Continued)

FOREIGN PATENT DOCUMENTS

| | | | |
|---|---|---|---|
| WO | WO 2010/126766 A1 | 11/2010 | |
| WO | WO 2012/065086 A1 | 5/2012 | |

(Continued)

OTHER PUBLICATIONS

Klingemann H., "Are natural killer cells superior CAR drivers?", Oncoimmunology, Apr. 15, 2014, vol. 3, pp. e28147.
Suarez E. R. et al., "Chimeric antigen receptor T cells secreting anti-PD-L1 antibodies more effectively regress renal cell carcinoma in a humanized mouse model", Oncotarget, Apr. 29, 2016, vol. 7, No. 23, pp. 34341-343555.
Yang Y. et al., CD4 CAR T Cells Mediate CD8-like Cytotoxic Anti-Leukemic Effects Resulting in Leukemic Clearance and Are Less Susceptible to Attenuation by Endogenous TCR Activation Than CD8 CAR T Cells. Blood., Dec. 3, 2015, vol. 126, No. 23, p. 100 (Abstract).
International Search Report and Written Opinion for International Patent Application No. PCT/US2017/041241 dated Sep. 19, 2017, 13 pages.

(Continued)

*Primary Examiner* — Laura B Goddard
(74) *Attorney, Agent, or Firm* — Christina A. MacDougall; Morgan, Lewis & Bockius, LLP

(57) ABSTRACT

The present disclosure provides proteins, such as antibodies, that include an antigen binding portion that specifically binds to Programmed Death 1 Ligand 1 (PD-L1). Also provided are nucleic acids encoding the proteins, and cells (e.g., genetically modified cytotoxic lymphocytes) that include such nucleic acids. In some embodiments, a subject method includes reducing the interaction between PD-L1 on a first-cell and PD-1 on a second cell. In some cases, the contacting is in vivo. For example, the methods and compositions provided can be used in the treatment of viral infection and cancer, such as the treatment of solid tumors via ACT or via administration of a subject protein that specifically binds to PD-L1.

27 Claims, 32 Drawing Sheets
Specification includes a Sequence Listing.

(56) References Cited

U.S. PATENT DOCUMENTS

| | | | |
|---|---|---|---|
| 2017/0044496 | A1 | 2/2017 | Sarnaik et al. |
| 2017/0081635 | A1 | 3/2017 | Sarnaik et al. |
| 2017/0107490 | A1 | 4/2017 | Maeurer |
| 2017/0152478 | A1 | 6/2017 | Rosenberg et al. |

FOREIGN PATENT DOCUMENTS

| | | | |
|---|---|---|---|
| WO | WO 2013/057500 A1 | | 4/2013 |
| WO | WO 2013/088147 A1 | | 6/2013 |
| WO | WO 2013/173835 A1 | | 11/2013 |
| WO | WO 2013/188427 A1 | | 12/2013 |
| WO | WO 2015/112805 | * | 7/2015 |
| WO | WO 2015/157636 A1 | | 10/2015 |
| WO | WO 2015/189357 A1 | | 12/2015 |
| WO | WO 2016/041945 A1 | | 3/2016 |
| WO | WO 2016/053338 A1 | | 4/2016 |
| WO | WO 2016/096903 A1 | | 6/2016 |
| WO | WO 2016100985 | | 6/2016 |
| WO | WO 2018/081473 A1 | | 5/2018 |
| WO | WO 2018129332 A1 | | 10/2018 |
| WO | WO 2018209115 A1 | | 11/2018 |
| WO | WO 2018226714 A1 | | 12/2018 |

OTHER PUBLICATIONS

Sznol et al., "Antagonist Antibodies to PD-1 and B7-H1 (PD-L1) in the Treatment of Advanced Human Cancer", Clinical Cancer Research, vol. 19, No. 5, Mar. 1, 2013, pp. 1021-1034.

Sunshine et al., "PD-1/PD/L1 inhibitors", Current Opinion in Pharmacology, vol. 23, Aug. 1, 2015, pp. 32-38.

Boyerinas et al., "Antibody-Dependent Cellular Cytotoxicity Activity of a Novel Anti-PD-L1 Antibody Avelumab (MSB0010718C) on Human Turmor Cells", Cancer Immunology Research, vol. 3, No. 10, May 26, 2015, pp. 1148-1157.

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Donia M, et al.. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al., "Cancer Regression and Autoimmunity in Patients After Clonal Repopulation with Antitumor Lymphocytes", Science, Oct. 2002, 298, 850-54.

International Search Report and Written Opinion for International Patent Application No. PCT/US2018/012633 dated May 25, 2018, 14 pages.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permiable flasks to numbers needed for patient treatment", J. Immunotherapy, 2012, 35:283-292.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. "Adoptive cell therapy for the treatment of patients with metastatic melanoma", Curr Opin Immunol. Apr. 2009;21(2):233-40.

Rosenberg, "IL-2: The First Effective Immunotherapy for Human Cancer," The Journal of Immunology, Col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

Somerville RP, et al., "Clinical scale rapid expansion of lymphocytes for adoptive cell transfer therapy in the WAVE® bioreactor", J Transl Med. Apr. 4, 2012;10:69.

Tran et al., "Minimally Cultured tumor-infiltrating lymphocytes display optimal characteristics for adoptive cell therapy", J. Immunother., Oct. 2008; 31(8), 742-751.

Lee et al., "Tumor-Infiltrating Lymphocytes in Melanoma", Curr Oncol Rep. Aug. 2012, 14, 468-474.

Holliger, et al., "Diabodies": Small bivalent and biospecific antibody fragments, Proc. Natl. Acad. Sci. USA, Jul. 1993, 90, 6444-6448.

Poljak, "Production and Structure of Diabodies", Structure, Dec. 1994, 2, 1121-1123.

Nelson, "IL-2, Regulatory T Cells, and Tolerance", J. Immunol. 2004, 172, 3983-88.

Malek et al., "The biology of interleukin-2", Annu. Rev. Immunol. 2008, 26, 453-79.

Fry and Mackall, "Interleukin-7: from bench to clinic", Blood 2002, 99, 3892-904.

Spolski and Leonard, "Interleukin-21: a double-edged sword with therapeutic potential", Nat. Rev. Drug. Disc. 2014, 13, 379-395.

Peyrottes et al., "Oligodeoxynucleoside phosphoramidates (P-NH2): synthesis and thermal stability of duplexes with DNA and RNA targets", 1996, Nucl. Acids Res. 24: 1841-1848.

Chaturvedi et al., "Stabilization of triple-stranded oligonucleotide complexes: use of probes containing alternating phosphodiester and stereo-uniform cationic phosphoramidate linkages", 1996, Nucl. Acids Res. 24: 2318-2323.

No et al., "Ecdysone-inducible gene expression in mammalian cells and transgenic Mice", Proc Natl. Acad. Sci. USA, Apr. 1996, 93, 3346-3351.

Gossen et al., "Tight control of gene expression in mammalian cells by tetracycline-responsive promoters", PNAS Jun. 15, 1992 89 (12) 5547-5551.

Gossen et al., "Transcriptional activation by tetracyclines in mammalian cells", Science Jun. 23, 1995: vol. 268, Issue 5218, pp. 1766-1769.

Harvey et al., "Inducible Control of Gene Expression: Prospects for Gene Therapy", Current Opinion in Chemical Biology, 1998, 2, 512-518.

Wang et al., "Ligand-Inducible and liver specific target gene expression in transgenic mice", Nature Biotechnology, Mar. 1997, 15, 239-243.

Wang et at., "Positive and Negative regulation of gene expression in eukaryotic cells with an inducible transcriptional regulator", Gene Therapy, 1997, 4, 432-441.

Magari et al., "Pharmacological Control of a Humanized Gene Therapy System Implanted into Nude Mice", J. Clin. Invest. Dec. 1997, 100(11), 2865-2872.

Nilsson et al., "Immobilization and Purification of Enzymes with Staphyloccal Protein A Gene Fusions", The EMBO Journal ,1985, 4(4), 1075-1080.

Nilsson et al., "Expression and Purification of Recombinant Insulin-Like growth factors from *Escherichia coli*", Methods in Enzymology, 1991, 198, 14 pages.

Smith et al., "Single-Step Purification of Polypeptides Expressed in *Escherichia coli* as fusions with glutathione S-Transferase", Gene, Mar. 1988, 67, 31-40.

(56) References Cited

OTHER PUBLICATIONS

Grussenmeyer et al., "Complexes of Polyoma virus medium T antigen and cellular proteins", Proc Natl. Acad. Sci., USA Dec. 1985, 82, 7952-7954.

Hopp et al., "A Short Polypeptide Marker Sequence Useful for Reconbinant Protein Identification and purification", Biotechnology 6: 1204 (1988).

Ford et al., "Fusion tails for the recovery and purification of recombinant proteins", Protein Expression and Purification 2:95 (1991).

Wang et al., "In Vitro Characterization of the Anti-PD-1 Antibody Nivolumab, BMS-936558, and in Vivo Toxicology in Non-Human primates", Cancer Immunol. Res., Sep. 2014, 2(9), 846-856.

Wang et al., "Development of a Hypoxia-inducible cytosine deaminase expression vector for gene-directed prodrug cancer therapy", Cancer Gene Therapy, Jan. 2005, 12, 276-283.

Liu et al., "Calcineurin is a Common Target of Cyclophilin-Cyclosporin A and FKBp-FK506 Complexes", Cell, Aug. 1991, 66, 807-815.

Henderson et al., "Comparison of th effects of FK-506, cyclosporine A and rapamycin on IL-2 production", Immun. 73:316-321, 1991.

Bierer et al., "Cyclosporin A and FK506: molecular mechanisms of immunosuppression and probes for transplantation of biology", Current Opinion in Immunology, 1993, 57, 763-773.

\* cited by examiner

*Figure 7*

Antibody 38A1

*Light Chain*

SYVLTQPPSVSVAPGQTARITCGGNNIGRKIVHWYQQRPGQAPVLVIYYDTDRPAGIPERFSGSN
SGNMATLTISTVGAGDEADYYCQVWDTGSDHVVFGGGTKLTVL (SEQ ID NO: 1)

```
CDR1(CDR-L1): NIGRKI              (SEQ ID NO: 2)
CDR2(CDR-L2): YDT                 (SEQ ID NO: 3)
CDR3(CDR-L3): QVWDTGSDHVV         (SEQ ID NO: 4)
```

*Heavy Chain*

EVQLVESGGGLVQPGGSLRLSCAASGFTFSNYAMSWVRQAPGKGLEWVSTISGSGGTTYYADSVK
GRFTISRDNSKNTLYLQMNSLRVEDTAVYYCAKDWFRSSSPDAFDIWGQGTTVTVSA (SEQ ID NO: 5)

```
CDR1(CDR-H1): GFTFSNYA            (SEQ ID NO: 6)
CDR2(CDR-H2): ISGSGGTT            (SEQ ID NO: 7)
CDR3(CDR-H3): AKDWFRSSSPDAFDI     (SEQ ID NO: 8)
```

Antibody 19H9

*Light Chain*

NFMLTQPHSVSESLGKTVTISCTGSSGSIARKFVQWYQQRPGSSPTTVIYENNQRPSGVSDRFSG
SIGSSSNSASLTISGLKTEDEADYYCQSYDSSNVVFGGGTKVTVL (SEQ ID NO: 9)

```
CDR1(CDR-L1): SGSIARKF            (SEQ ID NO: 10)
CDR2(CDR-L2): ENN                 (SEQ ID NO: 11)
CDR3(CDR-L3): QSYDSSNVV           (SEQ ID NO: 12)
```

*Heavy Chain*

QVQLQESGGGLVKPGGSLRLSCAASGFTFSSYSMNWVRQAPGKGLEWVSGINTAGDTHYPESVKG
RFTISRDNARNSLNLQMNSLRAEDTAVYYCVRERVEREYSGYDAFDIWGQGTTVTVSA (SEQ ID NO: 13)

```
CDR1(CDR-H1): GFTFSSYS            (SEQ ID NO: 14)
CDR2(CDR-H2): INTAGDT             (SEQ ID NO: 15)
CDR3(CDR-H3): VRERVEREYSGYDAFDI   (SEQ ID NO: 16)
```

Figure 7 (cont.)

Example of a 38A1 ScFv

EVQLVESGGGLVQPGGSLRLSCAASGFTFSNYAMSWVRQAPGKGLEWVSTISGSGGTTYYADSVK
GRFTISRDNSKNTLYLQMNSLRVEDTAVYYCAKDWFRSSSPDAFDIWGQGTTVTVSAGGGGSGGG
GSGGGGSGAPSYVLTQPPSVSVAPGQTARITCGGNNIGRKIVHWYQQRPGQAPVLVIYYDTDRPA
GIPERFSGSNSGNMATLTISTVGAGDEADYYCQVWDTGSDHVVFGGGTKLTVL
(SEQ ID NO: 17)
  *The 38A1 heavy chain (SEQ ID NO: 5) is followed by a
  linker (bold/underline), which is followed by the 38A1
  light chain (SEQ ID NO: 1).

Example of a protein with a 38A1 ScFv fused to an Fc domain (IgG1)

MGSTAILALLLAVLQGVSA*EVQLVESGGGLVQPGGSLRLSCAASGFTFSNYAMSWVRQAPGKGLE*
*WVSTISGSGGTTYYADSVKGRFTISRDNSKNTLYLQMNSLRVEDTAVYYCAKDWFRSSSPDAFDI*
*WGQGTTVTVSAGGGGSGGGGSGGGGSGAPSYVLTQPPSVSVAPGQTARITCGGNNIGRKIVHWYQ*
*QRPGQAPVLVIYYDTDRPAGIPERFSGSNSGNMATLTISTVGAGDEADYYCQVWDTGSDHVVFGG*
*GTKLTVL*GPRANFVYKSGPRPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

(SEQ ID NO: 18)
  *The protein of SEQ ID NO: 17 (italic/underline) is
  followed by an IgG1 Fc domain (bold/underline).

Example of a 19H9 ScFv

QVQLQESGGGLVKPGGSLRLSCAASGFTFSSYSMNWVRQAPGKGLEWVSGINTAGDTHYPESVKG
RFTISRDNARNSLNLQMNSLRAEDTAVYYCVRERVEREYSGYDAFDIWGQGTTVTVSAGGGGSGG
GGSGGGGSGAPNFMLTQPHSVSESLGKTVTISCTGSSGSIARKFVQWYQQRPGSSPTTVIYENNQ
RPSGVSDRFSGSIGSSSNSASLTISGLKTEDEADYYCQSYDSSNVVFGGGTKVTVL
(SEQ ID NO: 19)
  *The 19H9 heavy chain (SEQ ID NO: 13) is followed by a
  linker (bold/underline), which is followed by the 19H9
  light chain (SEQ ID NO: 9).

Example of a protein with a 19H9 ScFv fused to an Fc domain (IgG1)

MGSTAILALLLAVLQGVSA*QVQLQESGGGLVKPGGSLRLSCAASGFTFSSYSMNWVRQAPGKGLE*
*WVSGINTAGDTHYPESVKGRFTISRDNARNSLNLQMNSLRAEDTAVYYCVRERVEREYSGYDAFD*
*IWGQGTTVTVSAGGGGSGGGGSGGGGSGAPNFMLTQPHSVSESLGKTVTISCTGSSGSIARKFVQ*
*WYQQRPGSSPTTVIYENNQRPSGVSDRFSGSIGSSSNSASLTISGLKTEDEADYYCQSYDSSNVV*
*FGGGTKVTVL*GPRANFVYKSGPRPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

(SEQ ID NO: 20)
  *The protein of SEQ ID NO: 19 (italic/underline) is
  followed by an IgG1 Fc domain (bold/underline).

Figure 10A pLV430G (Lentiviral Vector) (SEQ ID NO:35)
cgataaccctaattcgatagcatatgcttcccgttgggtaacatatgctattgaattagggttagtctggatagtatatactactacccgggaa
gcatatgctacccgtttaggggttcaccggtgatgccggccacgatgcgtccggcgtagaggatctaatgtgagttagctcactcattaggcacc
ccaggctttacactttatgcttccggctcgtatgttgtgtggaattgtgagcggataacaatttcacacaggaaacagctatgaccatgattac
gccaagcgcgcaattaaccctcactaaagggaacaaaagctggagctgcaagcttaatgtagtcttatgcaatactcttgtagtcttgcaaca
tggtaacgatgagttagcaacatgccttacaaggagagaaaaagcaccgtgcatgccgattggtggaagtaaggtggtacgatcgtgcctta
ttaggaaggcaacagacgggtctgacatggattggacgaaccactgaattgccgcattgcagagatattgtatttaagtgcctagctcgatac
ataaacgggtctctctggttagaccagatctgagcctgggagctctctggctaactagggaacccactgcttaagcctcaataaagcttgcctt
gagtgcttcaagtagtgtgtgcccgtctgttgtgtgactctggtaactagagatccctcagacccttttagtcagtgtggaaaatctctagcagt
ggcgcccgaacagggacttgaaagcgaaagggaaaccagaggagctctctcgacgcaggactcggcttgctgaagcgcgcacggcaaga
ggcgaggggcggcgactggtgagtacgccaaaaattttgactagcggaggctagaaggagagagatgggtgcgagagcgtcagtattaag
cgggggagaattagatcgcgatgggaaaaaattcggttaaggccagggggaaagaaaaaatataaattaaaacatatagtatgggcaagc
agggagctagaacgattcgcagttaatcctggcctgttagaaacatcagaaggctgtagacaaatactgggacagctacaaccatcccttca
gacaggatcagaagaacttagatcattatataatacagtagcaaccctctattgtgtgcatcaaaggatagagataaaagacaccaaggaa
gctttagacaagatagaggaagagcaaaacaaaagtaagaccaccgcacagcaagcggccgctgatcttcagacctggaggaggagata
tgagggacaattggagaagtgaattatataaatataaagtagtaaaaattgaaccattaggagtagcacccaccaaggcaaagagaagag
tggtgcagagagaaaaagagcagtgggaataggagctttgttccttgggttcttgggagcagcaggaagcactatgggcgcagcgtcaat
gacgctgacggtacaggccagacaattattgtctggtatagtgcagcagcagaacaatttgctgagggctattgaggcgcaacagcatctgtt
gcaactcacagtctggggcatcaagcagctccaggcaagaatcctggctgtggaaagatacctaaaggatcaacagctcctggggatttgg
ggttgctctggaaaactcatttgcaccactgctgtgccttggaatgctagttggagtaataaatctctggaacagatttggaatcacacgacct
ggatggagtgggacagagaaattaacaattacacaagcttaatacactccttaattgaagaatcgcaaaaccagcaagaaaagaatgaac
aagaattattggaattagataaatgggcaagtttgtggaattggtttaacataacaaattggctgtggtatataaaattattcataatgatagt
aggaggcttggtaggtttaagaatagtttttgctgtactttctatagtgaatagagttaggcagggatattcaccattatcgtttcagacccacc
tcccaaccccgaggggacccgacaggcccgaaggaatagaagaagaaggtggagagagagacagagacagatccattcgattagtgaac
ggatctcgacggtatcggttttaaaagaaaaggggggattggggggtacagtgcaggggaaagaatagtagacataatagcaacagacat
acaaactaaagaattacaaaaacaaattacaaaaattcaaaattttatcgattttatttagtctccagaaaaaggggggaatgaaagacccc
acctgtaggtttggcaagctagcttaagtaacgccatttgcaaggcatggaaaatacataactgagaatagagaagttcagatcaaggtta
ggaacagagagacagcagaatatgggccaaacaggatatctgtggtaagcagttcctgccccggctcagggccaagaacagatggtcccc
agatgcggtcccgccctcagcagtttctagagaaccatcagatgtttccaggtgccccaaggacctgaaatgaccctgtgccttatttgaact
aaccaatcagttcgcttctcgcttctgttcgcgcgcttctgctccccgagctcaataaaagagcccacaacccctcactcggcgcgccagtcct
ccgatagactgcgtcgcccgggtaccgatatcacaagtttgtacaaaaaagctgaacgagaaacgtaaaatgatataaatatcaatatatta
aattagattttgcataaaaaacagactacataatactgtaaaacacaacatatccagtcactatggcggccgcattaggcaccccaggcttta
cactttatgcttccggctcgtataatgtgtggattttgagttaggatccgtcgagattttcaggagctaaggaagctaaaatggagaaaaaat
cactggatataccaccgttgatatatcccaatggcatcgtaaagaacattttgaggcatttcagtcagttgctcaatgtacctataaccagacc
gttcagctggatattacggcctttttaaagaccgtaaagaaaaataagcacaagtttatccggcctttattcacattcttgcccgcctgatgaa
tgctcatccggaattccgtatggcaatgaaagacggtgagctggtgatatgggatagtgttcacccttgttacaccgttttccatgagcaaact
gaaacgttttcatcgctctggagtgaataccacgacgatttccggcagtttctacacatatattcgcaagatggcgtgttacggtgaaaacc
tggcctatttccctaaagggtttattgagaatatgttttcgtctcagccaatccctgggtgagtttcaccagttttgatttaaacgtggccaatat
ggacaacttcttcgcccccgttttcaccatgggcaaatattatacgcaaggcgacaaggtgctgatgccgctggcgattcaggttcatcatgcc
gtttgtgatggcttccatgtcggcagaatgcttaatgaattacaacagtactgcgatgagtggcagggcggggcgtaaacgcgtggatccgg
cttactaaaagccagataacagtatgcgtatttgcgcgctgatttttgcggtataagaatatatactgatatgtatacccgaagtatgtcaaaa
agaggtatgctatgaagcagcgtattacagtgacagttgacagcgacagctatcagttgctcaaggcatatatgatgtcaatatctccggtct
ggtaagcacaaccatgcagaatgaagcccgtcgtctgcgtgccgaacgctggaaagcggaaaatcaggaagggatggctgaggtcgcccg
gtttattgaaatgaacggctcttttgctgacgagaacaggggctggtgaaatgcagtttaaggtttacacctataaaagagagagccgttatc
gtctgtttgtggatgtacagagtgatattattgacacgcccgggcgacggatggtgatccccctggccagtgcacgtctgctgtcagataaagt

Figure 10A (cont.)

ctcccgtgaactttacccggtggtgcatatcggggatgaaagctggcgcatgatgaccaccgatatggccagtgtgccggtctccgttatcgg
ggaagaagtggctgatctcagccaccgcgaaaatgacatcaaaaacgccattaacctgatgttctggggaatataaatgtcaggctccctta
tacacagccagtctgcaggtcgaccatagtgactggatatgttgtgttttacagtattatgtagtctgttttttatgcaaaatctaatttaatatat
tgatatttatatcattttacgtttctcgttcagctttcttgtacaaagtggtgattcgagttaattaagctagcctagtgccatttgttcagtggttc
gtagggctttccccactgtttggctttcagttatatggatgatgtggtattgggggccaagtctgtacagcatcttgagtccttttaccgctgt
taccaattttcttttgtctttgggtatacatttaaaccctaacaaaacaaagagatggggttactctctaaattttatgggttatgtcattggatgt
tatgggtccttgccacaagaacacatcatacaaaaaatcaaagaatgttttagaaaacttcctattaacaggcctattgattggaaagtatgt
caacgaattgtgggtcttttgggttttgctgccccttttacacaatgtggttatcctgcgttgatgcctttgtatgcatgtattcaatctaagcagg
ctttcactttctcgccaacttacaaggcctttctgtgtaaacaatacctgaacctttaccccgttgcccggcaacggccaggtctgtgccaagtg
tttgctgacgcaaccccccactggctggggcttggtcatgggccatcagcgcatgcgtggaaccttttcggctcctctgccgatccatactgcgg
aactcctagccgcttgttttgctcgcagcaggtctggagcaaacattatcgggactgataactctgttgtcctatcccgcaaatatacatcgttt
ccatggctgctaggctgtgctgccaactggatcctgcgcgggacgtcctttgtttacgtcccgtcggcgctgaatcctgcggacgacccttctcg
gggtcgcttgggactctctcgtcccttctccgtctgccgttccgaccgaccacggggcgcacctctctttacgcggactccccgtctgtgccttc
tcatctgccggaccgtgtgcacttcgcttcacctctgcacgtcgcatggagaccaccgtgaacgcccaccaaatattgcccaaggtcttacata
agaggactcttggactctcagcaatgtcaacgaccgaccttgaggcatacttcaaagactgtttgtttaaagactgggaggagttgggggag
gagattaggttaaaggtctttgtactaggaggctgtaggcataaattggtctgcgcaccagcaccatggcgcaatcactagagcggggtacct
ttaagaccaatgacttacaaggcagctgtagatcttagccactttttaaaagaaaagggggggactggaagggctaattcactcccaacgaag
acaagatctgcttttttgcttgtactgggtctctctggttagaccagatctgagcctgggagctctctggctaactagggaacccactgcttaagc
ctcaataaagcttgccttgagtgcttcaagtagtgtgtgcccgtctgttgtgtgactctggtaactagagatccctcagacccttttagtcagtgt
ggaaaatctctagcagtagtagttcatgtcatcttattattcagtatttataacttgcaaagaaatgaatatcagagagtgagaggaacttgtt
tattgcagcttataatggttacaaataaagcaatagcatcacaaatttcacaaataaagcatttttttcactgcattctagttgtggtttgtccaa
actcatcaatgtatcttatcatgtctggctctagctatcccgcccctaactccgcccatcccgcccctaactccgcccagttccgcccattctccg
ccccatggctgactaatttttttttatttatgcagaggccgaggccggatcccttgagtggctttcatcctggagcagactttgcagtctgtggact
gcaacacaacattgcctttatgtgtaactcttggctgaagctcttacaccaatgctgggggacatgtacctcccaggggcccaggaagactac
gggaggctacaccaacgtcaatcagaggggcctgtgtagctaccgataagcggaccctcaagagggcattagcaatagtgtttataaggcc
cccttgttaattcttgaagacgaaagggcctcgtgatacgcctatttttataggttaatgtcatgataataatggtttcttagacgtcaggtggc
acttttcggggaaatgtgcgcggaacccctatttgtttatttttctaaatacattcaaatatgtatccgctcatgagacaataaccctgataaat
gcttcaataatattgaaaaaggaagagtatgagtattcaactttccgtgtcgcccttattccctttttttgcggcattttgccttcctgtttttgctc
acccagaaacgctggtgaaagtaaaagatgctgaagatcagttgggtgcacgagtgggttacatcgaactggatctcaacagcggtaagat
ccttgagagttttcgccccgaagaacgttttccaatgatgagcacttttaaagttctgctatgtggcgcggtattatcccgtgttgacgccgggc
aagagcaactcggtcgccgcatacactattctcagaatgacttggttgagtactcaccagtcacagaaaagcatcttacggatggcatgaca
gtaagagaattatgcagtgctgccataaccatgagtgataacactgcggccaacttacttctgacaacgatcggaggaccgaaggagctaa
ccgcttttttgcacaacatgggggatcatgtaactcgccttgatcgttgggaaccggagctgaatgaagccataccaaacgacgagcgtgac
accacgatgcctgcagcaatggcaacaacgttgcgcaaactattaactggcgaactacttactctagcttcccggcaacaattaatagactgg
atggaggcggataaagttgcaggaccacttctgcgctcggcccttccggctggctggtttattgctgataaatctggagccggtgagcgtggg
tctcgcggtatcattgcagcactggggccagatggtaagccctcccgtatcgtagttatctacacgacggggagtcaggcaactatggatgaa
cgaaatagacagatcgctgagataggtgcctcactgattaagcattggtaactgtcagaccaagtttactcatatatactttagattgatttaa
aacttcattttaatttaaaaggatctaggtgaagatcctttttgataatctcatgaccaaaatcccttaacgtgagttttcgttccactgagcgt
cagaccccgtagaaaagatcaaaggatcttcttgagatcctttttttctgcgcgtaatctgctgcttgcaaacaaaaaaaccaccgctaccag
cggtggtttgtttgccggatcaagagctaccaactctttttccgaaggtaactggcttcagcagagcgcagataccaaatactgtccttctagt
gtagccgtagttaggccaccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacggggggttcgtgcacacagcc
cagcttggagcgaacgacctacaccgaactgagatacctacagcgtgagcattgagaaagcgccacgcttcccgaagggagaaaggcgga
caggtatccggtaagcggcagggtcggaacaggagagcgcacgagggagcttccaggggaaacgcctggtatctttatagtcctgtcggg
tttcgccacctctgacttgagcgtcgatttttgtgatgctcgtcaggggggcggagcctatggaaaaacgccagcaacgcggcctttttacggt

*Figure 10A (cont.)* tcctggccttttgctggccttttttgaagctgtccctgatggtcgtcatctacctgcctggacagcatggcctgcaacgcgggcatcccgatgccg
ccggaagcgagaagaatcataatggggaaggccatccagcctcgcgtcg

Figure 10B pCIGO-VSV.G (VSVG) (SEQ ID NO:36)

gtcgacggatcgggagatcaattccggcacctgtcctacgagttgcatgataaagaagacagtcataagtgcggcgacgatagtcatgcccc
gcgcccaccggaaggagctgactgggttgaaggctctcaagggcatcggtcgatgcaggaaaaggacaagcagcgaaaattcacgccccc
ttgggaggtggcggcatatgcaaaggatagcactcccactctactactgggtatcatatgctgactgtatatgcatgaggatagcatatgcta
cccggatacagattaggatagcatatactacccagatatagattaggatagcatatgctacccagatatagattaggatagcctatgctaccc
agatataaattaggatagcatatactacccagatatagattaggatagcatatgctacccagatatagattaggatagcctatgctacccaga
tatagattaggatagcatatgctacccagatatagattaggatagcatatgctatccagatatttgggtagtatatgctacccagatataaatt
aggatagcatatactaccctaatctctattaggatagcatatgctacccggatacagattaggatagcatatactacccagatatagattagg
atagcatatgctacccagatatagattaggatagcctatgctacccagatatagattaggatagcatatactacccagatatagattaggata
gcatatgctacccagatatagattaggatagcctatgctacccagatatagattaggatagcatatgctatccagatatttgggtagtatatgc
tacccatggcaacattagcccaccgtgctctcagcgacctcgtgaatatgaggaccaacaaccctgtgcttggcgctcaggcgcaagtgtgtg
taatttgtcctccagatcgcagcaatcgcgccccatcttggcccgcccacctacttatgcaggtattccccggggtgccattagtggttttgtgg
gcaagtggtttgaccgcagtggttagcggggttacaatcagccaagttattacacccttattttacagtccaaaaccgcagggcggcgtgtgg
gggctgacgcgtgcccccactccacaatttcaaaaaaaagagtggccacttgtctttgtttatgggccccattggcgtggagccccgtttaatt
ttcggggtgttagagacaaccagtggagtccgctgctgtcggcgtccactctctttcccttgttacaaatagagtgtaacaacatggttcac
ctgtcttggtccctgcctgggacacatcttaataaccccagtatcatattgcactaggattatgtgttgcccatagccataaattcgtgtgagat
ggacatccagtctttacggcttgtccccaccccatggatttctattgttaaagatattcagaatgtttcattcctacactagtatttattgcccaa
ggggtttgtgagggttatattggtgtcatagcacaatgccaccactgaaccccccgtccaaatttttattctggggggcgtcacctgaaaccttgtt
ttcgagcacctcacatacaccttactgttcacaactcagcagttattctattagctaaacgaaggagaatgaagaagcaggcgaagattcag
gagagttcactgcccgctccttgatcttcagccactgcccttgtgactaaaatggttcactaccctcgtggaatcctgaccccatgtaaataaa
accgtgacagctcatggggtgggagatatcgctgttccttaggacccttttactaaccctaattcgatagcatatgcttcccgttgggtaacata
tgctattgaattagggttagtctggatagtatatactactacccgggaagcatatgctacccgtttagggttaacaaggggggccttataaacac
tattgctaatgccctcttgagggtccgcttatcggtagctacacaggcccctctgattgacgttggtgtagcctcccgtagtcttcctgggcccct
gggaggtacatgtcccccagcattggtgtaagagcttcagccaagagttacacataaaggcaatgttgtgttgcagtccacagactgcaaag
tctgctccaggatgaaagccactcaagggatcttcaatattggccattagccatattattcattggttatatagcataaatcaatattggctatt
ggccattgcatacgttgtatctatatcataatatgtacatttatattggctcatgtccaatatgaccgccatgttggcattgattattgactagtta
ttaatagtaatcaattacggggtcattagttcatagcccatatatggagttccgcgttacataacttacggtaaatggcccgcctggctgaccg
cccaacgacccccgcccattgacgtcaataatgacgtatgttcccatagtaacgccaatagggactttccattgacgtcaatgggtggagtatt
tacggtaaactgcccacttggcagtacatcaagtgtatcatatgccaagtccgcccccattgacgtcaatgacggtaaatggcccgcctggc
attatgcccagtacatgaccttacgggactttcctacttggcagtacatctacgtattagtcatcgctattaccatggtgatgcggttttggcagt
acaccaatgggcgtggatagcggtttgactcacggggatttccaagtctccaccccattgacgtcaatgggagtttgttttggcaccaaaatca
acgggactttccaaaatgtcgtaataaccccgccccgttgacgcaaatgggcggtaggcgtgtacggtgggaggtctatataagcagagctc
gtttagtgaaccgtcagatcactagaagctttattgcggtagtttatcacagttaaattgctaacgcagtcagtgcttctgacacaacagtctcg
aacttaagctgcagaagttggtcgtgaggcactgggcaggtaagtatcaaggttacaagacaggtttaaggagaccaatagaaactgggct
tgtcgagacagagaagactcttgcgtttctgataggcacctattggtcttactgacatccactttgcctttctctccacaggtgtccactcccagt
tcaattacagctcttaaggctagagtacttaatacgactcactataggctagcggtaccgagctcggatccactagtaacggccgccagtgtg
ctggaattcaacagagatcgatctgtttccttgacactatgaagtgccttttgtacttagccttttattcattggggtgaattgcaagttccaccat
agttttttccacacaaccaaaaaggaaactggaaaaatgttccttctaattaccattattgcccgtcaagctcagatttaaattggcataatgac
ttaataggcacagccatacaagtcaaaatgcccaagagtcacaaggctattcaagcagacggttggatgtgtcatgcttccaaatgggtcac
tacttgtgatttccgctggtatggaccgaagtatataacacagtccatccgatccttcactccatctgtagaacaatgcaaggaaagcattgaa
caaacgaaacaaggaacttggctgaatccaggcttccctcctcaaagttgtggatatgcaactgtgacggatgccgaagcagtgattgtcca
ggtgactcctcaccatgtgctggttgatgaatacacaggagaatgggttgattcacagttcatcaacggaaaatgcagcaattacatatgccc
cactgtccataactctacaacctggcattctgactataaggtcaaagggctatgtgattctaacctcatttccatggacatcaccttcttctcag

Figure 10B (cont.)

aggacggagagctatcatccctgggaaaggagggcacagggttcagaagtaactactttgcttatgaaactggaggcaaggcctgcaaaat
gcaatactgcaagcattggggagtcagactcccatcaggtgtctggttcgagatggctgataaggatctctttgctgcagccagattccctga
atgcccagaagggtcaagtatctctgctccatctcagacctcagtggatgtaagtctaattcaggacgttgagaggatcttggattattccctct
gccaagaaacctggagcaaaatcagagcgggtcttccaatctctccagtggatctcagctatcttgctcctaaaaacccaggaaccggtcctg
ctttcaccataatcaatggtaccctaaaatactttgagaccagatacatcagagtcgatattgctgctccaatcctctcaagaatggtcggaat
gatcagtggaactaccacagaaagggaactgtgggatgactgggcaccatatgaagacgtggaaattggacccaatggagttctgaggacc
agttcaggatataagtttcctttatacatgattggacatggtatgttggactccgatcttcatcttagctcaaaggctcaggtgttcgaacatcct
cacattcaagacgctgcttcgcaacttcctgatgatgagagtttattttttggtgatactgggctatccaaaaatccaatcgagcttgtagaagg
ttggttcagtagttggaaaagctctattgcctctttttctttatcatagggttaatcattggactattcttggttctccgagttggtatccatctttg
cattaaattaaagcacaccaagaaaagacagatttatacagacatagagatgaaccgacttggaaagtaactcaaatcctgcacaacagat
tcttcatgtttggaccaaatcaacttgtgataccatgctcaaagaggcctcaattatatttgagtttttaattttatggaattctgcagatatcca
tcacactggcggccgctcgagcatgcatctagagggccctattctatagtgtcacctaaatgctagagctcgctgatcagcctcgactgtgcct
tctagttgccagccatctgttgtttgcccctcccccgtgccttccttgaccctggaaggtgccactcccactgtcctttcctaataaaatgaggaa
attgcatcgcattgtctgagtaggtgtcattctattctgggggtgtgggtggggcaggacagcaaggggggaggattgggaagacaatagcag
gcatgctggggatgcggtgggctctatggcttctgaggcggaaagaaccagctgcattaatgaatcggccaacgcgcggggagaggcggtt
tgcgtattgggcgctcttccgcttcctgctcactgactcgctgcgctcggtcgttcggctgcggcgagcggtatcagctcactcaaaggcggta
atacggttatccacagaatcaggggataacgcaggaaagaacatgtgagcaaaaggccagcaaaaggccaggaaccgtaaaaaggccgc
gttgctggcgtttttccataggctccgcccccctgacgagcatcacaaaaatcgacgctcaagtcagaggtggcgaaacccgacaggactat
aaagataccaggcgtttccccctggaagctccctcgtgcgctctcctgttccgaccctgccgcttaccggatacctgtccgcctttctcccttcgg
gaagcgtggcgctttctcaatgctcacgctgtaggtatctcagttcggtgtaggtcgttcgctccaagctgggctgtgtgcacgaaccccccgtt
cagcccgaccgctgcgccttatccggtaactatcgtcttgagtccaacccggtaagacacgacttatcgccactggcagcagccactggtaac
aggattagcagagcgaggtatgtaggcggtgctacagagttcttgaagtggtggcctaactacggctacactagaaggacagtatttggtat
ctgcgctctgctgaagccagttaccttcggaaaaagagttggtagctcttgatccggcaaacaaaccaccgctggtagcggtggtttttttgttt
gcaagcagcagattacgcgcagaaaaaaaggatctcaagaagatcctttgatcttttctacggggtctgacgctcagtggaacgaaaactca
cgttaagggattttggtcatgagattatcaaaaaggatcttcacctagatccttttaaattaaaaatgaagttttaaatcaatctaaagtatata
tgagtaaacttggtctgacagttaccaatgcttaatcagtgaggcacctatctcagcgatctgtctatttcgttcatccatagttgcctgactccc
cgtcgtgtagataactacgatacgggagggcttaccatctggccccagtgctgcaatgataccgcgagacccacgctcaccggctccagattt
atcagcaataaaccagccagccggaagggccgagcgcagaagtggtcctgcaactttatccgcctccatccagtctattaattgttgccggg
aagctagagtaagtagttcgccagttaatagtttgcgcaacgttgttgccattgctacaggcatcgtggtgtcacgctcgtcgtttggtatggct
tcattcagctccggttcccaacgatcaaggcgagttacatgatccccatgttgtgcaaaaaagcggttagctccttcggtcctccgatcgttgt
cagaagtaagttggccgcagtgttatcactcatggttatggcagcactgcataattctcttactgtcatgccatccgtaagatgcttttctgtga
ctggtgagtactcaaccaagtcattctgagaatagtgtatgcggcgaccgagttgctcttgcccggcgtcaatacgggataataccgcgccac
atagcagaactttaaaagtgctcatcattggaaaacgttcttcggggcgaaaactctcaaggatcttaccgctgttgagatccagttcgatgta
acccactcgtgcacccaactgatcttcagcatcttttactttcaccagcgtttctgggtgagcaaaaacaggaaggcaaaatgccgcaaaaaa
gggaataagggcgacacggaaatgttgaatactcatactcttcctttttcaatattattgaagcatttatcagggttattgtctcatgagcggat
acatatttgaatgtatttagaaaaataaacaatagggggttccgcgcacatttccccgaaaagtgccacctgac

Figure 11A

PLV4301G38A1 (also referred to as pLV4301G PDLV scFV 38A1) (SEQ ID NO:37)

cgataaccctaattcgatagcatatgcttcccgttgggtaacatatgctattgaattagggttagtctggatagtatatactactacccgggaa
gcatatgctacccgtttagggttcaccggtgatgccggccacgatgcgtccggcgtagaggatctaatgtgagttagctcactcattaggcacc
ccaggctttacactttatgcttccggctcgtatgttgtgtggaattgtgagcggataacaatttcacacaggaaacagctatgaccatgattac
gccaagcgcgcaattaaccctcactaaagggaacaaaagctggagctgcaagcttaatgtagtcttatgcaatactcttgtagtcttgcaaca
tggtaacgatgagttagcaacatgccttacaaggagagaaaaagcaccgtgcatgccgattggtggaagtaaggtggtacgatcgtgcctta
ttaggaaggcaacagacgggtctgacatggattggacgaaccactgaattgccgcattgcagagatattgtatttaagtgcctagctcgatac
ataaacgggtctctctggttagaccagatctgagcctgggagctctctggctaactagggaacccactgcttaagcctcaataaagcttgcctt
gagtgcttcaagtagtgtgtgcccgtctgttgtgtgactctggtaactagagatccctcagacccttttagtcagtgtggaaaatctctagcagt
ggcgcccgaacagggacttgaaagcgaaagggaaaccagaggagctctctcgacgcaggactcggcttgctgaagcgcgcacggcaaga
ggcgaggggcggcgactggtgagtacgccaaaaattttgactagcggaggctagaaggagagagatgggtgcgagagcgtcagtattaag
cgggggagaattagatcgcgatgggaaaaaattcggttaaggccaggggggaagaaaaaatataaattaaaacatatagtatgggcaagc
agggagctagaacgattcgcagttaatcctggcctgttagaaacatcagaaggctgtagacaaatactgggacagctacaaccatcccttca
gacaggatcagaagaacttagatcattatataatacagtagcaaccctctattgtgtgcatcaaaggatagagataaaagacaccaaggaa
gctttagacaagatagaggaagagcaaaacaaaagtaagaccaccgcacagcaagcggccgctgatcttcagacctggaggaggagata
tgagggacaattggagaagtgaattatataaatataaagtagtaaaaattgaaccattaggagtagcacccaccaaggcaaagagaagag
tggtgcagagagaaaaaagagcagtgggaataggagctttgttccttgggttcttgggagcagcaggaagcactatgggcgcagcgtcaat
gacgctgacggtacaggccagacaattattgtctggtatagtgcagcagcagaacaatttgctgagggctattgaggcgcaacagcatctgtt
gcaactcacagtctggggcatcaagcagctccaggcaagaatcctggctgtggaaagatacctaaaggatcaacagctcctggggatttgg
ggttgctctggaaaactcatttgcaccactgctgtgccttggaatgctagttggagtaataaatctctggaacagatttggaatcacacgacct
ggatggagtgggacagagaaattaacaattacacaagcttaatacactccttaattgaagaatcgcaaaaccagcaagaaaagaatgaac
aagaattattggaattagataaatgggcaagtttgtggaattggtttaacataacaaattggctgtggtatataaaattattcataatgatagt
aggaggcttggtaggtttaagaatagttttgctgtactttctatagtgaatagagttaggcagggatattcaccattatcgtttcagacccacc
tcccaaccccgaggggacccgacaggcccgaaggaatagaagaagaaggtggagagagagacagagacagatccattcgattagtgaac
ggatctcgacggtatcggttttaaaagaaaagggggggattgggggtacagtgcaggggaaagaatagtagacataatagcaacagacat
acaaactaaagaattacaaaaacaaattacaaaaattcaaaattttatcgattttatttagtctccagaaaaaggggggaatgaaagacccc
acctgtaggtttggcaagctagcttaagtaacgccattttgcaaggcatggaaaatacataactgagaatagagaagttcagatcaaggtta
ggaacagagagacagcagaatatgggccaaacaggatatctgtggtaagcagttcctgccccggctcagggccaagaacagatggtcccc
agatgcggtcccgccctcagcagtttctagagaaccatcagatgtttccaggtgccccaaggacctgaaatgaccctgtgccttatttgaact
aaccaatcagttcgcttctcgcttctgttcgcgcgcttctgctccccgagctcaataaaagagcccacaacccctcactcggcgcgccagtcct
ccgatagactgcgtcgcccgggtaccgatatcaccaactttgtacaaaaaagctgaacgatatcgccaccatgggcagcacagccattctgg
ccctgctgctggcagtgctgcagggcgtgtcagctGaagtgcagctggtggaatctggcggcggactggtgcagcctggcggatctctgaga
ctgagctgtgccgccagcggcttccttcagcaactacgccatgagctgggtgcgccaggcccctggaaaaggcctggaatgggtgtccac
catcagcggctctggcggaaccacctactacgccgatagcgtgaagggccggttcaccatctcccgggacaacagcaagaacacccctgtac
ctgcagatgaacagcctgcgggtggaagataccgccgtgtactactgcgccaaggactggttcagaagcagcagccccgacgccttcgaca
tctggggccagggaacaaccgtgaccgtgtctgctggcggaggcggatcaggcggcggaggatcaggggggaggcggaagcggagcacctt
cttacgtgctgacccagccccctagcgtgtcagtggctcctggacagaccgccagaatcacctgtggcggcaacaacatcggccggaagatc
gtgcactggtatcagcagaggcccggacaggctcccgtgctcgtgatctactacgacaccgacagacctgccggcatccccgagagattcag
cggcagcaacagcggcaacatggccaccctgaccatcagcacagtgggagccggcgacgaggccgactactactgtcaagtgtgggacac
cggcagcgatcacgtggtgtttggaggcggcaccaagctgacagtgctgggcccgcgggccaactttgtatacaaaagttgcagcgagagc
aagtacggccctccctgccccccttgccctgccccgagttcctgggcggaccagcgtgttcctgttccccccaagcccaaggacaccctga
tgatcagccggaccccgaggtgacctgtgtggtggtggacgtgtcccaggaggaccccgaggtccagttcaactggtacgtggacggcgtg
gaggtgcacaacgccaagaccaagcccgggaggagcagttcaatagcacctaccgggtggtgtccgtgctgaccgtgctgcaccaggact

Figure 11A (cont.)

ggctgaacggcaaggaatacaagtgtaaggtgtccaacaagggcctgcccagcagcatcgagaaaaccatcagcaaggccaagggccag
cctcgggagccccaggtgtacaccctgcccccctagccaagaggagatgaccaagaatcaggtgtccctgacctgcctggtgaagggcttcta
ccccagcgacatcgccgtggagtgggagagcaacggccagcccgagaacaactacaagaccacccccccctgtgctggacagcgacggcag
cttcttcctgtacagcaggctgaccgtggacaagagccggtggcaggagggcaacgtctttagctgctccgtgatgcacgaggccctgcaca
accactacacccagaagagcctgtccctgagcctgggcaagatgttcagatcttgtgatatttacatctgggcacccttggccggaatctgcgt
ggcccttctgctgtccttgatcatcactctcatctgctacggctccaccagcggctccggcaagcccggctctggcgagggctccaccagcggc
gactacaaggacgacgatgacaagtaataggatatcggttcagctttcttgtacaaagttgggattcgagttaattaagttaacgaattcccc
ccctctccctcccccccccctaacgttactggccgaagccgcttggaataaggccggtgtgcgtttgtctatatgttattttccaccatattgccg
tcttttggcaatgtgagggcccggaaacctggccctgtcttcttgacgagcattcctaggggtctttcccctctcgccaaaggaatgcaaggtct
gttgaatgtcgtgaaggaagcagttcctctggaagcttcttgaagacaaacaacgtctgtagcgaccctttgcaggcagcggaaccccccac
ctggcgacaggtgcctctgcggccaaaagccacgtgtataagatacacctgcaaaggcggcacaaccccagtgccacgttgtgagttggata
gttgtggaaagagtcaaatggctctcctcaagcgtattcaacaaggggctgaaggatgcccagaaggtacccattgtatgggatctgatctg
gggcctcggtgcacatgctttacatgtgtttagtcgaggttaaaaaacgtctaggcccccccgaaccacggggacgtggttttcctttgaaaaac
acgatgataatatggccacaaccatgggaggcggaagcggcggaggctcccctcgaggcaccatggtgagcaagggcgaggagctgttca
ccggggtggtgcccatcctggtcgagctggacggcgacgtaaacggccacaagttcagcgtgtccggcgagggcgagggcgatgccaccta
cggcaagctgaccctgaagttcatctgcaccaccggcaagctgcccgtgccctggcccaccctcgtgaccaccctgacctacggcgtgcagtg
cttcagccgctaccccgaccacatgaagcagcacgacttcttcaagtccgccatgcccgaaggctacgtccaggagcgcaccatcttcttcaa
ggacgacggcaactacaagacccgcgccgaggtgaagttcgagggcgacaccctggtgaaccgcatcgagctgaagggcatcgacttcaa
ggaggacggcaacatcctggggcacaagctggagtacaactacaacagccacaacgtctatatcatggccgacaagcagaagaacggcat
caaggtgaacttcaagatccgccacaacatcgaggacggcagcgtgcagctcgccgaccactaccagcagaacacccccatcggcgacgg
ccccgtgctgctgcccgacaaccactacctgagcacccagtccgccctgagcaaagaccccaacgagaagcgcgatcacatggtcctgctgg
agttcgtgaccgccgcgggatcactctcggcatggacgagctgtacaagtaacgcgtcccgggtctagagctagcggtaccatgcattacgt
agtcgacgacttaattaagctagcctagtgccatttgttcagtggttcgtagggctttccccactgtttggctttcagttatatggatgatgtgg
tattgggggccaagtctgtacagcatcttgagtccctttttaccgctgttaccaattttcttttgtctttgggtatacatttaaaccctaacaaaac
aaagagatggggttactctctaaatttatgggttatgtcattgatgttatgggtccttgccacaagaacacatcatacaaaaaatcaaaga
atgttttagaaaacttcctattaacaggcctattgattggaaagtatgtcaacgaattgtgggtcttttgggttttgctgccccttttacacaatgt
ggttatcctgcgttgatgcctttgtatgcatgtattcaatctaagcaggcttttcactttctcgccaacttacaaggcctttctgtgtaaacaatacc
tgaacctttaccccgttgcccggcaacggccaggtctgtgccaagtgtttgctgacgcaacccccactggctggggcttggtcatgggccatca
gcgcatgcgtggaaccttttcggctcctctgccgatccatactgcggaactcctagccgcttgttttgctcgcagcaggtctggagcaaacatta
tcgggactgataactctgttgtcctatcccgcaaatatacatcgtttccatggctgctaggctgtgctgccaactggatcctgcgcgggacgtcc
tttgtttacgtcccgtcggcgctgaatcctgcggacgacccttctcggggtcgcttgggactctctcgtcccttctccgtctgccgttccgaccg
accacggggcgcacctctctttacgcggactcccgtctgtgccttctcatctgccggaccgtgtgcacttcgcttcacctctgcacgtcgcatg
gagaccaccgtgaacgcccaccaaatattgcccaaggtcttacataagaggactcttggactctcagcaatgtcaacgaccgaccttgaggc
atacttcaaagactgtttgtttaaagactgggaggagttgggggaggagattaggttaaaggtctttgtactaggaggctgtaggcataaatt
ggtctgcgcaccagcaccatggcgcaatcactagagcggggtacctttaagaccaatgacttacaaggcagctgtagatcttagccactttt
aaaagaaaaggggggactggaagggctaattcactcccaacgaagacaagatctgcttttttgcttgtactgggtctctctggttagaccagat
ctgagcctgggagctctctggctaactagggaacccactgcttaagcctcaataaagcttgccttgagtgcttcaagtagtgtgtgcccgtctg
ttgtgtgactctggtaactagagatccctcagacccttttagtcagtgtggaaaatctctagcagtagtagttcatgtcatcttattattcagtat
ttataacttgcaaagaaatgaatatcagagagtgagaggaacttgtttattgcagcttataatggttacaaataaagcaatagcatcacaaat
ttcacaaataaagcattttttttcactgcattctagttgtggtttgtccaaactcatcaatgtatcttatcatgtctggctctagctatcccgcccct
aactccgcccatcccgcccctaactccgcccagttccgcccattctccgccccatggctgactaatttttttatttatgcagaggccgaggccg
gatcccttgagtggctttcatcctggagcagactttgcagtctgtggactgcaacacaacattgcctttatgtgtaactcttggctgaagctctta

*Figure 11A (cont.)* caccaatgctgggggacatgtacctcccaggggcccaggaagactacgggaggctacaccaacgtcaatcagaggggcctgtgtagctacc
gataagcggaccctcaagagggcattagcaatagtgtttataaggcccccttgttaattcttgaagacgaaagggcctcgtgatacgcctatt
tttataggttaatgtcatgataataatggtttcttagacgtcaggtggcacttttcggggaaatgtgcgcggaacccctatttgtttattttctaa
atacattcaaatatgtatccgctcatgagacaataaccctgataaatgcttcaataatattgaaaaaggaagagtatgagtattcaacatttc
cgtgtcgcccttattccctttttttgcggcattttgccttcctgttttttgctcacccagaaacgctggtgaaagtaaaagatgctgaagatcagttg
ggtgcacgagtgggttacatcgaactggatctcaacagcggtaagatccttgagagttttcgccccgaagaacgttttccaatgatgagcact
tttaaagttctgctatgtggcgcggtattatcccgtgttgacgccgggcaagagcaactcggtcgccgcatacactattctcagaatgacttgg
ttgagtactcaccagtcacagaaaagcatcttacggatggcatgacagtaagagaattatgcagtgctgccataaccatgagtgataacact
gcggccaacttacttctgacaacgatcggaggaccgaaggagctaaccgcttttttgcacaacatgggggatcatgtaactcgccttgatcgt
tgggaaccggagctgaatgaagccataccaaacgacgagcgtgacaccacgatgcctgcagcaatggcaacaacgttgcgcaaactatta
actggcgaactacttactctagcttcccggcaacaattaatagactggatggaggcggataaagttgcaggaccacttctgcgctcggccctt
ccggctggctggtttattgctgataaatctggagccggtgagcgtgggtctcgcggtatcattgcagcactggggccagatggtaagccctcc
cgtatcgtagttatctacacgacggggagtcaggcaactatggatgaacgaaatagacagatcgctgagataggtgcctcactgattaagca
ttggtaactgtcagaccaagtttactcatatatactttagattgatttaaaacttcattttaatttaaaaggatctaggtgaagatccttttttgat
aatctcatgaccaaaatcccttaacgtgagttttcgttccactgagcgtcagaccccgtagaaaagatcaaaggatcttcttgagatcctttttt
tctgcgcgtaatctgctgcttgcaaacaaaaaaaccaccgctaccagcggtggtttgtttgccggatcaagagctaccaactctttttccgaag
gtaactggcttcagcagagcgcagataccaaatactgtccttctagtgtagccgtagttaggccaccacttcaagaactctgtagcaccgcct
acatacctcgctctgctaatcctgttaccagtggctgctgccagtggcgataagtcgtgtcttaccgggttggactcaagacgatagttaccgg
ataaggcgcagcggtcgggctgaacggggggttcgtgcacacagcccagcttggagcgaacgacctacaccgaactgagatacctacagc
gtgagcattgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggccttttttacggttcctggccttttgctggccttttttgaagctgtccctgatggtcgtcat
ctacctgcctggacagcatggcctgcaacgcgggcatcccgatgccgccggaagcgagaagaatcataatggggaaggccatccagcctcg
cgtcg

Figure 11B

PLV4301G19H9 (also referred to as pLV4301G PDLV scFV 19H9) (SEQ ID NO:38)

cgataaccctaattcgatagcatatgcttcccgttgggtaacatatgctattgaattagggttagtctggatagtatatactactacccgggaa
gcatatgctacccgtttagggttcaccggtgatgccggccacgatgcgtccggcgtagaggatctaatgtgagttagctcactcattaggcacc
ccaggctttacactttatgcttccggctcgtatgttgtgtggaattgtgagcggataacaatttcacacaggaaacagctatgaccatgattac
gccaagcgcgcaattaaccctcactaaagggaacaaaagctggagctgcaagcttaatgtagtcttatgcaatactcttgtagtcttgcaaca
tggtaacgatgagttagcaacatgccttacaaggagagaaaaagcaccgtgcatgccgattggtggaagtaaggtggtacgatcgtgcctta
ttaggaaggcaacagacgggtctgacatggattggacgaaccactgaattgccgcattgcagagatattgtatttaagtgcctagctcgatac
ataaacgggtctctctggttagaccagatctgagcctgggagctctctggctaactagggaacccactgcttaagcctcaataaagcttgcctt
gagtgcttcaagtagtgtgtgcccgtctgttgtgtgactctggtaactagagatccctcagacccttttagtcagtgtggaaaatctctagcagt
ggcgcccgaacagggacttgaaagcgaaagggaaaccagaggagctctctcgacgcaggactcggcttgctgaagcgcgcacggcaaga
ggcgaggggcggcgactggtgagtacgccaaaaattttgactagcggaggctagaaggagagagatgggtgcgagagcgtcagtattaag
cgggggagaattagatcgcgatgggaaaaaattcggttaaggccaggggggaagaaaaaatataaattaaaacatatagtatgggcaagc
agggagctagaacgattcgcagttaatcctggcctgttagaaacatcagaaggctgtagacaaatactgggacagctacaaccatcccttca
gacaggatcagaagaacttagatcattatataatacagtagcaaccctctattgtgtgcatcaaaggatagagataaaagacaccaaggaa
gctttagacaagatagaggaagagcaaaacaaaagtaagaccaccgcacagcaagcggccgctgatcttcagacctggaggaggagata
tgagggacaattggagaagtgaattatataaatataaagtagtaaaaattgaaccattaggagtagcacccaccaaggcaaagagaagag
tggtgcagagagaaaaaagagcagtgggaataggagctttgttccttgggttcttgggagcagcaggaagcactatgggcgcagcgtcaat
gacgctgacggtacaggccagacaattattgtctggtatagtgcagcagcagaacaatttgctgagggctattgaggcgcaacagcatctgtt
gcaactcacagtctggggcatcaagcagctccaggcaagaatcctggctgtggaaagatacctaaaggatcaacagctcctggggatttgg
ggttgctctggaaaactcatttgcaccactgctgtgccttggaatgctagttggagtaataaatctctggaacagatttggaatcacacgacct
ggatggagtgggacagagaaattaacaattacacaagcttaatacactccttaattgaagaatcgcaaaaccagcaagaaaagaatgaac
aagaattattggaattagataaatgggcaagtttgtggaattggtttaacataacaaattggctgtggtatataaaattattcataatgatagt
aggaggcttggtaggtttaagaatagtttttgctgtactttctatagtgaatagagttaggcagggatattcaccattatcgtttcagacccacc
tcccaaccccgaggggacccgacaggcccgaaggaatagaagaagaaggtggagagagagacagagacagatccattcgattagtgaac
ggatctcgacggtatcggttttaaaagaaaaggggggattggggggtacagtgcaggggaaagaatagtagacataatagcaacagacat
acaaactaaagaattacaaaaacaaattacaaaaattcaaaattttatcgattttatttagtctccagaaaaagggggggaatgaaagacccc
acctgtaggtttggcaagctagcttaagtaacgccattttgcaaggcatggaaaatacataactgagaatagagaagttcagatcaaggtta
ggaacagagagacagcagaatatgggccaaacaggatatctgtggtaagcagttcctgccccggctcagggccaagaacagatggtcccc
agatgcggtcccgccctcagcagtttctagagaaccatcagatgtttccaggtgccccaaggacctgaaatgaccctgtgccttatttgaact
aaccaatcagttcgcttctcgcttctgttcgcgcgcttctgctccccgagctcaataaaagagcccacaacccctcactcggcgcgccagtcct
ccgatagactgcgtcgcccgggtaccgatatcaccaactttgtacaaaaaagctgaacgatatcgccaccatgggcagcacagccattctgg
ccctgctgctggcagtgctgcagggcgtgtcagctGaagtgcagctggtggaatctggcggcggactggtgcagcctggcggatctctgaga
ctgagctgtgccgccagcggcttcaccttcagcaactacgccatgagctgggtgcgccaggcccctggaaaaggcctggaatgggtgtccac
catcagcggtctggcggaaccacctactacgccgatagcgtgaagggccggttcaccatctcccgggacaacagcaagaacaccctgtac
ctgcagatgaacagcctgcgggtggaagataccgccgtgtactactgcgccaaggactggttcagaagcagcagccccgacgccttcgaca
tctggggccagggaacaaccgtgaccgtgtctgctggcggaggcggatcaggcggcggaggatcaggggggaggcggaagcggagcacctt
cttacgtgctgacccagccccctagcgtgtcagtggctcctggacagaccgccagaatcacctgtggcggcaacaacatcggccggaagatc
gtgcactggtatcagcagaggcccggacaggctcccgtgctcgtgatctactacgacaccgacagacctgccggcatccccgagagattcag
cggcagcaacagcggcaacatggccaccctgaccatcagcacagtgggagccggcgacgaggccgactactactgtcaagtgtgggacac
cggcagcgatcacgtggtgtttggaggcggcaccaagctgacagtgctgggcccgcgggccaactttgtatacaaaagttgcagcgagagc
aagtacggccctccctgccccccttgccctgccccgagttcctggcggacccagcgtgttcctgttccccccaagcccaaggacaccctga
tgatcagccggaccccgaggtgacctgtgtggtggtggacgtgtcccaggaggaccccgaggtccagttcaactggtacgtggacggcgtg

Figure 11B (cont.)

gaggtgcacaacgccaagaccaagccccggggaggagcagttcaatagcacctaccgggtggtgtccgtgctgaccgtgctgcaccaggact
ggctgaacggcaaggaatacaagtgtaaggtgtccaacaagggcctgcccagcagcatcgagaaaaccatcagcaaggccaagggccag
cctcgggagccccaggtgtacaccctgcccccctagccaagaggagatgaccaagaatcaggtgtccctgacctgcctggtgaagggcttcta
ccccagcgacatcgccgtggagtgggagagcaacggccagcccgagaacaactacaagaccacccccctgtgctggacagcgacggcag
cttcttcctgtacagcaggctgaccgtggacaagagccggtggcaggagggcaacgtctttagctgctccgtgatgcacgaggccctgcaca
accactacacccagaagagcctgtccctgagcctgggcaagatgttcagatcttgtgatatttacatctgggcacccttggccggaatctgcgt
ggcccttctgctgtccttgatcatcactctcatctgctacggctccaccagcggctccggcaagcccggctctggcgagggctccaccagcggc
gactacaaggacgacgatgacaagtaataggatatcggttcagctttcttgtacaaagttgggattcgagttaattaagttaacgaattcccc
ccctctccctcccccccccctaacgttactggccgaagccgcttggaataaggccggtgtgcgtttgtctatatgttattttccaccatattgccg
tcttttggcaatgtgagggcccggaaacctggccctgtcttcttgacgagcattcctaggggtctttcccctctcgccaaaggaatgcaaggtct
gttgaatgtcgtgaaggaagcagttcctctgggaagcttcttgaagacaaacaacgtctgtagcgaccctttgcaggcagcggaaccccccac
ctggcgacaggtgcctctgcggccaaaagccacgtgtataagatacacctgcaaaggcggcacaaccccagtgccacgttgtgagttggata
gttgtggaaagagtcaaatggctctcctcaagcgtattcaacaagggctgaaggatgcccagaaggtacccattgtatgggatctgatctg
gggcctcggtgcacatgctttacatgtgtttagtcgaggttaaaaaacgtctaggccccccgaaccacggggacgtggttttcctttgaaaaac
acgatgataatatggccacaaccatggggaggcggaagcggcggaggctcccctcgaggcaccatggtgagcaagggcgaggagctgttca
ccggggtggtgcccatcctggtcgagctggacggcgacgtaaacggccacaagttcagcgtgtccggcgagggcgagggcgatgccaccta
cggcaagctgaccctgaagttcatctgcaccaccggcaagctgcccgtgccctggcccaccctcgtgaccaccctgacctacggcgtgcagtg
cttcagccgctaccccgaccacatgaagcagcacgacttcttcaagtccgccatgcccgaaggctacgtccaggagcgcaccatcttcttcaa
ggacgacggcaactacaagacccgcgccgaggtgaagttcgagggcgacaccctggtgaaccgcatcgagctgaagggcatcgacttcaa
ggaggacggcaacatcctggggcacaagctggagtacaactacaacagccacaacgtctatatcatggccgacaagcagaagaacggcat
caaggtgaacttcaagatccgccacaacatcgaggacggcagcgtgcagctcgccgaccactaccagcagaacacccccatcggcgacgg
ccccgtgctgctgcccgacaaccactacctgagcacccagtccgcccctgagcaaagacccccaacgagaagcgcgatcacatggtcctgctgg
agttcgtgaccgccgccgggatcactctcggcatggacgagctgtacaagtaacgcgtcccgggtctagagctagcggtaccatgcattacgt
agtcgacgacttaattaagctagcctagtgccatttgttcagtggttcgtagggcttttccccactgtttggctttcagttatatggatgatgtgg
tattgggggccaagtctgtacagcatcttgagtcccttttttaccgctgttaccaattttcttttgtctttgggtatacatttaaaccctaacaaaac
aaagagatggggttactctctaaatttttatgggttatgtcattggatgttatgggtccttgccacaagaacacatcatacaaaaaatcaaaga
atgttttagaaaacttcctattaacaggcctattgattggaaagtatgtcaacgaattgtgggtcttttgggttttgctgccccttttacacaatgt
ggttatcctgcgttgatgcctttgtatgcatgtattcaatctaagcaggctttcactttctcgccaacttacaaggcctttctgtgtaaacaatacc
tgaacctttaccccgttgcccggcaacggccaggtctgtgccaagtgtttgctgacgcaaccccactggctggggcttggtcatgggccatca
gcgcatgcgtggaaccttttcggctcctctgccgatccatactgcggaactcctagccgcttgttttgctcgcagcaggtctggagcaaacatta
tcgggactgataactctgttgtcctatcccgcaaatatacatcgtttccatggctgctaggctgtgctgccaactggatcctgcgcgggacgtcc
tttgtttacgtcccgtcggcgctgaatcctgcggacgaccttctcggggtcgcttgggactctctcgtcccttctccgtctgccgttccgaccg
accacggggcgcacctctctttacgcggactccccgtctgtgccttctcatctgccggaccgtgtgcacttcgcttcacctctgcacgtcgcatg
gagaccaccgtgaacgcccaccaaatattgcccaaggtcttacataagaggactcttggactctcagcaatgtcaacgaccgaccttgaggc
atacttcaaagactgtttgtttaaagactgggaggagttgggggaggagattaggttaaaggtctttgtactaggaggctgtaggcataaatt
ggtctgcgcaccagcaccatggcgcaatcactagagcggggtacctttaagaccaatgacttacaaggcagctgtagatcttagccactttt
aaaagaaaaggggggactggaagggctaattcactcccaacgaagacaagatctgcttttttgcttgtactgggtctctctggttagaccagat
ctgagcctgggagctctctggctaactagggaacccactgcttaagcctcaataaagcttgccttgagtgcttcaagtagtgtgtgcccgtctg
ttgtgtgactctggtaactagagatccctcagacccttttagtcagtgtggaaaatctctagcagtagtagttcatgtcatcttattattcagtat
ttataacttgcaaagaaatgaatatcagagagtgagaggaacttgtttattgcagcttataatggttacaaataaagcaatagcatcacaaat
ttcacaaataaagcattttttttcactgcattctagttgtggtttgtccaaactcatcaatgtatcttatcatgtctggctctagctatcccgcccct
aactccgcccatcccgcccctaactccgcccagttccgcccattctccgcccatggctgactaattttttttatttatgcagaggccgaggccg
gatcccttgagtggctttcatcctggagcagactttgcagtctgtggactgcaacacaacattgcctttatgtgtaactcttggctgaagctctta

*Figure 11B (cont.)* caccaatgctgggggacatgtacctcccaggggcccaggaagactacgggaggctacaccaacgtcaatcagaggggcctgtgtagctacc
gataagcggaccctcaagagggcattagcaatagtgtttataaggcccccttgttaattcttgaagacgaaagggcctcgtgatacgcctatt
tttataggttaatgtcatgataataatggtttcttagacgtcaggtggcactttttcggggaaatgtgcgcggaacccctatttgtttattttctaa
atacattcaaatatgtatccgctcatgagacaataaccctgataaatgcttcaataatattgaaaaaggaagagtatgagtattcaacatttc
cgtgtcgcccttattccctttttgcggcattttgccttcctgttttgctcacccagaaacgctggtgaaagtaaaagatgctgaagatcagttg
ggtgcacgagtgggttacatcgaactggatctcaacagcggtaagatccttgagagttttcgccccgaagaacgttttccaatgatgagcact
tttaaagttctgctatgtggcgcggtattatcccgtgttgacgccgggcaagagcaactcggtcgccgcatacactattctcagaatgacttgg
ttgagtactcaccagtcacagaaaagcatcttacggatggcatgacagtaagagaattatgcagtgctgccataaccatgagtgataacact
gcggccaacttacttctgacaacgatcggaggaccgaaggagctaaccgcttttttgcacaacatggggatcatgtaactcgccttgatcgt
tgggaaccggagctgaatgaagccataccaaacgacgagcgtgacaccacgatgcctgcagcaatggcaacaacgttgcgcaaactatta
actggcgaactacttactctagcttcccggcaacaattaatagactggatggaggcggataaagttgcaggaccacttctgcgctcggcccct
ccggctggctggtttattgctgataaatctggagccggtgagcgtgggtctcgcggtatcattgcagcactggggccagatggtaagccctcc
cgtatcgtagttatctacacgacggggagtcaggcaactatggatgaacgaaatagacagatcgctgagataggtgcctcactgattaagca
ttggtaactgtcagaccaagtttactcatatatactttagattgatttaaaacttcatttttaatttaaaaggatctaggtgaagatcctttttgat
aatctcatgaccaaaatcccttaacgtgagttttcgttccactgagcgtcagaccccgtagaaaagatcaaaggatcttcttgagatccttttt
tctgcgcgtaatctgctgcttgcaaacaaaaaaaccaccgctaccagcggtggtttgtttgccggatcaagagctaccaactctttttccgaag
gtaactggcttcagcagagcgcagataccaaatactgtccttctagtgtagccgtagttaggccaccacttcaagaactctgtagcaccgcct
acatacctcgctctgctaatcctgttaccagtggctgctgccagtggcgataagtcgtgtcttaccgggttggactcaagacgatagttaccgg
ataaggcgcagcggtcgggctgaacggggggttcgtgcacacagcccagcttggagcgaacgacctacaccgaactgagatacctacagc
gtgagcattgagaaagcgccacgcttcccgaagggagaaaggcggacaggtatccggtaagcggcagggtcggaacaggagagcgcacg
agggagcttccaggggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttttgaagctgtccctgatggtcgtcat
ctacctgcctggacagcatggcctgcaacgcgggcatcccgatgccgccggaagcgagaagaatcataatggggaaggccatccagcctcg
cgtcg

Figure 12

|  | 19H9 | 38A1 |
|---|---|---|
| Cell Conc. (per ml) | 3.23e6 | 2.99e6 |
| Volume | 120 mL | 120 mL |
| Total Cells | 3.88E+08 | 3.59E+08 |
| aPDL1 Conc. | 31.76 ug/mL | 20.20 ug/mL |
| Total aPDL1 (mg) | 3.81 | 2.42 |
| Secretion capacity (ug per 1e6 cells) | 9.82 | 6.75 | pLV4301G PDLV scFV 19H9

| EU Index | 118 | 119 | 120 | 121 | 122 | 123 | 124 | 125 | 126 | 127 | 128 | 129 | 130 | 131 | 132 | 133 | 134 | 135 | 136 | 137 | 138 |
|---|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | E | S |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | E | S |

| EU Index | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU Index | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU Index | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | T | C | N |
| IgG3 | S | L | S | S | V | V | T | V | P | S | S | S | L | G | T | Q | T | Y | T | C | N |
| IgG4 | S | L | S | S | V | V | T | V | P | S | S | S | L | G | T | K | T | Y | T | C | N |

| EU Index | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|
| IgG1 | V | N | H | K | P | S | N | T | K | V | D | K | K | V | E | P | K | S | C |
| IgG2 | V | D | H | K | P | S | N | T | K | V | D | K | T | V | E | R | K | C | C |
| IgG3 | V | N | H | K | P | S | N | T | K | V | D | K | R | V | E | L | K | T | P |
| IgG4 | V | D | H | K | P | S | N | T | K | V | D | K | R | V | E | S | K | Y | G |

Hinge     Fc →

| EU Index | 221 | 222 | 223 | 224 | 225 | 226 | 227 | 228 |
|---|---|---|---|---|---|---|---|---|
| IgG1 | D |  | K | T | H | T | C | P | P |
| IgG2 |  |  | V |  | E |  | C | P | P |
| IgG3 | L | G | D | T | T | H | T | C | P | R | C | P | E | P | K | S | C | D | T | P | P |
| IgG4 |  |  |  |  | P | P | C | P | S |

| EU Index |
|---|
| IgG1 |
| IgG2 |
| IgG3 | P | C | P | R | C | P | E | P | K | S | C | D | T | P | P | C | P | R | C | P |
| IgG4 |

Fc →

| EU Index | 229 | 230 | 231 | 232 | 233 | 234 | 235 | 236 |
|---|---|---|---|---|---|---|---|---|
| IgG1 | C | P | A | P | E | L | L | G |
| IgG2 | C | P | A | P | P | V | A |  |
| IgG3 | E | P | K | S | C | D | T | P | P | P | C | P | R | C | P | A | P | E | L | L | G |
| IgG4 | C | P | A | P | E | F | L | G |

| EU Index | 237 | 238 | 239 | 240 | 241 | 242 | 243 | 244 | 245 | 246 | 247 | 248 | 249 | 250 | 251 | 252 | 253 | 254 | 255 | 256 | 257 |
|---|---|---|---|---|---|---|---|---|---|---|---|---|---|---|---|---|---|---|---|---|---|
| IgG1 | G | P | S | V | F | L | F | P | P | K | P | K | D | T | L | M | I | S | R | T | P |
| IgG2 | G | P | S | V | F | L | F | P | P | K | P | K | D | T | L | M | I | S | R | T | P |
| IgG3 | G | P | S | V | F | L | F | P | P | K | P | K | D | T | L | M | I | S | R | T | P |
| IgG4 | G | P | S | V | F | L | F | P | P | K | P | K | D | T | L | M | I | S | R | T | P |

| EU Index | 258 | 259 | 260 | 261 | 262 | 263 | 264 | 265 | 266 | 267 | 268 | 269 | 270 | 271 | 272 | 273 | 274 | 275 | 276 | 277 | 278 |
|---|---|---|---|---|---|---|---|---|---|---|---|---|---|---|---|---|---|---|---|---|---|
| IgG1 | E | V | T | C | V | V | V | D | V | S | H | E | D | P | E | V | K | F | N | W | Y |
| IgG2 | E | V | T | C | V | V | V | D | V | S | H | E | D | P | E | V | Q | F | N | W | Y |
| IgG3 | E | V | T | C | V | V | V | D | V | S | H | E | D | P | E | V | Q | F | N | W | Y |
| IgG4 | E | V | T | C | V | V | V | D | V | S | Q | E | D | P | E | V | Q | F | N | W | Y |

| EU Index | 279 | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|---|
| IgG1 | V | D | G | V | E | V | H | N | A | K | T | K | P | R | E | E | Q | Y | N | S | T |
| IgG2 | V | D | G | V | E | V | H | N | A | K | T | K | P | R | E | E | Q | F | N | S | T |
| IgG3 | V | D | G | V | E | V | H | N | A | K | T | K | P | R | E | E | Q | Y | N | S | T |
| IgG4 | V | D | G | V | E | V | H | N | A | K | T | K | P | R | E | E | Q | F | N | S | T |

| EU Index | 300 | 301 | 302 | 303 | 304 | 305 | 306 | 307 | 308 | 309 | 310 | 311 | 312 | 313 | 314 | 315 | 316 | 317 | 318 | 319 | 320 |
|---|---|---|---|---|---|---|---|---|---|---|---|---|---|---|---|---|---|---|---|---|---|
| IgG1 | Y | R | V | V | S | V | L | T | V | L | H | Q | D | W | L | N | G | K | E | Y | K |
| IgG2 | F | R | V | V | S | V | L | T | V | V | H | Q | D | W | L | N | G | K | E | Y | K |
| IgG3 | F | R | V | V | S | V | L | T | V | L | H | Q | D | W | L | N | G | K | E | Y | K |
| IgG4 | Y | R | V | V | S | V | L | T | V | L | H | Q | D | W | L | N | G | K | E | Y | K |

| EU Index | 321 | 322 | 323 | 324 | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|---|---|---|---|
| IgG1 | C | K | V | S | N | K | A | L | P | A | P | I | E | K | T | I | S | K | A | K |
| IgG2 | C | K | V | S | N | K | G | L | P | A | P | I | E | K | T | I | S | K | T | K |
| IgG3 | C | K | V | S | N | K | A | L | P | A | P | I | E | K | T | I | S | K | T | K |
| IgG4 | C | K | V | S | N | K | G | L | P | S | S | I | E | K | T | I | S | K | A | K |

CH3

| EU Index | 341 | 342 | 343 | 344 | 345 | 346 | 347 | 348 | 349 | 350 | 351 | 352 | 353 | 354 | 355 | 356 | 357 | 358 | 359 | 360 | 361 |
|---|---|---|---|---|---|---|---|---|---|---|---|---|---|---|---|---|---|---|---|---|---|
| IgG1 | G | Q | P | R | E | P | Q | V | Y | T | L | P | P | S | R | D | E | L | T | K | N |
| IgG2 | G | Q | P | R | E | P | Q | V | Y | T | L | P | P | S | R | E | E | M | T | K | N |
| IgG3 | G | Q | P | R | E | P | Q | V | Y | T | L | P | P | S | R | E | E | M | T | K | N |
| IgG4 | G | Q | P | R | E | P | Q | V | Y | T | L | P | P | S | Q | E | E | M | T | K | N |

| EU Index | 362 | 363 | 364 | 365 | 366 | 367 | 368 | 369 | 370 | 371 | 372 | 373 | 374 | 375 | 376 | 377 | 378 | 379 | 380 | 381 | 382 |
|---|---|---|---|---|---|---|---|---|---|---|---|---|---|---|---|---|---|---|---|---|---|
| IgG1 | Q | V | S | L | T | C | L | V | K | G | F | Y | P | S | D | I | A | V | E | W | E |
| IgG2 | Q | V | S | L | T | C | L | V | K | G | F | Y | P | S | D | I | A | V | E | W | E |
| IgG3 | Q | V | S | L | T | C | L | V | K | G | F | Y | P | S | D | I | A | V | E | W | E |
| IgG4 | Q | V | S | L | T | C | L | V | K | G | F | Y | P | S | D | I | A | V | E | W | E |

| EU Index | 383 | 384 | 385 | 386 | 387 | 388 | 389 | 390 | 391 | 392 | 393 | 394 | 395 | 396 | 397 | 398 | 399 | 400 | 401 | 402 | 403 |
|---|---|---|---|---|---|---|---|---|---|---|---|---|---|---|---|---|---|---|---|---|---|
| IgG1 | S | N | G | Q | P | E | N | N | Y | K | T | T | P | P | V | L | D | S | D | G | S |
| IgG2 | S | N | G | Q | P | E | N | N | Y | K | T | T | P | P | M | L | D | S | D | G | S |
| IgG3 | S | S | G | Q | P | E | N | N | Y | N | T | T | P | P | M | L | D | S | D | G | S |
| IgG4 | S | N | G | Q | P | E | N | N | Y | K | T | T | P | P | V | L | D | S | D | G | S |

| EU Index | 404 | 405 | 406 | 407 | 408 | 409 | 410 | 411 | 412 | 413 | 414 | 415 | 416 | 417 | 418 | 419 | 420 | 421 | 422 | 423 | 424 |
|---|---|---|---|---|---|---|---|---|---|---|---|---|---|---|---|---|---|---|---|---|---|
| IgG1 | F | F | L | Y | S | K | L | T | V | D | K | S | R | W | Q | Q | G | N | V | F | S |
| IgG2 | F | F | L | Y | S | K | L | T | V | D | K | S | R | W | Q | Q | G | N | V | F | S |
| IgG3 | F | F | L | Y | S | K | L | T | V | D | K | S | R | W | Q | Q | G | N | I | F | S |
| IgG4 | F | F | L | Y | S | R | L | T | V | D | K | S | R | W | Q | E | G | N | V | F | S |

| EU Index | 425 | 426 | 427 | 428 | 429 | 430 | 431 | 432 | 433 | 434 | 435 | 436 | 437 | 438 | 439 | 440 | 441 | 442 | 443 | 444 | 445 |
|---|---|---|---|---|---|---|---|---|---|---|---|---|---|---|---|---|---|---|---|---|---|
| IgG1 | C | S | V | M | H | E | A | L | H | N | H | Y | T | Q | K | S | L | S | L | S | P |
| IgG2 | C | S | V | M | H | E | A | L | H | N | H | Y | T | Q | K | S | L | S | L | S | P |
| IgG3 | C | S | V | M | H | E | A | L | H | N | R | F | T | Q | K | S | L | S | L | S | P |
| IgG4 | C | S | V | M | H | E | A | L | H | N | H | Y | T | Q | K | S | L | S | L | S | L |

| EU Index | 446 | 447 |
|---|---|---|
| IgG1 | G | K |
| IgG2 | G | K |
| IgG3 | G | K |
| IgG4 | G | K |

PROGRAMMED DEATH 1 LIGAND 1 (PD-L1) BINDING PROTEINS AND METHODS OF USE THEREOF

CROSS REFERENCE TO RELATED APPLICATIONS

This application claims the benefit of U.S. Provisional Application No. 62/359,612, filed on Jul. 7, 2016, all of which is expressly incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 7, 2017, is named 116983-5024_ST25.txt and is 101,943 bytes in size.

INTRODUCTION

Adoptive Cell Transfer (ACT) is a treatment approach in which a patient's autologous T-cells are expanded, manipulated ex vivo, and then re-introduced into the patient to exert a response, e.g., an anti-tumor response. Tumor Infiltrating Lymphocytes (TILs) generally refers to a heterogeneous population of lymphocytes which can be found in the tumor microenvironment. The general rationale of ACT therapy using TILs is that the anti-tumor immune response can be enhanced by removing cells with anti-tumor potential from the immunosuppressive tumor microenvironment, expanding the cells in vitro, and then returning the expanded population of cells to tumor sites to kill tumor cells and possibly other cell targets that sustain the tumor, such as vascular endothelial cells. Lee and Margolin, Curr. Oncol. Rep. 2012; 14(5) 468-474.

Programmed Death 1 (PD-1) is a well described inhibitory receptor expressed on activated human T-cells that, in cooperation with its ligands, Programmed Death 1 Ligand 1 (PD-L1) and Programmed Death 1 Ligand 2 (PD-L2), acts as checkpoint factor limiting T-cell mediated anti-tumor activity in a variety human cancers including melanoma. PD-1 is expressed by TILs and as such, expression of PD-L1 in the tumor microenvironment is inhibitory to cancer disease progression, including, for example, tumor growth.

Accordingly, there is a need in the art for new compositions and methods which interfere with the inhibitory effect of the PD-1-PD-L1 interaction, for example, in the context of ACT therapy using TILs.

SUMMARY

The present disclosure provides proteins, such as antibodies, that include an antigen binding portion that specifically binds to Programmed Death 1 Ligand 1 (PD-L1). Also provided are nucleic acids encoding the proteins, and cells (e.g., genetically modified cytotoxic lymphocytes) that include such nucleic acids. In some embodiments, a subject method includes reducing the interaction between PD-L1 on a first-cell and PD-1 on a second cell. For example, the methods and compositions provided can be used in the treatment of viral infection and cancer, such as the treatment of solid tumors via ACT or via administration of a subject protein that specifically binds to PD-L1.

The compositions and methods of the present disclosure can allow genetically modified cytotoxic lymphocytes, e.g., activated T-cells, TILs, and NK cells, to be propagated and infused as a cell therapy which allows for the secretion of a PD-L1 binding protein (e.g., an scFV, a maxibody) in the genetically modified cytotoxic lymphocytes to be administered to the subject. In this way, the cytotoxic lymphocytes of the present disclosure are able to "relieve" themselves of the inhibitory effect of the PD-1 checkpoint, providing for an improved anti-cancer effect in the subject to which the genetically modified cytotoxic lymphocytes are administered. Specific binding proteins of the disclosure (e.g., anti-PD-L1 antibodies) can also be administered to an individual directly, e.g., intravenous (i.v.) or intratumoral injection.

The disclosure provides a protein that specifically binds to PD-L1 and comprises an antigen binding portion that comprises: (a) a first polypeptide comprising the 3 CDR amino acid sequences set forth in SEQ ID NOs:2-4, and a second polypeptide comprising the 3 CDR amino acid sequences set forth in SEQ ID NOs:6-8; or (b) a first polypeptide comprising the 3 CDR amino acid sequences set forth in SEQ ID NOs: 10-12, and a second polypeptide comprising the 3 CDR amino acid sequences set forth in SEQ ID NOs:14-16, with the exception that each of the three CDR amino acid sequences of the first and/or second polypeptide comprises two or less conservative amino acid substitutions relative to the specified SEQ ID number.

In some embodiments, the antigen binding portion comprises a first polypeptide comprising the 3 CDR amino acid sequences set forth in SEQ ID NOs:2-4, and a second polypeptide comprising the 3 CDR amino acid sequences set forth in SEQ ID NOs:6-8.

In some embodiments, the first polypeptide comprises the amino acid sequence set forth in SEQ ID NO:1, and the second polypeptide comprises the amino acid sequence set forth in SEQ ID NO:5.

In some embodiments, the antigen binding portion comprises a first polypeptide comprising the 3 CDR amino acid sequences set forth in SEQ ID NOs:10-12, and a second polypeptide comprising the 3 CDR amino acid sequences set forth in SEQ ID NOs:14-16.

In some embodiments, the first polypeptide comprises the amino acid sequence set forth in SEQ ID NO:9, and the second polypeptide comprises the amino acid sequence set forth in SEQ ID NO:13.

In some embodiments, the first polypeptide is a light chain, and the second polypeptide is a heavy chain.

In some embodiments, the protein that specifically binds to PD-L1 is a single-chain antibody (scFv) and the first and second polypeptides are fused directly or via a linker to one another. In some embodiments, the scFv comprises the amino acid sequence set forth in SEQ ID NO:17 or SEQ ID NO:19.

In some embodiments, the protein that specifically binds to PD-L1 is a maxibody comprising an immunoglobulin Fc domain fused directly or via a linker to the antigen binding portion. In some embodiments, the immunoglobulin Fc domain is an IgG1 Fc domain. In some embodiments, the protein comprises the amino acid sequence set forth in SEQ ID NO:18 or SEQ ID NO:20. In some embodiments, the immunoglobulin Fc domain is an IgG4 Fc domain.

In some embodiments, the protein that specifically binds to PD-L1 is a humanized antibody.

The present disclosure also provides a nucleic acid comprising a nucleotide sequence encoding the protein that specifically binds to PD-L1, as discussed herein. In some embodiments, the nucleic acid comprises a promoter that is operably linked to the nucleotide sequence encoding the protein. In some embodiments, the promoter is a constitutive promoter. In some embodiments, the promoter is an inducible promoter.

The present disclosure also provides a cell comprising the nucleic acid that encodes the protein that specifically binds to PD-L1. In some embodiments, the nucleic acid is integrated into the cell's genome. In some embodiments, the cell is a cytotoxic lymphocyte genetically modified to express and secrete the protein. In some embodiments, the cytotoxic lymphocyte is a T-cell. In some embodiments, the T-cell is a CD8+ T-cell. In some embodiments, the T-cell is a CD4+ T-helper cell. In some embodiments, the T-cell is derived from peripheral blood. In some embodiments, the cytotoxic lymphocyte is a natural killer (NK) cell. In some embodiments, the NK is derived from peripheral blood.

In some embodiments, the cytotoxic lymphocyte is a tumor infiltrating lymphocyte (TIL) derived from a tumor from a subject.

In some embodiments, the TIL comprises a receptor specific for an antigen from the tumor.

In some embodiments, the cytotoxic lymphocyte exhibits an increased level of expression of one or more activation antigens relative to a nave T-cell. In some embodiments, the one or more activation antigens are selected from CD25, CD26, CD27, CD28, CD38, CD40L, CD69, CD134, CD137, BTLA, PD-1, HVEM, LIGHT, and HLA-DR.

In some embodiments, the cytotoxic lymphocyte comprises a T-cell receptor specific for a tumor associated antigen.

The present disclosure also provides a method comprising: genetically modifying a cytotoxic lymphocyte isolated from a tumor of a subject by introducing into the cytotoxic lymphocyte the nucleic acid encoding a protein that specifically binds to PD-L1, wherein the genetically modified cytotoxic lymphocyte expresses and secretes the protein that specifically binds to PD-L1; expanding the genetically modified cytotoxic lymphocyte to generate a population of genetically modified cytotoxic lymphocytes; and administering the population of genetically modified cytotoxic lymphocytes to the subject to treat the tumor.

In some embodiments, the genetically modified cytotoxic lymphocyte constitutively expresses the protein that specifically binds to PD-L1. In some embodiments, the genetically modified cytotoxic lymphocyte inducibly expresses the protein that specifically binds to PD-L1. In some embodiments, the nucleic acid integrates into the cytotoxic lymphocyte's genome.

In some embodiments, the cytotoxic lymphocyte is a T-cell. In some embodiments, the T-cell is a CD8+ T-cell. In some embodiments, the T-cell is a CD4+ T-helper cell. In some embodiments, the cytotoxic lymphocyte is a natural killer (NK) cell.

In some embodiments, the genetically modified cytotoxic lymphocyte comprises a receptor specific for an antigen from the tumor.

In some embodiments, the method comprises isolating the cytotoxic lymphocyte from the subject prior to genetically modifying.

In some embodiments of the method, the protein that specifically binds to PD-L1 and comprises an antigen binding portion that comprises: (a) a first polypeptide comprising the 3 CDR amino acid sequences set forth in SEQ ID NOs:2-4, and a second polypeptide comprising the 3 CDR amino acid sequences set forth in SEQ ID NOs:6-8; or (b) a first polypeptide comprising the 3 CDR amino acid sequences set forth in SEQ ID NOs: 10-12, and a second polypeptide comprising the 3 CDR amino acid sequences set forth in SEQ ID NOs:14-16, with the exception that each of the three CDR amino acid sequences of the first and/or second polypeptide comprises two or less conservative amino acid substitutions relative to the specified SEQ ID number.

In some embodiments of the method, the antigen binding portion comprises a first polypeptide comprising the 3 CDR amino acid sequences set forth in SEQ ID NOs:2-4, and a second polypeptide comprising the 3 CDR amino acid sequences set forth in SEQ ID NOs:6-8.

In some embodiments of the method, the first polypeptide comprises the amino acid sequence set forth in SEQ ID NO:1, and the second polypeptide comprises the amino acid sequence set forth in SEQ ID NO:5.

In some embodiments of the method, the antigen binding portion comprises a first polypeptide comprising the 3 CDR amino acid sequences set forth in SEQ ID NOs:10-12, and a second polypeptide comprising the 3 CDR amino acid sequences set forth in SEQ ID NOs:14-16.

In some embodiments of the method, the first polypeptide comprises the amino acid sequence set forth in SEQ ID NO:9, and the second polypeptide comprises the amino acid sequence set forth in SEQ ID NO:13.

In some embodiments of the method, the first polypeptide is a light chain, and the second polypeptide is a heavy chain.

In some embodiments of the method, the protein is a single-chain antibody (scFv) and the first and second polypeptides are fused directly or via a linker to one another.

In some embodiments of the method, the scFv comprises the amino acid sequence set forth in SEQ ID NO:17 or SEQ ID NO:19.

In some embodiments of the method, the protein is a maxibody comprising an immunoglobulin Fc domain fused directly or via a linker to the antigen binding portion.

In some embodiments of the method, the immunoglobulin Fc domain is an IgG1 Fc domain.

In some embodiments of the method, the protein comprises the amino acid sequence set forth in SEQ ID NO:18 or SEQ ID NO:20.

The present disclosure also provides a method of making a genetically modified cytotoxic lymphocyte, the method comprising: genetically modifying a cytotoxic lymphocyte isolated from a subject having or suspected of having cancer by introducing into the cytotoxic lymphocyte the nucleic acid encoding for the protein that specifically binds to PD-L1, wherein the genetically modified cytotoxic lymphocyte expresses and secretes the protein that specifically binds to PD-L1. In some embodiments, the genetically modified cytotoxic lymphocyte constitutively expresses the protein that specifically binds to PD-L1. In some embodiments, the genetically modified cytotoxic lymphocyte inducibly expresses the protein that specifically binds to PD-L1.

In some embodiments, the method comprises expanding the cytotoxic lymphocyte in vitro to provide an expanded population of genetically modified cytotoxic lymphocytes.

In some embodiments, the method comprises isolating the cytotoxic lymphocyte from the subject prior to the genetically modifying.

In some embodiments, the isolating comprises isolating the cytotoxic lymphocyte from a tumor of the subject. In some embodiments, the isolating comprises isolating the cytotoxic lymphocyte from peripheral blood of the subject.

In some embodiments of the method, the cytotoxic lymphocyte is a T-cell. In some embodiments of the method, the T-cell is a CD8+ T-cell. In some embodiments of the method, the T-cell is a CD4+ T-helper cell. In some embodiments of the method, the cytotoxic lymphocyte is a natural killer (NK) cell.

In some embodiments of the method, the nucleic acid integrates into the cytotoxic lymphocyte's genome.

In some embodiments of the method, the cytotoxic lymphocyte exhibits an increased level of expression of one or more activation antigens relative to a naïve T-cell. In some embodiments of the method, the one or more activation antigens are selected from CD25, CD26, CD27, CD28, CD38, CD40L, CD69, CD134, CD137, BTLA, PD-1, HVEM, LIGHT, and HLA-DR.

In some embodiments of the method, the genetically modified cytotoxic lymphocyte comprises a T-cell receptor specific for an antigen from a tumor of the subject.

The present disclosure also provides a method of treating an individual who has or is suspected of having cancer, the method comprising: administering the protein that specifically binds to PD-L1 to the individual (e.g., subject or patient, including for example a mammal such as a human).

In some embodiments of the method, the administering comprises introducing into the subject a nucleic acid encoding the protein that specifically binds to PD-L1.

In some embodiments of the method, administering comprises introducing into the subject a genetically modified cytotoxic lymphocyte that expresses and secretes the protein that specifically binds to PD-L1.

In some embodiments of the method, the genetically modified cytotoxic lymphocyte constitutively expresses the protein that specifically binds to PD-L1. In some embodiments of the method, the genetically modified cytotoxic lymphocyte inducibly expresses the protein that specifically binds to PD-L1. In some embodiments, the method, comprises inducing expression of the protein that specifically binds to PD-L1.

In some embodiments of the method, the cytotoxic lymphocyte is a T-cell. In some embodiments of the method, the T-cell is a CD8+ T-cell. In some embodiments of the method, the T-cell is a CD4+ T-helper cell. In some embodiments of the method, the cytotoxic lymphocyte is a natural killer (NK) cell.

In some embodiments of the method, the cytotoxic lymphocyte exhibits an increased level of expression of one or more activation antigens relative to a nave T-cell. In some embodiments of the method, the one or more activation antigens are selected from CD25, CD26, CD27, CD28, CD38, CD40L, CD69, CD134, CD137, BTLA, PD-1, HVEM, LIGHT, and HLA-DR.

In some embodiments of the method, the genetically modified cytotoxic lymphocyte comprises a T-cell receptor specific for an antigen from a tumor of the subject.

The present disclosure also provides a method of reducing the interaction between PD-L1 on a first-cell and PD-1 on a second cell, the method comprising: contacting PD-L1 on the first-cell with the protein that specifically binds to PD-L1.

In some embodiments of the method, the first and second cells are introduced to an individual, and the contacting comprises administering the protein that specifically binds to PD-L1. In some embodiments of the method, introducing comprises systemic administration. In some embodiments of the method, the introducing comprises local administration. In some embodiments of the method, the local administration comprises intratumoral administration. In some embodiments of the method, the individual has cancer. In some embodiments of the method, the individual has a solid tumor.

BRIEF DESCRIPTION OF THE DRAWINGS

The invention may be best understood from the following detailed description when read in conjunction with the accompanying drawings. Included in the drawings are the following figures:

FIG. 7 provides sequences of the antigen binding regions of the newly generated 38A1 and 19H9 antibodies, as well as examples of scFV proteins (e.g., scFV and scFV-FC fusions) that include antigen binding regions 38A1 or 19H9.

FIG. 10 provides the empty vector sequence for the pLEV vector used as an exemplary vector in the present methods. pLV430G (Lentiviral Vector) (SEQ ID NO:35) (A) and pCIGO-VSV.G (VSVG) (SEQ ID NO:36) (B).

FIG. 11A-11B provides the complete vector nucleotide sequences for the pLV4301G PDLV scFV 38A1 (SEQ NO: 37) (A) and pLV4301G PDLV scFV 19H9 (SEQ ID NO:38) (B).

FIG. 12 provides data showing that 19H9 exhibits greater secretion capacity. A comparison of the secretion capacity of Jurkat cells overexpressing anti-PD-L1 ScFV clone 19H9 versus 38A1 is provided. Supernatant from Jurkat cells overexpressing anti-PD-L1 ScFV clone 19H9 and 38A1 were harvested and concentrated for IgG ELISA assay to determine the anti-PD-L1 ScFV concentration. It was found that Jurkat cells clone 19H9 had greater secretion capacity as compared with 38A1 (9.82 versus 6.75 µg/cells).

FIG. 17 provides examples of IgG1 (SEQ ID NO:39), IgG2 (SEQ ID NO:40), IgG3 (SEQ ID NO:41), and IgG4 (SEQ ID NO:42) sequences.

DETAILED DESCRIPTION

Figure 1:
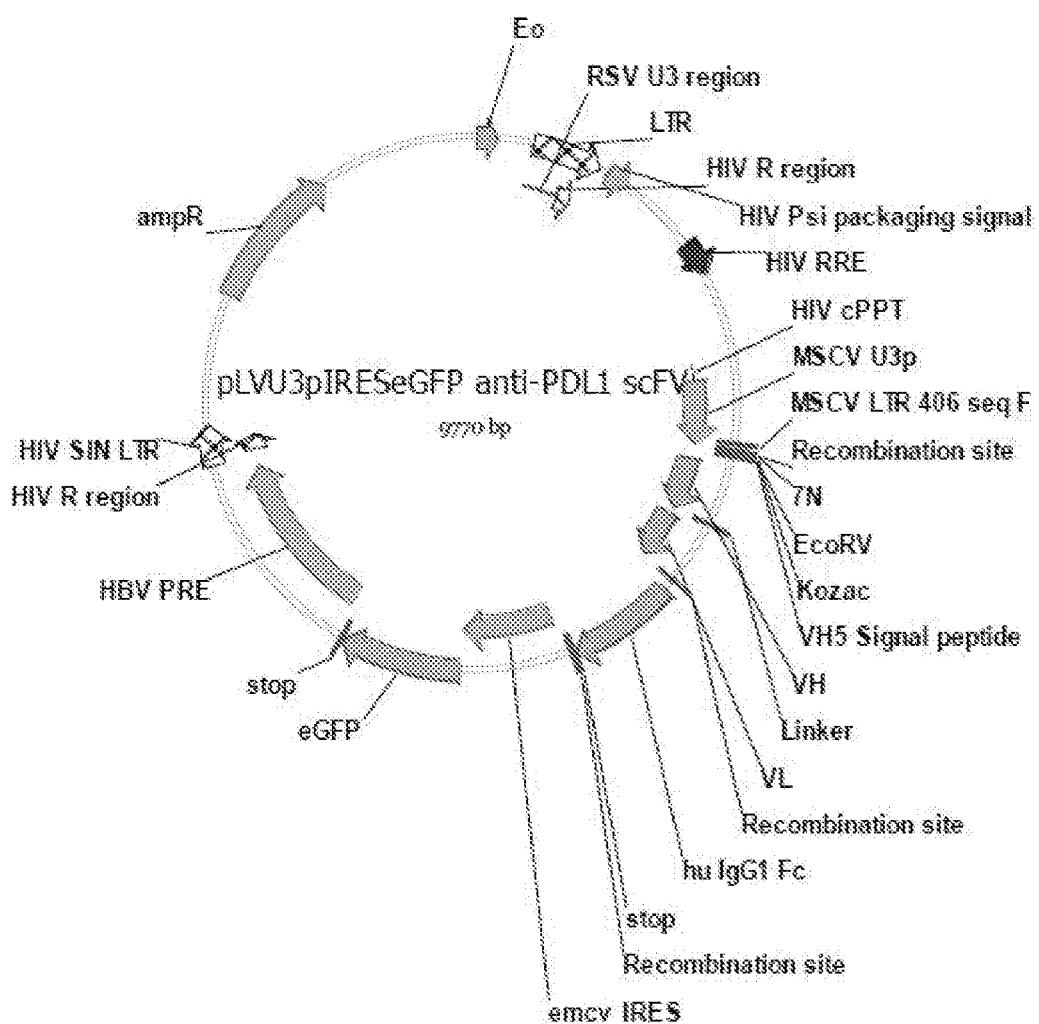
FIG. 1 provides a schematic representation of the lentiviral plasmid used to produce 38A1-Fc, 19H9-Fc and FMC63-Fc. Anti PD-L1 maxibodies are encoded downstream of the U3 promoter from MSCV promoter and upstream of an IRES-eGFP cassette.

The present disclosure provides proteins, such as antibodies, that include an antigen binding portion that specifically binds to Programmed Death 1 Ligand 1 (PD-L1). Also provided are nucleic acids encoding the proteins, and cells (e.g., genetically modified cytotoxic lymphocytes) that include such nucleic acids. In some embodiments, a subject method includes reducing the interaction between PD-L1 on a first-cell and PD-1 on a second cell. For example, the methods and compositions provided can be used in the treatment of viral infections and cancer, such as the treatment of solid tumors via ACT or via administration of a subject protein that specifically binds to PD-L1.

The compositions and methods of the present disclosure provide genetically modified cytotoxic lymphocytes, e.g., activated T-cells, TILs, and NK cells, that can be propagated and infused as a cell therapy, resulting in the secretion of a PD-L1 binding protein (e.g. an scFV, a maxibody, and the like) in the genetically modified cytotoxic lymphocytes infused into the subject. In this way, the cytotoxic lymphocytes of the present disclosure are able to "relieve" themselves of the inhibitory effect of the PD-1 checkpoint, providing for an improved anti-cancer effect. Specific binding proteins of the disclosure (e.g., anti-PD-L1 antibodies) can also be administered to an individual directly, e.g., intravenous (i.v.) or intratumoral injection.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Such terms are found defined and used in context in various standard references illustratively including J. Sambrook and D. W. Russell, Molecular Cloning: A Laboratory Manual, Cold Spring Harbor Laboratory Press; 4th Ed., 2012; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the disclosed compositions and methods to prevent the occurrence of tumor in the first place.

The term "antibody" is used in the broadest sense and includes, for example, an intact immunoglobulin or an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include Fab, Fab', F(ab')2, Fd, Fv, and domain antibodies (dAbs), and complementarity determining region (CDR) fragments, single-chain antibodies (single-chain variable domain fragment; scFv), diabodies, triabodies, tetrabodies, and polypeptides that contain at least a portion of an immunoglobulin that is sufficient to confer specific antigen binding to the polypeptide. Antibody includes a human antibody, a humanized antibody, chimeric antibody, a monoclonal antibody, a polyclonal antibody, a recombinant antibody, an antigen-binding antibody fragment, a single chain antibody, a maxibody (scFv fused by a linker or direct attachment to an Fc or an Fc fragment), a diabody, a triabody, a tetrabody, a Fab fragment, an F(fa')x fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region that alleviates a tendency to for intra H-chain disulfide bonds.

A "Fab fragment" is a monovalent fragment having the VL, VH, CL and CH1 domains; a F(ab')2 fragment is a bivalent fragment having two Fab fragments linked by a disulfide bridge at the hinge region; a Fd fragment has the VH and CH1 domains; an Fv fragment has the VL and VH domains of a single arm of an antibody; and a dAb fragment has a VH domain, a VL domain, or an antigen-binding fragment of a VH or VL domain.

A "single-chain antibody" (scFv) is an antibody in which a VL and a VH region are fused directly or joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al, 1988, Proc. Natl. Acad. Sci. USA 85:5879-83). Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

The term "human antibody" includes all antibodies that have one or more variable and constant regions derived from human immunoglobulin sequences. In one embodiment, all of the variable and constant domains are derived from human immunoglobulin sequences (a fully human antibody). Human antibodies may be prepared in a variety of ways, including immunization of a mouse that is genetically modified to express human antibodies. One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity fully human antibodies against any antigen of interest, including human antigens. Using the hybridoma technology, antigen-specific human MAbs with the desired specificity may be produced and selected. Human antibodies can also be prepared by panning human antibody libraries expressed on phage, phagemids, ribosomes, or other particles.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of methods for making humanized antibodies may be found in U.S. Pat. Nos. 6,054,297, 5,886,152 and 5,877,293, the disclosures of each of which are incorporated by reference herein.

The term "chimeric antibody" refers to an antibody that contains one or more regions from one antibody and one or more regions from one or more other antibodies. A "CDR grafted antibody" is an antibody comprising one or more CDRs derived from an antibody of a particular species or isotype and the framework of another antibody of the same or different species or isotype.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a Biacore® system.

As used herein, the term "high affinity" for an IgG antibody refers to an antibody having a $K_D$ of $10^{-8}$ M or less, in some embodiments, $10^{-9}$ M or less, and in some embodiments, $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, in some embodiments, $10^{-8}$ M or less, and in some embodiments, $10^{-9}$ M or less.

"Constitutive" expression includes a state in which a gene product is produced in a living cell under most or all physiological conditions of the cell.

A "coding region" of a gene includes the nucleotide residues of the coding strand of the gene and the nucleotides of the non-coding strand of the gene which are homologous with or complementary to, respectively, the coding region of an mRNA molecule which is produced by transcription of the gene. A "coding region" of a mRNA molecule also includes the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T-cells (lymphocytes), Th1 and Th17 CD4+ T-cells, natural killer cells, dendritic cells, and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs") as discussed herein.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cytotoxic lymphocyte" includes cytotoxic T (CTL) cells (including $CD8^+$ cytotoxic T lymphocytes and $CD4^+$ T-helper lymphocytes), natural killer T (NKT) cells and natural killer (NK) cells. Cytotoxic lymphocytes can include, for example, peripheral blood-derived αβ TCR-positive or γδ TCR-positive T-cells activated by tumor associated antigens and/or transduced with tumor specific chimeric antigen receptors or T-cell receptors, and tumor-infiltrating lymphocytes (TILs). Cytotoxic lymphocyte generally kill cancer cells, cells that are infected (particularly with viruses), or cells that are otherwise damaged or defective. A cytotoxic lymphocyte can also be referred to as a cytotoxic T-cell, TC, cytotoxic T lymphocyte, CTL, T-killer cell, cytolytic T-cell, CD8+ T-cell or killer T-cell is a T lymphocyte (a type of white blood cell).

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact-cells are employed.

The term "anti-CD3 antibody" refers to an antibody or variant thereof, e.g., a monoclonal antibody and including human, humanized, chimeric or murine antibodies which are directed against the CD3 receptor in the T-cell antigen receptor of mature T-cells. Anti-CD3 antibodies include OKT-3, also known as muromonab. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T-cell antigen receptor of mature T-cells, and includes commercially-available forms such as OKT-3 (30 ng/mL, MACS GMP CD3 pure, Miltenyi Biotech, Inc., San Diego, Calif., USA) and muromonab or variants, conservative amino acid substitutions, glycoforms, or biosimilars thereof. The amino acid sequences of the heavy and light chains of muromonab are given in Table 1 (SEQ ID NO:27 and SEQ ID NO:28). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:30). The term IL-2 also encompasses pegylated forms of IL-2, as described herein, including the pegylated IL2 prodrug NKTR-214, available from Nektar Therapeutics, South San Francisco, Calif., USA. NKTR-214 and pegylated IL-2 suitable for use in the invention is

TABLE 1

Amino acid sequences of muromonab.

| Identifier | Sequence (One-Letter Amino Acid Symbols) | |
|---|---|---|
| SEQ ID NO: 27<br>Muromonab<br>heavy chain | QVQLQQSGAE LARPGASVKM SCKASGYTFT RYTMHWVKQR PGQGLEWIGY INPSRGYTNY<br>NQKFKDKATL TTDKSSSTAY MQLSSLTSED SAVYYCARYY DDHYCLDYWG QGTTLTVSSA<br>KTTAPSVYPL APVCGGTTGS SVTLGCLVKG YFPEPVTLTW NSGSLSSGVH TFPAVLQSDL<br>YTLSSSVTVT SSTWPSQSIT CNVAHPASST KVDKKIEPRP KSCDCHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 28<br>Muromonab<br>light chain | QIVLTQSPAI MSASPGEKVT MTCSASSSVS INNWYQQKSG TSPKRWIYDT SKLASGVPAH<br>FRGSGSGTSY SLTISGMEAE DAATYYCQQW SSNPFTFGSG TKLEINRADT APTVSIFPPS<br>SEQLTSGGAS VVCFLNNFYP KDINVKWKID GSERQNGVLN SWTDQDSKDS TYSMSSTLTL<br>TKDEYERHNS YTCEATHKTS TSPIVKSFNR NEC | 60<br>120<br>180<br>213 |

The term "IL-2" (also referred to herein as "IL2") refers to the T-cell growth factor known as interleukin-2, and includes all forms of IL-2 including human and mammalian forms, conservative amino acid substitutions, glycoforms, biosimilars, and variants thereof. IL-2 is described, e.g., in Nelson, J. Immunol. 2004, 172, 3983-88 and Malek, Annu. Rev. Immunol. 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

As used herein, interleukins include IL-2, IL-4, IL-7, IL-15, and IL-21. Exemplary sequences for these interleukins are provided in Table 2 below.

TABLE 2

Amino acid sequences of interleukins.

| Identifier | Sequence (One-Letter Amino Acid Symbols) | |
|---|---|---|
| SEQ ID NO: 29<br>recombinant<br>human IL-2<br>(rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 30<br>Aldesleukin<br>(Proleukin ®) | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 31<br>recombinant<br>human IL-4<br>(rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 32<br>recombinant<br>human IL-7<br>(rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |

TABLE 2-continued

Amino acid sequences of interleukins.

| Identifier | Sequence (One-Letter Amino Acid Symbols) | |
|---|---|---|
| SEQ ID NO: 33 recombinant human IL-15 (rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 34 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

The term "IL-4" (also referred to herein as "IL4") refers to the cytokine known as interleukin 4, which is produced by Th2 T-cells and by eosinophils, basophils, and mast-cells. IL-4 regulates the differentiation of naïve helper T-cells (Th0 cells) to Th2 T-cells. Steinke and Borish, Respir. Res. 2001, 2, 66-70. Upon activation by IL-4, Th2 T-cells subsequently produce additional IL-4 in a positive feedback loop. IL-4 also stimulates B cell proliferation and class II MHC expression, and induces class switching to IgE and IgG1 expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, Mass., USA (human IL-15 recombinant protein, Cat. No. Gibco CTP0043). The amino acid sequence of recombinant human IL-4 suitable for use in the invention is given in Table 2 (SEQ ID NO:31).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T-cells. IL-7 binds to the IL-7 receptor, a heterodimer consisting of IL-7 receptor alpha and common gamma chain receptor, which in a series of signals important for T-cell development within the thymus and survival within the periphery. Recombinant human IL-4 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-15 recombinant protein, Cat. No. Gibco PHC0071). The amino acid sequence of recombinant human IL-7 suitable for use in the invention is given in Table 2 (SEQ ID NO:32).

The term "IL-15" (also referred to herein as "IL15") refers to the T-cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, Mass., USA (human IL-15 recombinant protein, Cat. No. 34-8159-82). The amino acid sequence of recombinant human IL-15 suitable for use in the invention is given in Table 2 (SEQ ID NO:33).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, Nat. Rev. Drug. Disc. 2014, 13, 379-95, the disclosure of which is incorporated by reference herein. IL-21 is primarily produced by natural killer T-cells and activated human CD4+ T-cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80). The amino acid sequence of recombinant human IL-21 suitable for use in the invention is given in Table 2 (SEQ ID NO:34).

A "disease" includes a state of health of an animal wherein the animal cannot maintain homeostasis, and wherein if the disease is not ameliorated then the animal's health continues to deteriorate.

In contrast, a "disorder" in an animal includes a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

With respect to the inventive methods, the term "tumor" or "cancer" can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin's lymphoma, hypopharynx cancer, kidney cancer, larynx cancer, liver cancer, lung cancer, malignant mesothelioma, melanoma, multiple myeloma, nasopharynx cancer, non-Hodgkin's lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colon cancer, and hepatobiliary cancer. In some embodiments, the cancer is melanoma. In some embodiments, the cancer is metastatic melanoma.

As used herein, the term "mammal" refers to any mammal, including, but not limited to, mammals of the order Rodentia, such as mice and hamsters, and mammals of the order Logomorpha, such as rabbits. In some embodiments, the mammals are from the order Carnivora, including felines (cats) and canines (dogs). In some embodiments, the mammals are from the order Artiodactyla, including bovines (cows) and swines (pigs) or of the order Perssodactyla, including Equines (horses). It is most preferred that the mammals are of the order Primates, Ceboids, or Simoids (monkeys) or of the order Anthropoids (humans and apes). In some embodiments, the mammal is the human.

The term "regression," as well as words stemming therefrom, as used herein, does not necessarily imply 100% or complete regression. Rather, there are varying degrees of regression of which one of ordinary skill in the art recognizes as having a potential benefit or therapeutic effect. In this respect, the inventive methods can provide any amount of any level of regression of cancer in a mammal. Furthermore, the regression provided by the inventive method can include regression of one or more conditions or symptoms of the disease, e.g., cancer. Also, for purposes herein, "regression" can encompass delaying the onset of the disease, or delaying the onset of a symptom and/or delaying the onset of a condition thereof.

An "effective amount" or "therapeutically effective amount" of a composition includes that amount of the composition which is sufficient to provide a beneficial effect to the subject to which the composition is administered. An "effective amount" of a delivery vehicle includes that amount sufficient to effectively bind or deliver a composition.

"Encoding" includes the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if, for example, transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" includes any material from or produced inside an organism, cell, tissue or system.

As used herein, the term "exogenous" includes any material introduced from or produced outside an organism, cell, tissue or system.

An "expression cassette" includes any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target-cells. Thus, the term includes cloning and expression vehicles, as well as viral vectors.

As used herein, the term "fragment," as applied to a nucleic acid or polypeptide, includes a subsequence of a larger nucleic acid or polypeptide. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between). A "fragment" of a polypeptide can be at least about 15 amino acids in length; for example, at least about 50 amino acids to about 100 amino acids; at least about 100 to about 500 amino acids, at least about 500 to about 1000 amino acids, at least about 1000 amino acids to about 1500 amino acids; or about 1500 amino acids to about 2500 amino acids; or about 2500 amino acids (and any integer value in between).

As used herein, the terms "gene" and "recombinant gene" includes nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

"Homologous" as used herein, includes the subunit sequence similarity between two polymeric molecules, e.g. between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g. if half (e.g., five positions in a polymer ten subunits in length) of the positions in two compound sequences are homologous then the two sequences are 50% homologous, if 90% of the positions, e.g. 9 of 10, are matched or homologous, the two sequences share 90% homology. By way of example, the DNA sequences 5'-ATTGCC-3' and 5'-TATGGC-3' share 50% homology.

"Inducible" expression includes a state in which a gene product is produced in a living cell in response to the presence of a signal in the cell.

As used herein, an "instructional material" includes a publication, a recording, a diagram, or any other medium of expression which can be used to communicate the usefulness and/or use of a compound, composition, vector, or delivery system of the present disclosure in a kit according to the present disclosure, e.g., a kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

The term "operably linked" as used herein includes a polynucleotide in functional relationship with a second polynucleotide, e.g. a single-stranded or double-stranded nucleic acid moiety comprising the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. The order specified when indicating operably linkage is not important. For example, the phrases: "the promoter is operably linked to the nucleotide sequence" and "the nucleotide sequence is operably linked to the promoter" are used interchangeably herein and are considered equivalent. In some cases, when the nucleic acid encoding the desired protein further comprises a promoter/regulatory sequence, the promoter/regulatory sequence is positioned at the 5' end of the desired protein coding sequence such that it drives expression of the desired protein in a cell.

The terms "oligonucleotide," "polynucleotide," and "nucleic acid molecule", used interchangeably herein, refer to a polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. The polynucleotide may comprise one or more L-nucleosides. A polynucleotide may comprise modified nucleotides, such as methylated nucleotides and nucleotide analogs, and may be interrupted by non-nucleotide components. If present, modifications to the nucleotide structure may be imparted before or after assembly of the polymer. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Polynucleotides can be single, double, or triplex, linear or circular, and can be of any length. In discussing polynucleotides, a sequence or structure of a particular polynucleotide may be described herein according to the convention of providing the sequence in the 5' to 3' direction.

The term "recombinant," as applied to a polynucleotide means the polynucleotide is the product of various combinations of cloning, restriction or ligation steps, and other procedures resulting in a construct distinct and/or different from a polynucleotide found in nature. The terms respectively include replicates of the original polynucleotide construct and progeny of the original virus construct.

The term "Programmed Death 1 Ligand 1 (PD-L1) binding protein" refers to a polypeptide (e.g., a fusion protein, an scFV, a maxibody, an antibody, and the like), which is capable of specifically binding to Programmed Death 1 Ligand 1 (PD-L1) protein (a.k.a. CD274 or B7-H1) expressed on the surface of a cell.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes polypeptide chains modified or derivatized in any manner, including, but not limited to, glycosylation, formylation, cyclization, acetylation, phosphorylation, and the like. The term includes naturally-occurring peptides, synthetic peptides, and peptides comprising one or more amino acid analogs. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "tumor-associated antigen" is a term well understood in the art, and refers to molecules that are differentially over-expressed in tumor cells relative to non-cancerous cells of the same cell type. As used herein, "tumor-associated antigen" includes not only complete tumor-associated antigens that can be expressed on the cell surface, but also epitope-comprising portions (fragments) thereof that are recognized by T-cells. A tumor-associated antigen (TAA) may be one found in nature, or may be a synthetic version of a TAA found in nature, or may be a variant of a naturally-occurring TAA, e.g., a variant which has enhanced immunogenic properties. The TAA may be a naturally occurring over-expressed protein or a mutated protein expressed only in tumor cells or other transformed cells in tumors.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors.

The terms "polypeptide," "peptide," and "protein" are used interchangeably herein to refer to polymers of amino acids of any length. The "polypeptides," "proteins" and "peptides" encoded by the "polynucleotide sequences," include full-length native sequences, as with naturally occurring proteins, as well as functional subsequences, modified forms or sequence variants so long as the subsequence, modified form, or variant retains some degree of functionality of the native full-length protein. In methods and uses of as described herein, such polypeptides, proteins, and peptides encoded by the polynucleotide sequences can be but are not required to be identical to the defective endogenous protein, or whose expression is insufficient, or deficient in the treated mammal. The terms also encompass a modified amino acid polymer; for example, disulfide bond formation, glycosylation, lipidation, phosphorylation, methylation, carboxylation, deamidation, acetylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, retaining the desired biochemical function of the intact protein.

A "recombinant polypeptide" includes one which is produced upon expression of a recombinant polynucleotide.

The term "specifically binds," as used herein, e.g., with respect to an antibody/antigen binding region, includes an antibody/antigen binding region which recognizes a specific antigen, but does not substantially recognize or bind other molecules in a sample. For example, an antibody (e.g., an scFV) that specifically binds to an antigen from one species may also bind to that antigen from one or more other species. But, such cross-species reactivity does not itself alter the classification of an antibody as specific. As another example, an antibody that specifically binds to an antigen may also bind to different allelic forms of the antigen. However, such cross reactivity does not itself alter the classification of an antibody as specific.

In some instances, the terms "specific binding" or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "synthetic antibody" as used herein includes an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Variant" as the term is used herein, includes a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions, and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "substitution" results from the replacement of one or more amino acids or nucleotides by different amino acids or nucleotides, respectively as compared to an amino acid sequence or nucleotide sequence of a polypeptide. If a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids ("conservative amino acid substitutions") usually result in a substitution of a first amino acid with second amino acid from the same group as the first amino acid, where examples of amino acid groups are as follows: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral non-polar amino acids such as alanine, leucine, isoleucine, valine, proline, phenylalanine, tryptophan, and methionine. In some embodiments, polypeptide variants may have "non-conservative" changes, where the substituted amino acid differs in structural and/or chemical properties.

A "deletion" is defined as a change in either amino acid or nucleotide sequence in which one or more amino acid or nucleotide residues, respectively, are absent as compared to an amino acid sequence or nucleotide sequence of a naturally occurring polypeptide or polynucleotide. In the context of a polypeptide or polynucleotide sequence, a deletion can involve deletion of 2, 5, 10, up to 20, up to 30, or up to 50 or more amino acids or nucleotide residues, taking into account the length of the polypeptide or polynucleotide sequence being modified.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide or polynucleotide. "Insertion" generally refers to addition of one or more amino acid residues within an amino acid sequence of a polypeptide (or nucleotide residues within a polynucleotide), while "addition" can be an insertion or refer to amino acid residues added at the N- or C-termini of a polypeptide (or nucleotide residues added at the 5' or 3' end of a polynucleotide). In the context of a polypeptide or polynucleotide sequence, an insertion or addition may be of up to 10, up to 20, up to 30, or up to 50 or more amino acids (or nucleotide residues).

An "isolated" plasmid, nucleic acid, vector, or other substance refers to a preparation of the substance devoid of at least some of the other components present where the substance or a similar substance naturally occurs or from which it is initially prepared. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, or other substance is in some embodiments purified, e.g., from about 80% to about 90% pure, at least about 90% pure, at least about 95% pure, at least about 98% pure, or at least about 99%, or more, pure.

A "vector" is capable of transferring gene sequences to target-cells. Typically, "vector construct," "expression vector," and "gene transfer vector," mean any nucleic acid construct capable of directing the expression of a gene of interest and which can transfer gene sequences to target-cells, which can be accomplished by genomic integration of all or a portion of the vector, or transient or inheritable maintenance of the vector as an extrachromosomal element. Thus, the term includes cloning, and expression vehicles, as well as integrating vectors.

The term "regulatory element" as used herein includes a nucleotide sequence which controls some aspect of the expression of nucleic acid sequences. Examples of regulatory elements illustratively include an enhancer, an internal ribosome entry site (IRES), an intron, an origin of replication, a polyadenylation signal (pA), a promoter, an enhancer, a transcription termination sequence, and an upstream regulatory domain, which contribute to the replication, transcription, and/or post-transcriptional processing of a nucleic acid sequence. In cases, regulatory elements can also include cis-regulatory DNA elements as well as transposable elements (TEs). Those of ordinary skill in the art are capable of selecting and using these and other regulatory elements in an expression construct with no more than routine experimentation. Expression constructs can be generated using a genetic recombinant approach or synthetically using well-known methodology.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "homologous tumor" is meant any tumor composed of tissue of the same type from which it develops. Additionally, a tumor can be homologous to TILs derived from said tumor. For example, a melanoma tumor can be homologous to TILs derived from the melanoma tumor and/or TILs derived from a melanoma tumor can be used to treat the homologous melanoma tumor from which they were derived. In some embodiments, TILs derived from the homologous tumor can be used to treat the homologous tumor.

By "individual" or "host" or "subject" or "patient" is meant any mammalian subject for whom diagnosis, treatment, or therapy is desired, particularly humans. Other subjects may include cattle, dogs, cats, guinea pigs, rabbits, rats, mice, horses, and so on.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, 75% free, or 90% free from other components with which it is naturally associated.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics,* 2:482-489 (1981). This algorithm can be applied to amino acid sequences by using the scoring matrix developed by Dayhoff, *Atlas of Protein Sequences and Structure,* M. O. Dayhoff ed., 5 suppl. 3:353-358, National Biomedical Research Foundation, Washington, D.C., USA, and normalized by Gribskov, *Nucl. Acids Res.* 14(6):6745-6763 (1986).

An example of an implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by Intelli-Genetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

Alternatively, in the context of polynucleotides, homology can be determined by hybridization of polynucleotides under conditions that form stable duplexes between homologous regions, followed by digestion with single-stranded-specific nuclease(s), and size determination of the digested fragments.

Two DNA, or two polypeptide sequences are "substantially homologous" to each other when the sequences exhibit at least about 80%-85%, at least about 85%-90%, at least about 90%-95%, or at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook and Russel, Molecular Cloning: A Laboratory Manual Third Edition, (2001) Cold Spring Harbor Laboratory Press, Cold Spring Harbor, N.Y.

A first polynucleotide is "derived from" a second polynucleotide if it has the same or substantially the same nucleotide sequence as a region of the second polynucleotide, its cDNA, complements thereof, or if it displays sequence identity as described above. This term is not meant to require or imply the polynucleotide must be obtained from the origin cited (although such is encompassed), but rather can be made by any suitable method.

A first polypeptide (or peptide) is "derived from" a second polypeptide (or peptide) if it is (i) encoded by a first polynucleotide derived from a second polynucleotide, or (ii) displays sequence identity to the second polypeptides as described above. This term is not meant to require or imply the polypeptide must be obtained from the origin cited (although such is encompassed), but rather can be made by any suitable method.

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

Any and all publications (including patents and patent application publications) mentioned herein are incorporated herein by reference to disclose and describe the methods and/or materials in connection with which the publications are cited.

The publications discussed herein are provided for their disclosure prior to the filing date of the present application. Further, the dates of publication provided may be different from the actual publication dates which may need to be independently confirmed. To the extent such publications may set out a definition which conflicts with an explicit or implicit definition or disclosure of the present disclosure, the definition or disclosure of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Compositions

Proteins (e.g., Antibodies) that Specifically Bind to PD-L1

Provided are proteins (e.g., antibodies) that specifically binds to PD-L1, nucleic acids encoding the proteins, and cells that include a subject protein and/or a nucleic acid encoding a subject protein. Throughout this disclosure, a "protein that specifically binds to PD-L1" that includes an antigen binding region as described herein is also referred to as a "PD-L1 binding protein."

Two new recombinant antibodies are provided (referred to herein as "38A1" and "19H9"), both of which specifically bind to human Programmed Death 1 Ligand (PD-L1). Human PD-L1, NCBI Accession NP_054862 (Version NP_054862.1 GI:7661534), is a 290 aa protein having the amino acid sequence (which includes a putative signal peptide at aa 1-18 and an ectodomain at amino acids 19-238):

```
                                         (SEQ ID NO: 21)
MRIFAVFIFMTYWHLLNAFTVTVPKDLYVVEYGSNMTIECKFPVE

KQLDLAALIVYWEMEDKNIIQFVHGEEDLKVQHSSYRQRARLLKD

QLSLGNAALQITDVKLQDAGVYRCMISYGGADYKRITVKVNAPYN

KINQRILVVDPVTSEHELTCQAEGYPKAEVIWTSSDHQVLSGKTT

TTNSKREEKLFNVTSTLRINTTTNEIFYCTFRRLDPEENHTAELV

IPELPLAHPPNERTHLVILGAILLCLGVALTFIFRLRKGRMMDVK

KCGIQDTNSKKQSDTHLEET
```

PD-L1 is also known as CD274 and B7-H1, and is expressed on the surface of a cell, e.g., a tumor cell.

Sequence details, including the CDR sequences, and additional information related to the 38A1 and 19H9 antibodies is presented in FIG. 7. As such in some cases, a subject protein that specifically binds to PD-L1 has an antigen binding portion that includes a first polypeptide that includes the 3 CDR amino acid sequences set forth in SEQ ID NOs:2-4 (light chain CDRs L1, L2, and L3, respectively of scFV 38A1), and a second polypeptide that includes the 3 CDR amino acid sequences set forth in SEQ ID NOs:6-8 (heavy chain CDRs H1, H2, and H3, respectively of scFV 38A1). In some cases, a subject protein that specifically binds to PD-L1 has an antigen binding portion that includes a first polypeptide that includes the 3 CDR amino acid sequences set forth in SEQ ID NOs:2-4 (light chain CDRs L1, L2, and L3, respectively of scFV 38A1), and a second polypeptide that includes the 3 CDR amino acid sequences set forth in SEQ ID NOs:6-8 (heavy chain CDRs H1, H2, and H3, respectively of scFV 38A1), with the exception that the first and/or the second polypeptide can include one or more conservative amino acid substitutions relative to the specified SEQ ID numbers as long as the protein specifically binds to PD-L1. In some cases, the first and/or the second polypeptide can include two or less (e.g., one or less) conservative amino acid substitutions within each amino acid stretch that corresponds to the specified SEQ ID numbers as long as the protein specifically binds to PD-L1. For example, such a subject protein can in some cases include two or less (e.g., one or less) conservative amino acid substitutions within each CDR.

In some cases, the first polypeptide comprises the amino acid sequence set forth in SEQ ID NO:1 (38A1 light chain), and the second polypeptide comprises the amino acid sequence set forth in SEQ ID NO:5 (38A1 heavy chain) (e.g., see FIG. 7). In some cases, the first polypeptide comprises the amino acid sequence set forth in SEQ ID NO:1, and the second polypeptide comprises the amino acid sequence set forth in SEQ ID NO:5, with the exception that the first and/or the second polypeptide can include one or more conservative amino acid substitutions relative to the specified SEQ ID numbers as long as the protein specifically binds to PD-L1. In some cases, the first and/or the second polypeptide can include two or less (e.g., one or less) conservative amino acid substitutions within each amino acid stretch that corresponds to the specified SEQ ID numbers as long as the protein specifically binds to PD-L1. For example, such a subject protein can in some cases include two or less (e.g., one or less) conservative amino acid substitutions within each CDR. In some embodiments, the first polypeptide comprises the CDRs recited in SEQ ID NOs:2, 3, and 4 and wherein the protein specifically binds to PD-L1. In some embodiments, the second polypeptide comprises the CDRs recited in SEQ ID NOs:6, 7, and 8 and wherein the protein specifically binds to PD-L1. In some embodiments, the PD-L1 binding protein exhibits greater or increased binding capacity in Jurkat cells as compared to 19H9. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway.

```
Light Chain-Antibody 38A1
                                         (SEQ ID NO: 1)
SYVLTQPPSVSVAPGQTARITCGGNNIGRKIVHWYQQRPGQAPVLVIY

YDTDRPAGIPERFSGSNSGNMATLTISTVGAGDEADYYCQVWDTGSDH

VVFGGGTKLTVL

CDR1 (CDR-L1):
                                         (SEQ ID NO: 2)
NIGRKI

CDR2 (CDR-L2):
                                         (SEQ ID NO: 3)
YDT

CDR3 (CDR-L3):
                                         (SEQ ID NO: 4)
QVWDTGSDHVV

Heavy Chain-Antibody 38A1
                                         (SEQ ID NO: 5)
EVQLVESGGGLVQPGGSLRLSCAASGFTFSNYAMSWVRQAPGKGLEWV

STISGSGGTTYYADSVKGRFTISRDNSKNTLYLQMNSLRVEDTAVYYC

AKDWFRSSSPDAFDIWGQGTTVTVSA

CDR1 (CDR-H1):
                                         (SEQ ID NO: 6)
GFTFSNYA

CDR2 (CDR-H2):
                                         (SEQ ID NO: 7)
ISGSGGTT

CDR3 (CDR-H3):
                                         (SEQ ID NO: 8)
AKDWFRSSSPDAFDI
```

In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3).

In some cases, a subject protein that specifically binds to PD-L1 has an antigen binding portion that includes a first polypeptide that includes the 3 CDR amino acid sequences set forth in SEQ ID NOs:10-12 (light chain CDRs L1, L2, and L3, respectively of scFV 19H9), and a second polypeptide that includes the 3 CDR amino acid sequences set forth in SEQ ID NOs:14-16 (heavy chain CDRs H1, H2, and H3, respectively of scFV 19H9). In some cases, a subject protein that specifically binds to PD-L1 has an antigen binding portion that includes a first polypeptide that includes the 3 CDR amino acid sequences set forth in SEQ ID NOs:10-12 (light chain CDRs L1, L2, and L3, respectively of scFV 19H9), and a second polypeptide that includes the 3 CDR amino acid sequences set forth in SEQ ID NOs:14-16 (heavy chain CDRs H1, H2, and H3, respectively of scFV 19H9), with the exception that the first and/or the second polypeptide can include one or more conservative amino acid substitutions relative to the specified SEQ ID numbers as long as the protein specifically binds to PD-L1. In some cases, the first and/or the second polypeptide can include two or less (e.g., one or less) conservative amino acid substitutions within each amino acid stretch that corresponds to the specified SEQ ID numbers as long as the protein specifically binds to PD-L1. For example, such a subject protein can in some cases include two or less (e.g., one or less) conservative amino acid substitutions within each CDR. In some embodiments, the first polypeptide comprises the CDRs recited in SEQ ID NOs:10, 11, and 12 and wherein the protein specifically binds to PD-L1. In some embodiments, the second polypeptide comprises the CDRs recited in SEQ ID NOs:14, 15, and 16 and wherein the protein specifically binds to PD-L1. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1.

Light Chain-Antibody 19H9
(SEQ ID NO: 9)
NFMLTQPHSVSESLGKTVTISCTGSSGSIARKFVQWYQQRPGSSPTTV

IYENNQRPSGVSDRFSGSIGSSSNSASLTISGLKTEDEADYYCQSYDS

SNVVFGGGTKVTVL

CDR1 (CDR-L1):
(SEQ ID NO: 10)
SGSIARKF

CDR2 (CDR-L2):
(SEQ ID NO: 11)
ENN

CDR3 (CDR-L3):
(SEQ ID NO: 12)
QSYDSSNVV

Heavy Chain-Antibody 19H9
(SEQ ID NO: 13)
QVQLQESGGGLVKPGGSLRLSCAASGFTFSSYSMNWVRQAPGKGLEWV

SGINTAGDTHYPESVKGRFTISRDNARNSLNLQMNSLRAEDTAVYYCV

RERVEREYSGYDAFDIWGQGTTVTVSA

CDR1 (CDR-H1):
(SEQ ID NO: 14)
GFTFSSYS

CDR2 (CDR-H2):
(SEQ ID NO: 15)
INTAGDT

CDR3 (CDR-H3):
(SEQ ID NO: 16)
VRERVEREYSGYDAFDI

In some embodiments, the first polypeptide comprises the amino acid sequence set forth in SEQ ID NO:9 (19H9 light chain), and the second polypeptide comprises the amino acid sequence set forth in SEQ ID NO:13 (19H9 heavy chain) (e.g., see FIG. 7). In some embodiments, the first polypeptide comprises the amino acid sequence 90%, 95%, or 98% identical to the amino acid sequence set forth in SEQ ID NO:9 (19H9 light chain), and the second polypeptide comprises the amino acid sequence 90%, 95%, or 98% identical to the amino acid sequence set forth in SEQ ID NO:13 (19H9 heavy chain). In some cases, the first polypeptide comprises the amino acid sequence set forth in SEQ ID NO:9, and the second polypeptide comprises the amino acid sequence set forth in SEQ ID NO:13, with the exception that the first and/or the second polypeptide can include one or more conservative amino acid substitutions relative to the specified SEQ ID numbers as long as the protein specifically binds to PD-L1. In some cases, the first and/or the second polypeptide can include two or less (e.g., one or less) conservative amino acid substitutions within each amino acid stretch that corresponds to the specified SEQ ID numbers as long as the protein specifically binds to PD-L1. For example, such a subject protein can in some cases include two or less (e.g., one or less) conservative amino acid substitutions within each CDR.

In some embodiments, a subject protein that specifically binds to PD-L1 is a single-chain antibody (scFv) (discussed above). As such, in some cases, a subject protein that specifically binds to PD-L1 is an scFv, and the first and second polypeptides of the antigen binding portion, as described above (e.g. in this section), are fused to one another (and are therefore part of the same polypeptide). Examples of suitable scFvs include, but are not limited to those set forth in SEQ ID NOs:17 and 19 (see FIG. 7). In some cases, the first and second polypeptides of an scFv are separated from one another via a linker (e.g., a flexible linker). Various linkers will be known to one of ordinary skill in the art and any convenient linker can be used. A flexible linker may include, for example, an amino acid sequence for a hinge region derived from an immunoglobulin heavy chain. A flexible linker can be positioned, for example, between an antigen binding portion (an antigen binding domain) of an antibody (e.g., an scFv) and an immunoglobulin Fc domain. A variety of flexible linkers are known in the art, including, e.g., flexible linkers including one or more Gly, Ser, Asn, and/or Asp amino acids. In some embodiments, the flexible linker is GGGGS. In some embodiments, the 1 flexible inker is (GGGGS)n (SEQ ID NO:35), wherein n is an integer between 1 and 10. In some embodiments, the flexible linker is GGGGS. In some embodiments, the flexible linker is GGGGSGGGGS (SEQ ID NO:36). In some embodiments, the flexible linker is GGGGSGGGGSGGGGS (SEQ ID NO:37). In some embodiments, the flexible linker is GGGGSGGGGSGGGGSGGGGS (SEQ ID NO:38). In some embodiments, the flexible linker is GGGGSGGGGSGGGGSGGGGSGGGGS (SEQ ID NO:39). In some embodiments, the flexible linker comprises a c-terminal Ala and Pro (AP). In some embodiments, the flexible linker is GGGSGG GGSGGGGSGAP (SEQ ID NO:40).

The flexible linkers of the scFvs of SEQ ID NOs:17 and 19 are bold and underlined in FIG. 7. In some cases, a subject protein that specifically binds to PD-L1 includes an amino acid sequence having 80% or more sequence identity (e.g., 85% or more, 90% or more, 95% or more, 98% or more, 99% or more, or 100% sequence identity) with the amino acid sequence set forth in any of SEQ ID NOs:17 and 19 (e.g., see FIG. 7).

In some embodiments, the scFv comprises the following sequence:

```
                                       (SEQ ID NO: 17)
EVQLVESGGGLVQPGGSLRLSCAASGFTFSNYAMSWVRQAPGK

GLEWVSTISGSGGTTYYADSVKGRFTISRDNSKNTLYLQMNSL

RVEDTAVYYCAKDWFRSSSPDAFDIWGQTTVTVSAGGGGSGG

GGSGGGGSGAPSYVLTQPPSVSVAPGQTARITCGGNNIGRKIV

HWYQQRPGQAPVLVIYYDTDRPAGIPERFSGSNSGNMATLTIS

TVGAGDEADYYCQVWDTGSDHVVFGGGTKLTVL.
```

In some embodiments, the scFv comprises the following sequence:

```
                                       (SEQ ID NO: 19)
QVQLQESGGGLVKPGGSLRLSCAASGFTFSSYSMNWVRQAPGK

GLEWVSGINTAGDTHYPESVKGRFTISRDNARNSLNLQMNSLR

AEDTAVYYCVRERVEREYSGYDAFDIWGQGTTVTVSAGGGGSG

GGGSGGGGSGAPNFMLTQPHSVSESLGKTVTISCTGSSGSIAR

KFVQWYQQRPGSSPTTVIYENNQRPSGVSDRFSGSIGSSSNSA

SLTISGLKTEDEADYYCQSYDSSNVVFGGGTKVTVL.
```

In some embodiments, a subject protein that specifically binds to PD-L1 (e.g., an scFv) is fused directly or via a linker to an Fc domain (or a fragment thereof) (e.g., an IgG1 Fc, an IgG2 Fc, an IgG3 Fc, an IgG4 Fc, or a fragment thereof) to provide a maxibody. In some cases, the Fc is an IgG1 Fc domain. In some cases, an IgG1 FC domain has the sequence:

```
                                       (SEQ ID NO: 22)
CPPCPAPEFEGGPSVFLFPPKPKDTLMetISRTPEVTCVVVDV

SQEDPEVQFNWYVDGVEVHNAKTKPREEQFQSTYRVVSVLTVL

HQDWLNGKEYKCKVSNKGLPSSIEKTISKAKGQPREPQVYTLP

PSQEEMetTKNQVSLTCLVKGFYPSDIAVEWESNGQPENNYKT

TPPVLDSDGSFFLYSRLTVDKSRWQEGNVFSCSVMetHEALHN

HYTQKSLSLSLGK
```

In some embodiments, the Fc is an IgG4 Fc domain. In some cases, an IgG4 FC domain has the sequence:

```
                                       (SEQ ID NO: 23)
CPPCPAPEFEGGPSVFLFPPKPKDTLMetISRTPEVTCVVVDV

SQEDPEVQFNWYVDGVEVHNAKTKPREEQFQSTYRVVSVLTVL

HQDWLNGKEYKCKVSNKGLPSSIEKTISKAKGQPREPQVYTLP

PSQEEMetTKNQVSLTCLVKGFYPSDIAVEWESNGQPENNYKT

TPPVLDSDGSFFLYSRLTVDKSRWQEGNVFSCSVMetHEALHN

HYTQKSLSLSLGK
```

In some embodiments, a subject protein that specifically binds to PD-L1 is a humanized antibody. In some cases, a subject protein that specifically binds to PD-L1 is an scFv (e.g., as described above) fused to an Fc domain (or a fragment thereof) (e.g., an IgG1 Fc, an IgG2 Fc, an IgG3 Fc, an IgG4 Fc, or a fragment thereof). In some cases, a subject protein that specifically binds to PD-L1 includes an amino acid sequence having 80% or more sequence identity (e.g., 85% or more, 90% or more, 95% or more, 98% or more, 99% or more, or 100% sequence identity) with the amino acid sequence set forth in any one of SEQ ID NOs:18 and 20 (e.g., see FIG. 7).

In some embodiments, the subject protein that specifically binds to PD-L1 comprises:

```
                                       (SEQ ID NO: 18)
MGSTAILALLLAVLQGVSAEVQLVESGGGLVQPGGSLRLSCAAS

GFTFSNYAMSWVRQAPGKGLEWVSTISGSGGTTYYADSVKGRFT

ISRDNSKNTLYLQMNSLRVEDTAVYYCAKDWFRSSSPDAFDIWG

QGTTVTVSAGGGGSGGGGSGGGGSGAPSYVLTQPPSVSVAPGQT

ARITCGGNNIGRKIVHWYQQRPGQAPVLVIYYDTDRPAGIPERF

SGSNSGNMATLTISTVGAGDEADYYCQVWDTGSDHVVFGGGTKL

TVLGPRANFVYKSGPRPKSCDKTHTCPPCPAPELLGGPSVFLFP

PKPKDTLMISRTPEVTCVVVDVSHEDPEVKFNWYVDGVEVHNAK

TKPREEQYNSTYRVVSVLTVLHQDWLNGKEYKCKVSNKALPAPI

EKTISKAKGQPREPQVYTLPPSREEMTKNQVSLTCLVKGFYPSD

IAVEWESNGQPENNYKTTPPVLDSDGSFFLYSKLTVDKSRWQQG

NVFSCSVMHEALHNHYTQKSLSLSPGK.
```

In some embodiments, the subject protein that specifically binds to PD-L1 comprises:

```
                                       (SEQ ID NO: 20)
MGSTAILALLLAVLQGVSAQVQLQESGGGLVKPGGSLRLSCAAS

GFTFSSYSMNWVRQAPGKGLEWVSGINTAGDTHYPESVKGRFTI
```

-continued

SRDNARNSLNLQMNSLRAEDTAVYYCVRERVEREYSGYDAFDIW

GQGTTVTVSAGGGGSGGGGSGGGGSGAPNFMLTQPHSVSESLGK

TVTISCTGSSGSIARKFVQWYQQRPGSSPTTVIYENNQRPSGVS

DRFSGSIGSSSNSASLTISGLKTEDEADYYCQSYDSSNVVFGGG

TKVTVLGPRANFVYKSGPRPKSCDKTHTCPPCPAPELLGGPSVF

LFPPKPKDTLMISRTPEVTCVVVDVSHEDPEVKFNWYVDGVEVH

NAKTKPREEQYNSTYRVVSVLTVLHQDWLNGKEYKCKVSNKALP

APIEKTISKAKGQPREPQVYTLPPSREEMTKNQVSLTCLVKGFY

PSDIAVEWESNGQPENNYKTTPPVLDSDGSFFLYSKLTVDKSRW

QQGNVFSCSVMHEALHNHYTQKSLSLSPGK.

A subject PD-L1 binding protein (e.g., an scFV) can be fused to a fusion partner. Examples of fusion partners for a subject PD-L1 binding protein (e.g., scFV) include but are not limited to: (a) a ligand for an NK activation receptor (e.g., ectodomain ULBP1), (b) the Fc domain of any human immunoglobulin (e.g. IgG4 or IgG1) and their variants (e.g. monomeric hinge mutant, FcR binding mutant), (c) a self-dimerizing protein (e.g., leucine zipper protein), (d) human CD4 domains 3 and 4 (3/4), and (e) the Carboxy-Terminal Peptide (CTP) of Human Chorionic Gonadotropin (hCG).

Example sequences of the above fusion partners are as follows, and include sel-dimerizing leucine zipper proteins, human CD4 domains 3 and 4 (3/4), and Carboxy-Terminal Peptide (CTP) of Human Chorionic Gonadotropin (hCG).

In some embodiments, the self-dimerizing leucine zipper protein comprises:

(SEQ ID NO: 24)
RSGSSRMetKQIEDKIEEILSKIYHIENEIARIKKLIGERGTSSRG

In some embodiments, the human CD4 domains 3 and 4 (3/4) comprises (SEQ ID NO: 25)
ASSIVYKKEGEQVEFSFPLAFTVEKLTGSGELWWQAERASSSKS WITFDLKNKEVSVKRVTQDPKLQMetGKKLPLHLTLPQALPQYA GSGNLTLALEAKTGKLHQEVNLVVMetRATQLQKNLTCEVWGPT SPKLMetLSLKLENKEAKVSKREKAVWVLNPEAGMetWQCLLSD

SGQVLLESNIKVL

In some embodiments, the Carboxy-Terminal Peptide (CTP) of Human Chorionic Gonadotropin (hCG) comprises:

(SEQ ID NO: 26)
SSSSKAPPPSLPSPSRLPGPSDTPILPQ

PD-L1 Binding Protein Properties & Co-Compositions

In some embodiments, the compositions and methods described include a PD-1 inhibitor that binds human PD-1 with a $K_D$ of about 100 pM or lower, binds human PD-1 with a $K_D$ of about 90 pM or lower, binds human PD-1 with a $K_D$ of about 80 pM or lower, binds human PD-1 with a $K_D$ of about 70 pM or lower, binds human PD-1 with a $K_D$ of about 60 pM or lower, binds human PD-1 with a $K_D$ of about 50 pM or lower, binds human PD-1 with a $K_D$ of about 40 pM or lower, binds human PD-1 with a $K_D$ of about 30 pM or lower, binds human PD-1 with a $K_D$ of about 20 pM or lower, binds human PD-1 with a $K_D$ of about 10 pM or lower, or binds human PD-1 with a $K_D$ of about 1 pM or lower.

In some embodiments, the compositions and methods described include a PD-1 inhibitor that binds to human PD-1 with a $k_{assoc}$ of about $7.5 \times 10^5$ 1/M·s or faster, binds to human PD-1 with a $k_{assoc}$ of about $7.5 \times 10^5$ 1/M·s or faster, binds to human PD-1 with a $k_{assoc}$ of about $8 \times 10^5$ 1/M·s or faster, binds to human PD-1 with a $k_{assoc}$ of about $8.5 \times 10^5$ 1/M·s or faster, binds to human PD-1 with a $k_{assoc}$ of about $9 \times 10^5$ 1/M·s or faster, binds to human PD-1 with a $k_{assoc}$ of about $9.5 \times 10^5$ 1/M·s or faster, or binds to human PD-1 with a $k_{assoc}$ of about $1 \times 10^6$ 1/M·s or faster.

In some embodiments, the compositions and methods described include a PD-1 inhibitor that binds to human PD-1 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower or binds to human PD-1 with a $k_{dissoc}$ of about $2.7 \times 10^{-5}$ 1/s or slower, binds to human PD-1 with a $k_{dissoc}$ of about $2.8 \times 10^{-5}$ 1/s or slower, binds to human PD-1 with a $k_{dissoc}$ of about $2.9 \times 10^{-5}$ 1/s or slower, or binds to human PD-1 with a $k_{dissoc}$ of about $3 \times 10^{-5}$ 1/s or slower.

In some embodiments, the compositions and methods described include a PD-1 inhibitor that blocks or inhibits binding of human PD-L1 or human PD-L2 to human PD-1 with an $IC_{50}$ of about 10 nM or lower, blocks or inhibits binding of human PD-L1 or human PD-L2 to human PD-1 with an $IC_{50}$ of about 9 nM or lower, blocks or inhibits binding of human PD-L1 or human PD-L2 to human PD-1 with an $IC_{50}$ of about 8 nM or lower, blocks or inhibits binding of human PD-L1 or human PD-L2 to human PD-1 with an $IC_{50}$ of about 7 nM or lower, blocks or inhibits binding of human PD-L1 or human PD-L2 to human PD-1 with an $IC_{50}$ of about 6 nM or lower, blocks or inhibits binding of human PD-L1 or human PD-L2 to human PD-1 with an $IC_{50}$ of about 5 nM or lower, blocks or inhibits binding of human PD-L1 or human PD-L2 to human PD-1 with an $IC_{50}$ of about 4 nM or lower, blocks or inhibits binding of human PD-L1 or human PD-L2 to human PD-1 with an $IC_{50}$ of about 3 nM or lower, blocks or inhibits binding of human PD-L1 or human PD-L2 to human PD-1 with an $IC_{50}$ of about 2 nM or lower, or blocks or inhibits binding of human PD-L1 or human PD-L2 to human PD-1 with an $IC_{50}$ of about 1 nM or lower.

In some embodiments, the PD-L1 binding protein is a PD-L1 antibody. In some embodiments, the PD-L1 antibody is a high affinity antibody. In some embodiments, the PD-L1 antibody is a human PD-L1 antibody. In some embodiments, the PD-L1 antibody is a murine antibody, a chimeric antibody, or humanized antibody. In some embodiments, the PD-L1 antibody is a monoclonal antibody. In some embodiments, the PD-L1 antibody binds to human PD-1 with a $K_D$ of $5 \times 10^{-8}$ M or less, binds to human PD-1 with a $K_D$ of $1 \times 10^{-8}$ M or less, binds to human PD-1 with a $K_D$ of $5 \times 10^{-9}$ M or less, or binds to human PD-1 with a $K_D$ of between $1 \times 10^{-8}$ M and $1 \times 10^{-10}$ M. In some embodiments, the PD-L1 antibody binds to human PD-1 with a KD of $1 \times 10^{-7}$ M or less.

Nucleic Acids Encoding a Subject Protein
Nucleic Acids and Vectors

Figure 16A:
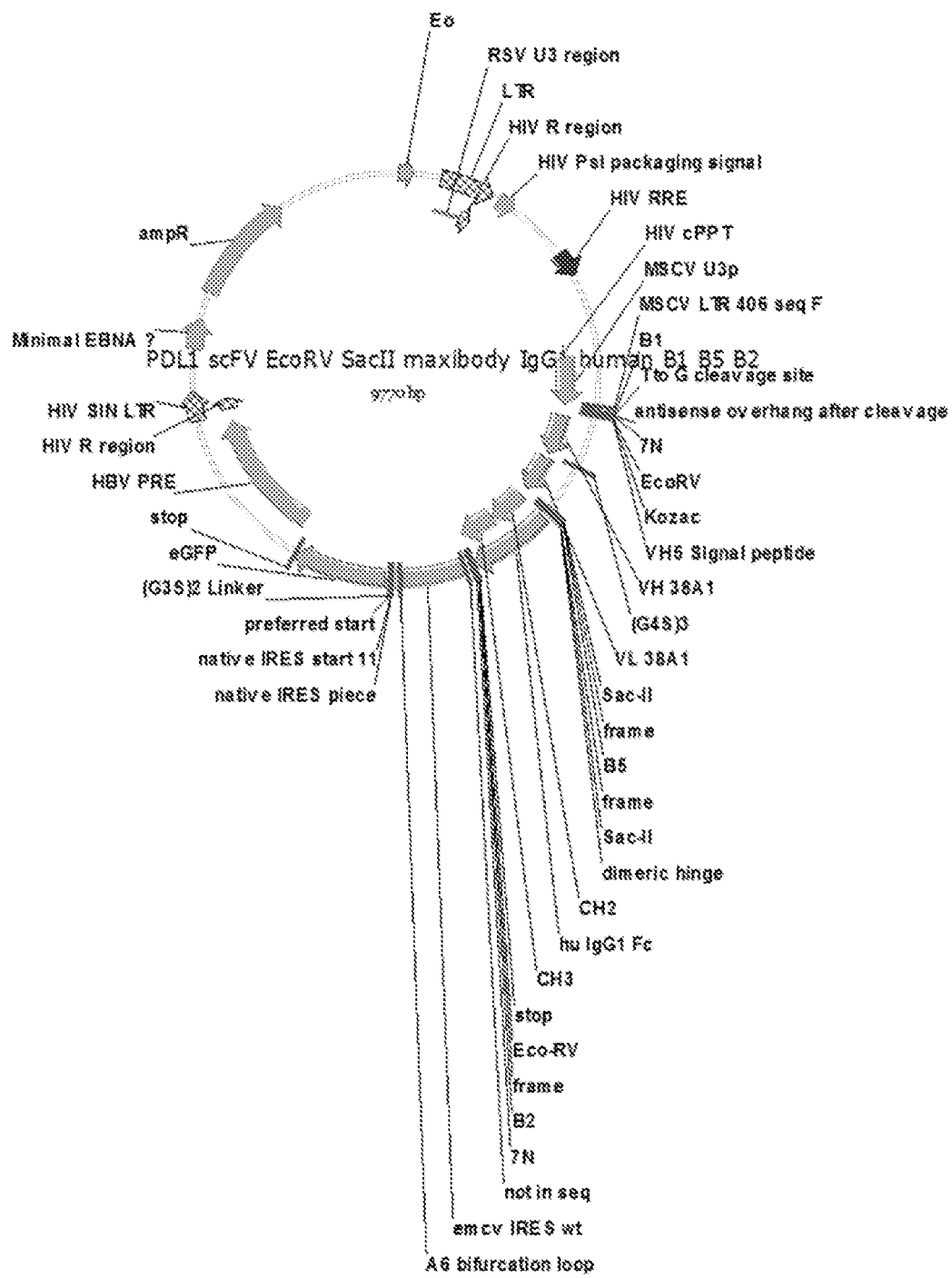
FIG. 16 provides the vector maps for pLV4301G PDLV scFV 38A1 (A) and pLV4301G PDLV scFV 19H9 (B).
Figure 16B:
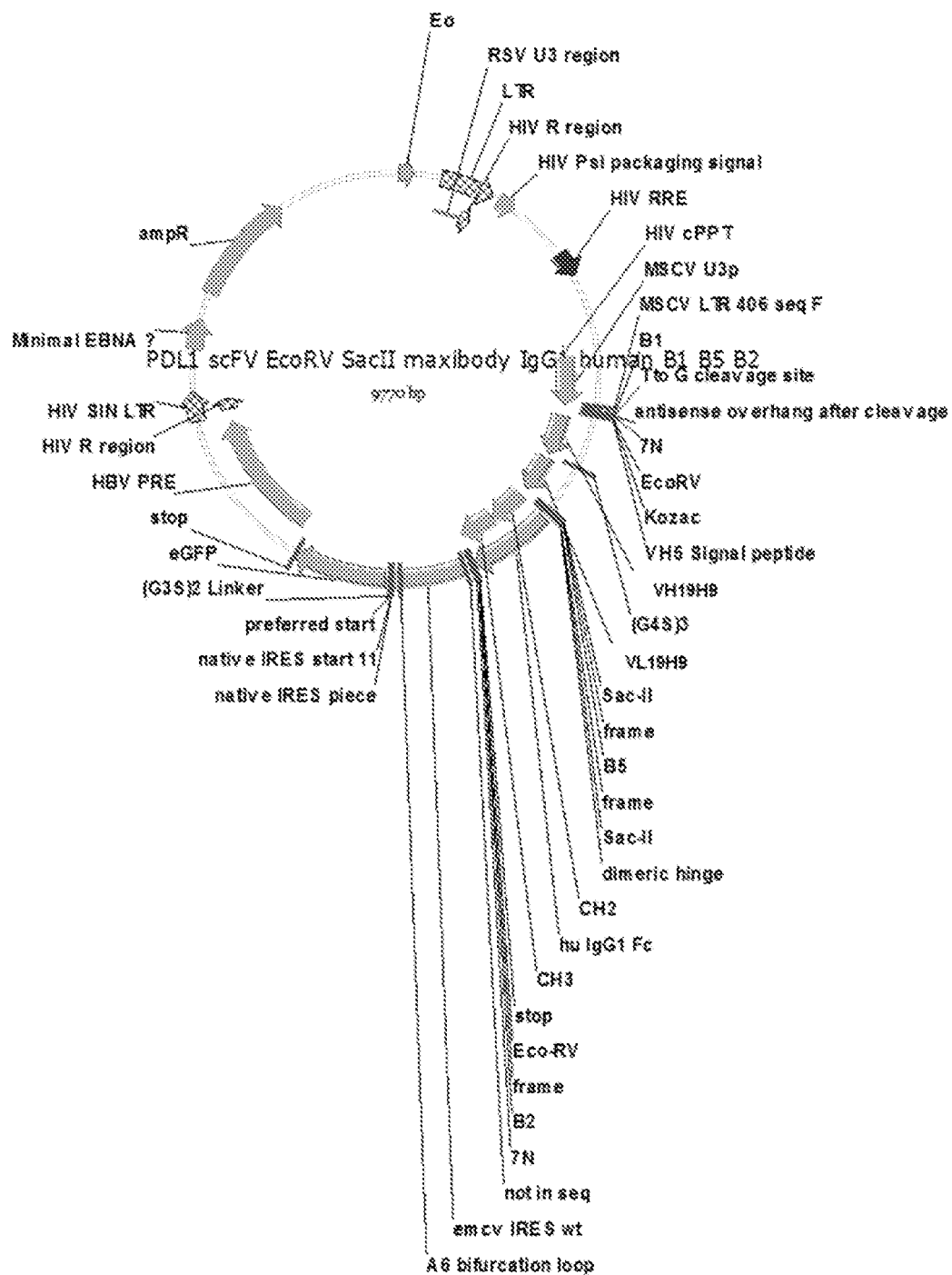

Provided are nucleic acids that encode a subject protein (that specifically binds to PD-L1). A subject protein can be encoded by one or more nucleic acids. For example, in cases where the first and second polypeptides of the antigen binding portion are separate polypeptides (i.e., are not fused to one another), the first and second polypeptides can be encoded on the same or on different nucleic acids. In some embodiments, the one or more nucleic acids that encode a subject PD-L1 binding protein (e.g., antibody, scFv, a maxibody, etc.) are included in an expression vector. In some embodiments, the first and second polypeptides are encoded on the same vector. In some embodiments, the first and second polypeptides are encoded on different vectors. In some embodiments, the first polypeptide is encoded on a first vector. In some embodiments, the second polypeptide is encoded on a second vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the viral vector encodes the PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression vector may be provided to a cell (e.g., introduced into a cell) in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to the desired cells.

The present disclosure also provides expression vectors in which a nucleic acid construct of the present disclosure is inserted. In some embodiments, an inducible expression system may be utilized. Where inducible expression is desired, a number of vectors facilitating such inducible expression are available, including, but not limited to, tetracycline- and tetracycline analogue-inducible vectors, tamoxifen-inducible vectors, as well as other inducible transcription system vectors known in the art.

The nucleic acid construct can be operably linked to control elements directing the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, can also be used. Such promoter sequences are commercially available from, e.g., Stratagene (San Diego, Calif.).

In some embodiments, a cell type-specific or a tissue-specific promoter can be operably linked to nucleic acid insert encoding the heterologous gene product, and allowing for selectively or preferentially producing a gene product in a particular cell type(s) or tissue(s), for example expression in cytotoxic lymphocytes. In some embodiments, an inducible promoter can be operably linked to the heterologous nucleic acid.

The vectors disclosed herein can also include conventional control elements operably linked to the nucleic acid insert (also referred to as a heterologous nucleotide sequence) in a manner permitting transcription, translation and/or expression in a cell transfected with the vector produced according to the present invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters selected from native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), murine cell virus (MSCV) promoter, the cytomegalovirus (CMV) promoter (optionally with the CMV enhancer) (see, e.g., Boshart et al., Cell, 41:521-530 (1985)), the SV40 promoter, the dihydrofolate reductase promoter, the beta-actin promoter, the phosphoglycerol kinase (PGK) promoter, and the EF1 promoter (Invitrogen). Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clonetech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., (1996) *Proc. Natl. Acad. Sci. USA,* 93:3346-3351), the tetracycline-repressible system (Gossen et al., (1992) *Proc. Natl. Acad. Sci. USA,* 89:5547-5551), the tetracycline-inducible system (Gossen et al., (1995) *Science,* 268:1766-1769, see also Harvey et al., (1998) *Curr. Opin. Chem. Biol.,* 2:512-518), the RU486-inducible system (Wang et al., (1997) *Nat. Biotech.,* 15:239-243 and Wang et al., (1997) *Gene Ther.,* 4:432-441) and the rapamycin-inducible system (Magari et al., (1997) *J. Clin. Invest.,* 100:2865-2872). Other types of inducible promoters useful in this context are those regulated by a specific physiological state, e.g., temperature, acute phase, a particular differentiation state of the cell, or in replicating cells only. In some embodiments, a lentiviral vector containing a murine cell virus (MSCV) promoter or a human elongation factor-1 alpha (EF-1 alpha) promoter is utilized to express a nucleic acid encoding a subject PD-L1 binding protein as described herein, e.g., in connection with any embodiment described herein.

In another embodiment, the native promoter for the nucleic acid insert will be used. The native promoter may be preferred when it is desired that expression of the nucleic acid insert should mimic the native expression. The native promoter may be used when expression of the nucleic acid insert must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the nucleic acid includes a gene operably linked to a tissue-specific promoter. For instance, if expression in T-cells and/or cytotoxic lymphocytes is desired, a promoter active in T-cells and/or cytotoxic lymphocytes should be employed.

In various embodiments, the vector carrying one or more nucleic acid inserts also include selectable markers or reporter genes, e.g., sequences encoding geneticin, hygromycin or puromycin resistance, among others. Selectable reporters or marker genes can be used to signal the presence of the plasmids/vectors in bacterial cells, including, for example, examining ampicillin resistance. Other components of the plasmid may include an origin of replication. Selection of these and other promoters and vector elements are conventional and many such sequences are available (see, e.g., Sambrook et al., and references cited therein).

In some cases, a subject nucleic acid includes a promoter that is operably linked to the nucleotide sequence encoding the subject PD-L1 binding protein. Suitable promoters include constitutive promoters (e.g., CMV promoter, EF1alpha promoter, MSCV, and the like) as well as inducible promoters (e.g., Tetracycline- and tetracycline analogue-inducible promoters, tamoxifen-inducible promoters and the like) and conditional promoters such as the NR4A1 promoter. In some embodiments, the vector comprises transposons.

In some embodiments, the vector is pLEV having a nucleotide sequence as provided in FIG. 10. In some embodiments, the pLEV vector containing the PD-L1 binding protein is provided in FIG. 11. In some embodiments, the vector is SEQ ID NO:41 (FIG. 11A). In some embodiments, the vector is SEQ ID NO:42 (FIG. 11B). In some embodiments, the vector is vector shown in FIG. 16A. In some embodiments, the vector is shown in FIG. 16B.

In some embodiments, the vector is a retroviral vector, such as a gammaretroviral vector.

In some cases, a subject nucleic acid encoding a PD-L1 binding protein is included in a plasmid, e.g., for transient expression in a eukaryotic cell, for genomic integration of an expression cassette (which includes the nucleotide sequence encoding the PD-L1 binding protein operably linked to a promoter) in a eukaryotic cell, for propagation in a bacterial cell, and the like.

Cells

The present disclosure provides cells that include a subject protein that specifically binds to PD-L1, and/or include a nucleic acid (e.g., as discussed above) encoding the protein. For cells that include a nucleic acid encoding a subject protein that specifically binds to PD-L1, the nucleic acid can be maintained episomally (e.g., can be a plasmid), or the nucleic acid can be integrated into the genome. In some embodiments, the first and second polypeptides are encoded on the same nucleic acid. In some embodiments, the first and second polypeptides are encoded on different nucleic acids. In some embodiments, the first polypeptide is encoded on a nucleic acid. In some embodiments, the second polypeptide is encoded on a nucleic acid. In some embodiments, the nucleic acid is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments the nucleic acid encodes a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Cells can be any convenient-cell type. For example, in some cases, a subject-cell is a prokaryotic cell. For example, the can be an *E. coli* cell used for propagating a nucleic acid (e.g., a plasmid) that encodes a subject protein. In some cases, the cell is a eukaryotic cell (e.g., a mammalian cell, a rat-cell, a mouse cell, a human cell). In some cases, the cell is a cytotoxic lymphocyte. In some embodiments, the cell is a cytotoxic lymphocyte and can be referred to as a cytotoxic lymphocyte that is genetically modified to express and secrete a soluble Programmed Death 1 Ligand (PD-L1) binding protein. In such cases, the term "genetically modified" encompasses scenarios in which the nucleic acid is maintained episomally as well as scenarios in which the nucleic acid is integrated into the cell's genome. In some cases, the cell is a cytotoxic lymphocyte that is genetically modified to express and secrete a soluble Programmed Death 1 Ligand (PD-L1) binding protein, where the genetic modification is a genome modification (i.e., a nucleic acid encoding a subject protein is integrated into the genome of the cell.

Cytotoxic lymphocytes which may be genetically modified to express and secrete a subject PD-L1 binding protein as described herein, e.g., in connection with any embodiment described herein, include cytotoxic T (CTL) cells, natural killer T (NKT) cells and natural killer (NK) cells. Cytotoxic lymphocytes can include, for example, peripheral blood-derived αβ TCR-positive or γδ TCR-positive T-cells activated by tumor associated antigens and/or transduced with tumor specific chimeric antigen receptors or T-cell receptors, and tumor-infiltrating lymphocytes (TILs). In some embodiments, the cytotoxic lymphocyte has been modified to express and secrete a subject PD-L1 binding protein selected from the group consisting of 38A1 and 19H9. In some embodiments, the cytotoxic lymphocyte has been modified to express and secrete 38A1. In some embodiments, the cytotoxic lymphocyte has been modified to express and secrete 19H9.

In some embodiments, a cytotoxic T-cell according to the present disclosure is a $CD8^+$ T-cell. In some embodiments, a cytotoxic T-cell according to the present disclosure is a $CD4^+$ T-helper cell. In some embodiments, a cytotoxic T-cell according to the present disclosure is a $CD8^+$ T-cell modified to express and secrete a subject PD-L1 binding protein as described herein. In some embodiments, a cytotoxic T-cell according to the present disclosure is a $CD4^+$ T-helper cell modified to express and secrete a subject PD-L1 binding protein as described herein. In some embodiments, a cytotoxic T-cell according to the present disclosure is a CD8⁺ T-cell modified to express and secrete 38A1. In some embodiments, a cytotoxic T-cell according to the present disclosure is a CD4⁺ T-helper cell modified to express and secrete 19H9. In some embodiments, a cytotoxic T-cell according to the present disclosure is a CD8⁺ T-cell modified to express and secrete a PD-L1 binding protein. In some embodiments, a cytotoxic T-cell according to the present disclosure is a CD4⁺ T-helper cell modified to express and secrete a PD-L1 binding protein. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

A cytotoxic lymphocyte which may be genetically modified to express and secrete a subject PD-L1 binding protein as described herein, e.g., in connection with any embodiment described herein, may express one or more activation antigens. For example, a cytotoxic lymphocyte according to the present disclosure may exhibit an increased level of expression of one or more activation antigens relative to a naïve T-cell. The one or more activation antigens may be selected from, e.g., CD25, CD26, CD27, CD28, CD38, CD40L, CD69, CD134, CD137, BTLA, PD-1, HVEM, LIGHT, and HLA-DR. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, a cytotoxic lymphocyte which may be genetically modified to express and secrete a subject PD-L1 binding protein as described herein, e.g., in connection with any embodiment described herein, includes or is genetically modified to include a receptor specific for a tumor associated antigen, e.g., a tumor associated antigen from a tumor of a subject to be treated with a genetically modified cytotoxic lymphocyte according to the present disclosure. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

A cytotoxic lymphocyte which may be genetically modified to express and secrete a subject PD-L1 binding protein as described herein, e.g., in connection with any embodiment described herein, may be obtained from any suitable tissue or fluid of a subject. For example, in some embodiments a cytotoxic lymphocyte may be obtained from peripheral blood of a subject. In some embodiments, a cytotoxic lymphocyte which may be genetically modified to express and secrete a subject PD-L1 binding protein as described herein, e.g., in connection with any embodiment described herein, is a TIL derived from a tumor of a subject. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Detectable Labels

In some embodiments, a subject protein that specifically binds to PD-L1 (i.e. a subject PD-L1 binding protein) as described herein, e.g., in connection with any embodiment described herein, includes one or more detectable labels. A variety of suitable detectable labels are known in the art including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range. Examples of detectable labels suitable for use as components of subject PD-L1 binding proteins include affinity tags and fluorescent proteins (e.g., GFP, YFP, RFP, CFP, and the like). In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

The term "affinity tag" is used herein to denote a peptide segment, e.g., a heterologous peptide segment that can be incorporated into a subject PD-L1 binding protein and detected using a molecule that binds the affinity tag and provides a detectable signal (e.g., a fluorescent compound or protein). In principal, any peptide or protein for which an antibody or other specific binding agent is available can be used as an affinity tag. Examples of affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.). In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Any fluorescent polypeptide (also referred to herein as a fluorescent label) well known in the art is suitable for use as a detectable label directly or in connection with an affinity tag. A suitable fluorescent polypeptide will be one that can be expressed in a desired hosT-cell, such as a bacterial cell or a mammalian cell, and will readily provide a detectable signal that can be assessed qualitatively (positive/negative) and quantitatively (e.g., comparative degree of fluorescence). Examples of fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Biotin-based labels may also find use in the subject PD-L1 binding proteins disclosed herein. Biotinylation of molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Methods

Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods.

In some embodiments, TILs and/or cytotoxic lymphocytes may be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

In some embodiments, an effective dosage of TILs and/or cytotoxic lymphocytes is about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, about $1\times10^8$, about $2\times10^8$, about $3\times10^8$, about $4\times10^8$, about $5\times10^8$, about $6\times10^8$, about $7\times10^8$, about $8\times10^8$, about $9\times10^8$, about $1\times10^9$, about $2\times10^9$, about $3\times10^9$, about $4\times10^9$, about $5\times10^9$, about $6\times10^9$, about $7\times10^9$, about $8\times10^9$, about $9\times10^9$, about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, about $5\times10^{11}$, about $6\times10^{11}$, about $7\times10^{11}$, about $8\times10^{11}$, about $9\times10^{11}$, about $1\times10^{12}$, about $2\times10^{12}$, about $3\times10^{12}$, about $4\times10^{12}$, about $5\times10^{12}$, about $6\times10^{12}$, about $7\times10^{12}$, about $8\times10^{12}$, about $9\times10^{12}$, about $1\times10^{13}$, about $2\times10^{13}$, about $3\times10^{13}$, about $4\times10^{13}$, about $5\times10^{13}$, about $6\times10^{13}$, about $7\times10^{13}$, about $8\times10^{13}$, and about $9\times10^{13}$. In some embodiments, an effective dosage of TILs and/or cytotoxic lymphocytes is in the range of about $1\times10^6$ to about $5\times10^6$, about $5\times10^6$ to about $1\times10^7$, about $1\times10^7$ to about $5\times10^7$, about $5\times10^7$ to about $1\times10^8$, about $1\times10^8$ to about $5\times10^8$, about $5\times10^8$ to about $1\times10^9$, about $1\times10^9$ to about $5\times10^9$, about $5\times10^9$ to about $1\times10^{10}$, about $1\times10^{10}$ to about $5\times10^{10}$, about $5\times10^{10}$ to about $1\times10^{11}$, about $5\times10^{11}$ to about $1\times10^{12}$, about $1\times10^{12}$ to about $5\times10^{12}$, and about $5\times10^{12}$ to about $1\times10^{13}$. In some embodiments, the TIL and/or cytotoxic lymphocytes are genetically modified to express and secrete 19H9 or 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete 19H9 from pLV4301G PDLV scFV 19H9 (SEQ ID NO:38; FIG. 11B, FIG. 16B). In some embodiments, the TIL and/or cytotoxic lymphocytes are genetically modified to express and secrete 38A1 from pLV4301G PDLV scFV 38A1 (SEQ ID NO:37; FIG. 11A, FIG. 16A). In some embodiments, the TIL and/or cytotoxic lymphocytes are genetically modified to express and secrete a PD-L1 binding protein. In some embodiments, the TIL and/or cytotoxic lymphocytes are genetically modified with a lentiviral vector to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector or nucleic acid. In some embodiments, the heavy and light chains are encoded on different vectors or nucleic acids. In some embodiments, the heavy chain is encoded on a first vector or nucleic acid. In some embodiments, the light chain is encoded on a second vector or nucleic acid. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Contacting Cells with a Subject Protein

Provided are methods of reducing the interaction between PD-L1 on a first-cell (e.g., a cancer cell such as a tumor cell) and PD-1 on another cell (e.g., an immune cell such as a T-cell). Such methods can include contacting PD-L1 on the first-cell with a subject PD-L1 binding protein (e.g., anti-PD-L1 antibody, anti-PD-L1 scFV, anti-PD-L1 maxibody, etc.). Any amount of reduction can be useful in some cases (depending on context). In some cases, the interaction between PD-L1 and PD-1 is reduced by 10% or more (e.g., 20% or more, 30% or more, 50% or more, 60% or more, 75% or more, 80% or more, 85% or more, 90% or more, 95% or more, or 100%). In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Any convenient assay can be used to measure the amount of reduction and such assays will be known to one of ordinary skill in the art. Examples of assays for measuring the amount of reduction (e.g., where the assays can be performed in the presence versus absence of a subject PD-L1 binding protein such as an anti-PD-L1 antibody, anti-PD-L1 scFV, anti-PD-L1 maxibody, and the like) can include but are not limited to: measuring the inhibition of cytokine production in mixed lymphocyte reaction assays (MLR assays, e.g., allo MLR assays), measuring interactions between tumor infiltrating lymphocytes (TILs) and a homologous tumor, measuring cytotoxicity (e.g., cytotoxicity assays such as assays to measure cytotoxic T-cell activity toward a PD-L1 expressing cell such as a cancer cell), measuring NFkB translocation to the nucleus, and measuring signaling activity/output of the PI3K/AKT/mTOR signaling pathway (e.g., see Wang et. al., Cancer Immunol Res. 2014 September; 2(9):846-56).

The contacting can take place in vitro (e.g., cells in culture). In some cases, the contacting is in vivo. For example, in some cases, the contacting includes administering a subject PD-L1 binding protein to an individual. In such cases, the method can be considered to be a method of treatment (for an individual who has cancer, for an individual who has a solid tumor, for an individual who has a chronic infection (e.g., a chronic viral infection), and the like). In some cases, contacting includes introducing into a cell (e.g., the cell expressing PD-L1, the cell expressing PD-1, or a third cell) a nucleic acid encoding a subject PD-L1 binding protein, and the cell into which the nucleic acid is introduced produces and secretes the PD-L1 binding protein. In cases where the nucleic acid is introduced into a third cell, the third cell can then be used to provide the PD-L1 binding protein via secretion. In some embodiments, where the nucleic acid is introduced into a third cell, the third cell can then be used to provide to the individual or subject in need thereof the PD-L1 binding protein via secretion. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Therapeutic formulations comprising one or more PD-L1 binding proteins of the disclosure can be prepared for storage by mixing the PD-L1 binding protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. PD-L1 binding protein composition can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the PD-L1 binding protein to be administered can be governed by such considerations, and is the minimum amount necessary to treat the patient's disease (e.g., cancer, chronic infection). In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

The therapeutic dose may be at least 0.01 mg/kg body weight, at least 0.05 mg/kg body weight; at least 0.1 mg/kg body weight, at least 0.5 mg/kg body weight, at least 1 mg/kg body weight, at least 2 mg/kg body weight, at least 2.5 mg/kg body weight, at least 5 mg/kg body weight, at least 7.5 mg/kg body weight, at least 10 mg/kg body weight, at least 15 mg/kg body weight, at least 20 mg/kg body weight, at least 25 mg/kg body weight, at least 30 mg/kg body weight, at least 35 mg/kg body weight, at least 40 mg/kg body weight, at least 45 mg/kg body weight, at least 50 mg/kg body weight, at least 55 mg/kg body weight, at least 60 mg/kg body weight, at least 65 mg/kg body weight, at least 70 mg/kg body weight, at least 75 mg/kg body weight, at least 80 mg/kg body weight, at least 85 mg/kg body weight, at least 90 mg/kg body weight, at least 95 mg/kg body weight, at least 100 mg/kg body weight, at least 110 mg/kg body weight, at least 120 mg/kg body weight, at least 130 mg/kg body weight, at least 140 mg/kg body weight, at least 150 mg/kg body weight, at least 160 mg/kg body weight, at least 170 mg/kg body weight, at least 180 mg/kg body weight, at least 190 mg/kg body weight, at least 200 mg/kg body weight, at least 210 mg/kg body weight, at least 220 mg/kg body weight, at least 230 mg/kg body weight, at least 240 mg/kg body weight, at least 250 mg/kg body weight, at least 260 mg/kg body weight, at least 270 mg/kg body weight, at least 280 mg/kg body weight, at least 290 mg/kg body weight, at least 300 mg/kg body weight, at least 310 mg/kg body weight, at least 320 mg/kg body weight, at least 330 mg/kg body weight, at least 340 mg/kg body weight, at least 350 mg/kg body weight, at least 360 mg/kg body weight, at least 370 mg/kg body weight, at least 380 mg/kg body weight, at least 390 mg/kg body weight, at least 400 mg/kg body weight, at least 410 mg/kg body weight, at least 420 mg/kg body weight, at least 430 mg/kg body weight, at least 440 mg/kg body weight, at least 450 mg/kg body weight, at least 460 mg/kg body weight, at least 470 mg/kg body weight, at least 480 mg/kg body weight, at least 490 mg/kg body weight, and at least 500 mg/kg body weight. In some embodiments, the dosage is not more than 500 mg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like. In some embodiments, the antibody administered is 19H9 or 38A1, or a combination thereof. In some embodiments, the antibody administered is 19H9. In some embodiments, a PD-L1 binding protein is administered. In some embodiments, the PD-L1 binding protein comprises an antigen binding portion. In some embodiments, the antibody administered is 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

The PD-L1 binding protein need not be, but is optionally formulated with one or more agents that potentiate activity, or that otherwise increase the therapeutic effect. These are generally used in the same dosages and with administration routes as used hereinbefore or about from 1 to 99% of the heretofore employed dosages. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR- L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration can be sterile. This is readily accomplished by filtration through sterile filtration membranes.

The PD-L1 binding protein (e.g., anti-PD-L1 antibody, anti-PD-L1 maxibody, anti-PD-L1 scFV, and the like) can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the PD-L1 binding protein (e.g., anti-PD-L1 antibody, anti-PD-L1 maxibody, anti-PD-L1 scFV, and the like) is suitably administered by pulse infusion, particularly with declining doses of the binding protein. In some cases, a subject PD-L1 binding protein is administered systemically (e.g., i.v.). In some cases, a subject PD-L1 binding protein is administered locally (e.g., intratumorally, e.g., via injection). In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

For the prevention or treatment of disease, the appropriate dosage of PD-L1 binding protein can depend on the type of disease to be treated, as defined above, the severity and course of the disease, whether the PD-L1 binding protein is administered for preventive purposes, previous therapy, the patient's clinical history and response to the PD-L1 binding protein, and the discretion of the attending physician. The PD-L1 binding protein can be administered to the patient at one time or over a series of treatments. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR- H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Methods of Adoptive Cell Transfer with Cytotoxic Lymphocytes Genetically Modified to Express and Secrete a Soluble Programmed Death 1 Ligand (PD-L1) Binding Protein Cytotoxic lymphocytes which express and secrete a subject PD-L1 binding protein as described herein, e.g., in connection with any embodiment described herein, find use in methods of adoptive cell transfer, e.g., in the context of treating cancer or chronic infection.

In some embodiments, suitable methods according to the present disclosure include, for example, isolating cytotoxic lymphocytes as described herein, e.g., in connection with any embodiment described herein, from a subject, e.g., from a tumor or peripheral blood of a subject.

In some embodiments, suitable methods according to the present disclosure include, for example, genetically modifying the cytotoxic lymphocytes by introducing into the cytotoxic lymphocytes a nucleic acid encoding a subject PD-L1 binding protein as described herein, e.g., in connection with any embodiment described herein, wherein the genetically modified cytotoxic lymphocytes express and secrete the subject PD-L1 binding protein as described herein, e.g., in connection with any embodiment described herein. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, suitable methods according to the present disclosure include, for example, expanding the genetically modified cytotoxic lymphocyte to provide a population of genetically modified cytotoxic lymphocytes. In some embodiments, the TIL and/or cytotoxic lymphocytes are genetically modified to express and secrete 19H9 or 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete 19H9 from pLV4301G PDLV scFV 19H9 (SEQ ID NO:38; FIG. 11B, FIG. 16B). In some embodiments, the TIL and/or cytotoxic lymphocytes are genetically modified to express and secrete 38A1 from pLV4301G PDLV scFV 38A1 (SEQ ID NO:37; FIG. 11A, FIG. 16A). In some embodiments, the TIL and/or cytotoxic lymphocytes are genetically modified to express and secrete a PD-L1 binding protein. In some embodiments, the TIL and/or cytotoxic lymphocytes are genetically modified with a lentiviral vector to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector or nucleic acid. In some embodiments, the heavy and light chains are encoded on different vectors or nucleic acids. In some embodiments, the heavy chain is encoded on a first vector or nucleic acid. In some embodiments, the light chain is encoded on a second vector or nucleic acid. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, suitable methods according to the present disclosure include, for example, administering the population of genetically modified cytotoxic lymphocytes to the subject to treat a disease or disorder of the subject, e.g., a cancer or chronic infection. In some embodiments, the TIL and/or cytotoxic lymphocytes are genetically modified to express and secrete 19H9 or 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete 19H9 from pLV4301G PDLV scFV 19H9 (SEQ ID NO:38; FIG. 11B, FIG. 16B). In some embodiments, the TIL and/or cytotoxic lymphocytes are genetically modified to express and secrete 38A1 from pLV4301G PDLV scFV 38A1 (SEQ ID NO:37; FIG. 11A, FIG. 16A). In some embodiments, the TIL and/or cytotoxic lymphocytes are genetically modified to express and secrete a PD-L1 binding protein. In some embodiments, the TIL and/or cytotoxic lymphocytes are genetically modified with a lentiviral vector to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector or nucleic acid. In some embodiments, the heavy and light chains are encoded on different vectors or nucleic acids. In some embodiments, the heavy chain is encoded on a first vector or nucleic acid. In some embodiments, the light chain is encoded on a second vector or nucleic acid. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Isolating Cytotoxic Lymphocytes from a Subject

Many suitable methods are known in the art to isolate cytotoxic lymphocytes from a subject, e.g., a human subject, and any convenient method can be used. For example, tumor infiltrating lymphocytes as described herein, e.g., in connection with any embodiment described herein, may be isolated from fresh patient biopsy specimens. Alternatively, cytotoxic lymphocytes may be obtained from peripheral blood of a subject. While the methods described herein are described primarily in the context of autologous cytotoxic lymphocytes used for ACT. It should be noted that in some embodiments cytotoxic lymphocytes may be obtained or generated from a source other than a subject to be treated, as discussed in further detail below.

Genetically Modifying the Cytotoxic Lymphocytes

Genetically modifying the cytotoxic lymphocytes to express and secrete a subject PD-L1 binding protein as described herein, e.g., in connection with any embodiment described herein, can include introducing into the cytotoxic lymphocytes a nucleic acid encoding a subject PD-L1 binding protein. In some embodiments, the PD-L1 binding protein comprises a first and second polypeptide. In some embodiments, the first and second polypeptides are encoded on the same vector. In some embodiments, the first and second polypeptides are encoded on different vectors. In some embodiments, the first polypeptide is encoded on a first vector. Many ways to accomplish this are known in the art and any convenient method can be used (e.g., using any convenient vector or vector combination, e.g., a retroviral vector, e.g., a lentiviral vector, an adenoviral vector, or other vectors, e.g., together with suitable packaging and envelope plasmids). Regulatory elements for lentiviral vectors, e.g., promoters, may be selected specifically for stable expression in cytotoxic lymphocytes. See, e.g., Jones et al. *Hum Gene Ther.* 2009 June; 20(6): 630-640, describing the use of a lentiviral vector containing a murine cell virus (MSCV) promoter for use with both minimally stimulated and highly activated lymphocytes. In some embodiments, the PD-L1 binding protein encoded by the vector is 38A1 or 19H9. In some embodiments, the PD-L1 binding protein encoded by the vector is 38A1. In some embodiments, the PD-L1 binding protein encoded by the vector is 19H9. In some embodiments the PD-L1 binding protein encoded by the vector comprises an antigen binding portion. In some embodiments the PD-L1 binding protein encoded by the one or more vectors is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein encoded by the one or more vectors is an antibody or fragment thereof comprising a heavy chain and a light chain, wherein said light chain comprises SEQ ID NO:1 and said heavy chain comprises SEQ ID NO:5. In some embodiments the PD-L1 binding protein encoded by the one or more vectors is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein encoded by the one or more vectors is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein encoded by the one or more vectors is an antibody or fragment thereof comprising a heavy chain and a light chain, wherein said light chain comprises SEQ ID NO:9 and said heavy chain comprises SEQ ID NO:13. In some embodiments the PD-L1 binding protein encoded by the one or more vectors is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the subject PD-L1 binding protein gene can be part of a larger gene expression cassette introduced into the cytotoxic lymphocytes that allows for an inducible expression of the subject PD-L1 binding protein, e.g., using a cell membrane permeant drug that activates the promoter elements driving the subject PD-L1 gene. Withdrawal of the drug would shut-down the gene expression allowing for a regulatable on/off subject PD-L1 binding protein expression. A number of vectors facilitating this inducible expression are available, including, but not limited to, tetracycline- and tetracycline analogue-inducible vectors, tamoxifen-inducible vectors, as well as other inducible transcription system vectors known in the art. In some embodiments, the PD-L1 binding protein is 38A1 or 19H9. In some embodiments, the PD-L1 binding protein is 38A1. In some embodiments, the PD-L1 binding protein is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Figure 8:
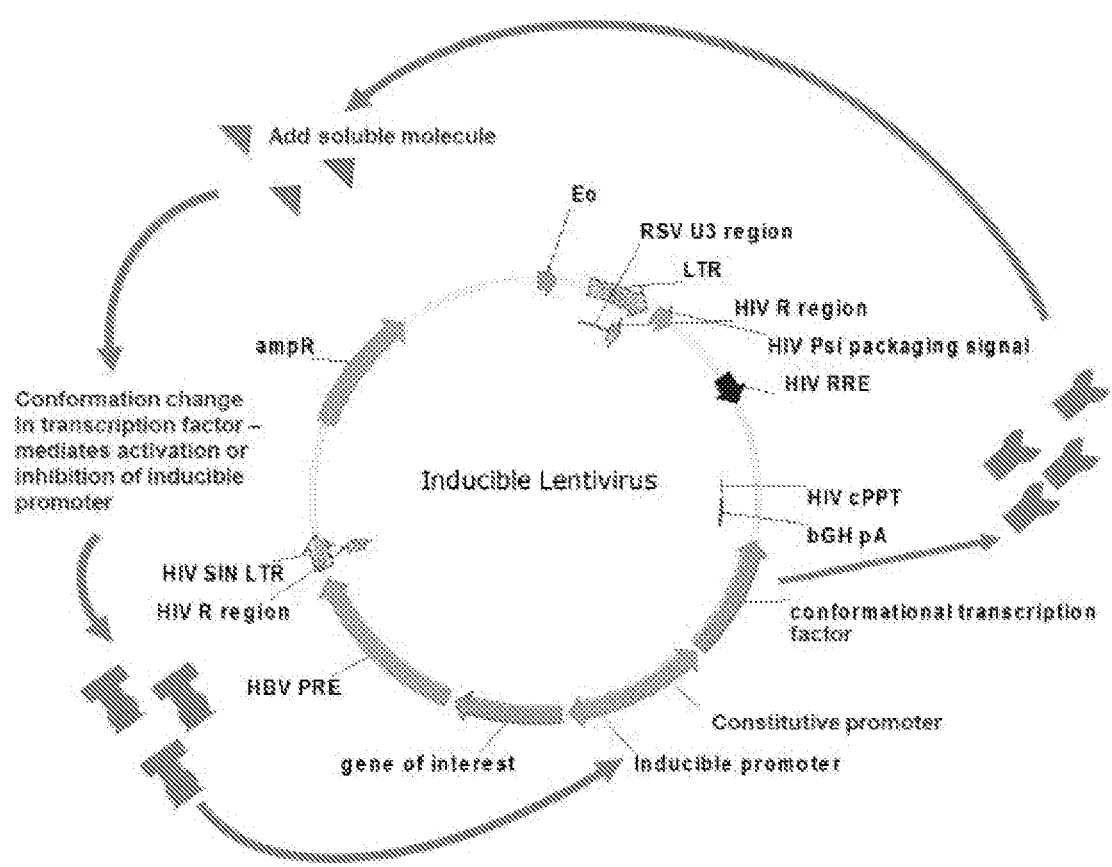
FIG. 8 depicts a schematic of an example of an expression vector (e.g., lentivector) encoding an inducible promoter

A schematic of an example of an expression vector (e.g., lentivector) encoding an inducible promoter is provided in FIG. 8. The basic design includes two promoters. One promoter is constitutively active and drives the transcription of a conformational transcription factor (CTF) which changes conformation upon binding to a soluble molecule (SM). The second promoter binds the CTF and drives the gene of interest. There are two possibilities. In both cases, binding of the CTF to its promoter mediates transcription. In case one, addition of the SM releases the CTF from the inducible promoter, stopping transcription. In the second case, addition of SM induces binding of the CTF to the inducible promoter and initiation of transcription.

Figure 9:
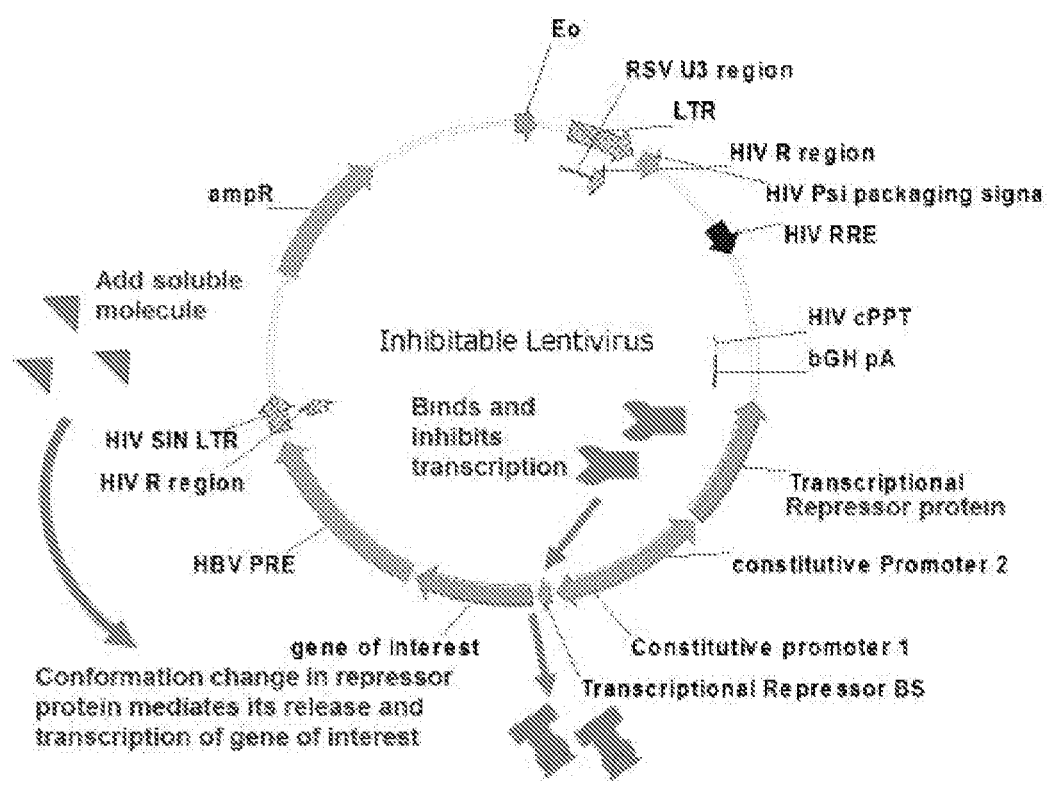
FIG. 9 depicts a schematic of an example of an expression vector (e.g., lentivector) encoding an inducible promoter.

A schematic of another example of an expression vector (e.g., lentivector) is provided in FIG. 9, which depicts schematically an inhibitable expression vector coding for a conformational repressor protein. The basic design includes two promoters. Both promoters are constitutively active. One drives the transcription of a conformational repressor protein (CRP) which changes conformation upon binding to a soluble molecule (SM). The CRP binds to a CRP binding site (CRP-BS) and inhibits transcription of the second constitutive promoter driving transcription of the gene of interest. Addition of the soluble molecule releases the CRP from the CRP-BS "releasing" transcription of the gene of interest.

FIG. 16 provides additional schematics of exemplary viral vectors for use with the present methods, including pLV4301G PDLV scFV 38A1 and pLV4301G PDLV scFV 19H9. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B).

The soluble molecule utilized as described above with the inducible expression vectors can be any suitable molecule known in the art for use with such inducible expression vectors, e.g., tetracycline (or analogs thereof) or tamoxifen. Such soluble molecules may be administered to a subject in accordance with one or more of the methods described herein, e.g., prior to, concurrently with, or subsequent to the administration of genetically modified cytotoxic lymphocytes as described herein, e.g., in connection with any embodiment described herein, to a subject. Alternatively, or in addition, expression vectors may be utilized which include elements responsive to conditions and/or molecules present at a desired site of action in a subject, e.g., a tumor microenvironment. For example, expression vectors including a hypoxia response element may be used to selectively induce expression in the hypoxic microenvironment of a solid tumor. See, e.g., Wang et al. *Cancer Gene Ther.* 2005 March; 12(3):276-83.

Additional transfection methods, which may include viral and non-viral methods, may be utilized as appropriate to introduce nucleic acids encoding subject PD-L1 binding proteins into cytotoxic lymphocytes. Methods which may be utilized to facilitate delivery into cytotoxic lymphocytes can include, e.g., electroporation, particle bombardment (gene gun), sonoporation, magnetofection, hydrodynamic delivery, nanoparticle delivery, lipofection, etc. In some embodiments, the PD-L1 binding protein encoded is 38A1 or 19H9. In some embodiments, the PD-L1 binding protein encoded is 38A1. In some embodiments, the PD-L1 binding protein encoded is 19H9. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein encoded by one or more vectors is an antibody or fragment thereof, wherein the light chain is encoded by a first vector and the heavy chain is encoded by a second vector. In some embodiments the PD-L1 binding protein encoded by one or more vectors is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein encoded by one or more vectors is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein encoded by one or more vectors is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein encoded by one or more vectors is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Viral Production

In some embodiments, the viral vector for transfection is produced using any methods well known in the art. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the viral vector is produced for transfection using a method comprising plating $5\times10^6$ phoenix cells in 10 mm tissue culture plate containing 5 ml cell culture media. In some embodiments, the virus is produced for transfection using a method further comprising transfecting cells with 10 μg pLEV (lentiviral vector) containing anti-PD-1 scFV and 6 μg pVSV-G using lipofectamine. In some embodiments, the virus is produced for transfection using a method further comprising collecting the supernatant and filter with 70 μM strainer into a 15 ml tube after 60 minutes In some embodiments, the virus is produced for transfection using a method comprising the following steps: 1) plating $5\times10^6$ phoenix cells in 10 mm tissue culture plate containing 5 ml cell culture media; 2) transfecting cells with 10 μg pLEV (lentiviral vector) containing anti-PD-1 scFV and 6 μg pVSV-G using lipofectamine; and 3) after 60 hours, collecting the supernatant and filter with 70 μM strainer into a 15 ml tube.

T-Cell Transduction

In some embodiments, T-cells, including for example, cytotoxic lymphocytes, are transduced with the viral vector (i.e., genetically modified with the viral vector). In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the viral vector is a pMSCIV based vector encoding a PD-L1 binding protein. In some embodiments, the T-cells, TIL and/or cytotoxic lymphocytes are genetically modified to express and secrete 19H9. In some embodiments, the T-cells, TIL and/or cytotoxic lymphocytes are genetically modified to express and secrete 38A1. In some embodiments, the T-cells, TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the T-cells are transduced using a method comprising activating $1 \times 10^6$ TIL with anti-CD3 at concentration of 300 ng/ml in 2 ml TIL culture media in 12-well-plate. In some embodiments, the transduction method further comprises splitting the TIL into two well and adding 1 ml of supernatant (from step 3 in viral production) into each well together with polybrene at a concentration of 8 µg/ml after 48 hours. In some embodiments, the transduction method further comprises centrifuging the cells for 30 minutes at 800×g at 32 C. In some embodiments, the transduction method further comprises removing virus containing medium and resuspending cell pellet with 2 ml of fresh complete culture media, and incubating the cells for 24 hours. In some embodiments, the transduction method further comprise propagating the cells using the Expanding the Genetically Modified Cytotoxic Lymphocytes provide below, as well as any other method know in the art for expanding TILs that could be applied to expanding cytotoxic lymphocytes within the TIL population.

Tumor Samples

In some embodiments, the method comprises obtaining a tumor tissue sample from the mammal, wherein the tumor sample comprises TILs containing the cytotoxic lymphocytes. The tumor tissue sample can be obtained from numerous sources, including but not limited to tumor biopsy or necropsy. The tumor tissue sample may be obtained from any cancer, including but not limited to any of the cancers described herein. In some embodiments, the cancer is melanoma. The tumor tissue sample may be obtained from any mammal. In some embodiments, the tumor tissue sample is obtained from a human. In some embodiments, the tumor tissue sample may be a tumor tissue fragment. The tumor tissue sample may be fragmented, e.g., by dissection, to provide a tumor tissue fragment. In some embodiments, alternatively or additionally, the tumor tissue sample may, optionally, be enzymatically or mechanically digested. Suitable enzymes for fragmenting the tumor tissue sample include, but are not limited to, collagenase. In some embodiments, the tumor tissue sample is fragmented without digestion. The tumor tissue fragment may be any suitable size. Preferably, the tumor tissue fragment has a size of about 1 $mm^3$ or less to about 8 $mm^3$ or larger, about 1 $mm^3$ to about 4 $mm^3$, about 1 $mm^3$ to about 2 $mm^3$, or about 1 $mm^3$.

The cancer treated by the disclosed compositions and methods can in some aspects be any solid tumor for which TILs can be produced. The cancer can also be metastatic and/or recurrent. The cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, digestive tract cancer, gastric cancer, gastrointestinal carcinoid tumor, glioma, hepatobiliary cancer, Hodgkin's lymphoma, hypopharynx cancer, kidney cancer, larynx cancer, liver cancer, lung cancer, malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer. In some embodiments, the cancer is melanoma. In some embodiments, the cancer is metastatic melanoma.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). In some embodiments, the mammal is the human.

TIL Containing Cytotoxic Lymphocyte General Expansion Methods

Tumor-infiltrating lymphocyte (TIL) containing cytotoxic lymphocyte production is generally a 2-step process: 1) the pre-REP (Rapid Expansion) stage where you the grow the cells in standard lab media such as RPMI and treat the TILs w/reagents such as irradiated feeder cells, and anti-CD3 antibodies to achieve the desired effect; and 2) the REP stage where you expand the TIL containing cytotoxic lymphocyte in a large enough culture amount for treating the patients. The REP stage requires cGMP (current good manufacturing procedures) grade reagents and 30-40 L of culture medium. However, the pre-REP stage can utilize lab grade reagents (under the assumption that the lab grade reagents get diluted out during the REP stage), making it easier to incorporate alternative strategies for improving TIL production. Therefore, in some embodiments, the disclosed TLR agonist and/or peptide or peptidomimetics can be included in the culture medium during the pre-REP stage. The pre-REP culture can in some embodiments, include IL-2.

In some embodiments, ACT can be performed by (i) obtaining autologous TIL containing cytotoxic lymphocytes from a mammal, (ii) culturing (including, for example, REP) the autologous TIL containing cytotoxic lymphocytes to produce expanded lymphocytes, and (ii) administering the expanded TIL containing cytotoxic lymphocytes to the mammal. In some embodiments, the TIL containing cytotoxic lymphocytes are tumor-derived, i.e., they are TILs containing cytotoxic, and are isolated from the mammal to be treated, i.e. autologous transfer. In some embodiments, the autologous TIL containing cytotoxic lymphocytes are genetically modified cytotoxic lymphocytes. In some embodiments, the autologous cytotoxic lymphocytes are genetically modified to express and secrete a PD-L1 binding protein. In some embodiments, the autologous lymphocytes are genetically modified cytotoxic lymphocytes using a viral vector. In some embodiments, the autologous lymphocytes are genetically modified before or after culturing, but prior to administration to the mammal. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, autologous ACT as described herein can also be performed by (i) culturing autologous TIL containing cytotoxic lymphocytes to produce expanded lymphocytes; (ii) optionally administering nonmyeloablative lymphodepleting chemotherapy to the mammal; and (iii) after optionally administering nonmyeloablative lymphodepleting chemotherapy, administering the expanded TIL containing cytotoxic lymphocytes to the mammal. Autologous TILs may be obtained from the stroma of resected tumors. For this, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). In some embodiments, the autologous cytotoxic lymphocytes are genetically modified to express and secrete a PD-L1 binding protein. In some embodiments, the autologous lymphocytes are genetically modified cytotoxic lymphocytes using a viral vector. In some embodiments, the autologous lymphocytes are genetically modified before or after culturing, but prior to administration to the mammal. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Expansion of lymphocytes, including tumor-infiltrating lymphocytes, such as T-cells can be accomplished by any of a number of methods as are known in the art, including those described herein below. For example, T-cells can be rapidly expanded using non-specific T-cell receptor stimulation in the presence of feeder lymphocytes and interleukin-2 (IL-2), IL-7, IL-15, IL-21, or combinations thereof. The non-specific T-cell receptor stimulus can e.g. include around 30 ng/ml of OKT3, a mouse monoclonal anti-CD3 antibody (available from Ortho-McNeil®, Raritan, N.J. or Miltenyi Biotec, Bergisch Gladbach, Germany). Alternatively, T-cells can be rapidly expanded by stimulation of peripheral blood mononuclear cells (PBMC) in vitro with one or more antigens (including antigenic portions thereof, such as epitope(s), or a cell of the cancer, which can be optionally expressed from a vector, such as an human leukocyte antigen A2 (HLA-A2) binding peptide, e.g., approximately 0.3 µM MART-1:26-35 (27 L) or gp100:209-217 (210M)), in the presence of a T-cell growth factor, such as around 200-400 µl/ml, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example. See, for example, International Patent Publication WO 2015/143328, incorporated by reference herein for all purposes.

Specific tumor reactivity of the expanded TILs can be tested by any method known in the art, e.g., by measuring cytokine release (e.g., interferon-gamma) following co-culture with tumor cells. In one embodiment, the autologous ACT method comprises enriching cultured TILs for CD8+ T-cells prior to rapid expansion of the cells. Following culture of the TILs in IL-2, the T-cells are depleted of CD4+ cells and enriched for CD8+ cells using, for example, a CD8 microbead separation (e.g., using a CliniMACS<plus>CD8 microbead system (Miltenyi Biotec)). In some embodiments, a T-cell growth factor that promotes the growth and activation of the autologous T-cells is administered to the mammal either concomitantly with the autologous T-cells or subsequently to the autologous T-cells. The T-cell growth factor can be any suitable growth factor that promotes the growth and activation of the autologous T-cells. Examples of suitable T-cell growth factors include interleukin (IL)-2, IL-7, IL-15, IL-12 and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. In some embodiments, 4-1BB co-stimulation enhancement can be employed to increase active TIL expansion for adoptive cell therapy.

Expanding the Genetically Modified Cytotoxic Lymphocytes

Expanding the TIL containing cytotoxic lymphocytes and/or expanding (i.e., REP) the genetically modified cytotoxic lymphocytes to provide a population of genetically modified cytotoxic lymphocytes includes culturing the TIL containing cytotoxic lymphocytes ex vivo to provide a population of TIL containing cytotoxic lymphocytes, e.g., for reintroduction to the subject (including, for example, a mammal). In some embodiments, cytotoxic lymphocytes are cultured in suitable media containing irradiated peripheral blood mononuclear cells (PBMCs) (feeder cells), isolated by leukapheresis from the subject or from allogeneic donors, and suitable reagents such as Interleukin 2 (IL-2), e.g., human IL-2, and OKT3 (anti-CD3 antibody). As an alternative to the use of PBMCs, artificial antigen presenting cells could be used in the expansion of cytotoxic lymphocytes, e.g., K562 cells genetically modified to express the human Fc receptors CD32 and CD64, such that the K562 cells can bind and present αCD3 and αCD28 monoclonal antibodies. Such artificial antigen presenting cells, including artificial antigen presenting cells expressing a variety of costimulatory molecules, are described, for example, in Turtle and Riddell *Cancer J.* 2010 July-August; 16(4): 374-381.

As part of the expanding step or as an additional step(s) one or more selection steps can be performed to enrich for TIL and/or cytotoxic lymphocytes of interest (e.g., cytotoxic lymphocytes expressing receptors for one or more tumor associated antigens), e.g., via one or more immunological assays.

In addition to TIL, cytotoxic lymphocytes, macrophages, monocytes, and natural killer (NK) cells may also be obtained from the tumor tissue sample, cultured, and expanded as described herein for TIL. Accordingly, the method may also comprise administering macrophages, monocytes, and natural killer (NK) cells to the mammal. In some embodiments, the methods can be employed for expanding cytotoxic lymphocytes, for example, including REPexpansion step(s).

After obtaining a tumor sample comprising TIL containing cytotoxic lymphocytes, the TIL and/or cytotoxic lymphocytes are expanded. In some embodiments, the method of propagating the TIL containing cytotoxic lymphocytes and/or genetically modified cytotoxic lymphocytes comprises (i) culturing (i.e., pre-REP) the TIL containing cytotoxic lymphocytes, including using IL-2; (ii) expanding (i.e., REP) the cultured cytotoxic lymphocytes using OKT3 antibody, IL-2, and feeder lymphocytes, wherein the cultured cytotoxic lymphocytes are enriched for CD8+ T-cells prior to expansion of the cytotoxic lymphocytes; (iii) optionally administering to the mammal nonmyeloablative lymphodepleting chemotherapy; and (iv) after optional administration of nonmyeloablative lymphodepleting chemotherapy, administering to the mammal the expanded cytotoxic lymphocytes, wherein the cytotoxic lymphocytes administered to the mammal are about 19 to about 35 days old and have not been screened for specific tumor reactivity, whereupon the regression of the cancer in the mammal is promoted. In some embodiments, the administered cytotoxic lymphocytes are less than about 35 days old, e.g., about 19 to about 26 days old. See, for example those methods described in U.S. Pat. No. 8,383,099, as well as the methods provided herein.

In some embodiments, TIL and/or cytotoxic lymphocytes are genetically modified after obtaining a tumor tissue sample from the mammal. In some embodiments, TIL and/or cytotoxic lymphocytes are genetically modified before or after culturing the TIL containing cytotoxic lymphocytes. In some embodiments, TIL and/or cytotoxic lymphocytes are genetically modified before or after expanding the cultured cytotoxic lymphocytes using OKT3 antibody, IL-2, and feeder lymphocytes, wherein the cultured cytotoxic lymphocytes are enriched for CD8+ T-cells prior to expansion of the TIL and/or cytotoxic lymphocytes. In some embodiments, TIL and/or cytotoxic lymphocytes are genetically modified before administering to the mammal. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the cytotoxic lymphocytes are genetically modified using a viral vector. In some embodiments, the first and second polypeptides are encoded on the same vector. In some embodiments, the first and second polypeptides are encoded on different vectors. In some embodiments, the first polypeptide is encoded on a first vector. In some embodiments, the second polypeptide is encoded on a second vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, cytotoxic lymphocytes that are about 19 to about 35 days old are believed to provide improved in vivo proliferation, survival, and antitumor activity as compared to cytotoxic lymphocytes that are about 44 days old or older. Moreover, in embodiments that include nonmyeloablative chemotherapy, the inventive methods can advantageously be used to treat patients that would not be eligible for treatments that involve total body irradiation (TBI) such as, for example, patients that have already undergone myeloablative therapy, e.g., radiotherapy, prior to treatment; patients with comorbid conditions; and patients with less than $2\times10^6$ CD34$^+$ cells/kg.

In some embodiments, the period of time required to generate cytotoxic lymphocytes for adoptive cell therapy (ACT) may be shortened from an average of about 44 days to a range of about 19 to about 35 days (or less than about 35 days, e.g., about 19 to about 29 days, or about 19 to about 26 days). Accordingly, more patients may be treated before their disease burden progresses to a stage in which administration of ACT may no longer be safe or possible. In some embodiments, methods do not require in vitro testing of specific antigen reactivity prior to administration, the inventive methods reduce the time, expense, and labor associated with the treatment of patients. Additionally, the inventive methods can employ administering cytotoxic lymphocytes that are pooled from bulk cultures instead of those derived from microcultures.

An embodiment of the method comprises culturing autologous cytotoxic lymphocytes. Tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2), e.g., in multiple wells. The cells are cultured until confluence (e.g., about $2\times10^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, preferably from 10 days, 10.5 days, or 10.8 days to 14 days, 14.5 days, or 14.8 days.

In some embodiments, the method comprises expanding cultured TILs containing cytotoxic lymphocytes. The cultured TILs containing cytotoxic lymphocytes are pooled and rapidly expanded. Rapid expansion provides an increase in the number of antigen-specific T-cells of at least about 50-fold (e.g., 50-fold, 60-fold, 70-fold, 80-fold, 90-fold, or 100-fold, or greater) over a period of about 10 days to about 14 days, and in some embodiments, about 14 days. In some embodiments, rapid expansion provides an increase of at least about 200-fold (e.g., 200-fold, 300-fold, 400-fold, 500-fold, 600-fold, 700-fold, 800-fold, 900-fold, or greater)

over a period of about 10 to about 14 days, in some embodiments, about 14 days. In some embodiments, rapid expansion provides an increase of at least about 1000-fold over a period of about 10 to about 14 days, in some embodiments, about 14 days. In some embodiments, rapid expansion provides an increase of about 1000-fold over a period of about 14 days. In some embodiments, the cultured TILs containing cytotoxic lymphocytes are genetically modified. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the cultured TILs containing cytotoxic lymphocytes are genetically modified using a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Expansion can be accomplished by any of a number of methods as are known in the art. For example, cytotoxic lymphocytes can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, cytotoxic lymphocytes can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, e.g., 0.3 µM MART-1:26-35 (27 L) or gp100:209-217 (210M), in the presence of a T-cell growth factor, such as 300 IU/ml IL-2 or IL-15. In some embodiments, the T-cell growth factor is IL-2 being preferred. The in vitro-induced cytotoxic lymphocytes are rapidly expanded by re-stimulation with the same antigen(s) of the cancer pulsed onto HLA-A2-expressing antigen-presenting cells. In some embodiments, the cytotoxic lymphocytes can be re-stimulated with irradiated, autologous lymphocytes or with irradiated HLA-A2+ allogeneic lymphocytes and IL-2, for example.

In some embodiments, a T-cell growth factor that promotes the growth and activation of the TIL and/or cytotoxic lymphocytes is administered to the mammal either concomitantly with the TIL or subsequently to the TIL. The T-cell growth factor can be any suitable growth factor that promotes the growth and activation of the TIL. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL-2. IL-2 is a preferred T-cell growth factor.

In some embodiments, the TIL and/or cytotoxic lymphocytes are further modified to express a T-cell growth factor that promotes the growth and activation of the TIL and/or cytotoxic lymphocytes. Suitable T-cell growth factors include, for example, any of those described above. Suitable methods of modification are known in the art. See, for instance, Sambrook et al., Molecular Cloning: A Laboratory Manual, 3$^{rd}$ ed., Cold Spring Harbor Press, Cold Spring Harbor, N.Y. 2001; and Ausubel et al., Current Protocols in Molecular Biology, Greene Publishing Associates and John Wiley & Sons, N Y, 1994. In some embodiments, modified TIL and/or cytotoxic lymphocytes express the T-cell growth factor at high levels. T-cell growth factor coding sequences, such as that of IL-12, are readily available in the art, as are promoters, the operable linkage of which to a T-cell growth factor coding sequence promote high-level expression. In some embodiments, the TIL and/or cytotoxic lymphocytes may be modified to express IL-12 as described in World Intellectual Property Organization Patent Application Publication No. WO 2010/126766, which is incorporated herein by reference.

In some embodiments, two cytokines can be more effective than a single cytokine, and, in some embodiments, three cytokines, e.g., IL-2, IL-7 and IL-15, can be more effective than any two cytokines. It is believed that IL-15 enhances a tumor-specific $CD8^+$ T-cell response. In this regard, the administration of IL-15-cultured cells with IL-2 (such as a bolus injection) can be particularly efficacious. In some embodiments, TIL and/or cytotoxic lymphocytes modified to express IL-15 may be administered with IL-2 as a bolus injection.

The T-cell growth factor can be administered by any suitable route. In embodiments where more than one T-cell growth factor is administered, they can be administered simultaneously or sequentially, in any order, and by the same route or different routes. In some embodiments, the T-cell growth factor, such as IL-2, is administered intravenously as a bolus injection. In some embodiments, the dosage of the T-cell growth factor, such as IL-2, is what is considered by those of ordinary skill in the art to be high. In some embodiments, a dose of about 720,000 IU/kg of IL-2 is administered three times daily until tolerance, particularly when the cancer is melanoma. In some embodiments, about 5 to about 15 doses of IL-2 are administered, with an average of around 8 doses.

TIL and/or cytotoxic lymphocytes can recognize any of the unique antigens produced as a result of the estimated 10,000 genetic mutations encoded by each tumor cell genome. The antigen, however, need not be unique. TIL and/or cytotoxic lymphocytes can recognize one or more antigens of a cancer, including an antigenic portion of one or more antigens, such as an epitope, or a cell of the cancer. An "antigen of a cancer" and an "antigen of the cancer" are intended to encompass all of the aforementioned antigens. If the cancer is melanoma, such as metastatic melanoma, the TIL and/or cytotoxic lymphocytes can recognize MART-1 (such as MART-1:26-35 (27L)), gp100 (such as gp100:209-217 (210M)), or a "unique" or patient-specific antigen derived from a tumor-encoded mutation. Other suitable melanoma antigens which may be recognized by TIL can include, but are not limited to, tyrosinase, tyrosinase related protein (TRP)1, TRP2, and MAGE. TIL can also recognize antigens such as, for example, NY-ESO-1, telomerase, p53, HER2/neu, carcinoembryonic antigen, or prostate-specific antigen, for treatment of lung carcinoma, breast cancer, colon cancer, prostate cancer, and the like.

In some embodiments, the method comprises optionally administering to the mammal nonmyeloablative lymphodepleting chemotherapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. In some embodiments, the route of administering cyclophosphamide and fludarabine is intravenously. Likewise, any suitable dose of cyclophosphamide and fludarabine can be administered. In some embodiments, around 60 mg/kg of cyclophosphamide is administered for two days after which around 25 $mg/m^2$ fludarabine is administered for five days. In some embodiments, around 60 mg/kg of cyclophosphamide is administered for two days after which around 25 mg/m² fludarabine is administered for five days and the cancer/tumor is melanoma.

In some embodiments, the method comprises, after optionally administering the nonmyeloablative lymphodepleting chemotherapy, administering to the mammal the expanded cytotoxic lymphocytes, wherein the cytotoxic lymphocytes administered to the mammal are about 19 to about 35 days old. For example, the administered cytotoxic lymphocytes may be 19 days, 19.5 days, or 19.8 days to 35 days, 35.5 days, or 35.8 days old. In some embodiments, the cytotoxic lymphocytes administered to the mammal are about 19 days to about 29 days or about 23 days to about 29 days old, or about 26 days old. For example, the administered cytotoxic lymphocytes may be 19 days, 19.5 days, or 19.8 days to 29, 29.5, or 29.8 days old; 23, 23.5, or 23.8 to 29, 29.5, or 29.8 days old; or 26, 26.5, or 26.8 days old. In some embodiments, the cytotoxic lymphocytes that are administered to the mammal are "young" cytotoxic lymphocytes, i.e., minimally cultured cytotoxic lymphocytes or cytotoxic lymphocytes between 19 days to about 29 days or about 23 days to about 29 days old, or about 26 days old.

Young cytotoxic lymphocytes cultures that are administered to the mammal in accordance with an embodiment of the invention advantageously have features associated with in vivo persistence, proliferation, and antitumor activity. For example, young cytotoxic lymphocytes cultures have a higher expression of CD27 and/or CD28 than cytotoxic lymphocytes that are about 44 days old. Without being bound to a particular theory, it is believed that CD27 and CD28 are associated with proliferation, in vivo persistence, and a less differentiated state of cytotoxic lymphocytes (while not being bound by theory, the increased differentiation of cytotoxic lymphocytes is believed to negatively affect the capacity of cytotoxic lymphocytes to function in vivo). Cytotoxic lymphocytes expressing higher levels of CD27 are believed to have better antitumor activity than CD27-low cells. Moreover, young cytotoxic lymphocyte cultures (e.g., 19 days to about 29 days or about 23 days to about 29 days old, or about 26 days old) have a higher frequency of $CD4^+$ cells than cytotoxic lymphocytes that are about 44 days old.

In addition, young cytotoxic lymphocytes cultures have a mean telomere length that is longer than that of cytotoxic lymphocytes that are about 44 days old. Without being bound to a particular theory, it is believed that cytotoxic lymphocytes lose an estimated telomere length of 0.8 kb per week in culture, and that young cytotoxic lymphocytes cultures have telomeres that are about 1.4 kb longer than cytotoxic lymphocytes that are about 44 days old. Without being bound to a particular theory, it is believed that longer telomere lengths are associated with positive objective clinical responses in subjects and persistence of the cells in vivo.

In some embodiments, the cytotoxic lymphocytes are not tested for specific tumor reactivity to identify tumor reactive cytotoxic lymphocytes prior to administration to the patient. Specific tumor reactivity can be tested by any method known in the art, e.g., by measuring cytokine release (e.g., interferon-γ) following co-culture with tumor cells. The inventive methods advantageously make it possible to promote regression of cancer in a mammal by administering cytotoxic lymphocytes to the mammal without the necessity of prior screening for specific tumor recognition. Embodiments of the methods may, if desired, include testing the cytotoxic lymphocytes for potency in a non-antigen-specific manner prior to administering the cytotoxic lymphocytes to the mammal. In some embodiments, cytotoxic lymphocyte potency may be optionally tested, e.g., by a non-specific potency assay measuring cytokine release following OKT3 stimulation. T-cells may be considered potent if, for example, interferon (IFN) release is greater than about 50 μg/mL, greater than about 100 μg/mL, greater than about 150 μg/mL, or greater than about 200 μg/mL. A less desired embodiment of the method comprises testing the expanded cytotoxic lymphocytes for specific tumor reactivity to identify tumor-reactive cytotoxic lymphocytes.

In some embodiments, the invention provides a method of promoting regression of a cancer in a mammal comprising (i) culturing (i.e., pre-REP) autologous cytotoxic lymphocytes and/or genetically modified cytotoxic lymphocytes (in some embodiments, autologous genetically modified cytotoxic lymphocytes), including using IL-2; (ii) expanding the cultured cytotoxic lymphocytes using OKT3 antibody, IL-2, and feeder lymphocytes, wherein the cultured cytotoxic lymphocytes are enriched for CD8+ T-cells prior to expansion of the cytotoxic lymphocytes; (iii) optionally administering to the mammal nonmyeloablative lymphodepleting chemotherapy; and (iv) after optionally administering nonmyeloablative lymphodepleting chemotherapy, administering to the mammal the expanded cytotoxic lymphocytes, wherein the cytotoxic lymphocytes administered to the mammal are about 19 days to about 29 days old, or about 23 days to about 29 days old, or about 26 days old, whereupon the regression of the cancer in the mammal is promoted. For example, the cytotoxic lymphocytes administered to the mammal may be 19 days to about 29 days or about 23 days to about 29 days old. In some embodiments, about 19 days to about 29 days, or about 23 days to about 29 days old, or about 26 days old. In some embodiments, the cultured TILs containing cytotoxic lymphocytes are genetically modified. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the cultured TILs containing cytotoxic lymphocytes are genetically modified using a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the cultured TILs containing cytotoxic lymphocytes are genetically modified before or after culturing. In some embodiments, the cultured TILs containing cytotoxic lymphocytes are genetically modified before or after expanding the cultured TILs containing cytotoxic lymphocytes using OKT3 antibody, IL-2, and feeder lymphocytes, wherein the cultured cytotoxic lymphocytes are enriched for CD8+ T-cells prior to expansion of the cytotoxic lymphocytes. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the method comprises culturing (for example, pre-REP) autologous T-cells as described herein from about 19 days to about 29 days, or about 23 days to about 29 days, or about 26 days. The method further comprises expanding (for example, REP) the cultured cytotoxic lymphocytes and optionally administering to the mammal nonmyeloablative lymphodepleting chemotherapy as described herein. After optionally administering nonmyeloablative lymphodepleting chemotherapy, the method comprises administering to the mammal the expanded cytotoxic lymphocytes as described herein, whereupon the regression of the cancer in the mammal is promoted. In some embodiments of the method, the administered cytotoxic lymphocytes have not been screened for specific tumor reactivity. In some embodiments, the expanded cytotoxic lymphocytes administered to the mammal are about 19 days to about 29 days or about 23 days to about 29 days old, or about 26 days old. For example, the administered cytotoxic lymphocytes may be 19 days, 19.5 days, or 19.8 days to 29, 29.5, or 29.8 days old; 23, 23.5, or 23.8 to 29, 29.5, or 29.8 days old; or 26, 26.5, or 26.8 days old.

In some embodiments, the method comprises enriching cultured T-cells containing the cytotoxic lymphocytes for CD8$^+$ T-cells prior to rapid expansion of the cells. Following culture of the TIL containing cytotoxic lymphocytes in IL-2, the TIL containing cytotoxic lymphocytes are depleted of CD4$^+$ cells and enriched for CD8$^+$ cells using, for example, a CD8 microbead separation (e.g., using a CliniMACS® Plus CD8 microbead system (commercially available from Miltenyi Biotec)). In some embodiments, CD4$^+$ and CD25$^+$ regulatory T-cells can impede anti-tumor responses. In some embodiments, enriching cultured cytotoxic lymphocytes for CD8$^+$ cytotoxic lymphocytes and reducing or eliminating CD4$^+$ cells may improve the impact of adoptively transferred anti-tumor CD8$^+$ cells, improve the response rates in patients, and/or reduce the toxicities seen by production of cytokines by CD4$^+$ cells. In some embodiments, CD8$^+$ enrichment of some T-cell cultures reveals in vitro tumor recognition that may not be evident in the bulk culture, and improved in vitro recognition of tumor in other cultures. In some embodiments, the enriched CD8$^+$ young cytotoxic lymphocytes can function more reliably and predictably in clinical scale rapid expansions than the bulk T-cells.

Expanding the Genetically Modified Cytotoxic Lymphocytes Using Gas Permeable Containers An embodiment of the invention provides a method of promoting regression of cancer in a mammal comprising obtaining a tumor tissue sample from the mammal; culturing (i.e., pre-REP) the tumor tissue sample in a first gas permeable container containing cell medium therein; obtaining cytotoxic lymphocytes from the tumor tissue sample; expanding (i.e., REP) the number of cytotoxic lymphocytes in a second gas permeable container containing cell medium therein using irradiated allogeneic feeder cells and/or irradiated autologous feeder cells; and administering the expanded number of cytotoxic lymphocytes to the mammal. In some embodiments, the cytotoxic lymphocytes are genetically modified after isolation from the tumor tissue sample, but prior to culturing in said first gas permeable container. In some embodiments, the cytotoxic lymphocytes are genetically modified after culturing in said first gas permeable container but prior to culturing in said a second gas permeable container. In some embodiments, the cytotoxic lymphocytes are genetically modified prior to administration of the expanded number of cytotoxic lymphocytes to the mammal. See, for example, the methods described in U.S. Patent Publication 2017/0152478, as well as those described herein. In some embodiments, the cytotoxic lymphocytes are genetically modified using a vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the present methods of promoting regression of cancer using cytotoxic lymphocytes and/or genetically modified cytotoxic lymphocytes which have been expanded using gas permeable containers are simpler, less labor-intensive, use less reagents, and can be performed using simpler equipment than procedures using non-gas permeable containers (e.g., T-flasks or T-175 flasks, bags, and multi-well plates). In addition, gas permeable containers can in some embodiments protect the cells from microbial contamination more effectively than non-gas permeable containers which may be "open" systems. In addition, methods using gas permeable containers can in some embodiments, reduce the number of containers that are used compared to methods using non-gas permeable containers, thereby reducing the amount of labor necessary to carry out the methods and also reducing the risk of microbial contamination. Thus, producing cells in gas permeable containers may be more suitable for compliance with the current good manufacturing practice (cGMP) conditions that are required for, e.g., Phase III clinical trials. In some embodiments, methods using gas-permeable containers reduce the final culture volume to lower than that obtained with non-gas permeable containers, which can lower the incubator capacity required to grow the cells, reduces the amount of reagents (e.g., cell culture medium and additives) necessary to grow the cells, and simplifies the equipment and/or procedures for concentrating and washing the cells. In some embodiments, the cells may be fed less frequently in gas-permeable containers (e.g., about every three to four days) than in non-gas permeable containers (e.g., every other day), particularly when the cells and/or tumor tissue sample are cultured submerged under at least about 1.3 cm of cell culture medium in a gas permeable container. In some embodiments, cells in gas permeable containers can be handled less frequently than cells in non-gas permeable containers (e.g., bags), which may minimize disturbance of the tumor fragment and provide more reproducible cytotoxic lymphocyte growth. In some embodiments, various portions of the method, including, but not limited to, culturing and/or expanding cytotoxic lymphocytes, can be automated. In some embodiments, the use of gas permeable flasks allows for generation of sufficient numbers of cytotoxic lymphocytes allowing for treatment of subjects who previously may not have been successfully treated because sufficient numbers of cytotoxic lymphocytes were not generated due to the technical and logistical complexities of previous methods that do not use gas permeable flasks.

In some embodiments, the method further comprises culturing the tumor tissue sample in a first gas permeable container containing cell medium therein. In an embodiment, the tumor tissue sample is cultured directly on the gas permeable material in the gas permeable container without digestion. In another embodiment, an enzymatically or mechanically digested tumor tissue sample may be cultured directly on the gas permeable material. Any suitable cell medium may be used. The cell culture medium may further comprise any suitable T-cell growth factor such as, e.g., interleukin (IL)-2. The cell culture medium may optionally further comprise human AB serum. In some embodiments, the tumor tissue sample may contain TILs that are autologous to the subject. In some embodiments, culturing the tumor tissue sample includes culturing the TILs present in the tumor sample.

The method also comprises obtaining TIL from the tumor tissue sample. The tumor tissue sample comprises TIL. As the tumor tissue sample is cultured in the gas permeable container, e.g., on gas permeable material in the container, TIL present in the tumor tissue sample also begin to grow in the gas permeable container, e.g., on the gas permeable material. TIL may be obtained from the tumor tissue sample in any suitable manner.

In some embodiments, the first gas permeable container may be any suitable gas permeable container. In some embodiments, the first gas permeable container comprises a base, sides, and a cap. In some embodiments, the container comprises a gas permeable support and a gas permeable material, e.g., a gas permeable membrane. In some embodiments, the base of the container comprises a gas permeable support and a gas permeable material, e.g., a gas permeable membrane. In some embodiments, the gas permeable material may be positioned inside the container directly on the gas permeable support which comprises openings (e.g., channels) in fluid communication with ambient gas in order to facilitate gas exchange between the interior of the container and the ambient gas. In some embodiments, the cap may comprise a vent and/or a port (e.g., an access port). In some embodiments, the access port may have an opening greater than about 1 mm to about 1 cm (e.g., greater than about 1 mm or greater than about 1 cm). An access port with an opening greater than about 1 mm to about 1 cm may advantageously eliminate or reduce disturbance of the TIL. In some embodiments, the gas permeable container comprises a vent or a vented port, which can be advantageous in the event that the temperature in the container drops during handling. In some embodiments, the first gas permeable container is a gas permeable container as described in U.S. Patent Application Publication No. 2005/0106717, which is incorporated herein by reference, and is commercially available from Wilson Wolf Manufacturing Corporation (e.g., G-Rex10, GP200, G-Rex100, GP2000 containers) (New Brighton, Minn.).

In some embodiments, the first gas permeable container has any suitable cell medium volume capacity. For example, the first gas permeable container can have a medium volume capacity of about 40 mL or more; about 200 mL or more; about 500 mL or more; about 2,000 mL or more; or about 5,000 mL or more. Although the first gas permeable container can have any suitable medium volume capacity, the tumor tissue sample and/or TIL containing cytotoxic lymphocytes can be cultured in any suitable volume of medium. In some embodiments, the tumor tissue sample and/or TIL containing cytotoxic lymphocytes are cultured submerged under a height of at least about 1.3 cm of cell culture medium. In some embodiments, the tumor tissue sample and/or TIL containing cytotoxic lymphocytes are cultured submerged under a height of at least about 2.0 cm of cell culture medium. Tumor tissue samples and/or TIL cultured on a gas permeable material submerged under a height of at least about 1.3 cm or a height of at least about 2.0 cm of medium may, advantageously, be handled and fed less frequently.

In some embodiments, the first gas permeable container can provide any suitable surface area for the growth of the TIL containing cytotoxic lymphocytes. In some embodiments, the gas permeable container can have a surface area for growth of the TIL of about 10 cm$^2$ or more; about 100 cm$^2$ or more; or about 650 cm$^2$ or more.

In some embodiments, the tumor tissue sample and/or TIL containing cytotoxic lymphocytes are cultured inside the first gas permeable container in contact with the gas permeable material and submerged under a suitable volume of culture medium. Culturing the tumor tissue sample and/or TIL in contact with the gas permeable material facilitates gas exchange between the cells and the ambient air. Facilitating gas exchange between the cells and the ambient air facilitates the respiration, growth, and viability of the cells. In some embodiments, the gas exchange across the gas permeable material can facilitate circulation of the medium (e.g., by convection and diffusion) within the container, which facilitates feeding of the TIL containing cytotoxic lymphocytes. In some embodiments, the cytotoxic lymphocytes are genetically modified before or after culturing in the first gas permeable container. In some embodiments, the cytotoxic lymphocytes are genetically modified using a vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the method further comprises expanding the number of TIL containing cytotoxic lymphocytes in a second gas permeable container containing cell medium therein using irradiated allogeneic feeder cells and/or irradiated autologous feeder cells. In some embodiments, the number of TIL containing cytotoxic lymphocytes is expanded using a ratio of about 1 TIL to at least about 20 feeder cells, about 1 TIL to at least about 25 feeder cells, about 1 TIL to at least about 50 feeder cells, about 1 TIL to at least about 100 feeder cells, about 1 TIL to at least about 200 feeder cells, e.g., a TIL-to-feeder cell ratio of about 1 to about 20, about 1 to about 25, about 1 to about 50, about 1 to about 100, or about 1 to about 200. In some embodiments, the second gas permeable container can be as described for the first container.

In some embodiments, the cultured TIL containing the cytotoxic lymphocytes are expanded. In some embodiments, the cultured TIL containing the cytotoxic lymphocytes are rapidly expanded. Rapid expansion provides an increase in the number of TIL containing the cytotoxic lymphocytes of at least about 50-fold (or 60-fold, 70-fold, 80-fold, 90-fold, or 100-fold, or greater) over a period of about 10 days to about 14 days, and in some embodiments, over about 14 days. In some embodiments, the rapid expansion provides an increase of at least about 200-fold (or 300-fold, 400-fold, 500-fold, 600-fold, 700-fold, 800-fold, 900-fold, or greater) over a period of about 10 days to about 14 days, and in some embodiments, over about 14 days. In some embodiments, the rapid expansion provides an increase of at least about 1000-fold over a period of about 10 to about 14 days, and in some embodiments, about 14 days. In some embodiments, rapid expansion provides an increase of about 1000-fold to about 2000-fold, e.g., about 1000-fold, about 1500-fold, or about 2,000-fold over a period of about 14 days. In some embodiments, the cytotoxic lymphocytes are genetically modified before or after expanding. In some embodiments, the cytotoxic lymphocytes are genetically modified using a vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, expansion (i.e., REP) can be accomplished in the gas permeable container by any suitable method. For example, TIL containing cytotoxic lymphocytes can be rapidly expanded using non-specific T-cell receptor stimulation in the presence of feeder cells (e.g., irradiated allogeneic feeder cells, irradiated autologous feeder cells, and/or artificial antigen presenting cells (e.g., K562 leukemia cells transduced with nucleic acids encoding CD3 and/or CD8)) and either interleukin-2 (IL-2) or interleukin-15 (IL-15), and in some embodiments, IL-2. In some embodiments, expanding the number of TIL containing cytotoxic lymphocytes uses about $1 \times 10^9$ to about $4 \times 10^9$ allogeneic feeder cells and/or autologous feeder cells, preferably about $2 \times 10^9$ to about $3 \times 10^9$ allogeneic feeder cells and/or autologous feeder cells. The non-specific T-cell receptor stimulus can include, for example, about 30 ng/ml of OKT3, a mouse monoclonal anti-CD3 antibody (available from ORTHO-MCNEIL, Raritan, N.J. or MILTENYI BIOTECH, Auburn, Calif.). Alternatively, TIL containing cytotoxic lymphocytes can be rapidly expanded by, for example, stimulation of the TIL containing cytotoxic lymphocytes in vitro with an antigen (one or more, including antigenic portions thereof, such as epitope(s), or a cell) of the cancer, which can be optionally expressed from a vector, such as an human leukocyte antigen A2 (HLA-A2) binding peptide, e.g., 0.3 µM MART-1:26-35 (27L) or gp100:209-217 (210M), in the presence of a T-cell growth factor, such as 300 IU/ml IL-2 or IL-15, and in some embodiments with IL-2. Other suitable antigens may include, e.g., NY-ESO-1, TRP-1, TRP-2, tyrosinase cancer antigen, MAGE-A3, SSX-2, and VEGFR2, or antigenic portions thereof. The in vitro-induced TIL are rapidly expanded by re-stimulation with the same antigen(s) of the cancer pulsed onto HLA-A2-expressing antigen-presenting cells. Alternatively, the TIL can be re-stimulated with, for example, irradiated, autologous lymphocytes or with irradiated HLA-A2+ allogeneic lymphocytes and IL-2, for example.

In some embodiments, expanding the number of TIL can comprise using about 5,000 mL to about 10,000 mL of cell medium, preferably about 5,800 mL to about 8,700 mL of cell medium. In an embodiment, expanding the number of TIL uses no more than one type of cell culture medium. Any suitable cell culture medium may be used, e.g., AIM-V cell medium (L-glutamine, 50 µg/ml streptomycin sulfate, and 10 µg/ml gentamicin sulfate) cell culture medium (Invitrogen, Carlsbad Calif.). In this regard, the inventive methods advantageously reduce the amount of medium and the number of types of medium required to expand the number of TIL containing cytotoxic lymphocytes.

In some embodiments, expanding the number of TIL containing cytotoxic lymphocytes can comprise feeding the cells no more frequently than every third or fourth day. Expanding the number of cells in a gas permeable container advantageously simplifies the procedures necessary to expand the number of cells by reducing the feeding frequency necessary to expand the cells.

In some embodiments, the cell medium in the first and/or second gas permeable container is unfiltered. Without being bound to a particular theory, it is believed that particulate serum components present in some cell medium supplements (e.g., AB serum) have little or no detrimental effects on TIL growth. The use of unfiltered cell medium may, advantageously, simplify the procedures necessary to expand the number of cells.

In some embodiments, the cell medium in the first and/or second gas permeable container lacks beta-mercaptoethanol (BME). In some embodiments, the absence of BME from the cell medium can be advantageously more compliant with cGMP (current good manufacturing procedures) and, thus, can advantageously make it easier to gain regulatory approval.

In some embodiments, the duration of the method comprising obtaining a tumor tissue sample from the mammal; culturing (i.e., pre-REP) the tumor tissue sample in a first gas permeable container containing cell medium therein; obtaining TIL containing cytotoxic lymphocytes from the tumor tissue sample; expanding (i.e., REP) the number of TIL containing cytotoxic lymphocytes in a second gas permeable container containing cell medium therein using irradiated allogeneic feeder cells and/or irradiated autologous feeder cells may be about 28 to about 42 days, e.g., about 28 days. In some embodiments, the cytotoxic lymphocytes are genetically modified before or after culturing, before or after obtaining the TIL-containing cytotoxic lymphocytes, or before or after expanding. In some embodiments, the cytotoxic lymphocytes are genetically modified using a vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the method comprises administering the expanded TIL containing cytotoxic lymphocytes to the mammal. The TIL containing cytotoxic lymphocytes can be administered by any suitable route as known in the art. In some embodiments the TIL and/or cytotoxic lymphocytes are administered as an intra-arterial or intravenous infusion, which preferably lasts about 30 to about 60 minutes. Other examples of routes of administration include intraperitoneal, intrathecal and intralymphatic. In some embodiments, the cytotoxic lymphocytes are genetically modified prior to administration. In some embodiments, the cytotoxic lymphocytes are genetically modified using a vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the heavy and light chains are encoded on the same vector. In some embodiments, the heavy and light chains are encoded on different vectors. In some embodiments, the heavy chain is encoded on a first vector. In some embodiments, the light chain is encoded on a second vector. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In addition to TIL, cytotoxic lymphocytes, macrophages, monocytes, and natural killer (NK) cells may also be obtained from the tumor tissue sample, cultured, and expanded as described herein for TIL. Accordingly, the method may also comprise administering macrophages, monocytes, and natural killer (NK) cells to the mammal. In some embodiments, the methods can be employed for expanding cytotoxic lymphocytes.

In some embodiments, a T-cell growth factor that promotes the growth and activation of the TIL and/or cytotoxic lymphocytes is administered to the mammal either concomitantly with the TIL or subsequently to the TIL. The T-cell growth factor can be any suitable growth factor that promotes the growth and activation of the TIL. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL-2. IL-2 is a preferred T-cell growth factor.

In some embodiments, the TIL and/or cytotoxic lymphocytes are modified to express a T-cell growth factor that promotes the growth and activation of the TIL and/or cytotoxic lymphocytes. Suitable T-cell growth factors include, for example, any of those described above. Suitable methods of modification are known in the art. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. In some embodiments, modified TIL and/or cytotoxic lymphocytes express the T-cell growth factor at high levels. T-cell growth factor coding sequences, such as that of IL-12, are readily available in the art, as are promoters, the operable linkage of which to a T-cell growth factor coding sequence promote high-level expression. In some embodiments, the TIL and/or cytotoxic lymphocytes may be modified to express IL-12 as described in World Intellectual Property Organization Patent Application Publication No. WO 2010/126766, which is incorporated herein by reference.

In some embodiments, two cytokines can be more effective than a single cytokine, and, in some embodiments, three cytokines, e.g., IL-2, IL-7 and IL-15, can be more effective than any two cytokines. It is believed that IL-15 enhances a tumor-specific CD8$^+$ T-cell response. In this regard, the administration of IL-15-cultured cells with IL-2 (such as a bolus injection) can be particularly efficacious. In some embodiments, TIL and/or cytotoxic lymphocytes modified to express IL-15 may be administered with IL-2 as a bolus injection.

The T-cell growth factor can be administered by any suitable route. In embodiments where more than one T-cell growth factor is administered, they can be administered simultaneously or sequentially, in any order, and by the same route or different routes. In some embodiments, the T-cell growth factor, such as IL-2, is administered intravenously as a bolus injection. In some embodiments, the dosage of the T-cell growth factor, such as IL-2, is what is considered by those of ordinary skill in the art to be high. In some embodiments, a dose of about 720,000 IU/kg of IL-2 is administered three times daily until tolerance, particularly when the cancer is melanoma. In some embodiments, about 5 to about 15 doses of IL-2 are administered, with an average of around 8 doses.

TIL and/or cytotoxic lymphocytes can recognize any of the unique antigens produced as a result of the estimated 10,000 genetic mutations encoded by each tumor cell genome. The antigen, however, need not be unique. TIL and/or cytotoxic lymphocytes can recognize one or more antigens of a cancer, including an antigenic portion of one or more antigens, such as an epitope, or a cell of the cancer. An "antigen of a cancer" and an "antigen of the cancer" are intended to encompass all of the aforementioned antigens. If the cancer is melanoma, such as metastatic melanoma, the TIL and/or cytotoxic lymphocytes can recognize MART-1 (such as MART-1:26-35 (27L)), gp100 (such as gp100:209-217 (210M)), or a "unique" or patient-specific antigen derived from a tumor-encoded mutation. Other suitable melanoma antigens which may be recognized by TIL can include, but are not limited to, tyrosinase, tyrosinase related protein (TRP)1, TRP2, and MAGE. TIL can also recognize antigens such as, for example, NY-ESO-1, telomerase, p53, HER2/neu, carcinoembryonic antigen, or prostate-specific antigen, for treatment of lung carcinoma, breast cancer, colon cancer, prostate cancer, and the like.

In some embodiments, the method provided is a method of obtaining an expanded number of TIL and/or cytotoxic lymphocytes from a mammal for adoptive cell immunotherapy comprising obtaining a tumor tissue sample from the mammal; culturing the tumor tissue sample in a first gas permeable container containing cell medium therein; obtaining TIL and/or cytotoxic lymphocytes from the tumor tissue sample; expanding the number of TIL and/or cytotoxic lymphocytes in a second gas permeable container containing cell medium therein using irradiated allogeneic feeder cells and/or irradiated autologous feeder cells. In some embodiments, the TIL and/or cytotoxic lymphocytes are genetically modified. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, TIL and/or cytotoxic lymphocytes are genetically modified after obtaining a tumor tissue sample from the mammal. In some embodiments, TIL and/or cytotoxic lymphocytes are genetically modified before or after culturing (i.e., pre-REP) the tumor tissue sample in a first gas permeable container containing cell medium therein. In some embodiments, TIL and/or cytotoxic lymphocytes are genetically modified after obtaining the TIL and/or cytotoxic lymphocytes from the tumor tissue sample. In some embodiments, TIL and/or cytotoxic lymphocytes are genetically modified after expanding (i.e., REP) the number of TIL and/or cytotoxic lymphocytes in a second gas permeable container containing cell medium therein using irradiated allogeneic feeder cells and/or irradiated autologous feeder cells. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the method comprises obtaining a tumor tissue sample from the mammal. The tumor tissue sample may be obtained as described herein with respect to any embodiments of the invention.

In some embodiments, the method comprises culturing the tumor tissue sample in a first gas permeable container containing cell medium therein. The tumor tissue sample may be cultured in a first gas permeable container as described herein with respect to any embodiments of the invention.

In some embodiments, the method comprises obtaining TIL containing cytotoxic lymphocytes from the tumor tissue sample. The TIL containing cytotoxic lymphocytes may be obtained from the tumor tissue sample as described herein with respect to any embodiments of the invention.

In some embodiments, the method comprises expanding the number of TIL and/or cytotoxic lymphocytes in a second gas permeable container containing cell medium therein using irradiated allogeneic feeder cells and/or irradiated autologous feeder cells. The number of TIL and/or cytotoxic lymphocytes may be expanded as described herein with respect to any embodiments of the invention.

In some embodiments, the method involves obtaining an expanded number of TIL and/or cytotoxic lymphocytes from a mammal for adoptive cell immunotherapy, wherein the method comprises obtaining a tumor tissue sample from the mammal; obtaining TIL containing cytotoxic lymphocytes from the tumor tissue sample; expanding the number of TIL and/or cytotoxic lymphocytes in a gas permeable container containing cell medium therein using irradiated allogeneic feeder cells and/or irradiated autologous feeder cells. In some embodiments, the gas permeable container is a first gas permeable container. Obtaining a tumor tissue sample from the mammal, obtaining TIL and/or cytotoxic lymphocytes from the tumor tissue sample, and expanding the number of TIL and/or cytotoxic lymphocytes in a second gas permeable container containing cell medium therein using irradiated allogeneic feeder cells and/or irradiated autologous feeder cells may be carried out as described herein with respect to any embodiments of the invention. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the method provided is a method of promoting regression of cancer in a mammal comprising obtaining a tumor tissue sample from the mammal; obtaining TIL containing cytotoxic lymphocytes from the tumor tissue sample; expanding the number of TIL and/or cytotoxic lymphocytes in a first gas permeable container and a second gas permeable container containing cell medium therein using irradiated allogeneic feeder cells and/or irradiated autologous feeder cells; and administering the expanded number of TIL and/or cytotoxic lymphocytes to the mammal. In some embodiments, obtaining a tumor tissue sample from the mammal, obtaining TIL from the tumor tissue sample, expanding the number of TIL and/or cytotoxic lymphocytes in a gas permeable container containing cell medium therein using irradiated allogeneic feeder cells and/or irradiated autologous feeder cells, and administering the expanded number of TIL and/or cytotoxic lymphocytes to the mammal can be carried out as described herein with respect to any embodiments described herein. In some embodiments, the method further comprises selecting TIL and/or cytotoxic lymphocytes capable of lysing cancer cells. The TIL and/or cytotoxic lymphocytes may be selected as described herein with respect to any embodiments of the invention. In some embodiments, the TIL and/or cytotoxic lymphocytes are genetically modified. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, the TIL and/or cytotoxic lymphocytes are genetically modified after obtaining a tumor tissue sample from the mammal. In some embodiments, the TIL and/or cytotoxic lymphocytes are genetically modified before or after isolating the TIL containing cytotoxic lymphocytes from the tumor tissue sample. In some embodiments, the TIL and/or cytotoxic lymphocytes are genetically modified before or after expanding the number of TIL and/or cytotoxic lymphocytes in a second gas permeable container containing cell medium therein using irradiated allogeneic feeder cells and/or irradiated autologous feeder cells. In some embodiments, the TIL and/or cytotoxic lymphocytes are genetically modified prior to administering the expanded number of TIL and/or cytotoxic lymphocytes to the mammal.

In some embodiments, the cytotoxic lymphocytes are not tested for specific tumor reactivity to identify tumor reactive cytotoxic lymphocytes prior to administration to the patient. Specific tumor reactivity can be tested by any method known in the art, e.g., by measuring cytokine release (e.g., interferon-γ) following co-culture with tumor cells. The inventive methods advantageously make it possible to promote regression of cancer in a mammal by administering cytotoxic lymphocytes to the mammal without the necessity of prior screening for specific tumor recognition. Embodiments of the methods may, if desired, include testing the cytotoxic lymphocytes for potency in a non-antigen-specific manner prior to administering the cytotoxic lymphocytes to the mammal. In some embodiments, cytotoxic lymphocyte potency may be optionally tested, e.g., by a non-specific potency assay measuring cytokine release following OKT3 stimulation. T-cells may be considered potent if, for example, interferon (IFN) release is greater than about 50 μg/mL, greater than about 100 μg/mL, greater than about 150 μg/mL, or greater than about 200 μg/mL. A less desired embodiment of the method comprises testing the expanded cytotoxic lymphocytes for specific tumor reactivity to identify tumor-reactive cytotoxic lymphocytes.

Further Methods for Culturing TIL and/or Cytotoxic Lymphocytes

In some embodiments, the method can further comprise culturing the tumor tissue by any suitable method that facilitates the obtaining of TIL and/or cytotoxic lymphocytes from the tumor tissue sample. In this regard, culturing the tumor tissue may comprise establishing multiple independent cultures, e.g., microcultures. For example, culturing the tumor tissue may comprise culturing tumor fragments in plates, e.g., 24-well plates. In some embodiments, the tumor tissue is cultured without a gas permeable container.

In some embodiments, the method further comprises selecting TIL and/or cytotoxic lymphocytes capable of lysing cancer cells while in other embodiments, the method does not include selecting TIL capable of lysing cancer cells. TIL capable of lysing cancer cells may be selected by identifying TILs having any suitable trait associated with the lysis of cancer cells and/or the regression of cancer. Exemplary suitable TIL traits that may serve as the basis for selecting TILs may include any one or more of IFN-γ release upon co-culture with autologous tumor cells; cell surface expression of one or more of CD8, CD27, and CD28; and telomere length. Without being bound to a particular theory, it is believed that cell surface expression of one or more of CD8, CD27, and CD28 and longer telomere lengths are associated with positive objective clinical responses in patients and persistence of the cells in vivo. Preferably the trait is IFN-γ release upon co-culture with autologous tumor cells. In an embodiment of the invention, selected TIL release about 200 pg/ml or more of IFN-γ upon co-culture with tumor cells.

In some embodiments, selecting TIL capable of lysing cancer cells comprises testing individual cultures for presence of the trait and identifying TIL possessing the trait. Methods of testing cultures for the presence of any one or more of IFN-γ release upon co-culture with autologous tumor cells; cell surface expression of one or more of CD8, CD27, and CD28; and telomere length (longer telomeres being associated with regression of cancer) are known in the art.

In some embodiments, any number of cultures can be selected. For example, one, two, three, four, five, or more cultures may be selected. In embodiments in which two or more cultures are selected, the selected cultures may be combined and the number of TIL expanded in one (or more) gas permeable containers. In embodiments in which two or more cultures are selected, each selected culture is separately expanded in separate containers, including gas permeable containers when such containers are employed.

In some embodiments, the method can further comprise expanding the number of TIL and/or cytotoxic lymphocytes in an identified culture in a second gas permeable container containing cell medium therein using irradiated allogeneic feeder cells and/or irradiated autologous feeder cells as described herein with respect to any embodiments of the invention. In some embodiments, the cytotoxic lymphocytes that are expanded in a second gas permeable container are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Administering the Population of Genetically Modified Cytotoxic Lymphocytes

Once expanded to a suitable number, the population of genetically modified cytotoxic lymphocytes may be administered, e.g., infused, to the subject using any suitable method and/or device known in the art. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

The compositions of the present disclosure, e.g., the genetically modified cytotoxic lymphocytes of the present disclosure, may be administered either alone, or as a pharmaceutical composition in combination with diluents and/or with other components such as IL-2 or other cytokines or cell populations. Briefly, pharmaceutical compositions of the present disclosure may include a population of genetically modified cytotoxic lymphocytes as described herein, e.g., in connection with any embodiment described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration or injection at a tumor site.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the genetically modified cytotoxic lymphocytes described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Genetically modified cytotoxic lymphocytes compositions may also be administered multiple times at these dosages. The genetically modified cytotoxic lymphocytes can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient systemically or locally (e.g., at the site of a tumor). The compositions described herein may be administered to a patient subcutaneously, intradermally, intratumorally, intranodally, intramedullary, intramuscularly, by intravenous (i.v.) injection, or intraperitoneally. In some embodiments, the compositions of the present disclosure are administered to a patient by intradermal or subcutaneous injection. In some cases, the compositions of the present disclosure are administered by i.v. injection. The compositions of the present disclosure may be injected directly into a tumor, lymph node, or site of infection.

In some embodiments, the expanded TIL containing cytotoxic lymphocytes, cytotoxic lymphocytes, and/or genetically modified cytotoxic lymphocytes produced by the disclosed methods are administered as an intra-arterial or intravenous infusion. In some embodiments, administration lasts about 30 to about 60 minutes. In some embodiments, routes of administration include intraperitoneal, intrathecal and intralymphatic. In some embodiments, TIL and/or cytotoxic lymphocytes are genetically modified after obtaining a tumor tissue sample from the mammal, anytime during expansion, but prior to administration to a mammal. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, TIL and/or cytotoxic lymphocytes are genetically modified using a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Lymphodepleting Methods

In some embodiments, nonmyeloablative lymphodepleting chemotherapy is administered to the mammal prior to administering to the mammal the expanded cytotoxic lymphocytes obtained from the tumor-infiltrating lymphocytes. The purpose of lymphodepletion is to make room for the infused lymphocytes, in particular by eliminating regulatory T-cells and other non-specific T-cells which compete for homeostatic cytokines. Nonmyeloablative lymphodepleting chemotherapy can be any suitable such therapy, which can be administered by any suitable route known to a person of skill. The nonmyeloablative lymphodepleting chemotherapy can comprise, for example, the administration of cyclophosphamide and fludarabine, particularly if the cancer is melanoma, which can be metastatic. In some embodiments, the route of administering cyclophosphamide and fludarabine is intravenously. Likewise, any suitable dose of cyclophosphamide and fludarabine can be administered. Preferably, around 40-80 mg/kg, such as around 60 mg/kg of cyclophosphamide is administered for approximately two days after which around 15-35 mg/m$^2$, such as around 25 mg/m$^2$ fludarabine is administered for around five days, particularly if the cancer is melanoma.

In some embodiments, nonmyeloablative lymphodepleting chemotherapy is administered to the mammal prior to administering to the mammal the cytotoxic lymphocytes that are genetically modified. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Combination Therapies

In some embodiments, a suitable therapy will include exposing a subject to one or more lymphodepletion measures prior to administration of the genetically modified cytotoxic lymphocytes of the present disclosure. Lymphodepletion measures may take the form of chemo- or radiotherapy. Suitable chemotherapy measures may include, e.g., treatment with cyclophosphamide and/or fludarabine.

In some embodiments of the present disclosure, cells expanded using the methods described herein, e.g., in connection with any embodiment described herein or other methods known in the art where lymphocytes are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the genetically modified cytotoxic lymphocytes of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, my cophenolic acid, steroids, FR901228, cytokines, and irradiation, These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, 1991; Henderson et al., *Immun.* 73:316-321, 1991; Bierer et al., *Curr. Opin, Immun.* 5:763-773, 1993). In a further embodiment, the cell compositions of the present disclosure are administered to a patient in conjunction with (e.g., before, simultaneously or following) bone marrow transplantation, T-cell ablative therapy using either chemotherapy agents such as, fludarabine, external-beam radiation therapy (XRT), cyclophosphamide, or antibodies such as OKT3 or CAMPATH. In another embodiment, the cell compositions of the present disclosure are administered following B-cell ablative therapy such as agents that react with CD20, e.g., Rittman. For example, in one embodiment, subjects may undergo standard treatment with high dose chemotherapy followed by peripheral blood stem cell transplantation. In certain embodiments, following the transplant, subjects receive an infusion of the expanded genetically modified cytotoxic lymphocytes of the present disclosure. In an additional embodiment, expanded cells are administered before or following surgery.

In some embodiments, the expanded cells administered before or following surgery are genetically modified. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some embodiments, genetically modified cytotoxic lymphocytes are administered simultaneously with a standard anti-cancer drug or therapy. Numerous anti-cancer drugs and therapies are available for combination with the present methods and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 1131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safngol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Subjects Suitable for Treatment

Subjects suitable for treatment with the disclosed methods and compositions include, but are not limited to, those having (e.g., diagnosed as having) or at risk of having cancer and/or a chronic viral infection. Types of cancer which may be amenable to treatment via the methods and compositions disclosed herein include, but are not limited to, metastatic melanoma, lymphoma, leukemia, and solid tumors of pancreatic or brain origin. Types of chronic viral infection which may be amenable to treatment via the methods and compositions disclosed herein include, but are not limited to, post-transplant lymphoproliferative diseases (PTLD) associated with Epstein-Barr virus (EBV) infection, human papillomavirus (HPV), cytomegalovirus, and adenovirus infection. Subjects infected with hepatitis C and B viruses may also be amendable to treatment via the methods and compositions disclosed herein.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the methods and compositions of the present disclosure to include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

In some embodiments, the methods promote cancer regression. Promoting regression of cancer in a mammal can comprise treating or preventing cancer in the mammal. The terms "treat," "prevent," and "regression," as well as words stemming therefrom, as used herein, does not necessarily imply 100% or complete regression. Rather, there are varying degrees of treatment, prevention, and regression of which one of ordinary skill in the art recognizes as having a potential benefit or therapeutic effect. In this respect, the inventive methods can provide any amount of any level of treatment, prevention, or regression of cancer in a mammal. Furthermore, the treatment, prevention, or regression provided by the inventive method can include treatment, prevention, or regression of one or more conditions or symptoms of the disease, e.g., cancer. Also, for purposes herein, "treatment," "prevention," and "regression" can encompass delaying the onset of the disease, or a symptom or condition thereof.

In some embodiments, cytotoxic lymphocytes are administered as part of the treatment regimen. In some embodiments, a PD-L1 binding protein is administered as part of the treatment regimen. In some embodiments, cytotoxic lymphocytes in combination with a PD-L1 binding protein are administered as part of the treatment regimen. In some embodiments, genetically modified cytotoxic lymphocytes are administered as part of the treatment regimen. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Methods of Making Cytotoxic Lymphocytes Genetically Modified to Express and Secrete a Soluble Programmed Death 1 Ligand 1 (PD-L1) Binding Protein Methods of making genetically modified cytotoxic lymphocytes according to the present disclosure may include one or more of the isolating, genetically modifying, and expanding steps described above.

In some embodiments, the genetically cytotoxic lymphocytes are genetically modified to express and secrete a PD-L1 binding protein. In some embodiments, the genetically modified cytotoxic lymphocytes made according to the present invention have been genetically modified using viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the genetically modified cytotoxic lymphocytes are genetically modified to express and secrete 19H9. In some embodiments, the genetically modified cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

Kits

The present disclosure also provides kits including one or more compositions of the present disclosure, e.g., selected from: (i) a subject PD-L1 binding protein (e.g., scFV, maxibody, and the like), e.g., in connection with any embodiment described herein, (ii) one or more nucleic acids (e.g., vectors) including a nucleotide sequence(s) encoding a subject PD-L1 binding protein according to the present disclosure, e.g., in connection with any embodiment described herein, and (iii) one or more genetically modified cells (e.g., a cytotoxic lymphocyte) (e.g., in a composition including one or more pharmaceutically acceptable excipients) according to the present disclosure, e.g., in connection with any embodiment described herein. In some embodiments, cytotoxic lymphocytes are included in the kit. In some embodiments, a PD-L1 binding protein is included in the kit. In some embodiments, cytotoxic lymphocytes in combination with a PD-L1 binding protein are included in the kit. In some embodiments, genetically modified cytotoxic lymphocytes in the kit. In some embodiments, the cytotoxic lymphocytes are genetically modified cytotoxic lymphocytes. In some embodiments, the cytotoxic lymphocytes are genetically modified to express and secrete a PD-L1 binding protein. In some embodiments, the TIL and/or cytotoxic lymphocytes are genetically modified with a viral vector. In some embodiments, the viral vector is a lentiviral based vector. In some embodiments, the viral vector is pLV4301G PDLV scFV 38A1 (SEQ ID NO:37; FIG. 11A, FIG. 16A). In some embodiments, the viral vector is pLV4301G PDLV scFV 19H9 (SEQ ID NO:38; FIG. 11B, FIG. 16B). In some embodiments, the viral vector is a pLEV based viral vector. In some embodiments, the viral vector is a gammaretroviral based vector. In some embodiments, the viral vector is a pMSCIV based vector. In some embodiments, the viral vector encodes 19H9. In some embodiments, the viral vector is a lentiviral based vector encoding 19H9. In some embodiments, the viral vector is a pLEV based viral vector encoding 19H9. In some embodiments, the viral vector encodes 38A1. In some embodiments, the viral vector is a lentiviral based vector encoding 38A1. In some embodiments, the viral vector is a pLEV based viral vector encoding 38A1. In some embodiments, the TIL and/or cytotoxic lymphocytes are genetically modified to express and secrete 19H9. In some embodiments, the TIL and/or cytotoxic lymphocytes are genetically modified to express and secrete 38A1. In some embodiments, the TIL and/or cytotoxic lymphocytes are genetically modified to express and secrete a PD-L1 binding protein. In some embodiments the PD-L1 binding protein comprises an antigen binding portion. In some embodiments, the 38A1 protein exhibits greater or increased binding capacity in Jurkat cells as compared to 19H9. In some embodiments, the PD-L1 binding protein exhibits greater or increased binding capacity in melanoma as compared to 19H9. In some embodiments, the 38A1 protein exhibits greater or increased binding capacity in melanoma as compared to 19H9. In some embodiments, the increased binding capacity is measured by (i) determining the percentage of PD-L1 positive cells detected in a flow cytometry assay using a PD-L1 binding protein labeled with or detectable by a fluorescent label, and (ii) comparing the number of PD-L1 positive cells obtained with the PD-L1 binding protein to a control antibody or comparing to 19H9, wherein an increase in the percentage of PD-L1 positive cells detected by flow cytometry as compared to a control antibody or 19H9 indicates an increase in binding capacity (see, for example, the assay in Example 3). In some embodiments, the increased binding capacity is measured by (i) determining the mean fluorescence intensity (MFI) of PD-L1 positive cells in a flow cytometry assay which have been labeled with a PD-L1 binding protein labeled with or detectable by a fluorescent label and (ii) comparing the MFI obtained with the PD-L1 binding protein to a control antibody or comparing to 19H9, wherein an increase in the MFI of the total cell population by flow cytometry with the PD-L1 binding protein as compared to a control antibody or 19H9 indicates an increase in binding capacity (see, for example, the assay in Example 3). In some embodiments, the PD-L1 binding protein exhibits greater or increased biological function in Jurkat cells as compared to 19H9. In some embodiments, the 38A1 protein exhibits greater or increased biological function in Jurkat cells as compared to 19H9. In some embodiments, biological function includes blockade of the engagement of PD-1 and PD-L1. In some embodiments, biological function includes inhibition of the PD-1 and PD-L1 signaling pathway. In some embodiments, the PD-L1 binding protein exhibits greater or increased secretion capacity in Jurkat cells as compared to 38A1. In some embodiments, the 19H9 protein exhibits greater or increased secretion capacity in Jurkat cells as compared to 38A1. In some embodiments the PD-L1 binding protein is an antibody or fragment thereof comprising a heavy chain and a light chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments the PD-L1 binding protein is an antibody or fragment thereof comprising a heavy chain and a light chain, wherein said light chain comprises SEQ ID NO:1 and said heavy chain comprises SEQ ID NO:5. In some embodiments the PD-L1 binding protein is an antibody or fragment thereof comprising a light chain and a heavy chain, wherein said light chain comprises CDRs of SEQ ID NO:2 (CDR-L1), SEQ ID NO:3 (CDR-L2), and SEQ ID NO:4 (CDR-L3) and said heavy chain comprises CDRs of SEQ ID NO:6 (CDR-H1), SEQ ID NO:7 (CDR-H2), and SEQ ID NO:8 (CDR-H3). In some embodiments the PD-L1 binding protein is an antibody or fragment thereof comprising a heavy chain and a light chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments the PD-L1 binding protein is an antibody or fragment thereof comprising a heavy chain and a light chain, wherein said light chain comprises SEQ ID NO:9 and said heavy chain comprises SEQ ID NO:13. In some embodiments the PD-L1 binding protein is an antibody or fragment thereof comprising a light chain and a heavy chain, wherein said light chain comprises CDRs of SEQ ID NO:10 (CDR-L1), SEQ ID NO:11 (CDR-L2), and SEQ ID NO:12 (CDR-L3) and said heavy chain comprises CDRs comprising SEQ ID NO:14 (CDR-H1), SEQ ID NO:15 (CDR-H2), and SEQ ID NO:16 (CDR-H3). In some embodiments, the PD-L1 binding protein is a single-chain Fv (scFv) comprising a light chain and a heavy chain, wherein said light chain comprises a sequence having 90%, 95%, or 98% identity to SEQ ID NO:1 and said heavy chain comprises a sequence having 90%, 95%, or 98% identity to SEQ ID NO:5. In some embodiments, the PD-L1 binding protein is a single-chain Fv (scFv) comprising a light chain and a heavy chain, wherein said light chain comprises SEQ ID NO:1 and said heavy chain comprises SEQ ID NO:5. In some embodiments, the PD-L1 binding protein is a single-chain Fv (scFv) comprising SEQ ID NO:17. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:18. In some embodiments, conjugation is direct. In some embodiments, conjugation is via a linker. In some embodiments, the PD-L1 binding protein is a single-chain Fv (scFv) comprising a light chain and a heavy chain, wherein said light chain comprises a sequence having 90%, 95%, or 98% identity to SEQ ID NO:9 and said heavy chain comprises a sequence having 90%, 95%, or 98% identity to SEQ ID NO:13. In some embodiments, the PD-L1 binding protein is a single-chain Fv (scFv) comprising a light chain and a heavy chain, wherein said light chain comprises SEQ ID NO:9 and said heavy chain comprises SEQ ID NO:13. In some embodiments, the PD-L1 binding protein is a single-chain Fv (scFv) comprising SEQ ID NO:19. In some embodiments, the PD-L1 binding protein is a single-chain Fv (scFv) further comprising an IgG1, IgG2, IgG3, or IgG4 sequence (i.e., conjugated to an IgG1, IgG2, IgG3, or IgG4 sequence). In some embodiments, the PD-L1 binding protein is a single-chain Fv (scFv) further comprising an IgG1 sequence (i.e., conjugated to an IgG1 sequence). In some embodiments, the PD-L1 binding protein is a single-chain Fv (scFv) comprising SEQ ID NO:20. In some embodiments, conjugation is direct. In some embodiments, conjugation is via a linker.

In some cases, a subject kit includes suitable instructional material, e.g., to practice methods as described herein, e.g., in connection with any embodiment described herein.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-76 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A protein that specifically binds to PD-L1 and comprises an antigen binding portion that comprises:
(a) a first polypeptide comprising the 3 CDR amino acid sequences set forth in SEQ ID NOs:2-4, and a second polypeptide comprising the 3 CDR amino acid sequences set forth in SEQ ID NOs:6-8; or
(b) a first polypeptide comprising the 3 CDR amino acid sequences set forth in SEQ ID NOs: 10-12, and a second polypeptide comprising the 3 CDR amino acid sequences set forth in SEQ ID NOs:14-16, with the exception that each of the three CDR amino acid sequences of the first and/or second polypeptide comprises two or less conservative amino acid substitutions relative to the specified SEQ ID number.
2. The protein of 1, wherein the antigen binding portion comprises a first polypeptide comprising the 3 CDR amino acid sequences set forth in SEQ ID NOs:2-4, and a second polypeptide comprising the 3 CDR amino acid sequences set forth in SEQ ID NOs:6-8.
3. The protein of 2, wherein the first polypeptide comprises the amino acid sequence set forth in SEQ ID NO:1, and the second polypeptide comprises the amino acid sequence set forth in SEQ ID NO:5.
4. The protein of 1, wherein the antigen binding portion comprises a first polypeptide comprising the 3 CDR amino acid sequences set forth in SEQ ID NOs:10-12, and a second polypeptide comprising the 3 CDR amino acid sequences set forth in SEQ ID NOs:14-16.
5. The protein of 4, wherein the first polypeptide comprises the amino acid sequence set forth in SEQ ID NO:9, and the second polypeptide comprises the amino acid sequence set forth in SEQ ID NO:13.
6. The protein of any of 1-5, wherein the first polypeptide is a light chain, and the second polypeptide is a heavy chain.
7. The protein of any of 1-6, wherein the protein is a single-chain antibody (scFv) and the first and second polypeptides are fused directly or via a linker to one another.
8. The protein of 7, wherein the scFv comprises the amino acid sequence set forth in SEQ ID NO:17 or SEQ ID NO:19.
9. The protein of any of 1-8, wherein the protein is a maxibody comprising an immunoglobulin Fc domain fused directly or via a linker to the antigen binding portion.
10. The protein of 9, wherein the immunoglobulin Fc domain is an IgG1 Fc domain.
11. The protein of 10, wherein the protein comprises the amino acid sequence set forth in SEQ ID NO:18 or SEQ ID NO:20.
12. The protein of 9, wherein the immunoglobulin Fc domain is an IgG4 Fc domain.
13. The protein of any of 1-6, wherein the protein is a humanized antibody.
14. A nucleic acid comprising a nucleotide sequence encoding the protein of any one of 1-13.
15. The nucleic acid of 14, wherein the nucleic acid comprises a promoter that is operably linked to the nucleotide sequence encoding the protein.
16. The nucleic acid of 15, wherein the promoter is a constitutive promoter.
17. The nucleic acid of 15, wherein the promoter is an inducible promoter.
18. A cell comprising the nucleic acid of any one of 14-17.
19. The cell of 18, wherein the nucleic acid is integrated into the cell's genome.
20. The cell of 18 or 19, wherein the cell is a cytotoxic lymphocyte genetically modified to express and secrete the protein.
21. The cell of 20, wherein the cytotoxic lymphocyte is a T-cell.
22. The cell of 21, wherein the T-cell is a CD8+ T-cell.
23. The cell of 21, wherein the T-cell is a CD4+ T-helper cell.
24. The cell of 21, wherein the T-cell is derived from peripheral blood
25. The cell of 20, wherein the cytotoxic lymphocyte is a natural killer (NK) cell.
26. The cell of 25, wherein the NK is derived from peripheral blood.
27. The cell of 20, wherein the cytotoxic lymphocyte is a tumor infiltrating lymphocyte (TIL) derived from a tumor from a subject.
28. The cell of 27, wherein the TIL comprises a receptor specific for an antigen from the tumor.
29. The cell of any of 20-28, wherein the cytotoxic lymphocyte exhibits an increased level of expression of one or more activation antigens relative to a naïve T-cell.
30. The cell of 29, wherein the one or more activation antigens are selected from CD25, CD26, CD27, CD28, CD38, CD40L, CD69, CD134, CD137, BTLA, PD-1, HVEM, LIGHT, and HLA-DR.

31. The cell of 29 or 30, wherein the cytotoxic lymphocyte comprises a T-cell receptor specific for a tumor associated antigen.

32. A method comprising:
   genetically modifying a cytotoxic lymphocyte isolated from a tumor of a subject by introducing into the cytotoxic lymphocyte the nucleic acid of any of claims 14-17, wherein the genetically modified cytotoxic lymphocyte expresses and secretes the protein that specifically binds to PD-L1;
   expanding the genetically modified cytotoxic lymphocyte to generate a population of genetically modified cytotoxic lymphocytes; and
   administering the population of genetically modified cytotoxic lymphocytes to the subject to treat the tumor.

33. The method of claim 32, wherein the genetically modified cytotoxic lymphocyte constitutively expresses the protein that specifically binds to PD-L1.

34. The method of claim 32, wherein the genetically modified cytotoxic lymphocyte inducibly expresses the protein that specifically binds to PD-L1.

35. The method of any one of claims 32-34, wherein the nucleic acid integrates into the cytotoxic lymphocyte's genome.

36. The method of any one of claims 32-35, wherein the cytotoxic lymphocyte is a T-cell.

37. The method of claim 36, wherein the T-cell is a CD8+ T-cell.

38. The method of claim 36, wherein the T-cell is a CD4+ T-helper cell.

39. The method of any one of claims 32-35, wherein the cytotoxic lymphocyte is a natural killer (NK) cell.

40. The method of any one of claims 32-39, wherein the genetically modified cytotoxic lymphocyte comprises a receptor specific for an antigen from the tumor.

41. The method of any one of claims 32-40, comprising isolating the cytotoxic lymphocyte from the subject prior to the genetically modifying.

42. The method of any one of claims 32-41, wherein said protein that specifically binds to PD-L1 and comprises an antigen binding portion that comprises:
   (a) a first polypeptide comprising the 3 CDR amino acid sequences set forth in SEQ ID NOs:2-4, and a second polypeptide comprising the 3 CDR amino acid sequences set forth in SEQ ID NOs:6-8; or
   (b) a first polypeptide comprising the 3 CDR amino acid sequences set forth in SEQ ID NOs: 10-12, and a second polypeptide comprising the 3 CDR amino acid sequences set forth in SEQ ID NOs:14-16,
   with the exception that each of the three CDR amino acid sequences of the first and/or second polypeptide comprises two or less conservative amino acid substitutions relative to the specified SEQ ID number.

43. The method of claim 42, wherein said wherein the antigen binding portion comprises a first polypeptide comprising the 3 CDR amino acid sequences set forth in SEQ ID NOs:2-4, and a second polypeptide comprising the 3 CDR amino acid sequences set forth in SEQ ID NOs:6-8.

44. The method of claim 43, wherein the first polypeptide comprises the amino acid sequence set forth in SEQ ID NO:1, and the second polypeptide comprises the amino acid sequence set forth in SEQ ID NO:5.

45. The method of claim 42, wherein the antigen binding portion comprises a first polypeptide comprising the 3 CDR amino acid sequences set forth in SEQ ID NOs:10-12, and a second polypeptide comprising the 3 CDR amino acid sequences set forth in SEQ ID NOs:14-16.

46. The method of claim 45, wherein the first polypeptide comprises the amino acid sequence set forth in SEQ ID NO:9, and the second polypeptide comprises the amino acid sequence set forth in SEQ ID NO:13.

47. The method of any of claims 42-46, wherein the first polypeptide is a light chain, and the second polypeptide is a heavy chain.

48. The method of any of claims 42-47, wherein the protein is a single-chain antibody (scFv) and the first and second polypeptides are fused directly or via a linker to one another.

49. The method of claim 48, wherein the scFv comprises the amino acid sequence set forth in SEQ ID NO:17 or SEQ ID NO:19.

50. The method of any of claims 42-49, wherein the protein is a maxibody comprising an immunoglobulin Fc domain fused directly or via a linker to the antigen binding portion.

51. The method of claim 50, wherein the immunoglobulin Fc domain is an IgG1 Fc domain.

52. The method of claim 51, wherein the protein comprises the amino acid sequence set forth in SEQ ID NO:18 or SEQ ID NO:20.

53. A method of making a genetically modified cytotoxic lymphocyte, the method comprising:
   genetically modifying a cytotoxic lymphocyte isolated from a subject having or suspected of having cancer by introducing into the cytotoxic lymphocyte the nucleic acid of any of claims 14-17, wherein the genetically modified cytotoxic lymphocyte expresses and secretes the protein that specifically binds to PD-L1.

54. The method of claim 53, wherein the genetically modified cytotoxic lymphocyte constitutively expresses the protein that specifically binds to PD-L1.

55. The method of claim 53, wherein the genetically modified cytotoxic lymphocyte inducibly expresses the protein that specifically binds to PD-L1.

56. The method of any one of claims 53-55, comprising expanding the cytotoxic lymphocyte in vitro to provide an expanded population of genetically modified cytotoxic lymphocytes.

57. The method of any one of claims 53-56, comprising isolating the cytotoxic lymphocyte from the subject prior to the genetically modifying.

58. The method of claim 57, wherein the isolating comprises isolating the cytotoxic lymphocyte from a tumor of the subject.

59. The method of any of claim 57, wherein the isolating comprises isolating the cytotoxic lymphocyte from peripheral blood of the subject.

60. The method of any one of claims 53-59, wherein the cytotoxic lymphocyte is a T-cell.

61. The method of claim 60, wherein the T-cell is a CD8+ T-cell.

62. The method of claim 60, wherein the T-cell is a CD4+ T-helper cell.

63. The method of any one of claims 53-59, wherein the cytotoxic lymphocyte is a natural killer (NK) cell.

64. The method of any one of claims 53-63, wherein the nucleic acid integrates into the cytotoxic lymphocyte's genome.

65. The method of any one of claims 53-64, wherein the cytotoxic lymphocyte exhibits an increased level of expression of one or more activation antigens relative to a naïve T-cell.

66. The method of claim 65, wherein the one or more activation antigens are selected from CD25, CD26, CD27, CD28, CD38, CD40L, CD69, CD134, CD137, BTLA, PD-1, HVEM, LIGHT, and HLA-DR.

67. The method of claim 65 or claim 66, wherein the genetically modified cytotoxic lymphocyte comprises a T-cell receptor specific for an antigen from a tumor of the subject.
68. A method of treating an individual who has or is suspected of having cancer, the method comprising:
administering the protein that specifically binds to PD-L1 according to any of claims 1-13 to the individual.
69. The method of claim 68, wherein the administering comprises introducing into the subject a nucleic acid encoding the protein.
70. The method of claim 68, wherein the administering comprises introducing into the subject a genetically modified cytotoxic lymphocyte that expresses and secretes the protein.
71. The method of claim 70, wherein the genetically modified cytotoxic lymphocyte constitutively expresses the protein.
72. The method of claim 71, wherein the genetically modified cytotoxic lymphocyte inducibly expresses the protein.
73. The method of claim 72, comprising inducing expression of the protein.
74. The method of any one of claims 70-73, wherein the cytotoxic lymphocyte is a T-cell.
75. The method of claim 74, wherein the T-cell is a CD8+ T-cell.
76. The method of claim 74, wherein the T-cell is a CD4+ T-helper cell.
77. The method of any one of claims 70-73, wherein the cytotoxic lymphocyte is a natural killer (NK) cell.
78. The method of any one of claims 70-77, wherein the cytotoxic lymphocyte exhibits an increased level of expression of one or more activation antigens relative to a naïve T-cell.
79. The method of claim 78, wherein the one or more activation antigens are selected from CD25, CD26, CD27, CD28, CD38, CD40L, CD69, CD134, CD137, BTLA, PD-1, HVEM, LIGHT, and HLA-DR.
80. The method of claim 78 or claim 79, wherein the genetically modified cytotoxic lymphocyte comprises a T-cell receptor specific for an antigen from a tumor of the subject.
81. A method of reducing the interaction between PD-L1 on a first-cell and PD-1 on a second cell, the method comprising:
contacting PD-L1 on the first-cell with the protein of any one of claims 1-13.
82. The method of claim 81, wherein the first and second cells are in an individual, and the contacting comprises administering the protein of any of claims 1-13 to the individual.
83. The method of claim 82, wherein the introducing comprises systemic administration.
84. The method of claim 82, wherein the introducing comprises local administration.
85. The method of claim 84, wherein the local administration comprises intratumoral administration.
86. The method of any of claims 81-85, wherein the individual has cancer.
87. The method of claim 87, wherein the individual has a solid tumor.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Example 1: PD-L1 Binding Proteins with an Antigen Binding Portion

Figure 2:
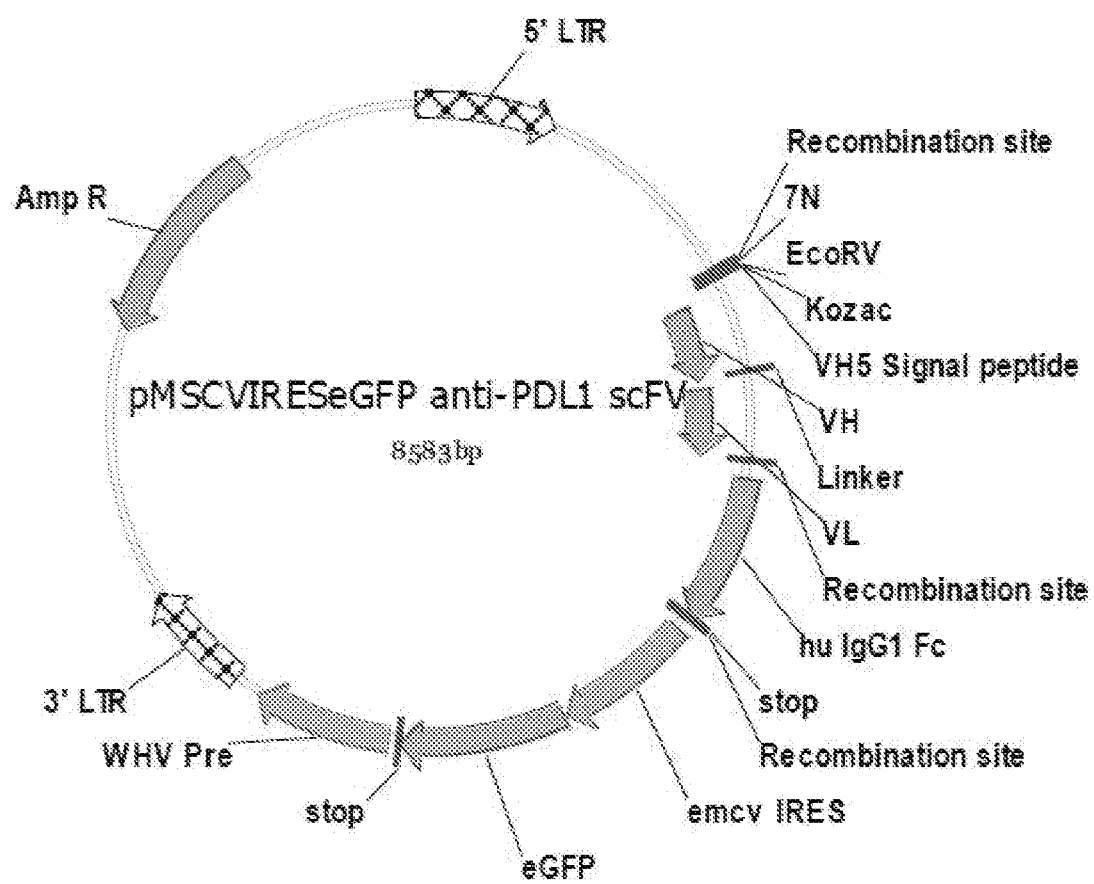
FIG. 2 provides a schematic representation of the retroviral plasmid used to produce 38A1-Fc, 19H9-Fc and FMC63-Fc. Anti PD-L1 maxibodies are encoded downstream of the U3 promoter from MSCV promoter and upstream of an IRES-eGFP cassette.
Figure 3:
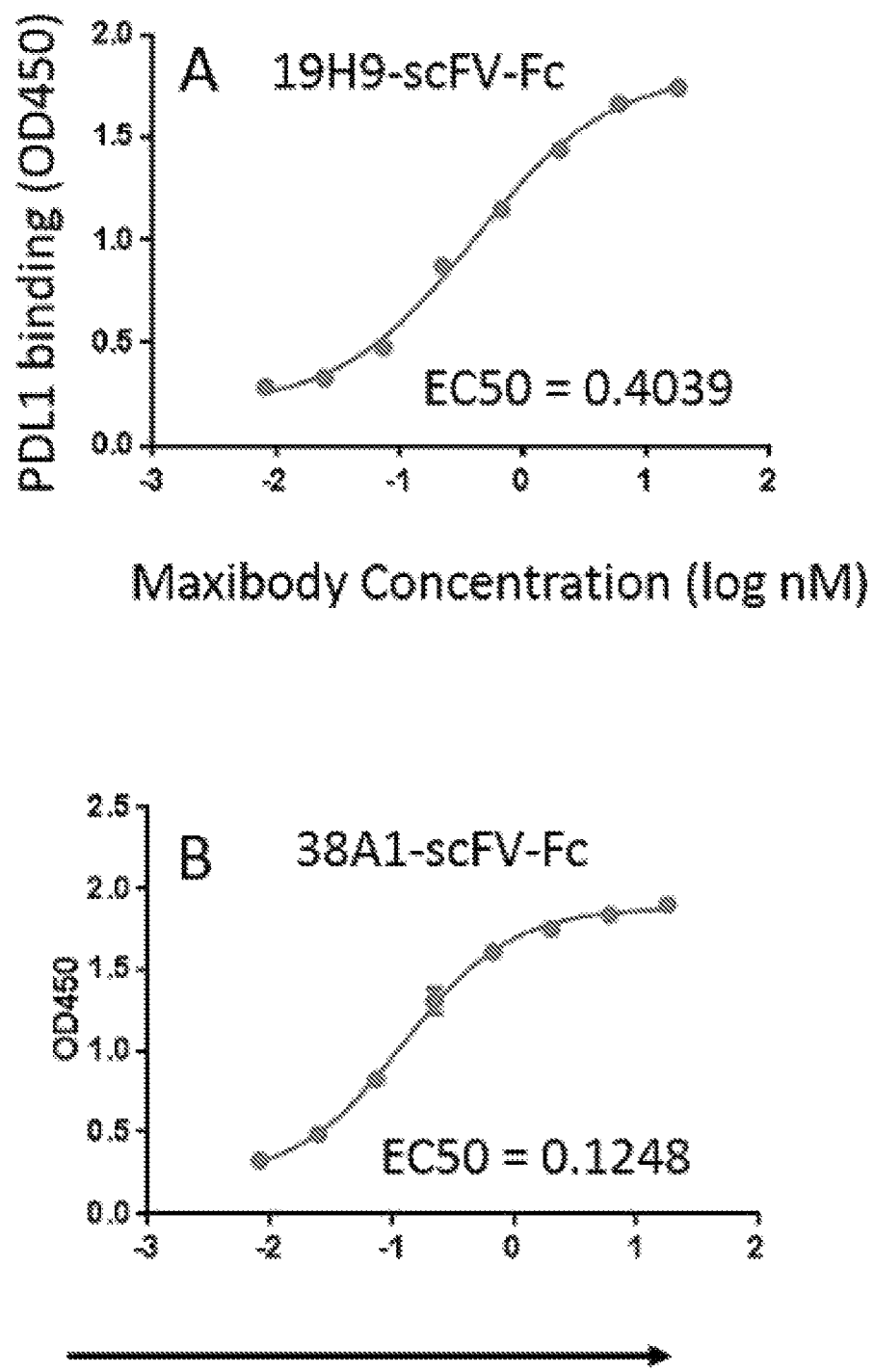
FIG. 3A-3B provides data from cell based ELISA to determine affinity of 38A1-seFV-Fe and 19H9-seFV-Fe for PD-L1. 293-PD-L1 were stained with 19H9-seFV-Fe (panel A) or 38A1-seFV-Fe (panel B). Maxibodies were titrated from 100 nM to 0.01 nM on 293-PD-L1, washed and stained with HRP labelled anti-human Fcγ specific antibody. Binding was determined by optical density at 450 nm following addition of TMB (3,3',5,5'-tetramethylbenzidine). 12D10-seFV-Fe was used as the negative control.
Figure 4:
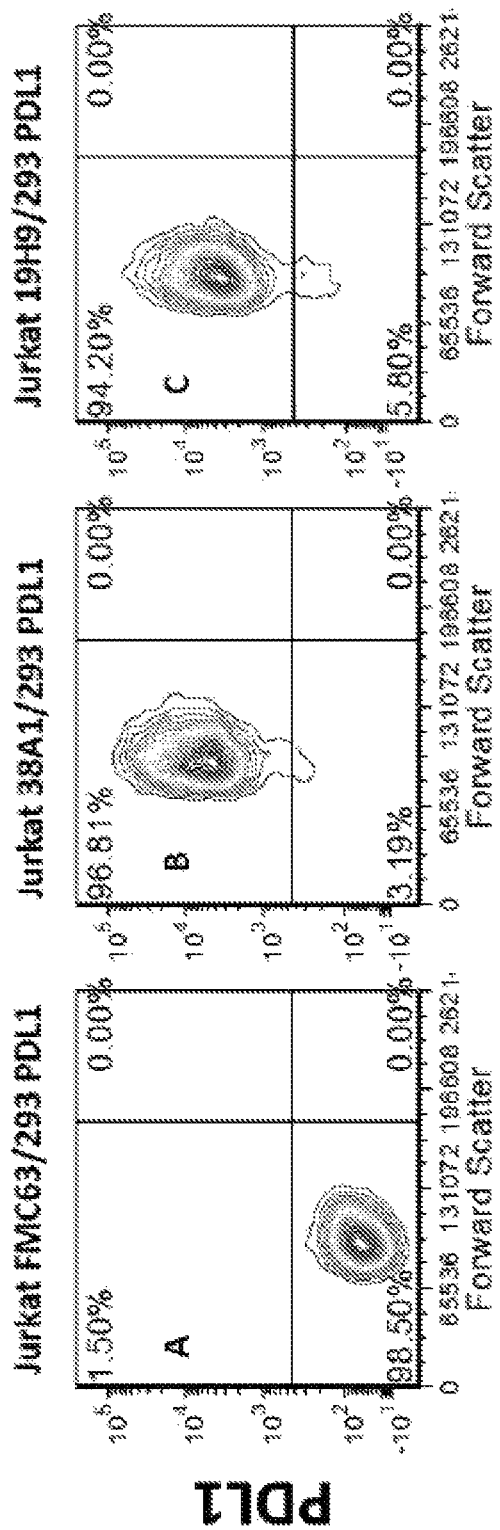
FIG. 4A-4C provides data showing that 293-PD-L1 cells bind anti-PD-L1 maxibodies secreted by Jurkat T-cells. Jurkat T-cells stably expressing FMC63-scFV-Fc (panel A), 38A1-seFV-Fe (panel B) or 19H9-seFV-Fe (panel C) were co-cultured at a ratio of 1:1 for 16 hour. The cells were harvested and stained with Alexa 647 labelled anti-human Fcγ specific antibody. Compared to the negative control maxibody (FMC63-scFV-Fc), between a 100 fold and 300 fold increase mean fluorescent intensity (binding of maxibody) was observed for 19H9-seFV-Fe and 38A1-seFV-Fe, respectively.

Recombinant antibodies specific for PD-L1 (anti-PD-L1 scFV fused to the human Fc domain of human IgG) were generated. Using a scFV phage display library (Viva Biotechnologies), several scFVs specific for PD-L1 were isolated. Two scFVs bound to native PD-L1, and were named 38A1 and 19H9. 38A1-scFV, 19H9-scFV and FMC63-scFV (anti-CD19 scFV negative control) were fused to the Fc domain of human IgG1 (38A1-scFV-Fc, 19H9-scFV-Fc and FMC63-scFV-Fc). These were constructed in lentiviral and retroviral plasmids using multisite lambda phage "Gateway" recombination (e.g., see FIG. 1). Each scFV sequence was flanked by the recombination sites attL1 and attR5, synthesized by Geneart (Life Technologies) and subcloned into pMK. The sequence for IgG1 Fc was flanked by the recombination sites attL5 and attL2, synthesized by Geneart (Life Technologies) and subcloned into pMK. Each scFV was recombined with IgG1-Fc in either a lentiviral plasmid (pLVU3pIRESeGFP; FIG. 2) or a retroviral plasmid (pMSCVIRESeGFP; FIG. 3). The recombined constructs consist of a fusion of the scFV (38A1, 19H9 or FMC63) fused to IgG1-Fc via an attB5 recombination site.

Figure 5:
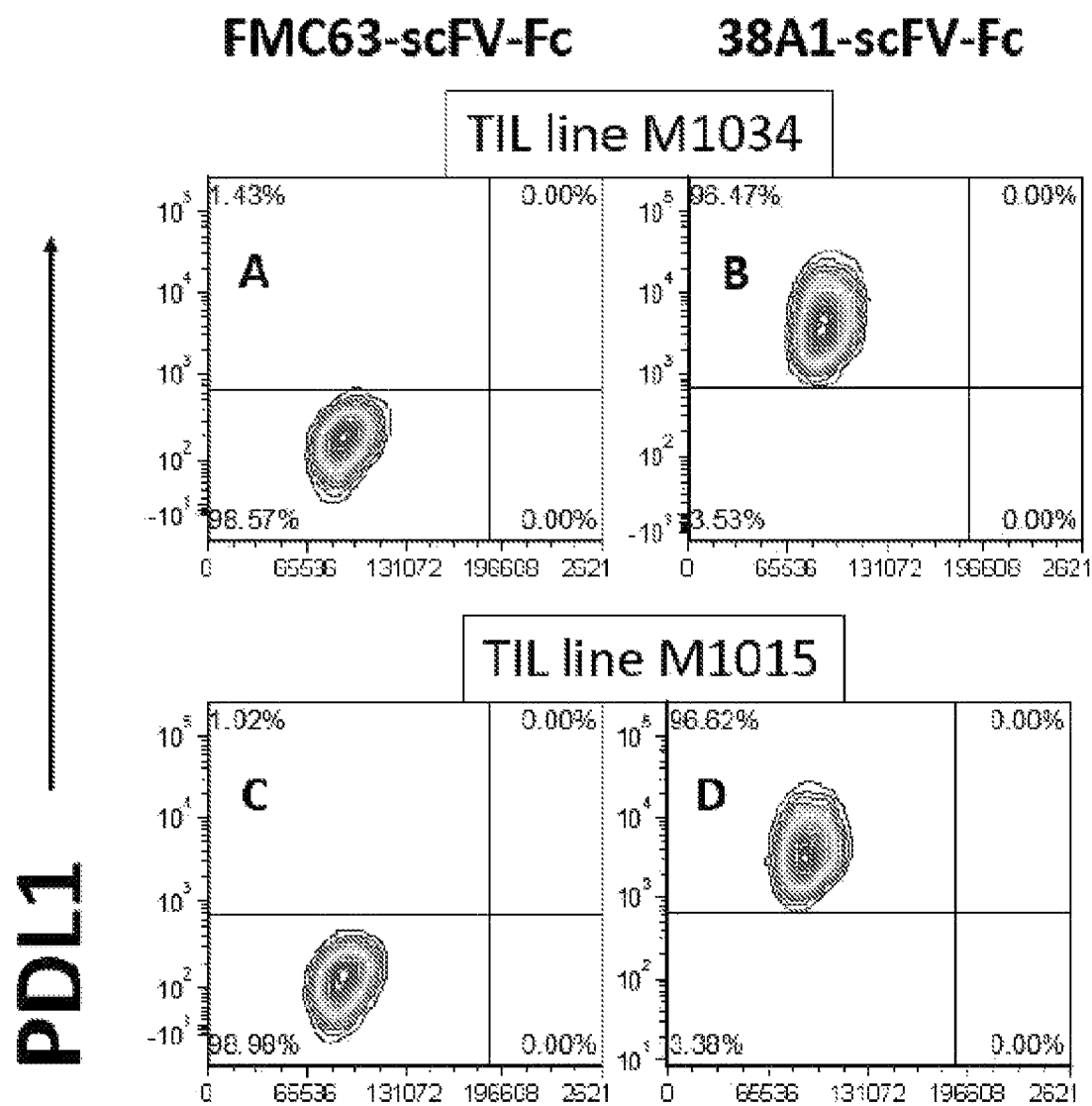
FIG. 5A-5D provides data showing that 293-PD-L1 cells bind anti-PD-L1 maxibodies secreted by tumor infiltrating lymphocytes (TIL). Supernatant from TIL lines M1034 (panel A, panel B) and M1015 (panel C, panel D) stably expressing FMC63-scFV-Fc (panel A, panel C) or 38A1-seFV-Fe (panel B, panel D) were concentrated 10 fold and used to stain 293-PD-L1. The maxibodies were detected using Alexa 647 labelled anti-human Fcγ specific antibody. Compared to the negative control maxibody (FMC63-scFV-Fc), we observed greater than a 50 fold in increase in mean fluorescent intensity (binding of maxibody) for 38A1-seFV-Fe.

To determine the affinity of the 38A1-scFV-Fc (SEQ ID NO:17) and 19H9-scFV-Fc (SEQ ID NO:19) maxibodies for PD-L1 (using 12D10-scFV-Fc, a microtubule associated protein specific reagent, as a negative control), a "cell based ELISA" was performed using 293-PD-L1. The affinity of 38A1-scFV-Fc (EC50=0.1248) was observed to be 3.2 fold greater than that for 19H9-scFV-Fc (EC50=0.4039; FIG. 5).

Jurak T-cells were transduced with lentivirus encoding either 38A1-scFV-Fc, 19H9-scFV-Fc or FMC63-scFV-Fc. 293-PD-L1 were co-cultured at a ratio of 1:1 for 16 hours with Jurkat T-cells stably secreting 38A1-scFV-Fc, 19H9-scFV-Fc or FMC63-scFV-Fc. We found that 38A1-scFV-Fc, 19H9-scFV-Fc but not FMC63-scFV-Fc bound to 293-PD-L1. Compared to 19H9-scFV-Fc, we observed greater than 1.5-fold enhanced binding of 38A1-scFV-Fc to 293-PD-L1 (FIG. 5). This result was consistent with a greater affinity of 38A1-scFV-Fc compared to 19H9-scFV-Fc for PD-L1.

Figure 6:
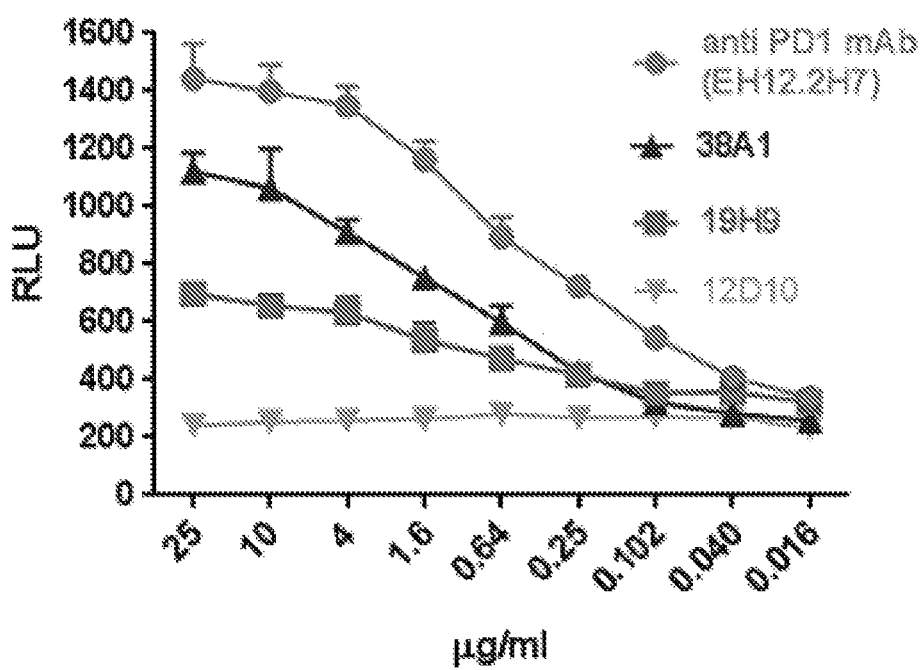
FIG. 6 provides data showing the capacity of anti-PD-L1 maxibodies to limit PD-L1 mediated inhibition of NFAT activity. Jurkat T-cells expressing PD1 and firefly luciferase downstream of the NFAT promoter were co-cultured at a 2:1 ratio with CHO cells expressing PD-L1 and a proprietary T-cell agonistic protein (PD1/PD-L1 Blockade Bioassay Kit, Promega catalog number CS187111) and one of 12D10-seFV-Fe (negative control; grey), 19H9-seFV-Fe (red), 38A1-seFV-Fe (blue) or the positive control PD1 specific antibody EH12.2H7 (Biolegend; green). The maxibodies were titrated from 25 µg/ml to 0.016 µg/ml. Jukat T-cell activation (de-inhibition of PD-L1) was measured as bioluminescent activity (Relative Luminescent Units; RLU) following addition of 5'-Fluoroluciferin.

TIL lines M1034 and M1015 were transduced with lentivirus encoding either 38A1-scFV-Fc, 19H9-scFV-Fc or FMC63-scFV-Fc. After sorting for the eGFP co-reporter and expanding in-vitro, supernatants were collected from TIL secreting FMC63-scFV-Fc and 38A1-scFV-Fc, concentrated ten-fold and used to stain 293-PD-L1. Compared to the negative control maxibody (FMC63-scFV-Fc), we observed greater than a 50 fold in increase binding of 38A1-scFV-Fc to 293-PD-L1 (FIG. 6).

The capacity of 38A1-scFV-Fc and 19H9-scFV-Fc to relinquish inhibition of T-cell activity blocked by PD-L1 was next tested. To do so, 12D10-scFV-Fc (microtubule associated protein specific negative control), 19H9-scFV-Fc, and 38A1-scFV-Fc were added to a co-culture of Jurkat T-cells that produce firefly luciferase when activated and CHO cells engineered to activate T-cells but also inhibit such activation via over-expression of PD-L1 as described above. The addition of 38A1-scFV-Fc and 19H9-scFV-Fc but not 12D10-scFV-Fc to the Jurkat/CHO co-culture led to increased bioluminescent activity. In both cases, "de-inhibition" of PD-L1 was dose dependent. The capacity of 38A1-scFV-Fc to induce bioluminescent activity was greater than 3.6 fold that for 19H9-scFV-Fc, consistent with the observed 3.2-fold difference in affinity for PD-L1 (FIG. 7).

Example 2: Production of TILs Expressing the PD-L1 scFv

Viral Production
  Method steps:
  1) Plate 5×10$^6$ phoenix cells in 10 mm tissue culture plate containing 5 ml cell culture media
  2) Transfect cells with 10 ug pLEV (lentiviral vector) containing anti-PD-1 scFV and 6 ug pVSV-G using lipofectamine.
  3) After 60 hours, collect the supernatant and filter with 70 uM strainer into a 15 ml tube.
T-Cell Transduction
  Method steps:
  1) Activate 1×10$^6$ TIL with anti-CD3 at concentration of 300 ng/ml in 2 ml TIL culture media in 12-well-plate.
  2) After 48 hours, split TIL into two well and add 1 ml of supernatant (from step 3 in viral production) into each well together with polybrene at a concentration of 8 ug/ml.
  3) Centrifuge cells for 30 minutes at 800×g at 32 C.
  4) Remove virus containing medium and resuspend cell pellet with 2 ml of fresh complete culture media, and incubate the cells for 24 hours.
  5) Propagate the cells using Rapid Expansion Protocol (REP).

Example 3: Characterization of 19H9 and 38A1

Figure 13A:
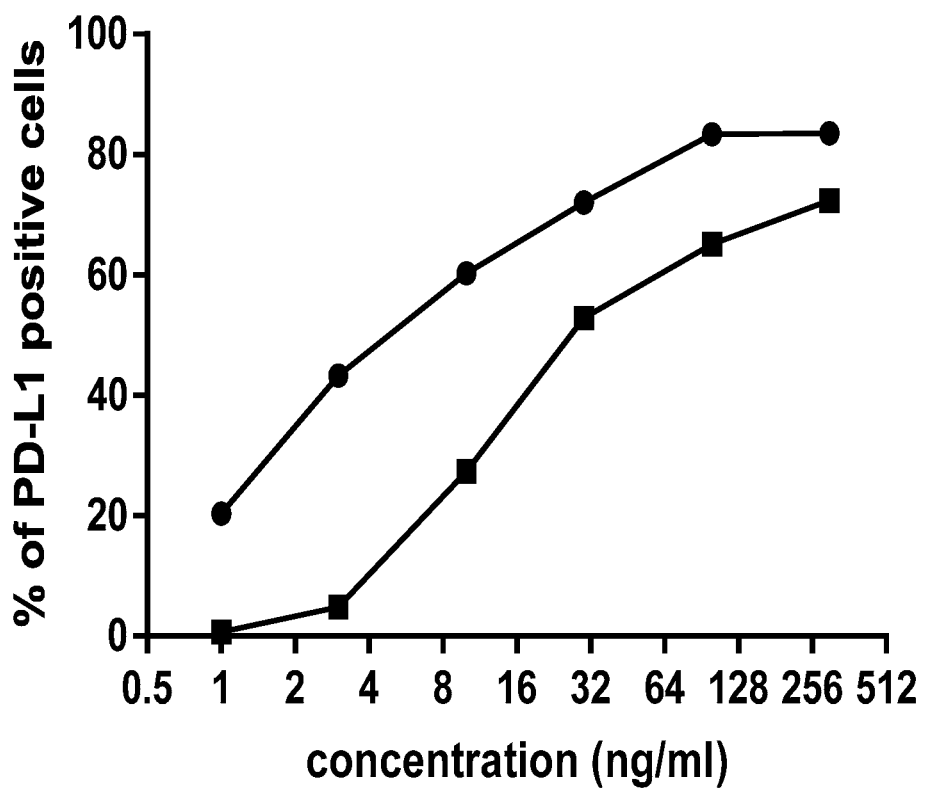
FIG. 13A-13B provides data showing that 38A1 exhibits greater binding capacity in Jurkat cells overexpressing PD-L1. The binding affinity of anti-PD-L1 ScFV clone 19H9 and 38A1 using EL4 PD-L1 cells was examined. EL4 PD-L1 were incubated with either anti-PD-L1 ScFV clone 19H9 or 38A1 at concentration of 1, 3, 10, 30, 100, and 300 ng/ml, and stained with Amcyan and goat anti-human FITC. The cells were washed with FACs buffer and analyzed by flow cytometry. Clone 38A1 exhibited greater binding capacity in Jurkat cells overexpressing PD-L1 in both the percentage of PD-L1 positive cells (A) and Mean of Fluorescence Intensity (MFI) (B).
Figure 13B:
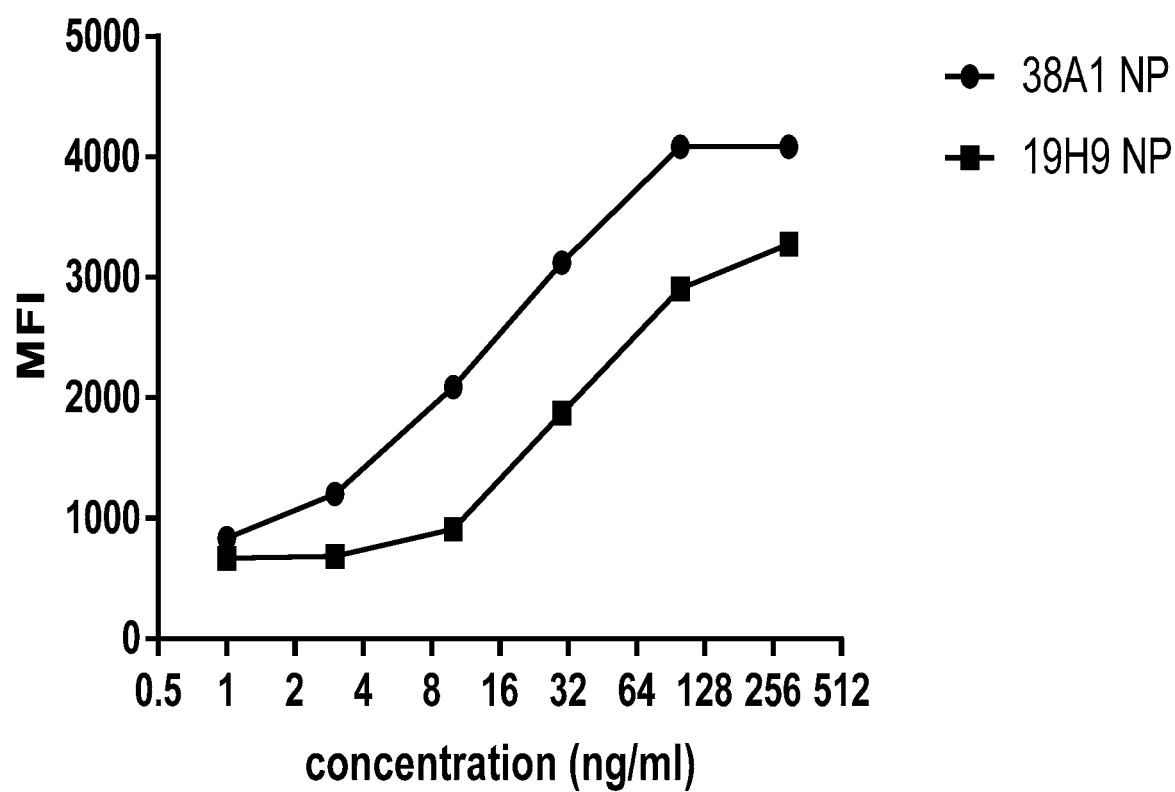
Figure 14A:
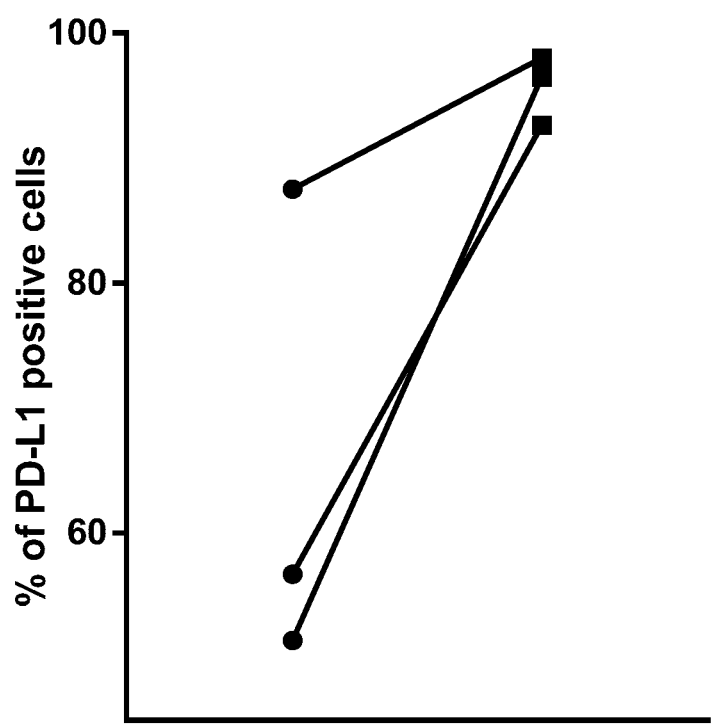
FIG. 14A-14B provides data showing that 38A1 exhibits greater binding capacity in melanoma tumor cells. A comparison of the binding affinity of anti-PD-L1 ScFV clone 19H9 and 38A1 using EL4 PD-L1 cells is provided. EL4 PD-L1 were incubated with either anti-PD-L1 ScFV clone 19H9 or 38A1 at concentration of 1, 3, 10, 30, 100, and 300 ng/ml, and stained with Amcyan and goat anti-human FITC. The cells were washed with FACs buffer and analyzed by flow cytometry. Clone 38A1 exhibited greater binding capacity in Jurkat cells overexpressing PD-L1 in both the percentage of PD-L1 positive cells (A) and Mean of Fluorescence Intensity (MFI) (B). To validate the binding of anti-PD-L1 ScFV in tumor cells, three melanoma tumor cells were treated with IFN-gamma (100 ng/ml) to enhance PD-L1 expression. After three days, the cells were harvested with cell dissociation buffer, incubated with either anti-PD-L1 ScFV clone 19H9 or 38A1 at concentration of 100 ng/ml, and stained with goat anti-human FITC. The cells were washed with FACs buffer and analyzed by flow cytometry. We found that clone 38A1 exhibited greater binding affinity in both the percentage of PD-L1 positive cells and MFI. Overall, clone 38A1 has greater binding affinity, but slightly less secretion capacity when compared to Clone 19H9.
Figure 14B:
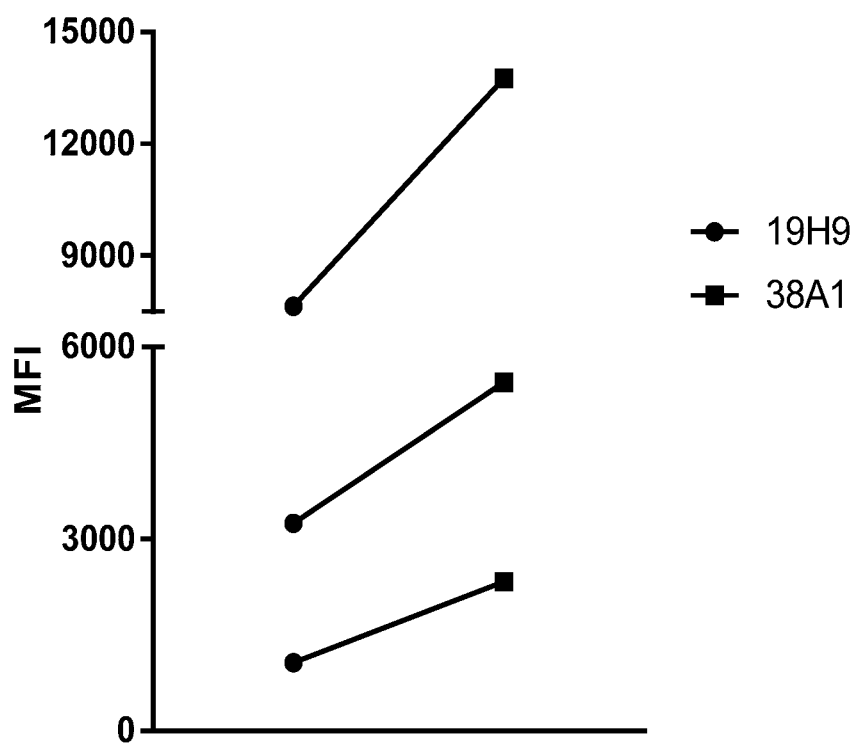
Figure 15A:
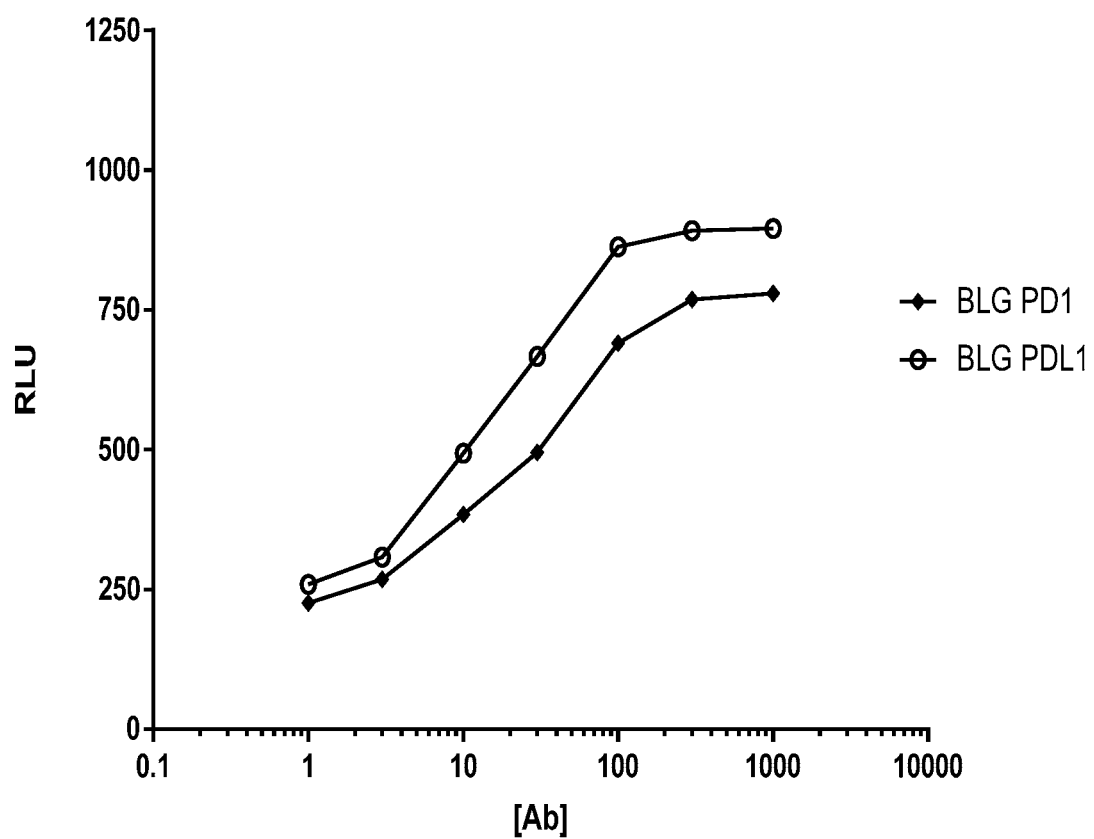
FIG. 15A-15B provides data showing that 38A1 exhibits greater biological function than 19H9. To further determine the biological function of two clones of anti-PD-L1 ScFV (19H9 and 38A1), a PD-L1 blockade assay was conducted, which can be used to determine the potency of either anti PD-1 or PD-L1 antibody that block the engagement of PD-1 and PD-L1 interaction. The assay consists of two genetically engineered cell lines: PD-1 effector cell (Jurkat T-cells stably expressing human PD-1 and NFAT-induced luciferase) and PD-L1 aAPC/CHO-K1 Cells stably expressing human PD-L1 with a cell surface protein activating cognate TCRs. When two cell types were co-cultured, the engagement of PD-1 and PD-L1 inhibited TCR signaling and decreased luciferase activity. Addition of either anti-PD-1 or PD-L1 blockade antibody helped release the inhibitory signal, resulting in enhanced TCR signaling and NFAT-mediated luciferase activity. Luciferase signal (RLU) was found to be greater when blocked with anti-PD-L1 as compared to anti-PD1, suggesting that blocking PD-L1 seemed to be more effective than PD-1 in this context (A). Expectedly, anti-PD-L1 ScFV clone 38A1, which previously shown to have greater binding affinity, provided greater biological function due to highly increased in luciferase signal in both purified ScFV (P) and non-purified (NP) settings (B).
Figure 15B:
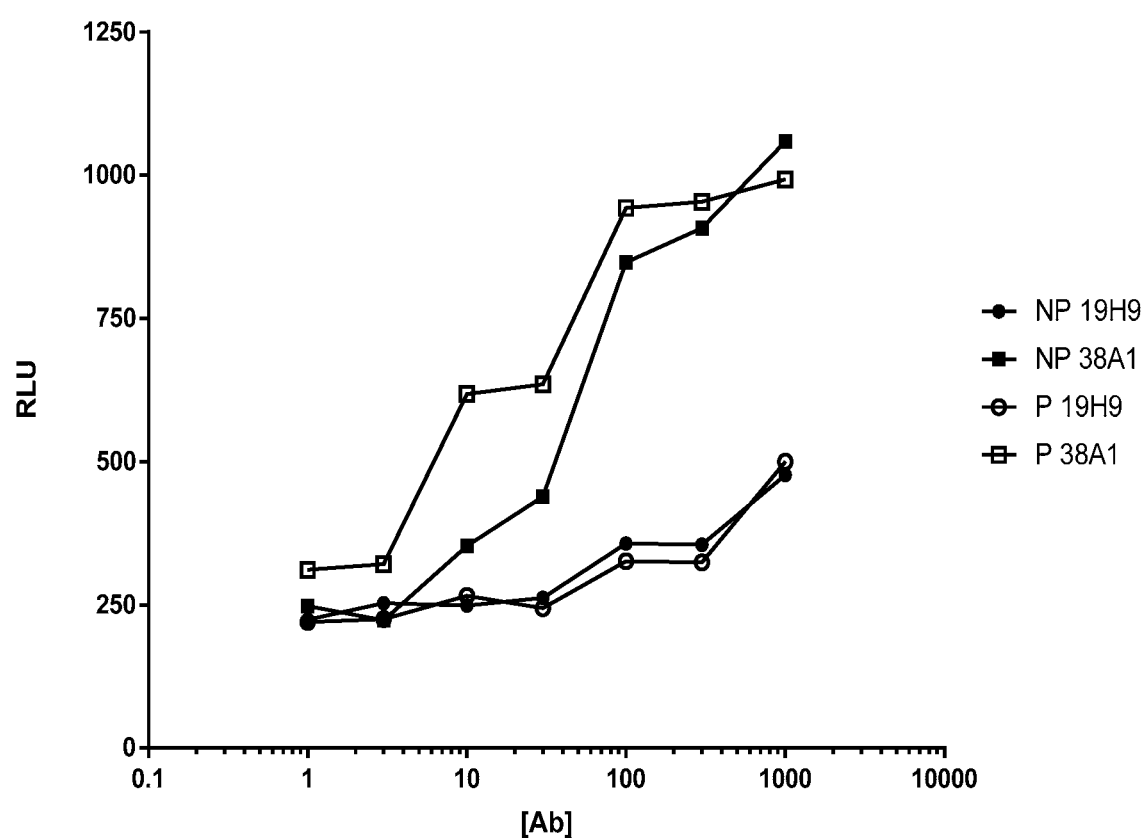

19H9 Exhibits Greater Secretion Capacity
  Goal: To compare secretion capacity of Jurkat cells overexpressing anti-PD-L1 ScFV clone 19H9 versus 38A1.
  Overall, 19H9 exhibits greater secretion capacity. A comparison of the secretion capacity of Jurkat cells overexpressing anti-PD-L1 ScFV clone 19H9 versus 38A1 is provided in FIG. 12. Supernatant from Jurkat cells overexpressing anti-PD-L1 ScFV clone 19H9 and 38A1 were harvested and concentrated for IgG ELISA assay to determine the anti-PD-L1 ScFV concentration. It was found that Jurkat cells clone 19H9 had greater secretion capacity as compared with 38A1 (9.82 versus 6.75 µg/cells).
38A1 Exhibits Greater Binding Capacity in Jurkat Cells Overexpressing PD-L1
  Goal: To examine the binding affinity of anti-PD-L1 ScFV clone 19H9 and 38A1 using EL4 PD-L1 cells.
  Overall, 38A1 exhibits greater binding capacity in Jurkat cells overexpressing PD-L1. The binding affinity of anti-PD-L1 ScFV clone 19H9 and 38A1 using EL4 PD-L1 cells was examined (FIG. 13). EL4 PD-L1 were incubated with either anti-PD-L1 ScFV clone 19H9 or 38A1 at concentration of 1, 3, 10, 30, 100, and 300 ng/ml, and stained with Amcyan and goat anti-human FITC. The cells were washed with FACs buffer and analyzed by flow cytometry. Clone 38A1 exhibited greater binding capacity in Jurkat-cells overexpressing PD-L1 in both the percentage of PD-L1 positive cells (FIG. 13A) and Mean of Fluorescence Intensity (MFI) (FIG. 13B).
38A1 Exhibits Greater Binding Capacity in Melanoma Tumor Cells
  Goal: To validate the binding of anti-PD-L1 ScFV in tumor cells,
  Overall, 38A1 exhibits greater binding capacity in melanoma tumor cells. A comparison of the binding affinity of anti-PD-L1 ScFV clone 19H9 and 38A1 using EL4 PD-L1 cells is provided in FIG. 14. EL4 PD-L1 were incubated with either anti-PD-L1 ScFV clone 19H9 or 38A1 at concentration of 1, 3, 10, 30, 100, and 300 ng/ml, and stained with Amcyan and goat anti-human FITC. The cells were washed with FACs buffer and analyzed by flow cytometry. Clone 38A1 exhibited greater binding capacity in Jurkat cells overexpressing PD-L1 in both the percentage of PD-L1 positive cells (FIG. 14A) and Mean of Fluorescence Intensity (MFI) (FIG. 14B). To validate the binding of anti-PD-L1 ScFV in tumor cells, three melanoma tumor cells were treated with IFN-gamma (100 ng/ml) to enhance PD-L1 expression. After three days, the cells were harvested with cell dissociation buffer, incubated with either anti-PD-L1 ScFV clone 19H9 or 38A1 at concentration of 100 ng/ml, and stained with goat anti-human FITC. The cells were washed with FACs buffer and analyzed by flow cytometry. We found that clone 38A1 exhibited greater binding affinity in both the percentage of PD-L1 positive cells and MFI. Overall, clone 38A1 has greater binding affinity, but slightly less secretion capacity when compared to Clone 19H9.
38A1 Exhibits Greater Biological Function
  Goal: To further characterize the biological function of two clones of anti-PD-L1 ScFV (19H9 and 38A1).
  Overall, 38A1 exhibits greater biological function than 19H9. To further determine the biological function of two clones of anti-PD-L1 ScFV (19H9 and 38A1), a PD-L1 blockade assay was conducted, which can be used to determine the potency of either anti PD-1 or PD-L1 antibody that block the engagement of PD-1 and PD-L1 interaction (FIG. 15). The assay consists of two genetically engineered cell lines: PD-1 effector cell (Jurkat T-cells stably expressing human PD-1 and NFAT-induced luciferase) and PD-L1 aAPC/CHO-K1 Cells stably expressing human PD-L1 with a cell surface protein activating cognate TCRs. When two cell types were co-cultured, the engagement of PD-1 and PD-L1 inhibited TCR signaling and decreased luciferase activity. Addition of either anti-PD-1 or PD-L1 blockade antibody helped release the inhibitory signal, resulting in enhanced TCR signaling and NFAT-mediated luciferase activity. Luciferase signal (RLU) was found to be greater when blocked with anti-PD-L1 as compared to anti-PD-1, suggesting that blocking PD-L1 seemed to be more effective than PD-1 in this context (FIG. 15A). Expectedly, anti-PD-L1 ScFV clone 38A1, which previously shown to have greater binding affinity, provided greater biological function due to highly increased in luciferase signal in both purified ScFV (P) and non-purified (NP) settings (FIG. 15B).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the example embodiments shown and described herein. Rather, the scope and spirit of present invention is embodied by the appended claims.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A protein that specifically binds to PD-L1 and comprises an antigen binding portion that comprises:
   (a) a first polypeptide comprising the 3 CDR amino acid sequences set forth in SEQ ID NOs:2-4, and a second polypeptide comprising the 3 CDR amino acid sequences set forth in SEQ ID NOs:6-8; or
   (b) a first polypeptide comprising the 3 CDR amino acid sequences set forth in SEQ ID NOs: 10-12, and a second polypeptide comprising the 3 CDR amino acid sequences set forth in SEQ ID NOs: 14-16.

2. A nucleic acid comprising a nucleotide sequence encoding the protein of claim 1.

3. A cell comprising the nucleic acid of claim 2.

4. A method comprising:
   genetically modifying a cytotoxic lymphocyte isolated from a tumor of a subject by introducing into the cytotoxic lymphocyte the nucleic acid of claim 2, wherein the genetically modified cytotoxic lymphocyte expresses and secretes the protein that specifically binds to PD-L1;
   expanding the genetically modified cytotoxic lymphocyte to generate a population of genetically modified cytotoxic lymphocytes; and
   administering the population of genetically modified cytotoxic lymphocytes to the subject to treat the tumor.

5. The method of claim 4, wherein the genetically modified cytotoxic lymphocyte constitutively expresses the protein that specifically binds to PD-L1.

6. The method of claim 4, wherein the genetically modified cytotoxic lymphocyte inducibly expresses the protein that specifically binds to PD-L1.

7. The method of claim 4, wherein the nucleic acid integrates into the cytotoxic lymphocyte's genome.

8. The method of claim 4, wherein the cytotoxic lymphocyte is a T-cell.

9. The method of claim 8, wherein the T-cell is a CD8+ T-cell.

10. The method of claim 8, wherein the T-cell is a CD4+ T-helper cell.

11. The method of claim 4, wherein the cytotoxic lymphocyte is a natural killer (NK) cell.

12. The method of claim 4, wherein the genetically modified cytotoxic lymphocyte comprises a receptor specific for an antigen from the tumor.

13. The method of claim 4, comprising isolating the cytotoxic lymphocyte from the subject prior to the genetically modifying.

14. The method of claim 4, wherein said protein that specifically binds to PD-L1 and comprises an antigen binding portion that comprises:

(a) a first polypeptide comprising the 3 CDR amino acid sequences set forth in SEQ ID NOs:2-4, and a second polypeptide comprising the 3 CDR amino acid sequences set forth in SEQ ID NOs:6-8; or
(b) a first polypeptide comprising the 3 CDR amino acid sequences set forth in SEQ ID NOs: 10-12, and a second polypeptide comprising the 3 CDR amino acid sequences set forth in SEQ ID NOs: 14-16.

15. The method of claim 14, wherein said wherein the antigen binding portion comprises a first polypeptide comprising the 3 CDR amino acid sequences set forth in SEQ ID NOs:2-4, and a second polypeptide comprising the 3 CDR amino acid sequences set forth in SEQ ID NOs:6-8.

16. The method of claim 15, wherein the first polypeptide comprises the amino acid sequence set forth in SEQ ID NO:1, and the second polypeptide comprises the amino acid sequence set forth in SEQ ID NO:5.

17. The method of claim 14, wherein the antigen binding portion comprises a first polypeptide comprising the 3 CDR amino acid sequences set forth in SEQ ID NOs:10-12, and a second polypeptide comprising the 3 CDR amino acid sequences set forth in SEQ ID NOs:14-16.

18. The method of claim 17, wherein the first polypeptide comprises the amino acid sequence set forth in SEQ ID NO:9, and the second polypeptide comprises the amino acid sequence set forth in SEQ ID NO:13.

19. The method of claim 14, wherein the first polypeptide is a light chain, and the second polypeptide is a heavy chain.

20. The method of claim 14, wherein the protein is a single-chain antibody (scFv) and the first and second polypeptides are fused directly or via a linker to one another.

21. The method of claim 20, wherein the scFv comprises the amino acid sequence set forth in SEQ ID NO:17 or SEQ ID NO:19.

22. The method of claim 14, wherein the protein is a maxibody comprising an immunoglobulin Fc domain fused directly or via a linker to the antigen binding portion.

23. The method of claim 22, wherein the immunoglobulin Fc domain is an IgG1 Fc domain.

24. The method of claim 23, wherein the protein comprises the amino acid sequence set forth in SEQ ID NO:18 or SEQ ID NO:20.

25. A method of making a genetically modified cytotoxic lymphocyte, the method comprising:
genetically modifying a cytotoxic lymphocyte isolated from a subject having or suspected of having cancer by introducing into the cytotoxic lymphocyte the nucleic acid of claim 2, wherein the genetically modified cytotoxic lymphocyte expresses and secretes the protein that specifically binds to PD-L1.

26. A method of treating an individual who has or is suspected of having cancer, the method comprising:
administering the protein that specifically binds to PD-L1 according to claim 1 to the individual.

27. A method of reducing the interaction between PD-L1 on a first-cell and PD-1 on a second cell, the method comprising:
contacting PD-L1 on the first-cell with the protein of claim 1.

* * * * *

UNITED STATES PATENT AND TRADEMARK OFFICE
CERTIFICATE OF CORRECTION

Page 1 of 1

PATENT NO. : 11,141,434 B2
APPLICATION NO. : 16/316019
DATED : October 12, 2021
INVENTOR(S) : Rabinovich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Eighteenth Day of February, 2025

Coke Morgan Stewart
*Acting Director of the United States Patent and Trademark Office*

SEQUENCE LISTING

```
<160> NUMBER OF SEQ ID NOS: 42

<210> SEQ ID NO 1
<211> LENGTH: 108
<212> TYPE: PRT
<213> ORGANISM: Artificial Sequence
<220> FEATURE:
<223> OTHER INFORMATION: synthetic sequence

<400> SEQUENCE: 1

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Arg Lys Ile Val
            20                  25                  30

His Trp Tyr Gln Gln Arg Pro Gly Gln Ala Pro Val Leu Val Ile Tyr
        35                  40                  45

Tyr Asp Thr Asp Arg Pro Ala Gly Ile Pro Glu Arg Phe Ser Gly Ser
    50                  55                  60

Asn Ser Gly Asn Met Ala Thr Leu Thr Ile Ser Thr Val Gly Ala Gly
65                  70                  75                  80

Asp Glu Ala Asp Tyr Tyr Cys Gln Val Trp Asp Thr Gly Ser Asp His
                85                  90                  95

Val Val Phe Gly Gly Gly Thr Lys Leu Thr Val Leu
            100                 105

<210> SEQ ID NO 2
<211> LENGTH: 6
<212> TYPE: PRT
<213> ORGANISM: Artificial Sequence
<220> FEATURE:
<223> OTHER INFORMATION: synthetic sequence

<400> SEQUENCE: 2

Asn Ile Gly Arg Lys Ile
1               5
```

-continued

```
<210> SEQ ID NO 3
<211> LENGTH: 3
<212> TYPE: PRT
<213> ORGANISM: Artificial Sequence
<220> FEATURE:
<223> OTHER INFORMATION: synthetic sequence

<400> SEQUENCE: 3

Tyr Asp Thr
1

<210> SEQ ID NO 4
<211> LENGTH: 11
<212> TYPE: PRT
<213> ORGANISM: Artificial Sequence
<220> FEATURE:
<223> OTHER INFORMATION: synthetic sequence

<400> SEQUENCE: 4

Gln Val Trp Asp Thr Gly Ser Asp His Val Val
1               5                   10

<210> SEQ ID NO 5
<211> LENGTH: 122
<212> TYPE: PRT
<213> ORGANISM: Artificial Sequence
<220> FEATURE:
<223> OTHER INFORMATION: synthetic sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Trp Phe Arg Ser Ser Pro Ala Phe Asp Ile Trp
            100                 105                 110

Gly Gln Gly Thr Thr Val Thr Val Ser Ala
        115                 120

<210> SEQ ID NO 6
<211> LENGTH: 8
<212> TYPE: PRT
<213> ORGANISM: Artificial Sequence
<220> FEATURE:
<223> OTHER INFORMATION: synthetic sequence

<400> SEQUENCE: 6

Gly Phe Thr Phe Ser Asn Tyr Ala
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic sequence
```

```
<400> SEQUENCE: 7

Ile Ser Gly Ser Gly Gly Thr Thr
1               5

<210> SEQ ID NO 8
<211> LENGTH: 15
<212> TYPE: PRT
<213> ORGANISM: Artificial Sequence
<220> FEATURE:
<223> OTHER INFORMATION: synthetic sequence

<400> SEQUENCE: 8

Ala Lys Asp Trp Phe Arg Ser Ser Ser Pro Asp Ala Phe Asp Ile
1               5                   10                  15

<210> SEQ ID NO 9
<211> LENGTH: 110
<212> TYPE: PRT
<213> ORGANISM: Artificial Sequence
<220> FEATURE:
<223> OTHER INFORMATION: synthetic sequence

<400> SEQUENCE: 9

Asn Phe Met Leu Thr Gln Pro His Ser Val Ser Glu Ser Leu Gly Lys
1               5                   10                  15

Thr Val Thr Ile Ser Cys Thr Gly Ser Ser Ser Ile Ala Arg Lys
            20                  25                  30

Phe Val Gln Trp Tyr Gln Gln Arg Pro Gly Ser Ser Pro Thr Thr Val
        35                  40                  45

Ile Tyr Glu Asn Asn Gln Arg Pro Ser Gly Val Ser Asp Arg Phe Ser
    50                  55                  60

Gly Ser Ile Gly Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Val Thr Val Leu
            100                 105                 110

<210> SEQ ID NO 10
<211> LENGTH: 8
<212> TYPE: PRT
<213> ORGANISM: Artificial Sequence
<220> FEATURE:
<223> OTHER INFORMATION: synthetic sequence

<400> SEQUENCE: 10

Ser Gly Ser Ile Ala Arg Lys Phe
1               5

<210> SEQ ID NO 11
<211> LENGTH: 3
<212> TYPE: PRT
<213> ORGANISM: Artificial Sequence
<220> FEATURE:
<223> OTHER INFORMATION: synthetic sequence

<400> SEQUENCE: 11

Glu Asn Asn
1

<210> SEQ ID NO 12
<211> LENGTH: 9
```

```
<212> TYPE: PRT
<213> ORGANISM: Artificial Sequence
<220> FEATURE:
<223> OTHER INFORMATION: synthetic sequence

<400> SEQUENCE: 12

Gln Ser Tyr Asp Ser Ser Asn Val Val
1               5

<210> SEQ ID NO 13
<211> LENGTH: 123
<212> TYPE: PRT
<213> ORGANISM: Artificial Sequence
<220> FEATURE:
<223> OTHER INFORMATION: synthetic sequence

<400> SEQUENCE: 13

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Gly Ile Asn Thr Ala Gly Asp Thr His Tyr Pro Glu Ser Val Lys
    50                  55                  60

Gly Arg Phe Thr Ile Ser Arg Asp Asn Ala Arg Asn Ser Leu Asn Leu
65                  70                  75                  80

Gln Met Asn Ser Leu Arg Ala Glu Asp Thr Ala Val Tyr Tyr Cys Val
                85                  90                  95

Arg Glu Arg Val Glu Arg Glu Tyr Ser Gly Tyr Asp Ala Phe Asp Ile
            100                 105                 110

Trp Gly Gln Gly Thr Thr Val Thr Val Ser Ala
        115                 120

<210> SEQ ID NO 14
<211> LENGTH: 8
<212> TYPE: PRT
<213> ORGANISM: Artificial Sequence
<220> FEATURE:
<223> OTHER INFORMATION: synthetic sequence

<400> SEQUENCE: 14

Gly Phe Thr Phe Ser Ser Tyr Ser
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic sequence

<400> SEQUENCE: 15

Ile Asn Thr Ala Gly Asp Thr
1               5

<210> SEQ ID NO 16
<211> LENGTH: 17
<212> TYPE: PRT
<213> ORGANISM: Artificial Sequence
<220> FEATURE:
<223> OTHER INFORMATION: synthetic sequence

<400> SEQUENCE: 16
```

```
Val Arg Glu Arg Val Glu Arg Glu Tyr Ser Gly Tyr Asp Ala Phe Asp
1               5                   10                  15

Ile

<210> SEQ ID NO 17
<211> LENGTH: 248
<212> TYPE: PRT
<213> ORGANISM: Artificial Sequence
<220> FEATURE:
<223> OTHER INFORMATION: synthetic sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Trp Phe Arg Ser Ser Pro Asp Ala Phe Asp Ile Trp
            100                 105                 110

Gly Gln Gly Thr Thr Val Thr Val Ser Ala Gly Gly Gly Ser Gly
            115                 120                 125

Gly Gly Gly Ser Gly Gly Gly Ser Gly Ala Pro Ser Tyr Val Leu
        130                 135                 140

Thr Gln Pro Pro Ser Val Ser Val Ala Pro Gly Gln Thr Ala Arg Ile
145                 150                 155                 160

Thr Cys Gly Gly Asn Asn Ile Gly Arg Lys Ile Val His Trp Tyr Gln
                165                 170                 175

Gln Arg Pro Gly Gln Ala Pro Val Leu Val Ile Tyr Tyr Asp Thr Asp
            180                 185                 190

Arg Pro Ala Gly Ile Pro Glu Arg Phe Ser Gly Ser Asn Ser Gly Asn
        195                 200                 205

Met Ala Thr Leu Thr Ile Ser Thr Val Gly Ala Gly Asp Glu Ala Asp
    210                 215                 220

Tyr Tyr Cys Gln Val Trp Asp Thr Gly Ser Asp His Val Val Phe Gly
225                 230                 235                 240

Gly Gly Thr Lys Leu Thr Val Leu
                245

<210> SEQ ID NO 18
<211> LENGTH: 511
<212> TYPE: PRT
<213> ORGANISM: Artificial Sequence
<220> FEATURE:
<223> OTHER INFORMATION: synthetic sequence

<400> SEQUENCE: 18

Met Gly Ser Thr Ala Ile Leu Ala Leu Leu Leu Ala Val Leu Gln Gly
1               5                   10                  15

Val Ser Ala Glu Val Gln Leu Val Glu Ser Gly Gly Gly Leu Val Gln
            20                  25                  30
```

-continued

```
Pro Gly Gly Ser Leu Arg Leu Ser Cys Ala Ala Ser Gly Phe Thr Phe
        35                  40                  45
Ser Asn Tyr Ala Met Ser Trp Val Arg Gln Ala Pro Gly Lys Gly Leu
    50                  55                  60
Glu Trp Val Ser Thr Ile Ser Gly Ser Gly Gly Thr Thr Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Val Glu Asp Thr Ala Val
            100                 105                 110
Tyr Tyr Cys Ala Lys Asp Trp Phe Arg Ser Ser Pro Asp Ala Phe
            115                 120                 125
Asp Ile Trp Gly Gln Gly Thr Thr Val Thr Val Ser Ala Gly Gly Gly
        130                 135                 140
Gly Ser Gly Gly Gly Gly Ser Gly Gly Gly Gly Ser Gly Ala Pro Ser
145                 150                 155                 160
Tyr Val Leu Thr Gln Pro Pro Ser Val Ser Val Ala Pro Gly Gln Thr
                165                 170                 175
Ala Arg Ile Thr Cys Gly Gly Asn Asn Ile Gly Arg Lys Ile Val His
            180                 185                 190
Trp Tyr Gln Gln Arg Pro Gly Gln Ala Pro Val Leu Val Ile Tyr Tyr
            195                 200                 205
Asp Thr Asp Arg Pro Ala Gly Ile Pro Glu Arg Phe Ser Gly Ser Asn
        210                 215                 220
Ser Gly Asn Met Ala Thr Leu Thr Ile Ser Thr Val Gly Ala Gly Asp
225                 230                 235                 240
Glu Ala Asp Tyr Tyr Cys Gln Val Trp Asp Thr Gly Ser Asp His Val
                245                 250                 255
Val Phe Gly Gly Gly Thr Lys Leu Thr Val Leu Gly Pro Arg Ala Asn
            260                 265                 270
Phe Val Tyr Lys Ser Gly Pro Arg Pro Lys Ser Cys Asp Lys Thr His
            275                 280                 285
Thr Cys Pro Pro Cys Pro Ala Pro Glu Leu Leu Gly Gly Pro Ser Val
        290                 295                 300
Phe Leu Phe Pro Pro Lys Pro Lys Asp Thr Leu Met Ile Ser Arg Thr
305                 310                 315                 320
Pro Glu Val Thr Cys Val Val Asp Val Ser His Glu Asp Pro Glu
                325                 330                 335
Val Lys Phe Asn Trp Tyr Val Asp Gly Val Glu Val His Asn Ala Lys
            340                 345                 350
Thr Lys Pro Arg Glu Glu Gln Tyr Asn Ser Thr Tyr Arg Val Val Ser
            355                 360                 365
Val Leu Thr Val Leu His Gln Asp Trp Leu Asn Gly Lys Glu Tyr Lys
        370                 375                 380
Cys Lys Val Ser Asn Lys Ala Leu Pro Ala Pro Ile Glu Lys Thr Ile
385                 390                 395                 400
Ser Lys Ala Lys Gly Gln Pro Arg Glu Pro Gln Val Tyr Thr Leu Pro
                405                 410                 415
Pro Ser Arg Glu Glu Met Thr Lys Asn Gln Val Ser Leu Thr Cys Leu
            420                 425                 430
Val Lys Gly Phe Tyr Pro Ser Asp Ile Ala Val Glu Trp Glu Ser Asn
            435                 440                 445
```

```
Gly Gln Pro Glu Asn Asn Tyr Lys Thr Thr Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys
            500                 505                 510

<210> SEQ ID NO 19
<211> LENGTH: 251
<212> TYPE: PRT
<213> ORGANISM: Artificial Sequence
<220> FEATURE:
<223> OTHER INFORMATION: synthetic sequence

<400> SEQUENCE: 19

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Gly Ile Asn Thr Ala Gly Asp Thr His Tyr Pro Glu Ser Val Lys
50                  55                  60

Gly Arg Phe Thr Ile Ser Arg Asp Asn Ala Arg Asn Ser Leu Asn Leu
65                  70                  75                  80

Gln Met Asn Ser Leu Arg Ala Glu Asp Thr Ala Val Tyr Tyr Cys Val
                85                  90                  95

Arg Glu Arg Val Glu Arg Glu Tyr Ser Gly Tyr Asp Ala Phe Asp Ile
            100                 105                 110

Trp Gly Gln Gly Thr Thr Val Thr Val Ser Ala Gly Gly Gly Gly Ser
        115                 120                 125

Gly Gly Gly Gly Ser Gly Gly Gly Ser Gly Ala Pro Asn Phe Met
    130                 135                 140

Leu Thr Gln Pro His Ser Val Ser Glu Ser Leu Gly Lys Thr Val Thr
145                 150                 155                 160

Ile Ser Cys Thr Gly Ser Ser Gly Ser Ile Ala Arg Lys Phe Val Gln
                165                 170                 175

Trp Tyr Gln Gln Arg Pro Gly Ser Ser Pro Thr Thr Val Ile Tyr Glu
            180                 185                 190

Asn Asn Gln Arg Pro Ser Gly Val Ser Asp Arg Phe Ser Gly Ser Ile
        195                 200                 205

Gly Ser Ser Ser Asn Ser Ala Ser Leu Thr Ile Ser Gly Leu Lys Thr
    210                 215                 220

Glu Asp Glu Ala Asp Tyr Tyr Cys Gln Ser Tyr Asp Ser Ser Asn Val
225                 230                 235                 240

Val Phe Gly Gly Gly Thr Lys Val Thr Val Leu
                245                 250

<210> SEQ ID NO 20
<211> LENGTH: 514
<212> TYPE: PRT
<213> ORGANISM: Artificial Sequence
<220> FEATURE:
<223> OTHER INFORMATION: synthetic sequence

<400> SEQUENCE: 20
```

-continued

```
Met Gly Ser Thr Ala Ile Leu Ala Leu Leu Ala Val Leu Gln Gly
1               5                   10                  15

Val Ser Ala Gln Val Gln Leu Gln Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Gly Ile Asn Thr Ala Gly Asp Thr His Tyr Pro Glu
65                  70                  75                  80

Ser Val Lys Gly Arg Phe Thr Ile Ser Arg Asp Asn Ala Arg Asn Ser
                85                  90                  95

Leu Asn Leu Gln Met Asn Ser Leu Arg Ala Glu Asp Thr Ala Val Tyr
                100                 105                 110

Tyr Cys Val Arg Glu Arg Val Glu Arg Glu Tyr Ser Gly Tyr Asp Ala
            115                 120                 125

Phe Asp Ile Trp Gly Gln Gly Thr Thr Val Thr Val Ser Ala Gly Gly
        130                 135                 140

Gly Gly Ser Gly Gly Gly Ser Gly Gly Gly Ser Gly Ala Pro
145                 150                 155                 160

Asn Phe Met Leu Thr Gln Pro His Ser Val Ser Glu Ser Leu Gly Lys
                165                 170                 175

Thr Val Thr Ile Ser Cys Thr Gly Ser Ser Gly Ser Ile Ala Arg Lys
            180                 185                 190

Phe Val Gln Trp Tyr Gln Gln Arg Pro Gly Ser Ser Pro Thr Thr Val
            195                 200                 205

Ile Tyr Glu Asn Asn Gln Arg Pro Ser Gly Val Ser Asp Arg Phe Ser
        210                 215                 220

Gly Ser Ile Gly Ser Ser Asn Ser Ala Ser Leu Thr Ile Ser Gly
225                 230                 235                 240

Leu Lys Thr Glu Asp Glu Ala Asp Tyr Tyr Cys Gln Ser Tyr Asp Ser
                245                 250                 255

Ser Asn Val Val Phe Gly Gly Gly Thr Lys Val Thr Val Leu Gly Pro
            260                 265                 270

Arg Ala Asn Phe Val Tyr Lys Ser Gly Pro Arg Pro Lys Ser Cys Asp
            275                 280                 285

Lys Thr His Thr Cys Pro Pro Cys Pro Ala Pro Glu Leu Leu Gly Gly
        290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415
```

```
Thr Leu Pro Pro Ser Arg Glu Glu Met Thr Lys Asn Gln Val Ser Leu
            420                 425                 430

Thr Cys Leu Val Lys Gly Phe Tyr Pro Ser Asp Ile Ala Val Glu Trp
        435                 440                 445

Glu Ser Asn Gly Gln Pro Glu Asn Asn Tyr Lys Thr Thr Pro Pro Val
    450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Gly Lys

<210> SEQ ID NO 21
<211> LENGTH: 290
<212> TYPE: PRT
<213> ORGANISM: Artificial Sequence
<220> FEATURE:
<223> OTHER INFORMATION: synthetic sequence

<400> SEQUENCE: 21

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
```

```
                    260                 265                 270
Gly Ile Gln Asp Thr Asn Ser Lys Lys Gln Ser Asp Thr His Leu Glu
            275                 280                 285

Glu Thr
    290

<210> SEQ ID NO 22
<211> LENGTH: 228
<212> TYPE: PRT
<213> ORGANISM: Artificial Sequence
<220> FEATURE:
<223> OTHER INFORMATION: synthetic sequence

<400> SEQUENCE: 22

Cys Pro Pro Cys Pro Ala Pro Glu Phe Glu Gly Gly Pro Ser Val Phe
1               5                   10                  15

Leu Phe Pro Pro Lys Pro Lys Asp Thr Leu Met Glu Thr Ile Ser Arg
            20                  25                  30

Thr Pro Glu Val Thr Cys Val Val Val Asp Val Ser Gln Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Gln Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Gln Glu Glu Met Glu Thr Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Arg Leu Thr Val Asp
            180                 185                 190

Lys Ser Arg Trp Gln Glu Gly Asn Val Phe Ser Cys Ser Val Met Glu
        195                 200                 205

Thr His Glu Ala Leu His Asn His Tyr Thr Gln Lys Ser Leu Ser Leu
    210                 215                 220

Ser Leu Gly Lys
225

<210> SEQ ID NO 23
<211> LENGTH: 228
<212> TYPE: PRT
<213> ORGANISM: Artificial Sequence
<220> FEATURE:
<223> OTHER INFORMATION: synthetic sequence

<400> SEQUENCE: 23

Cys Pro Pro Cys Pro Ala Pro Glu Phe Glu Gly Gly Pro Ser Val Phe
1               5                   10                  15

Leu Phe Pro Pro Lys Pro Lys Asp Thr Leu Met Glu Thr Ile Ser Arg
            20                  25                  30
```

Thr Pro Glu Val Thr Cys Val Val Asp Val Ser Gln Glu Asp Pro
                35                  40                  45

Glu Val Gln Phe Asn Trp Tyr Val Asp Gly Val Glu Val His Asn Ala
 50                  55                  60

Lys Thr Lys Pro Arg Glu Gln Phe Gln Ser Thr Tyr Arg Val Val
 65                  70                  75                  80

Ser Val Leu Thr Val Leu His Gln Asp Trp Leu Asn Gly Lys Glu Tyr
                85                  90                  95

Lys Cys Lys Val Ser Asn Lys Gly Leu Pro Ser Ser Ile Glu Lys Thr
                100                 105                 110

Ile Ser Lys Ala Lys Gly Gln Pro Arg Glu Pro Gln Val Tyr Thr Leu
                115                 120                 125

Pro Pro Ser Gln Glu Glu Met Glu Thr Thr Lys Asn Gln Val Ser Leu
 130                 135                 140

Thr Cys Leu Val Lys Gly Phe Tyr Pro Ser Asp Ile Ala Val Glu Trp
 145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Arg Leu Thr Val Asp
                180                 185                 190

Lys Ser Arg Trp Gln Glu Gly Asn Val Phe Ser Cys Ser Val Met Glu
                195                 200                 205

Thr His Glu Ala Leu His Asn His Tyr Thr Gln Lys Ser Leu Ser Leu
 210                 215                 220

Ser Leu Gly Lys
225

<210> SEQ ID NO 24
<211> LENGTH: 46
<212> TYPE: PRT
<213> ORGANISM: Artificial Sequence
<220> FEATURE:
<223> OTHER INFORMATION: synthetic sequence

<400> SEQUENCE: 24

Arg Ser Gly Ser Ser Arg Met Glu Thr Lys Gln Ile Glu Asp Lys Ile
 1               5                  10                  15

Glu Glu Ile Leu Ser Lys Ile Tyr His Ile Glu Asn Glu Ile Ala Arg
                20                  25                  30

Ile Lys Lys Leu Ile Gly Glu Arg Gly Thr Ser Ser Arg Gly
                35                  40                  45

<210> SEQ ID NO 25
<211> LENGTH: 189
<212> TYPE: PRT
<213> ORGANISM: Artificial Sequence
<220> FEATURE:
<223> OTHER INFORMATION: synthetic sequence

<400> SEQUENCE: 25

Ala Ser Ser Ile Val Tyr Lys Lys Glu Gly Glu Gln Val Glu Phe Ser
 1               5                  10                  15

Phe Pro Leu Ala Phe Thr Val Glu Lys Leu Thr Gly Ser Gly Glu Leu
                20                  25                  30

Trp Trp Gln Ala Glu Arg Ala Ser Ser Lys Ser Trp Ile Thr Phe
                35                  40                  45

Asp Leu Lys Asn Lys Glu Val Ser Val Lys Arg Val Thr Gln Asp Pro
 50                  55                  60

```
Lys Leu Gln Met Glu Thr Gly Lys Lys Leu Pro Leu His Leu Thr Leu
 65                  70                  75                  80

Pro Gln Ala Leu Pro Gln Tyr Ala Gly Ser Gly Asn Leu Thr Leu Ala
                 85                  90                  95

Leu Glu Ala Lys Thr Gly Lys Leu His Gln Glu Val Asn Leu Val Val
            100                 105                 110

Met Glu Thr Arg Ala Thr Gln Leu Gln Lys Asn Leu Thr Cys Glu Val
        115                 120                 125

Trp Gly Pro Thr Ser Pro Lys Leu Met Glu Thr Leu Ser Leu Lys Leu
130                 135                 140

Glu Asn Lys Glu Ala Lys Val Ser Lys Arg Glu Lys Ala Val Trp Val
145                 150                 155                 160

Leu Asn Pro Glu Ala Gly Met Glu Thr Trp Gln Cys Leu Leu Ser Asp
                165                 170                 175

Ser Gly Gln Val Leu Leu Glu Ser Asn Ile Lys Val Leu
            180                 185

<210> SEQ ID NO 26
<211> LENGTH: 28
<212> TYPE: PRT
<213> ORGANISM: Artificial Sequence
<220> FEATURE:
<223> OTHER INFORMATION: synthetic sequence

<400> SEQUENCE: 26

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 27
<211> LENGTH: 450
<212> TYPE: PRT
<213> ORGANISM: Artificial Sequence
<220> FEATURE:
<223> OTHER INFORMATION: synthetic sequence

<400> SEQUENCE: 27

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
```

```
            145                 150                 155                 160
Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 28
<211> LENGTH: 213
<212> TYPE: PRT
<213> ORGANISM: Artificial Sequence
<220> FEATURE:
<223> OTHER INFORMATION: synthetic sequence

<400> SEQUENCE: 28

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
```

```
                50                  55                  60
Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg Ala Asp Thr Ala Pro
                100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 29
<211> LENGTH: 134
<212> TYPE: PRT
<213> ORGANISM: Artificial Sequence
<220> FEATURE:
<223> OTHER INFORMATION: synthetic sequence

<400> SEQUENCE: 29

Met Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
                20                  25                  30

Lys Asn Pro Lys Leu Thr Arg Met Leu Thr Phe Lys Phe Tyr Met Pro
            35                  40                  45

Lys Lys Ala Thr Glu Leu Lys His Leu Gln Cys Leu Glu Glu Glu Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
            130

<210> SEQ ID NO 30
<211> LENGTH: 132
<212> TYPE: PRT
<213> ORGANISM: Artificial Sequence
<220> FEATURE:
<223> OTHER INFORMATION: synthetic sequence

<400> SEQUENCE: 30
```

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
                115                 120                 125

Ser Thr Leu Thr
        130

<210> SEQ ID NO 31
<211> LENGTH: 130
<212> TYPE: PRT
<213> ORGANISM: Artificial Sequence
<220> FEATURE:
<223> OTHER INFORMATION: synthetic sequence

<400> SEQUENCE: 31

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
            35                  40                  45

Ala Ala Thr Val Leu Arg Gln Phe Tyr Ser His His Glu Lys Asp Thr
        50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
                115                 120                 125

Ser Ser
    130

<210> SEQ ID NO 32
<211> LENGTH: 153
<212> TYPE: PRT
<213> ORGANISM: Artificial Sequence
<220> FEATURE:
<223> OTHER INFORMATION: synthetic sequence

<400> SEQUENCE: 32

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30
```

```
Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
 50                  55                  60

Arg Gln Phe Leu Lys Met Asn Ser Thr Gly Asp Phe Asp Leu His Leu
 65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
                100                 105                 110

Ser Leu Glu Glu Asn Lys Ser Leu Lys Glu Gln Lys Lys Leu Asn Asp
                115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 33
<211> LENGTH: 115
<212> TYPE: PRT
<213> ORGANISM: Artificial Sequence
<220> FEATURE:
<223> OTHER INFORMATION: synthetic sequence

<400> SEQUENCE: 33

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
                20                  25                  30

His Pro Ser Cys Lys Val Thr Ala Met Lys Cys Phe Leu Leu Glu Leu
            35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
                100                 105                 110

Asn Thr Ser
        115

<210> SEQ ID NO 34
<211> LENGTH: 132
<212> TYPE: PRT
<213> ORGANISM: Artificial Sequence
<220> FEATURE:
<223> OTHER INFORMATION: synthetic sequence

<400> SEQUENCE: 34

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
                20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
```

```
                50                  55                  60
Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130

<210> SEQ ID NO 35
<211> LENGTH: 8449
<212> TYPE: DNA
<213> ORGANISM: Artificial Sequence
<220> FEATURE:
<223> OTHER INFORMATION: pLV430G (Lentiviral Vector)

<400> SEQUENCE: 35
cgataaccct aattcgatag catatgcttc ccgttgggta acatatgcta ttgaattagg    60
gttagtctgg atagtatata ctactacccg ggaagcatat gctacccgtt tagggttcac   120
cggtgatgcc ggccacgatg cgtccggcgt agaggatcta atgtgagtta gctcactcat   180
taggcacccc aggctttaca ctttatgctt ccggctcgta tgttgtgtgg aattgtgagc   240
ggataacaat ttcacacagg aaacagctat gaccatgatt acgccaagcg cgcaattaac   300
cctcactaaa gggaacaaaa gctggagctg caagcttaat gtagtcttat gcaatactct   360
tgtagtcttg caacatggta acgatgagtt agcaacatgc cttacaagga gagaaaaagc   420
accgtgcatg ccgattggtg gaagtaaggt ggtacgatcg tgccttatta ggaaggcaac   480
agacgggtct gacatggatt ggacgaacca ctgaattgcc gcattgcaga gatattgtat   540
ttaagtgcct agctcgatac ataaacgggt ctctctggtt agaccagatc tgagcctggg   600
agctctctgg ctaactaggg aacccactgc ttaagcctca ataaagcttg ccttgagtgc   660
ttcaagtagt gtgtgcccgt ctgttgtgtg actctggtaa ctagagatcc ctcagaccct   720
tttagtcagt gtggaaaatc tctagcagtg gcgcccgaac agggacttga aagcgaaagg   780
gaaaccagag gagctctctc gacgcaggac tcggcttgct gaagcgcgca cggcaagagg   840
cgaggggcgg cgactggtga gtacgccaaa aattttgact agcggaggct agaaggagag   900
agatgggtgc gagagcgtca gtattaagcg gggagaatt  agatcgcgat gggaaaaaat   960
tcggttaagg ccaggggaa agaaaaaata taaattaaaa catatagtat gggcaagcag  1020
ggagctagaa cgattcgcag ttaatcctgg cctgttagaa acatcagaag gctgtagaca  1080
aatactggga cagctacaac catcccttca gacaggatca aagaactta gatcattata  1140 taatacagta gcaaccctct attgtgtgca tcaaaggata gagataaaag acaccaagga  1200
agctttagac aagatagagg aagagcaaaa caaaagtaag accaccgcac agcaagcggc  1260
cgctgatctt cagacctgga ggaggagata tgagggacaa ttggagaagt gaattatata  1320
aatataaagt agtaaaaatt gaaccattag gagtagcacc caccaaggca agagaagag  1380 tggtgcagag agaaaaaaga gcagtgggaa taggagcttt gttccttggg ttcttgggag  1440
cagcaggaag cactatgggc gcagcgtcaa tgacgctgac ggtacaggcc agacaattat  1500
tgtctggtat agtgcagcag cagaacaatt tgctgagggc tattgaggcg caacagcatc  1560
```

-continued

```
tgttgcaact cacagtctgg ggcatcaagc agctccaggc aagaatcctg gctgtggaaa    1620
gatacctaaa ggatcaacag ctcctggga tttggggttg ctctggaaaa ctcatttgca    1680
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaaccccga    2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280
ggggggaatg aaagaccca cctgtaggtt tggcaagcta gcttaagtaa cgccattttg    2340
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaacccct cactcggcgc gccagtcctc cgatagactg cgtcgcccgg gtaccgatat    2700
cacaagtttg tacaaaaaag ctgaacgaga acgtaaaat gatataaata tcaatatatt    2760
aaattagatt ttgcataaaa aacagactac ataatactgt aaaacacaac atatccagtc    2820
actatggcgg ccgcattagg caccccaggc tttacacttt atgcttccgg ctcgtataat    2880
gtgtggattt tgagttagga tccgtcgaga ttttcaggag ctaaggaagc taaaatggag    2940
aaaaaaatca ctggatatac caccgttgat atatcccaat ggcatcgtaa agaacatttt    3000
gaggcatttc agtcagttgc tcaatgtacc tataaccaga ccgttcagct ggatattacg    3060 gccttttttaa agaccgtaaa gaaaaataag cacaagtttt atccggcctt tattcacatt    3120
cttgcccgcc tgatgaatgc tcatccggaa ttccgtatgg caatgaaaga cggtgagctg    3180
gtgatatggg atagtgttca cccttgttac accgttttcc atgagcaaac tgaaacgttt    3240
tcatcgctct ggagtgaata ccacgacgat ttccggcagt ttctacacat atattcgcaa    3300
gatgtggcgt gttacggtga aaacctggcc tatttcccta aagggtttat tgagaatatg    3360 ttttcgtct cagccaatcc ctgggtgagt ttcaccagtt ttgatttaaa cgtggccaat    3420
atggacaact tcttcgcccc cgttttcacc atgggcaaat attatacgca aggcgacaag    3480
gtgctgatgc cgctggcgat tcaggttcat catgccgttt gtgatggctt ccatgtcggc    3540
agaatgctta atgaattaca acagtactgc gatgagtggc agggcgggc gtaaacgcgt    3600 ggatccggct tactaaaagc cagataacag tatgcgtatt tgcgcgctga ttttttgcggt    3660 ataagaatat atactgatat gtatacccga agtatgtcaa aaagaggtat gctatgaagc    3720
agcgtattac agtgacagtt gacagcgaca gctatcagtt gctcaaggca tatatgatgt    3780
caatatctcc ggtctggtaa gcacaaccat gcagaatgaa gcccgtcgtc tgcgtgccga    3840
acgctggaaa gcggaaaatc aggaagggat ggctgaggtc gcccggttta ttgaaatgaa    3900
cggctctttt gctgacgaga acaggggctg gtgaaatgca gtttaaggtt tacacctata    3960
```

```
aaagagagag ccgttatcgt ctgtttgtgg atgtacagag tgatattatt gacacgcccg    4020
ggcgacggat ggtgatcccc ctggccagtg cacgtctgct gtcagataaa gtctcccgtg    4080
aactttaccc ggtggtgcat atcggggatg aaagctggcg catgatgacc accgatatgg    4140
ccagtgtgcc ggtctccgtt atcggggaag aagtggctga tctcagccac cgcgaaaatg    4200
acatcaaaaa cgccattaac ctgatgttct ggggaatata aatgtcaggc tcccttatac    4260
acagccagtc tgcaggtcga ccatagtgac tggatatgtt gtgttttaca gtattatgta    4320
gtctgttttt tatgcaaaat ctaatttaat atattgatat ttatatcatt ttacgtttct    4380
cgttcagctt tcttgtacaa agtggtgatt cgagttaatt aagctagcct agtgccattt    4440
gttcagtggt tcgtagggct ttcccccact gtttggcttt cagttatatg gatgatgtgg    4500
tattgggggc caagtctgta cagcatcttg agtccctttt taccgctgtt accaattttc    4560
ttttgtcttt gggtatacat ttaaacccta acaaaacaaa gagatggggt tactctctaa    4620
attttatggg ttatgtcatt ggatgttatg ggtccttgcc acaagaacac atcatacaaa    4680
aaatcaaaga atgttttaga aaacttccta ttaacaggcc tattgattgg aaagtatgtc    4740
aacgaattgt gggtctttttg ggttttgctg ccccttttac acaatgtggt tatcctgcgt    4800
tgatgccttt gtatgcatgt attcaatcta agcaggcttt cactttctcg ccaacttaca    4860
aggcctttct gtgtaaacaa tacctgaacc tttaccccgt tgcccggcaa cggccaggtc    4920
tgtgccaagt gtttgctgac gcaacccca ctggctgggg cttggtcatg ggccatcagc    4980
gcatgcgtgg aaccttttcg gctcctctgc cgatccatac tgcggaactc ctagccgctt    5040
gttttgctcg cagcaggtct ggagcaaaca ttatcgggac tgataactct gttgtcctat    5100
cccgcaaata tacatcgttt ccatggctgc taggctgtgc tgccaactgg atcctgcgcg    5160
ggacgtcctt tgtttacgtc ccgtcggcgc tgaatcctgc ggacgaccct tctcggggtc    5220
gcttgggact ctctcgtccc cttctccgtc tgccgttccg accgaccacg gggcgcacct    5280
ctctttacgc ggactccccg tctgtgcctt ctcatctgcc ggaccgtgtg cacttcgctt    5340
cacctctgca cgtcgcatgg agaccaccgt gaacgcccac caaatattgc ccaaggtctt    5400
acataagagg actcttggac tctcagcaat gtcaacgacc gaccttgagg catacttcaa    5460
agactgtttg tttaaagact gggaggagtt gggggaggag attaggttaa aggtctttgt    5520
actaggaggc tgtaggcata aattggtctg cgcaccagca ccatggcgca atcactagag    5580
cggggtacct ttaagaccaa tgacttacaa ggcagctgta gatcttagcc actttttaaa    5640
agaaaagggg gactggaag ggctaattca ctcccaacga agacaagatc tgcttttttgc    5700 ttgtactggg tctctctggt tagaccagat ctgagcctgg gagctctctg gctaactagg    5760
gaacccactg cttaagcctc aataaagctt gccttgagtg cttcaagtag tgtgtgcccg    5820
tctgttgtgt gactctggta actagagatc cctcagaccc ttttagtcag tgtggaaaat    5880
ctctagcagt agtagttcat gtcatcttat tattcagtat ttataacttg caaagaaatg    5940
aatatcagag agtgagagga acttgtttat tgcagcttat aatggttaca ataaagcaa     6000 tagcatcaca aatttcacaa ataaagcatt ttttcactg cattctagtt gtggtttgtc    6060
caaactcatc aatgtatctt atcatgtctg gctctagcta tcccgcccct aactccgccc    6120
atcccgcccc taactccgcc cagttccgcc cattctccgc ccatggctg actaattttt    6180 tttatttatg cagaggccga ggccggatcc cttgagtggc tttcatcctg gagcagactt    6240
tgcagtctgt ggactgcaac acaacattgc ctttatgtgt aactcttggc tgaagctctt    6300
```

```
acaccaatgc tgggggacat gtacctccca ggggcccagg aagactacgg gaggctacac   6360
caacgtcaat cagagggggcc tgtgtagcta ccgataagcg gaccctcaag agggcattag   6420
caatagtgtt tataaggccc ccttgttaat tcttgaagac gaaagggcct cgtgatacgc   6480 ctattttat aggttaatgt catgataata atggtttctt agacgtcagg tggcactttt   6540
cggggaaatg tgcgcggaac ccctatttgt ttattttct aaatacattc aaatatgtat   6600
ccgctcatga caataaacc ctgataaatg cttcaataat attgaaaaag gaagagtatg   6660
agtattcaac atttccgtgt cgcccttatt ccctttttg cggcattttg ccttcctgtt   6720
tttgctcacc cagaaacgct ggtgaaagta aaagatgctg aagatcagtt gggtgcacga   6780
gtgggttaca tcgaactgga tctcaacagc ggtaagatcc ttgagagtttt cgccccgaa   6840 gaacgttttc caatgatgag cacttttaaa gttctgctat gtggcgcggt attatcccgt   6900
gttgacgccg ggcaagagca actcggtcgc cgcatacact attctcagaa tgacttggtt   6960
gagtactcac cagtcacaga aaagcatctt acggatggca tgacagtaag agaattatgc   7020
agtgctgcca taaccatgag tgataacact gcggccaact tacttctgac aacgatcgga   7080
ggaccgaagg agctaaccgc ttttttgcac aacatggggg atcatgtaac tcgccttgat   7140
cgttgggaac cggagctgaa tgaagccata ccaaacgacg agcgtgacac cacgatgcct   7200
gcagcaatgg caacaacgtt gcgcaaacta ttaactggcg aactacttac tctagcttcc   7260
cggcaacaat taatagactg gatggaggcg gataaagttg caggaccact tctgcgctcg   7320
gcccttccgg ctggctggtt tattgctgat aaatctggag ccggtgagcg tgggtctcgc   7380
ggtatcattg cagcactggg gccagatggt aagccctccc gtatcgtagt tatctacacg   7440
acggggagtc aggcaactat ggatgaacga atagacaga tcgctgagat aggtgcctca   7500
ctgattaagc attggtaact gtcagaccaa gtttactcat atatacttta gattgattta   7560
aaacttcatt tttaatttaa aaggatctag gtgaagatcc ttttttgataa tctcatgacc   7620 aaaatccctt aacgtgagtt ttcgttccac tgagcgtcag accccgtaga aaagatcaaa   7680
ggatcttctt gagatccttt ttttctgcgc gtaatctgct gcttgcaaac aaaaaaacca   7740
ccgctaccag cggtggtttg tttgccggat caagagctac caactctttt tccgaaggta   7800
actggcttca gcagagcgca gataccaaat actgtccttc tagtgtagcc gtagttaggc   7860
caccacttca agaactctgt agcaccgcct acatacctcg ctctgctaat cctgttacca   7920
gtggctgctg ccagtggcga taagtcgtgt cttaccgggt tggactcaag acgatagtta   7980
ccggataagg cgcagcggtc gggctgaacg ggggggttcgt gcacacagcc cagcttggag   8040
cgaacgacct acaccgaact gagatacctta cagcgtgagc attgagaaag cgccacgctt   8100
cccgaaggga gaaaggcgga caggtatccg gtaagcggca gggtcggaac aggagagcgc   8160
acgagggagc ttccaggggg aaacgcctgg tatctttata gtcctgtcgg gtttcgccac   8220
ctctgacttg agcgtcgatt tttgtgatgc tcgtcagggg ggcggagcct atggaaaaac   8280
gccagcaacg cggcctttt acggttcctg gccttttgct ggccttttg aagctgtccc   8340 tgatggtcgt catctacctg cctggacagc atggcctgca acgcgggcat cccgatgccg   8400
ccggaagcga agaatcat aatggggaag gccatccagc ctcgcgtcg                8449
```

<210> SEQ ID NO 36
<211> LENGTH: 7298
<212> TYPE: DNA
<213> ORGANISM: Artificial Sequence
<220> FEATURE:
<223> OTHER INFORMATION: pCIGO-VSV.G (VSVG)

<400> SEQUENCE: 36

```
gtcgacggat cgggagatca attccggcac ctgtcctacg agttgcatga taaagaagac      60
agtcataagt gcggcgacga tagtcatgcc ccgcgcccac cggaaggagc tgactgggtt     120
gaaggctctc aagggcatcg gtcgatgcag gaaaaggaca agcagcgaaa attcacgccc     180
ccttgggagg tggcggcata tgcaaaggat agcactccca ctctactact gggtatcata     240
tgctgactgt atatgcatga ggatagcata tgctacccgg atacagatta ggatagcata     300
tactacccag atatagatta ggatagcata tgctacccag atatagatta ggatagccta     360
tgctacccag atataaatta ggatagcata tactacccag atatagatta ggatagcata     420
tgctacccag atatagatta ggatagccta tgctacccag atatagatta ggatagcata     480
tgctacccag atatagatta ggatagcata tgctatccag atatttgggt agtatatgct     540
acccagatat aaattaggat agcatatact accctaatct ctattaggat agcatatgct     600
acccggatac agattaggat agcatatact acccagatat agattaggat agcatatgct     660
acccagatat agattaggat agcctatgct acccagatat aaattaggat agcatatact     720
acccagatat agattaggat agcatatgct acccagatat agattaggat agcctatgct     780
acccagatat agattaggat agcatatgct atccagatat ttgggtagta tatgctaccc     840
atggcaacat tagcccaccg tgctctcagc gacctcgtga atatgaggac caacaaccct     900
gtgcttggcg ctcaggcgca agtgtgtgta atttgtcctc cagatcgcag caatcgcgcc     960
cctatcttgg cccgcccacc tacttatgca ggtattcccc ggggtgccat tagtggtttt    1020
gtgggcaagt ggtttgaccg cagtggttag cggggttaca atcagccaag ttattacacc    1080
cttattttac agtccaaaac cgcagggcgg cgtgtggggg ctgacgcgtg cccccactcc    1140
acaatttcaa aaaaagagt ggccacttgt ctttgtttat gggccccatt ggcgtggagc    1200
cccgttaat tttcgggggt gttagagaca accagtggag tccgctgctg tcggcgtcca    1260
ctctctttcc ccttgttaca aatagagtgt aacaacatgg ttcacctgtc ttggtccctg    1320
cctgggacac atcttaataa ccccagtatc atattgcact aggattatgt gttgcccata    1380
gccataaatt cgtgtgagat ggacatccag tctttacggc ttgtcccccac ccatggatt    1440
tctattgtta aagatattca gaatgtttca ttcctacact agtatttatt gcccaagggg    1500
tttgtgaggg ttatattggt gtcatagcac aatgccacca ctgaaccccc cgtccaaatt    1560
ttattctggg ggcgtcacct gaaaccttgt tttcgagcac ctcacataca ccttactgtt    1620
cacaactcag cagttattct attagctaaa cgaaggagaa tgaagaagca ggcgaagatt    1680
caggagagtt cactgcccgc tccttgatct tcagccactg cccttgtgac taaaatggtt    1740
cactaccctc gtggaatcct gacccatgt aaataaaacc gtgacagctc atggggtggg    1800
agatatcgct gttccttagg acccttttac taaccctaat tcgatagcat atgcttcccg    1860
ttgggtaaca tatgctattg aattagggtt agtctggata gtatatacta ctacccggga    1920
agcatatgct acccgtttag ggttaacaag ggggccttat aaacactatt gctaatgccc    1980
tcttgagggt ccgcttatcg gtagctacac aggcccctct gattgacgtt ggtgtagcct    2040
cccgtagtct tcctgggccc ctgggaggta catgtccccc agcattggtg taagagcttc    2100
agccaagagt tacacataaa ggcaatgttg tgttgcagtc cacagactgc aaagtctgct    2160
ccaggatgaa agccactcaa gggatcttca atattggcca ttagccatat tattcattgg    2220
ttatatagca taaatcaata ttggctattg gccattgcat acgttgtatc tatatcataa    2280
```

-continued

| | | | | | |
|---|---|---|---|---|---|
| tatgtacatt | tatattggct | catgtccaat | atgaccgcca | tgttggcatt | gattattgac | 2340 |
| tagttattaa | tagtaatcaa | ttacggggtc | attagttcat | agcccatata | tggagttccg | 2400 |
| cgttacataa | cttacggtaa | atggcccgcc | tggctgaccg | cccaacgacc | cccgcccatt | 2460 |
| gacgtcaata | atgacgtatg | ttcccatagt | aacgccaata | gggactttcc | attgacgtca | 2520 |
| atgggtggag | tatttacggt | aaactgccca | cttggcagta | catcaagtgt | atcatatgcc | 2580 |
| aagtccgccc | cctattgacg | tcaatgacgg | taaatggccc | gcctggcatt | atgcccagta | 2640 |
| catgacctta | cgggactttc | ctacttggca | gtacatctac | gtattagtca | tcgctattac | 2700 |
| catggtgatg | cggttttggc | agtacaccaa | tgggcgtgga | tagcggtttg | actcacgggg | 2760 |
| atttccaagt | ctccacccca | ttgacgtcaa | tgggagtttg | ttttggcacc | aaaatcaacg | 2820 |
| ggactttcca | aaatgtcgta | ataacccgc | ccgttgacg | caaatgggcg | gtaggcgtgt | 2880 |
| acggtgggag | gtctatataa | gcagagctcg | tttagtgaac | cgtcagatca | ctagaagctt | 2940 |
| tattgcggta | gtttatcaca | gttaaattgc | taacgcagtc | agtgcttctg | acacaacagt | 3000 |
| ctcgaactta | agctgcagaa | gttggtcgtg | aggcactggg | caggtaagta | tcaaggttac | 3060 |
| aagacaggtt | taaggagacc | aatagaaact | gggcttgtcg | agacagagaa | gactcttgcg | 3120 |
| tttctgatag | gcacctattg | gtcttactga | catccacttt | gcctttctct | ccacaggtgt | 3180 |
| ccactcccag | ttcaattaca | gctcttaagg | ctagagtact | taatacgact | cactataggc | 3240 |
| tagcggtacc | gagctcggat | ccactagtaa | cggccgccag | tgtgctggaa | ttcaacagag | 3300 |
| atcgatctgt | ttccttgaca | ctatgaagtg | ccttttgtac | ttagccttt | tattcattgg | 3360 |
| ggtgaattgc | aagttcacca | tagttttcc | acacaaccaa | aaaggaaact | ggaaaaatgt | 3420 |
| tccttctaat | taccattatt | gcccgtcaag | ctcagattta | aattggcata | atgacttaat | 3480 |
| aggcacagcc | atacaagtca | aaatgcccaa | gagtcacaag | gctattcaag | cagacggttg | 3540 |
| gatgtgtcat | gcttccaaat | gggtcactac | ttgtgatttc | cgctggtatg | gaccgaagta | 3600 |
| tataacacag | tccatccgat | ccttcactcc | atctgtagaa | caatgcaagg | aaagcattga | 3660 |
| acaaacgaaa | caaggaactt | ggctgaatcc | aggcttccct | cctcaaagtt | gtggatatgc | 3720 |
| aactgtgacg | gatgccgaag | cagtgattgt | ccaggtgact | cctcaccatg | tgctggttga | 3780 |
| tgaatacaca | ggagaatggg | ttgattcaca | gttcatcaac | ggaaaatgca | gcaattacat | 3840 |
| atgccccact | gtccataact | ctacaacctg | gcattctgac | tataaggtca | aagggctatg | 3900 |
| tgattctaac | ctcatttcca | tggacatcac | cttcttctca | gaggacggag | agctatcatc | 3960 |
| cctgggaaag | gagggcacag | ggttcagaag | taactacttt | gcttatgaaa | ctggaggcaa | 4020 |
| ggcctgcaaa | atgcaatact | gcaagcattg | gggagtcaga | ctcccatcag | gtgtctggtt | 4080 |
| cgagatggct | gataaggatc | tctttgctgc | agccagattc | cctgaatgcc | agaagggtc | 4140 |
| aagtatctct | gctccatctc | agacctcagt | ggatgtaagt | ctaattcagg | acgttgagag | 4200 |
| gatcttggat | tattccctct | gccaagaaac | ctggagcaaa | atcagagcgg | tcttccaat | 4260 |
| ctctccagtg | gatctcagct | atcttgctcc | taaaaaccca | ggaaccggtc | ctgctttcac | 4320 |
| cataatcaat | ggtaccctaa | aatactttga | gaccagatac | atcagagtcg | atattgctgc | 4380 |
| tccaatcctc | tcaagaatgg | tcggaatgat | cagtggaact | accacagaaa | gggaactgtg | 4440 |
| ggatgactgg | gcaccatatg | aagacgtgga | aattggaccc | aatggagttc | tgaggaccag | 4500 |
| ttcaggatat | aagtttcctt | tatacatgat | tggacatggt | atgttggact | ccgatcttca | 4560 |
| tcttagctca | aaggctcagg | tgttcgaaca | tcctcacatt | caagacgctg | cttcgcaact | 4620 |
| tcctgatgat | gagagtttat | ttttggtga | tactgggcta | tccaaaaatc | caatcgagct | 4680 |

```
tgtagaaggt tggttcagta gttggaaaag ctctattgcc tcttttttct ttatcatagg   4740
gttaatcatt ggactattct tggttctccg agttggtatc catctttgca ttaaattaaa   4800
gcacaccaag aaaagacaga tttatacaga catagagatg aaccgacttg gaaagtaact   4860
caaatcctgc acaacagatt cttcatgttt ggaccaaatc aacttgtgat accatgctca   4920
aagaggcctc aattatattt gagtttttaa ttttttatgga attctgcaga tatccatcac   4980
actggcggcc gctcgagcat gcatctagag ggcccattc tatagtgtca cctaaatgct   5040
agagctcgct gatcagcctc gactgtgcct tctagttgcc agccatctgt tgtttgcccc   5100 tccccccgtgc cttccttgac cctggaaggt gccactccca ctgtcctttc ctaataaaat   5160
gaggaaattg catcgcattg tctgagtagg tgtcattcta ttctgggggg tggggtgggg   5220
caggacagca agggggagga ttgggaagac aatagcaggc atgctgggga tgcggtgggc   5280
tctatggctt ctgaggcgga agaaccagc tgcattaatg aatcggccaa cgcgcgggga   5340
gaggcggttt gcgtattggg cgctcttccg cttcctcgct cactgactcg ctgcgctcgg   5400
tcgttcggct gcggcgagcg gtatcagctc actcaaaggc ggtaatacgg ttatccacag   5460
aatcagggga taacgcagga aagaacatgt gagcaaaagg ccagcaaaag gccaggaacc   5520
gtaaaaaggc cgcgttgctg gcgttttttcc ataggctccg ccccctgac gagcatcaca   5580 aaaatcgacg ctcaagtcag aggtggcgaa acccgacagg actataaaga taccaggcgt   5640
ttccccctgg aagctccctc gtgcgctctc ctgttccgac cctgccgctt accggatacc   5700
tgtccgcctt tctcccttcg ggaagcgtgg cgctttctca atgctcacgc tgtaggtatc   5760
tcagttcggt gtaggtcgtt cgctccaagc tgggctgtgt gcacgaaccc cccgttcagc   5820
ccgaccgctg cgccttatcc ggtaactatc gtcttgagtc caacccggta agacacgact   5880
tatcgccact ggcagcagcc actggtaaca ggattagcag agcgaggtat gtaggcggtg   5940
ctacagagtt cttgaagtgg tggcctaact acggctacac tagaaggaca gtatttggta   6000
tctgcgctct gctgaagcca gttaccttcg gaaaaagagt tggtagctct tgatccggca   6060
aacaaaccac cgctggtagc ggtggttttt ttgtttgcaa gcagcagatt acgcgcagaa   6120
aaaaaggatc tcaagaagat cctttgatct ttttctacggg gtctgacgct cagtggaacg   6180
aaaactcacg ttaagggatt ttggtcatga gattatcaaa aaggatcttc acctagatcc   6240
ttttaaatta aaaatgaagt tttaaatcaa tctaaagtat atatgagtaa acttggtctg   6300
acagttacca atgcttaatc agtgaggcac ctatctcagc gatctgtcta tttcgttcat   6360
ccatagttgc ctgactcccc gtcgtgtaga taactacgat acgggagggc ttaccatctg   6420
gccccagtgc tgcaatgata ccgcgagacc cacgctcacc ggctccagat ttatcagcaa   6480
taaaccagcc agccggaagg gccgagcgca gaagtggtcc tgcaacttta tccgcctcca   6540
tccagtctat taattgttgc cgggaagcta gagtaagtag ttcgccagtt aatagtttgc   6600
gcaacgttgt tgccattgct acaggcatcg tggtgtcacg ctcgtcgttt ggtatggctt   6660
cattcagctc cggttcccaa cgatcaaggc gagttacatg atccccatg ttgtgcaaaa   6720 aagcggttag ctccttcggt cctccgatcg ttgtcagaag taagttggcc gcagtgttat   6780
cactcatggt tatggcagca ctgcataatt ctcttactgt catgccatcc gtaagatgct   6840
tttctgtgac tggtgagtac tcaaccaagt cattctgaga atagtgtatg cggcgaccga   6900
gttgctcttg cccggcgtca atacgggata ataccgcgcc acatagcaga actttaaaag   6960
tgctcatcat tggaaaacgt tcttcggggc gaaaactctc aaggatctta ccgctgttga   7020
```

| | |
|---|---|
| gatccagttc gatgtaaccc actcgtgcac ccaactgatc ttcagcatct tttactttca | 7080 |
| ccagcgtttc tgggtgagca aaaacaggaa ggcaaaatgc cgcaaaaaag ggaataaggg | 7140 |
| cgacacggaa atgttgaata ctcatactct tcctttttca atattattga agcatttatc | 7200 |
| agggttattg tctcatgagc ggatacatat ttgaatgtat ttagaaaaat aaacaaatag | 7260 |
| gggttccgcg cacatttccc cgaaaagtgc cacctgac | 7298 |

<210> SEQ ID NO 37
<211> LENGTH: 9932
<212> TYPE: DNA
<213> ORGANISM: Artificial Sequence
<220> FEATURE:
<223> OTHER INFORMATION: PLV4301G38A1

<400> SEQUENCE: 37

| | |
|---|---|
| cgataaccct aattcgatag catatgcttc ccgttgggta acatatgcta ttgaattagg | 60 |
| gttagtctgg atagtatata ctactacccg gaagcatat gctacccgtt tagggttcac | 120 |
| cggtgatgcc ggccacgatg cgtccggcgt agaggatcta atgtgagtta gctcactcat | 180 |
| taggcacccc aggctttaca ctttatgctt ccggctcgta tgttgtgtgg aattgtgagc | 240 |
| ggataacaat ttcacacagg aaacagctat gaccatgatt acgccaagcg cgcaattaac | 300 |
| cctcactaaa gggaacaaaa gctggagctg caagcttaat gtagtcttat gcaatactct | 360 |
| tgtagtcttg caacatggta acgatgagtt agcaacatgc cttacaagga gagaaaaagc | 420 |
| accgtgcatg ccgattggtg gaagtaaggt ggtacgatcg tgccttatta ggaaggcaac | 480 |
| agacgggtct gacatggatt ggacgaacca ctgaattgcc gcattgcaga gatattgtat | 540 |
| ttaagtgcct agctcgatac ataaacgggt ctctctggtt agaccagatc tgagcctggg | 600 |
| agctctctgg ctaactaggg aacccactgc ttaagcctca ataaagcttg ccttgagtgc | 660 |
| ttcaagtagt gtgtgcccgt ctgttgtgtg actctggtaa ctagagatcc ctcagaccct | 720 |
| tttagtcagt gtggaaaatc tctagcagtg gcgcccgaac agggacttga aagcgaaagg | 780 |
| gaaaccagag gagctctctc gacgcaggac tcggcttgct gaagcgcgca cggcaagagg | 840 |
| cgaggggcgg cgactggtga gtacgccaaa aattttgact agcggaggct agaaggagag | 900 |
| agatgggtgc gagagcgtca gtattaagcg gggagaatt agatcgcgat gggaaaaaat | 960 |
| tcggttaagg ccaggggaa agaaaaaata taaattaaaa catatagtat gggcaagcag | 1020 |
| ggagctagaa cgattcgcag ttaatcctgg cctgttagaa acatcagaag gctgtagaca | 1080 |
| aatactggga cagctacaac catcccttca gacaggatca aagaactta gatcattata | 1140 |
| taatacagta gcaaccctct attgtgtgca tcaaggata gagataaaag acaccaagga | 1200 |
| agctttagac aagatagagg aagagcaaaa caaaagtaag accaccgcac agcaagcggc | 1260 |
| cgctgatctt cagacctgga ggaggagata tgagggacaa ttggagaagt gaattatata | 1320 |
| aatataaagt agtaaaaatt gaaccattag gagtagcacc caccaaggca agagaagag | 1380 |
| tggtgcagag agaaaaaaga gcagtgggaa taggagcttt gttccttggg ttcttgggag | 1440 |
| cagcaggaag cactatgggc gcagcgtcaa tgacgctgac ggtacaggcc agacaattat | 1500 |
| tgtctggtat agtgcagcag cagaacaatt tgctgagggc tattgaggcg caacagcatc | 1560 |
| tgttgcaact cacagtctgg ggcatcaagc agctccaggc aagaatcctg gctgtggaaa | 1620 |
| gatacctaaa ggatcaacag ctcctgggga tttggggttg ctctggaaaa ctcatttgca | 1680 |
| ccactgctgt gccttggaat gctagttgga gtaataaatc tctggaacag atttggaatc | 1740 |
| acacgacctg gatggagtgg gacagagaaa ttaacaatta cacaagctta atacactcct | 1800 |

```
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaacccga     2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280
gggggaatg  aaagacccca cctgtaggtt tggcaagcta gcttaagtaa cgccattttg    2340
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaaccct  cactcggcgc gccagtcctc cgatagactg cgtcgcccgg gtaccgatat    2700
caccaacttt gtacaaaaaa gctgaacgat atcgccacca tgggcagcac agccattctg    2760
gccctgctgc tggcagtgct gcagggcgtg tcagctgaag tgcagctggt ggaatctggc    2820
ggcggactgg tgcagcctgg cggatctctg agactgagct gtgccgccag cggcttcacc    2880
ttcagcaact acgccatgag ctgggtgcgc caggcccctg gaaaaggcct ggaatgggtg    2940
tccaccatca gcggctctgg cggaaccacc tactacgccg atagcgtgaa gggccggttc    3000
accatctccc gggacaacag caagaacacc ctgtacctgc agatgaacag cctgcgggtg    3060
gaagataccg ccgtgtacta ctgcgccaag gactggttca aagcagcag  ccccgacgcc    3120
ttcgacatct ggggccaggg aacaaccgtg accgtgtctg ctggcggagg cggatcaggc    3180
ggcggaggat caggggagg  cggaagcgga gcaccttctt acgtgctgac ccagccccct    3240
agcgtgtcag tggctcctgg acagaccgcc agaatcacct gtgcgcggcaa caacatcggc    3300
cggaagatcg tgcactggta tcagcagagg ccccgacagg ctcccgtgct cgtgatctac    3360
tacgacaccg acagacctgc cggcatcccc gagagattca gcggcagcaa cagcggcaac    3420
atggccaccc tgaccatcag cacagtggga gccggcgacg aggccgacta ctactgtcaa    3480
gtgtgggaca ccggcagcga tcacgtggtg tttggaggcg gcaccaagct gacagtgctg    3540
ggcccgcggg ccaactttgt atacaaaagt tgcagcgaga gcaagtacgg ccctccctgc    3600
ccccttgcc  ctgcccccga gttcctgggc ggacccagcg tgttcctgtt ccccccaag    3660
cccaaggaca ccctgatgat cagccggacc cccgaggtga cctgtgtggt ggtggacgtg    3720
tcccaggagg accccgaggt ccagttcaac tggtacgtgg acggcgtgga ggtgcacaac    3780
gccaagacca agcccgggga ggagcagttc aatagcacct accgggtggt gtccgtgctg    3840
accgtgctgc accaggactg gctgaacggc aaggaataca agtgtaaggt gtccaacaag    3900
ggcctgccca gcagcatcga aaaaccatc  agcaaggcca agggccagcc tcgggagccc    3960
caggtgtaca ccctgccccc tagccaagag gagatgacca agaatcaggt gtccctgacc    4020
tgcctggtga agggcttcta ccccagcgac atcgccgtgg agtgggagag caacggccag    4080
cccgagaaca actacaagac cacccccct  gtgctggaca gcgacggcag cttcttcctg    4140
```

```
tacagcaggc tgaccgtgga caagagccgg tggcaggagg gcaacgtctt tagctgctcc   4200
gtgatgcacg aggccctgca caaccactac acccagaaga gcctgtccct gagcctgggc   4260
aagatgttca gatcttgtga tatttacatc tgggcaccct tggccggaat ctgcgtggcc   4320
cttctgctgt ccttgatcat cactctcatc tgctacggct ccaccagcgg ctccggcaag   4380
cccggctctg gcgagggctc caccagcggc gactacaagg acgacgatga caagtaatag   4440
gatatcggtt cagcttttct tgtacaaagt tgggattcga gttaattaag taacgaattc   4500 ccccccctctc cctccccccc ccctaacgtt actggccgaa gccgcttgga ataaggccgg   4560
tgtgcgtttg tctatatgtt attttccacc atattgccgt cttttggcaa tgtgagggcc   4620
cggaaacctg gccctgtctt cttgacgagc attcctaggg gtctttcccc tctcgccaaa   4680
ggaatgcaag gtctgttgaa tgtcgtgaag gaagcagttc ctctggaagc ttcttgaaga   4740
caaacaacgt ctgtagcgac cctttgcagg cagcggaacc ccccacctgg cgacaggtgc   4800
ctctgcggcc aaaagccacg tgtataagat acacctgcaa aggcggcaca accccagtgc   4860
cacgttgtga gttggatagt tgtggaaaga gtcaaatggc tctcctcaag cgtattcaac   4920
aaggggctga aggatgccca gaaggtaccc cattgtatgg gatctgatct ggggcctcgg   4980
tgcacatgct ttacatgtgt ttagtcgagg ttaaaaaacg tctaggcccc ccgaaccacg   5040
gggacgtggt tttcctttga aaaacacgat gataatatgg ccacaaccat gggaggcgga   5100
agcggcggag gctcccctcg aggcaccatg gtgagcaagg gcgaggagct gttcaccggg   5160
gtggtgccca tcctggtcga gctggacggc gacgtaaacg gccacaagtt cagcgtgtcc   5220
ggcgagggcg agggcgatgc cacctacggc aagctgaccc tgaagttcat ctgcaccacc   5280
ggcaagctgc ccgtgccctg gcccaccctc gtgaccaccc tgacctacgg cgtgcagtgc   5340
ttcagccgct accccgacca catgaagcag cacgacttct tcaagtccgc catgcccgaa   5400
ggctacgtcc aggagcgcac catcttcttc aaggacgacg gcaactacaa gacccgcgcc   5460
gaggtgaagt tcgagggcga caccctggtg aaccgcatcg agctgaaggg catcgacttc   5520
aaggaggacg gcaacatcct ggggcacaag ctggagtaca actacaacag ccacaacgtc   5580
tatatcatgg ccgacaagca gaagaacggc atcaaggtga acttcaagat ccgccacaac   5640
atcgaggacg gcagcgtgca gctcgccgac cactaccagc agaacacccc catcggcgac   5700
ggccccgtgc tgctgcccga caaccactac ctgagcaccc agtccgccct gagcaaagac   5760
cccaacgaga agcgcgatca catggtcctg ctggagttcg tgaccgccgc cgggatcact   5820
ctcggcatgg acgagctgta caagtaacgc gtcccgggtc tagagctagc ggtaccatgc   5880
attacgtagt cgacgactta attaagctag cctagtgcca tttgttcagt ggttcgtagg   5940
gctttccccc actgtttggc tttcagttat atggatgatg tggtattggg ggccaagtct   6000
gtacagcatc ttgagtccct ttttaccgct gttaccaatt ttcttttgtc tttgggtata   6060
catttaaacc ctaacaaaac aaagagatgg ggttactctc taaattttat gggttatgtc   6120
attggatgtt atgggtcctt gccacaagaa cacatcatac aaaaaatcaa agaatgtttt   6180
agaaaacttc ctattaacag gcctattgat tggaaagtat gtcaacgaat tgtgggtctt   6240
ttgggttttg ctgccccttt tacacaatgt ggttatcctg cgttgatgcc tttgtatgca   6300
tgtattcaat ctaagcaggc tttcactttc tcgccaactt acaaggcctt tctgtgtaaa   6360
caatacctga acctttaccc cgttgcccgg caacggccag gtctgtgcca agtgtttgct   6420
gacgcaaccc ccactggctg gggcttggtc atgggccatc agcgcatgcg tggaaccttt   6480
tcggctcctc tgccgatcca tactgcggaa ctcctagccg cttgttttgc tcgcagcagg   6540
```

```
tctggagcaa acattatcgg gactgataac tctgttgtcc tatcccgcaa atatacatcg   6600
tttccatggc tgctaggctg tgctgccaac tggatcctgc gcgggacgtc ctttgtttac   6660
gtcccgtcgg cgctgaatcc tgcggacgac ccttctcggg gtcgcttggg actctctcgt   6720
cccttctcc gtctgccgtt ccgaccgacc acggggcgca cctctcttta cgcggactcc    6780
ccgtctgtgc cttctcatct gccggaccgt gtgcacttcg cttcacctct gcacgtcgca   6840
tggagaccac cgtgaacgcc caccaaatat tgcccaaggt cttacataag aggactcttg   6900
gactctcagc aatgtcaacg accgaccttg aggcatactt caaagactgt ttgtttaaag   6960
actgggagga gttgggggag gagattaggt taaaggtctt tgtactagga ggctgtaggc   7020
ataaattggt ctgcgcacca gcaccatggc gcaatcacta gagcggggta cctttaagac   7080
caatgactta caaggcagct gtagatctta gccactttt aaaagaaaag gggggactgg    7140
aagggctaat tcactcccaa cgaagacaag atctgctttt tgcttgtact gggtctctct   7200
ggttagacca gatctgagcc tgggagctct ctggctaact agggaaccca ctgcttaagc   7260
ctcaataaag cttgccttga gtgcttcaag tagtgtgtgc ccgtctgttg tgtgactctg   7320
gtaactagag atccctcaga ccctttagt cagtgtggaa atctctagc agtagtagtt     7380
catgtcatct tattattcag tatttataac ttgcaaagaa atgaatatca gagagtgaga   7440
ggaacttgtt tattgcagct tataatggtt acaaataaag caatagcatc acaaatttca   7500
caaataaagc attttttca ctgcattcta gttgtggttt gtccaaactc atcaatgtat     7560
cttatcatgt ctggctctag ctatcccgcc cctaactccg cccatcccgc ccctaactcc   7620
gcccagttcc gcccattctc cgccccatgg ctgactaatt ttttttattt atgcagaggc   7680
cgaggccgga tcccttgagt ggctttcatc ctggagcaga cttgcagtc tgtggactgc    7740
aacacaacat tgcctttatg tgtaactctt ggctgaagct cttacaccaa tgctggggga   7800
catgtacctc ccaggggccc aggaagacta cgggaggcta caccaacgtc aatcagaggg   7860
gcctgtgtag ctaccgataa gcggaccctc aagagggcat tagcaatagt gtttataagg   7920
cccccttgtt aattcttgaa gacgaaaggg cctcgtgata cgcctatttt tataggttaa   7980
tgtcatgata ataatggttt cttagacgtc aggtggcact tttcggggaa atgtgcgcgg   8040
aaccccattt tgtttatttt tctaaataca ttcaaatatg tatccgctca tgagacaata   8100
accctgataa atgcttcaat aatattgaaa aggaagagt atgagtattc aacatttccg    8160
tgtcgccctt attcccttt ttgcggcatt ttgccttcct gttttgctc acccagaaac     8220
gctggtgaaa gtaaaagatg ctgaagatca gttgggtgca cgagtgggtt acatcgaact   8280
ggatctcaac agcggtaaga tccttgagag ttttcgcccc gaagaacgtt ttccaatgat   8340
gagcactttt aaagttctgc tatgtggcgc ggtattatcc cgtgttgacg ccgggcaaga   8400
gcaactcggt cgccgcatac actattctca gaatgacttg gttgagtact caccagtcac   8460
agaaaagcat cttacggatg gcatgacagt aagagaatta tgcagtgctg ccataaccat   8520
gagtgataac actgcggcca acttacttct gacaacgatc ggaggaccga aggagctaac   8580
cgcttttttg cacaacatgg ggatcatgt aactcgcctt gatcgttggg aaccggagct     8640
gaatgaagcc ataccaaacg acgagcgtga caccacgatg cctgcagcaa tggcaacaac   8700
gttgcgcaaa ctattaactg gcgaactact tactctagct tcccggcaac aattaataga   8760
ctggatggag gcggataaag ttgcaggacc acttctgcgc tcggcccttc cggctggctg   8820
gtttattgct gataaatctg gagccggtga gcgtgggtct cgcggtatca ttgcagcact   8880
```

| | |
|---|---|
| ggggccagat ggtaagccct cccgtatcgt agttatctac acgacgggga gtcaggcaac | 8940 |
| tatggatgaa cgaaatagac agatcgctga gataggtgcc tcactgatta agcattggta | 9000 |
| actgtcagac caagtttact catatatact ttagattgat ttaaaacttc attttttaatt | 9060 |
| taaaaggatc taggtgaaga tccttttttga taatctcatg accaaaatcc cttaacgtga | 9120 |
| gttttcgttc cactgagcgt cagaccccgt agaaaagatc aaaggatctt cttgagatcc | 9180 |
| ttttttttctg cgcgtaatct gctgcttgca acaaaaaaaa ccaccgctac cagcggtggt | 9240 |
| ttgtttgccg gatcaagagc taccaactct ttttccgaag gtaactggct tcagcagagc | 9300 |
| gcagatacca atactgtcc ttctagtgta gccgtagtta ggccaccact tcaagaactc | 9360 |
| tgtagcaccg cctacatacc tcgctctgct aatcctgtta ccagtggctg ctgccagtgg | 9420 |
| cgataagtcg tgtcttaccg ggttggactc aagacgatag ttaccggata aggcgcagcg | 9480 |
| gtcgggctga acggggggtt cgtgcacaca gcccagcttg gagcgaacga cctacaccga | 9540 |
| actgagatac ctacagcgtg agcattgaga aagcgccacg cttcccgaag ggagaaaggc | 9600 |
| ggacaggtat ccggtaagcg gcagggtcgg aacaggagag cgcacgaggg agcttccagg | 9660 |
| gggaaacgcc tggtatcttt atagtcctgt cgggtttcgc cacctctgac ttgagcgtcg | 9720 |
| atttttgtga tgctcgtcag ggggggcgag cctatgaaaa acgccagca acgcggcctt | 9780 |
| tttacggttc ctggcctttt gctggccttt tgaagctgt ccctgatggt cgtcatctac | 9840 |
| ctgcctggac agcatggcct gcaacgcggg catcccgatg ccgccggaag cgagaagaat | 9900 |
| cataatgggg aaggccatcc agcctcgcgt cg | 9932 |

<210> SEQ ID NO 38
<211> LENGTH: 9932
<212> TYPE: DNA
<213> ORGANISM: Artificial Sequence
<220> FEATURE:
<223> OTHER INFORMATION: PLV4301G19H9

<400> SEQUENCE: 38

| | |
|---|---|
| cgataaccct aattcgatag catatgcttc ccgttgggta acatatgcta ttgaattagg | 60 |
| gttagtctgg atagtatata ctactacccg ggaagcatat gctacccgtt tagggttcac | 120 |
| cggtgatgcc ggccacgatg cgtccggcgt agaggatcta atgtgagtta gctcactcat | 180 |
| taggcacccc aggctttaca ctttatgctt ccggctcgta tgttgtgtgg aattgtgagc | 240 |
| ggataacaat ttcacacagg aaacagctat gaccatgatt acgccaagcg cgcaattaac | 300 |
| cctcactaaa gggaacaaaa gctggagctg caagcttaat gtagtcttat gcaatactct | 360 |
| tgtagtcttg caacatggta acgatgagtt agcaacatgc cttacaagga gagaaaaagc | 420 |
| accgtgcatg ccgattggtg gaagtaaggt ggtacgatcg tgccttatta ggaaggcaac | 480 |
| agacgggtct gacatggatt ggacgaacca ctgaattgcc gcattgcaga gatattgtat | 540 |
| ttaagtgcct agctcgatac ataaacgggt ctctctggtt agaccagatc tgagcctggg | 600 |
| agctctctgg ctaactaggg aacccactgc ttaagcctca ataaagcttg ccttgagtgc | 660 |
| ttcaagtagt gtgtgcccgt ctgttgtgtg actctggtaa ctagagatcc ctcagaccct | 720 |
| tttagtcagt gtggaaaatc tctagcagtg gcgcccgaac agggacttga aagcgaaagg | 780 |
| gaaaccagag gagctctctc gacgcaggac tcggcttgct gaagcgcgca cggcaagagg | 840 |
| cgaggggcgg cgactggtga gtacgccaaa aattttgact agcggaggct agaaggagag | 900 |
| agatgggtgc gagagcgtca gtattaagcg ggggagaatt agatcgcgat gggaaaaaat | 960 |
| tcggttaagg ccagggggaa agaaaaaata taaattaaaa catatagtat gggcaagcag | 1020 |

```
ggagctagaa cgattcgcag ttaatcctgg cctgttagaa acatcagaag gctgtagaca    1080
aatactggga cagctacaac catcccttca gacaggatca gaagaactta gatcattata    1140
taatacagta gcaaccctct attgtgtgca tcaaaggata gagataaaag acaccaagga    1200
agctttagac aagatagagg aagagcaaaa caaaagtaag accaccgcac agcaagcggc    1260
cgctgatctt cagacctgga ggaggagata tgagggacaa ttggagaagt gaattatata    1320
aatataaagt agtaaaaatt gaaccattag gagtagcacc caccaaggca agagaagag     1380
tggtgcagag agaaaaaaga gcagtgggaa taggagcttt gttccttggg ttcttgggag    1440
cagcaggaag cactatgggc gcagcgtcaa tgacgctgac ggtacaggcc agacaattat    1500
tgtctggtat agtgcagcag cagaacaatt tgctgagggc tattgaggcg caacagcatc    1560
tgttgcaact cacagtctgg ggcatcaagc agctccaggc aagaatcctg gctgtggaaa    1620
gataccctaaa ggatcaacag ctcctgggga tttggggttg ctctggaaaa ctcatttgca   1680
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaaccccga    2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280
gggggggaatg aaagacccca cctgtaggtt tggcaagcta gcttaagtaa cgccatttg    2340
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgttccc agggtgcccc aaggacctga atgaccctg tgccttattt gaactaacca    2580
atcagttcgc ttctcgcttc tgttcgcgcg cttctgctcc ccgagctcaa taaaagagcc    2640
cacaacccct cactcggcgc gccagtcctc cgatagactg cgtcgcccgg gtaccgatat    2700
caccaacttt gtacaaaaaa gctgaacgat atcgccacca tgggcagcac agccattctg    2760
gccctgctgc tggcagtgct gcagggcgtg tcagctgaag tgcagctggt ggaatctggc    2820
ggcggactgg tgcagcctgg cggatctctg agactgagct gtgccgccag cggcttcacc    2880
ttcagcaact acgccatgag ctgggtgcgc caggcccctg aaaaggcct ggaatgggtg     2940
tccaccatca gcggctctgg cggaaccacc tactacgccg atagcgtgaa gggccggttc    3000
accatctccc gggacaacag caagaacacc ctgtacctgc agatgaacag cctgcgggtg    3060
gaagataccg ccgtgtacta ctgcgccaag gactggttca aagcagcag ccccgacgcc     3120
ttcgacatct ggggccaggg aacaaccgtg accgtgtctg ctggcggagg cggatcaggc    3180
ggcggaggat caggggggagg cggaagcgga gcaccttctt acgtgctgac ccagccccct    3240
agcgtgtcag tggctcctgg acagaccgcc agaatcacct gtggcggcaa caacatcggc    3300
cggaagatcg tgcactggta tcagcagagg cccggacagg ctcccgtgct cgtgatctac    3360
```

-continued

```
tacgacaccg acagacctgc cggcatcccc gagagattca gcggcagcaa cagcggcaac  3420
atggccaccc tgaccatcag cacagtggga gccggcgacg aggccgacta ctactgtcaa  3480
gtgtgggaca ccggcagcga tcacgtggtg tttggaggcg gcaccaagct gacagtgctg  3540
ggcccgcggg ccaactttgt atacaaaagt tgcagcgaga gcaagtacgg ccctcccctgc 3600
cccccttgcc ctgcccccga gttcctgggc ggacccagcg tgttcctgtt cccccccaag  3660
cccaaggaca ccctgatgat cagccggacc cccgaggtga cctgtgtggt ggtggacgtg  3720
tcccaggagg accccgaggt ccagttcaac tggtacgtgg acggcgtgga ggtgcacaac  3780
gccaagacca gccccgggga ggagcagttc aatagcacct accgggtggt gtccgtgctg  3840
accgtgctgc accaggactg gctgaacggc aaggaataca agtgtaaggt gtccaacaag  3900
ggcctgccca gcagcatcga aaaaccatc agcaaggcca agggccagcc tcgggagccc  3960
caggtgtaca ccctgccccc tagccaagag gagatgacca agaatcaggt gtccctgacc  4020
tgcctggtga agggcttcta ccccagcgac atcgccgtgg agtgggagag caacggccag  4080
cccgagaaca actacaagac cacccccct gtgctggaca gcgacggcag cttcttcctg  4140
tacagcaggc tgaccgtgga caagagccgg tggcaggagg caacgtcttagctgctcc   4200
gtgatgcacg aggccctgca caaccactac acccagaaga gcctgtccct gagcctgggc  4260
aagatgttca gatcttgtga tatttacatc tgggcaccct tggccggaat ctgcgtggcc  4320
cttctgctgt ccttgatcat cactctcatc tgctacggct ccaccagcgg ctccggcaag  4380
cccggctctg gcgagggctc caccagcggc gactacaagg acgacgatga caagtaatag  4440
gatatcggtt cagcttcttt gtacaaagtt gggattcgag ttaattaagt taacgaattc  4500
ccccctctc cctccccccc cctaacgtt actggccgaa gccgcttgga ataaggccgg  4560
tgtgcgtttg tctatatgtt attttccacc atattgccgt cttttggcaa tgtgagggcc  4620
cggaaacctg gccctgtctt cttgacgagc attcctaggg gtctttcccc tctcgccaaa  4680
ggaatgcaag gtctgttgaa tgtcgtgaag gaagcagttc ctctggaagc ttcttgaaga  4740
caaacaacgt ctgtagcgac cctttgcagg cagcggaacc ccccacctgg cgacaggtgc  4800
ctctgcggcc aaaagccacg tgtataagat acacctgcaa aggcggcaca accccagtgc  4860
cacgttgtga gttggatagt tgtggaaaga gtcaaatggc tctcctcaag cgtattcaac  4920
aaggggctga aggatgccca gaaggtaccc cattgtatgg gatctgatct ggggcctcgg  4980
tgcacatgct ttacatgtgt ttagtcgagg ttaaaaaacg tctaggcccc ccgaaccacg  5040
gggacgtggt tttcctttga aaaacacgat gataatatgg ccacaaccat gggaggcgga  5100
agcggcggag gctcccctcg aggcaccatg gtgagcaagg gcgaggagct gttcaccggg  5160
gtggtgccca tcctggtcga gctggacggc gacgtaaacg gccacaagtt cagcgtgtcc  5220
ggcgagggcg agggcgatgc cacctacggc aagctgaccc tgaagttcat ctgcaccacc  5280
ggcaagctgc ccgtgccctg gcccaccctc gtgaccaccc tgacctacgg cgtgcagtgc  5340
ttcagccgct accccgacca catgaagcag cacgacttct tcaagtccgc catgcccgaa  5400
ggctacgtcc aggagcgcac catcttcttc aaggacgacg gcaactacaa gacccgcgcc  5460
gaggtgaagt tcgagggcga caccctggtg aaccgcatcg agctgaaggg catcgacttc  5520
aaggaggacg gcaacatcct ggggcacaag ctggagtaca actacaacag ccacaacgtc  5580
tatatcatgg ccgacaagca gaagaacggc atcaaggtga acttcaagat ccgccacaac  5640
atcgaggacg gcagcgtgca gctcgccgac cactaccagc agaacacccc catcggcgac  5700
ggccccgtgc tgctgcccga caaccactac ctgagcaccc agtccgccct gagcaaagac  5760
```

```
cccaacgaga agcgcgatca catggtcctg ctggagttcg tgaccgccgc cgggatcact   5820
ctcggcatgg acgagctgta caagtaacgc gtcccgggtc tagagctagc ggtaccatgc   5880
attacgtagt cgacgactta attaagctag cctagtgcca tttgttcagt ggttcgtagg   5940
gctttccccc actgtttggc tttcagttat atggatgatg tggtattggg ggccaagtct   6000
gtacagcatc ttgagtccct ttttaccgct gttaccaatt ttcttttgtc tttgggtata   6060
catttaaacc ctaacaaaac aaagagatgg ggttactctc taaattttat ggttatgtc    6120 attggatgtt atgggtcctt gccacaagaa cacatcatac aaaaaatcaa agaatgtttt   6180
agaaaacttc ctattaacag gcctattgat tggaaagtat gtcaacgaat gtgggtctt    6240 ttgggttttg ctgccccttt tacacaatgt ggttatcctg cgttgatgcc tttgtatgca   6300
tgtattcaat ctaagcaggc tttcactttc tcgccaactt acaaggcctt tctgtgtaaa   6360
caatacctga acctttaccc cgttgcccgg caacggccag gtctgtgcca agtgtttgct   6420
gacgcaaccc ccactggctg gggcttggtc atgggccatc agcgcatgcg tggaaccttt   6480
tcggctcctc tgccgatcca tactgcggaa ctcctagccg cttgttttgc tcgcagcagg   6540
tctggagcaa acattatcgg gactgataac tctgttgtcc tatcccgcaa atatacatcg   6600
tttccatggc tgctaggctg tgctgccaac tggatcctgc gcgggacgtc ctttgtttac   6660
gtcccgtcgg cgctgaatcc tgcggacgac ccttctcggg gtcgcttggg actctctcgt   6720
ccccttctcc gtctgccgtt ccgaccgacc acggggcgca cctctcttta cgcggactcc   6780
ccgtctgtgc cttctcatct gccggaccgt gtgcacttcg cttcacctct gcacgtcgca   6840
tggagaccac cgtgaacgcc caccaaatat tgcccaaggt cttacataag aggactcttg   6900
gactctcagc aatgtcaacg accgaccttg aggcatactt caaagactgt ttgtttaaag   6960
actgggagga gttgggggag gagattaggt taaaggtctt tgtactagga ggctgtaggc   7020
ataaattggt ctgcgcacca gcaccatggc gcaatcacta gagcgggggta cctttaagac   7080 caatgactta caaggcagct gtagatctta gccacttttt aaaagaaaag gggggactgg   7140
aagggctaat tcactcccaa cgaagacaag atctgctttt tgcttgtact gggtctctct   7200
ggttagacca gatctgagcc tgggagctct ctggctaact agggaaccca ctgcttaagc   7260
ctcaataaag cttgccttga gtgcttcaag tagtgtgtgc ccgtctgttg tgtgactctg   7320
gtaactagag atccctcaga ccccttttagt cagtgtggaa aatctctagc agtagtagtt   7380
catgtcatct tattattcag tatttataac ttgcaaagaa atgaatatca gagagtgaga   7440
ggaacttgtt tattgcagct tataatggtt acaaataaag caatagcatc acaaatttca   7500
caaataaagc attttttttca ctgcattcta gttgtggttt gtccaaactc atcaatgtat   7560
cttatcatgt ctggctctag ctatcccgcc cctaactccg cccatcccgc cctaactcc    7620 gcccagttcc gcccattctc cgccccatgg ctgactaatt ttttttattt atgcagaggc   7680
cgaggccgga tcccttgagt ggctttcatc ctggagcaga ctttgcagtc tgtgactgc    7740 aacacaacat tgcctttatg tgtaactctt ggctgaagct cttacaccaa tgctggggga   7800
catgtacctc ccaggggccc aggaagacta cgggaggcta caccaacgtc aatcagaggg   7860
gcctgtgtag ctaccgataa gcggaccctc aagagggcat tagcaatagt gtttataagg   7920
cccccttgtt aattcttgaa gacgaaaggg cctcgtgata cgcctatttt tataggttaa   7980
tgtcatgata ataatggttt cttagacgtc aggtggcact tttcggggaa atgtgcgcgg   8040
aacccctatt tgtttatttt tctaaataca ttcaaatatg tatccgctca tgagacaata   8100
```

-continued

```
accctgataa atgcttcaat aatattgaaa aaggaagagt atgagtattc aacatttccg    8160
tgtcgccctt attcccttt ttgcggcatt ttgccttcct gtttttgctc acccagaaac    8220
gctggtgaaa gtaaaagatg ctgaagatca gttgggtgca cgagtgggtt acatcgaact    8280
ggatctcaac agcggtaaga tccttgagag ttttcgcccc gaagaacgtt ttccaatgat    8340
gagcactttt aaagttctgc tatgtggcgc ggtattatcc cgtgttgacg ccgggcaaga    8400
gcaactcggt cgccgcatac actattctca gaatgacttg gttgagtact caccagtcac    8460
agaaaagcat cttacggatg gcatgacagt aagagaatta tgcagtgctg ccataaccat    8520
gagtgataac actgcggcca acttacttct gacaacgatc ggaggaccga aggagctaac    8580
cgcttttttg cacaacatgg ggatcatgt aactcgcctt gatcgttggg aaccggagct    8640
gaatgaagcc ataccaaacg acgagcgtga caccacgatg cctgcagcaa tggcaacaac    8700
gttgcgcaaa ctattaactg gcgaactact tactctagct tcccggcaac aattaataga    8760
ctggatggag gcggataaag ttgcaggacc acttctgcgc tcggcccttc cggctggctg    8820
gtttattgct gataaatctg gagccggtga gcgtgggtct cgcggtatca ttgcagcact    8880
ggggccagat ggtaagccct cccgtatcgt agttatctac acgacgggga gtcaggcaac    8940
tatggatgaa cgaaatagac agatcgctga gataggtgcc tcactgatta gcattggta    9000
actgtcagac caagtttact catatatact ttagattgat ttaaaacttc attttttaatt    9060
taaaaggatc taggtgaaga tcctttttga taatctcatg accaaaatcc cttaacgtga    9120
gttttcgttc cactgagcgt cagaccccgt agaaaagatc aaaggatctt cttgagatcc    9180
ttttttttctg cgcgtaatct gctgcttgca acaaaaaaa ccaccgctac cagcggtggt    9240
ttgtttgccg gatcaagagc taccaactct ttttccgaag gtaactggct tcagcagagc    9300
gcagatacca aatactgtcc ttctagtgta gccgtagtta ggccaccact tcaagaactc    9360
tgtagcaccg cctacatacc tcgctctgct aatcctgtta ccagtggctg ctgccagtgg    9420
cgataagtcg tgtcttaccg ggttggactc aagacgatag ttaccggata aggcgcagcg    9480
gtcgggctga acggggggtt cgtgcacaca gcccagcttg gagcgaacga cctacaccga    9540
actgagatac ctacagcgtg agcattgaga aagcgccacg cttcccgaag ggagaaaggc    9600
ggacaggtat ccggtaagcg cagggtcgg aacaggagag cgcacgaggg agcttccagg    9660
gggaaacgcc tggtatcttt atagtcctgt cgggtttcgc cacctctgac ttgagcgtcg    9720
atttttgtga tgctcgtcag ggggcggag cctatggaaa aacgccagca acgcggcctt    9780
tttacggttc ctggcctttt gctggccttt tgaagctgt ccctgatggt cgtcatctac    9840
ctgcctggac agcatggcct gcaacgcggg catcccgatg ccgccggaag cgagaagaat    9900
cataatgggg aaggccatcc agcctcgcgt cg                                  9932
```

<210> SEQ ID NO 39
<211> LENGTH: 330
<212> TYPE: PRT
<213> ORGANISM: Artificial Sequence
<220> FEATURE:
<223> OTHER INFORMATION: IgG1

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

-continued

```
                35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 40
<211> LENGTH: 326
<212> TYPE: PRT
<213> ORGANISM: Artificial Sequence
<220> FEATURE:
<223> OTHER INFORMATION: IgG2

<400> SEQUENCE: 40

Ala Ser Thr Lys Gly Pro Ser Val Phe Pro Leu Ala Pro Cys Ser Arg
1                5                  10                  15
Ser Thr Ser Glu Ser Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Asn Phe Gly Thr Gln Thr
```

```
                65                  70                  75                  80
Tyr Thr Cys Asn Val Asp His Lys Pro Ser Asn Thr Lys Val Asp Lys
                    85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 41
<211> LENGTH: 377
<212> TYPE: PRT
<213> ORGANISM: Artificial Sequence
<220> FEATURE:
<223> OTHER INFORMATION: IgG3

<400> SEQUENCE: 41

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
```

```
                100             105             110
Arg Cys Pro Glu Pro Lys Ser Cys Asp Thr Pro Pro Cys Pro Arg
        115             120             125

Cys Pro Glu Pro Lys Ser Cys Asp Thr Pro Pro Cys Pro Arg Cys
        130             135             140

Pro Glu Pro Lys Ser Cys Asp Thr Pro Pro Cys Pro Arg Cys Pro
145             150             155             160

Ala Pro Glu Leu Leu Gly Gly Pro Ser Val Phe Leu Phe Pro Lys
        165             170             175

Pro Lys Asp Thr Leu Met Ile Ser Arg Thr Pro Glu Val Thr Cys Val
        180             185             190

Val Val Asp Val Ser His Glu Asp Pro Glu Val Gln Phe Lys Trp Tyr
        195             200             205

Val Asp Gly Val Glu Val His Asn Ala Lys Thr Lys Pro Arg Glu Glu
        210             215             220

Gln Tyr Asn Ser Thr Phe Arg Val Val Ser Val Leu Thr Val Leu His
225             230             235             240

Gln Asp Trp Leu Asn Gly Lys Glu Tyr Lys Cys Lys Val Ser Asn Lys
        245             250             255

Ala Leu Pro Ala Pro Ile Glu Lys Thr Ile Ser Lys Thr Lys Gly Gln
        260             265             270

Pro Arg Glu Pro Gln Val Tyr Thr Leu Pro Pro Ser Arg Glu Glu Met
        275             280             285

Thr Lys Asn Gln Val Ser Leu Thr Cys Leu Val Lys Gly Phe Tyr Pro
        290             295             300

Ser Asp Ile Ala Val Glu Trp Glu Ser Ser Gly Gln Pro Glu Asn Asn
305             310             315             320

Tyr Asn Thr Thr Pro Pro Met Leu Asp Ser Asp Gly Ser Phe Phe Leu
        325             330             335

Tyr Ser Lys Leu Thr Val Asp Lys Ser Arg Trp Gln Gln Gly Asn Ile
        340             345             350

Phe Ser Cys Ser Val Met His Glu Ala Leu His Asn Arg Phe Thr Gln
        355             360             365

Lys Ser Leu Ser Leu Ser Pro Gly Lys
        370             375

<210> SEQ ID NO 42
<211> LENGTH: 327
<212> TYPE: PRT
<213> ORGANISM: Artificial Sequence
<220> FEATURE:
<223> OTHER INFORMATION: IgG4

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

-continued

```
                85                  90                  95
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```